(12) United States Patent
Takahashi et al.

(10) Patent No.: US 11,117,963 B2
(45) Date of Patent: Sep. 14, 2021

(54) ANTIBODY WHICH BINDS TO MYELIN OLIGODENDROCYTE GLYCOPROTEIN

(71) Applicants: Kyowa Kirin Co., Ltd., Tokyo (JP); KAGOSHIMA UNIVERSITY, Kagoshima (JP)

(72) Inventors: Nobuaki Takahashi, Tokyo (JP); Ryosuke Nakano, Tokyo (JP); Sayaka Maeda, Tokyo (JP); Yuji Ito, Kagoshima (JP)

(73) Assignees: KYOWA HAKKO KIRIN CO., LTD., Tokyo (JP); KAGOSHIMA UNIVERSITY, Kagoshima (JP)

( * ) Notice: Subject to any disclaimer, the term of this patent is extended or adjusted under 35 U.S.C. 154(b) by 0 days.

(21) Appl. No.: 16/473,482

(22) PCT Filed: Dec. 25, 2017

(86) PCT No.: PCT/JP2017/046445
§ 371 (c)(1),
(2) Date: Jun. 25, 2019

(87) PCT Pub. No.: WO2018/123979
PCT Pub. Date: Jul. 5, 2018

(65) Prior Publication Data
US 2019/0352397 A1 Nov. 21, 2019

(30) Foreign Application Priority Data

Dec. 26, 2016 (JP) .............................. JP2016-251106

(51) Int. Cl.
| | |
|---|---|
| *C07K 16/28* | (2006.01) |
| *A61K 47/10* | (2017.01) |
| *A61K 47/36* | (2006.01) |
| *C12N 5/12* | (2006.01) |
| *G01N 33/563* | (2006.01) |

(52) U.S. Cl.
CPC .......... *C07K 16/2803* (2013.01); *A61K 47/10* (2013.01); *A61K 47/36* (2013.01); *C12N 5/12* (2013.01); *G01N 33/563* (2013.01); *C07K 2317/24* (2013.01); *C07K 2317/31* (2013.01); *C07K 2317/565* (2013.01)

(58) Field of Classification Search
CPC ............ C07K 16/2803; C07K 2317/24; C07K 2317/31; C07K 2317/565; C07K 2319/43; C07K 2319/21; C07K 14/82; C07K 14/71; C07K 14/4713; C07K 2317/33; C07K 16/32; C07K 16/40; C07K 2319/30; C07K 2319/33; C07K 2317/77; C07K 2317/569; C07K 2317/92; C07K 2317/94; C07K 2317/622; C07K 2317/21; C07K 16/18; C07K 16/46; A61K 47/10; A61K 47/36; A61K 2039/505; A61K 39/395; C12N 5/12; C12N 5/10; C12N 15/09; G01N 33/563; G01N 33/53; C12Y 301/04012; A61P 25/00
See application file for complete search history.

(56) References Cited

U.S. PATENT DOCUMENTS

| | | |
|---|---|---|
| 6,333,033 B1 | 12/2001 | Genain et al. |
| 2002/0068058 A1 | 6/2002 | Genain et al. |
| 2002/0072588 A1 | 6/2002 | Budingen et al. |

FOREIGN PATENT DOCUMENTS

| | | |
|---|---|---|
| CA | 2 623 841 | 4/2007 |
| JP | 5-170667 | 7/1993 |
| JP | 9-502346 | 3/1997 |
| JP | 2002-523472 | 7/2002 |
| JP | 2004-511570 | 4/2004 |
| WO | 95/06727 | 3/1995 |
| WO | 95/07096 | 3/1995 |
| WO | 2006/116155 | 11/2006 |
| WO | 2007/036021 | 4/2007 |
| WO | 2012/023623 | 2/2012 |
| WO | 2014/033074 | 3/2014 |
| WO | 2016/081640 | 5/2016 |
| WO | 2016/081643 | 5/2016 |

OTHER PUBLICATIONS

Rogers et al., "Therapeutic monoclonal antibodies and derivatives: Historical perspectives and future directions", Biotechnology Advances, 34: 1149-1158 (2016).

(Continued)

*Primary Examiner* — Kimberly Ballard
*Assistant Examiner* — Stacey N MacFarlane
(74) *Attorney, Agent, or Firm* — Wenderoth, Lind & Ponack, L.L.P.

(57) ABSTRACT

The invention relates to an antibody which binds to myelin oligodendrocyte glycoprotein (MOG), an antibody fragment thereof, a hybridoma which produces the antibody or the antibody fragment, a nucleic acid containing a nucleotide sequence which encodes the antibody or the antibody fragment, a transformant cell containing a vector containing the nucleic acid, a method for producing the antibody or the antibody fragment, a composition containing the antibody or the antibody fragment and a method for detecting or measuring an antigen that is present in the brain, a method for diagnosing or treating a brain disease, a method for improving the property of an antibody of accumulating in the brain and a method for increasing the amount of an antibody in the brain which use the antibody or the antibody fragment.

8 Claims, 27 Drawing Sheets

Specification includes a Sequence Listing.

(56) References Cited

OTHER PUBLICATIONS

Partridge, "Re-Engineering Biopharmaceuticals for Delivery to Brain with Molecular Trojan Horses", Bioconjugate Chemistry, 19(7): 1327-1338 (2008).
Wang et al., "Monoclonal Antibody Pharmacokinetics and Pharmacodynamics", Clin. Pharma. Ther., 84(5): 548-558 (2008).
Garg et al., "Investigation of the Influence of FcRn on the Distribution of IgG to the Brain", The AAPS Journal, 11(3): 553-557 (2009).
Blennow et al., "Effect of Immunotherapy with Bapineuzumab on Cerebrospinal Fluid Biomarker Levels in Patients With Mild to Moderate Alzheimer Disease", Arch Neurol, 69(8): 1002-1010 (2012).
Wraith et al., "Enzyme Replacement Therapy for Mucopolysaccharidosis I: A randomized, double-blinded, placebo-controlled, multinational study of recombinant human a-L-Iduronidase (Laronidase)", J. Pediatrics, 144(5): 581-588 (2004).
Muenzer et al., "A phase II/III clinical study of enzyme replacement therapy with idursulfase in mucopolysaccharidosis II (Hunter Syndrome)", Genetics in Medicine 8(8): 465-473 (2006).
Document attached to intravenous infusion 2.9 mg of Aldurazyme (registered trademark) (Jul. 2016, 8th edition), with partial English translation.
Document attached to intravenous infusion 6 mg of Elaprase (registered trademark) (Jul. 2016, 6th edition), with partial English translation.
Brooks et al., "Significance of immune response to enzyme-replacement therapy for patients with a lysosomal storage disorder", Trends in Molecular Medicine, 9(10): 450-453 (2003).
Sorrentino et al., "Brain Targeting in MPS-IIIA", Pediatric Endocrinology Reviews (PER), 13(Supplement 1): 630-638 (2016).
Couch et al., "Addressing Safety Liabilities of TfR Bispecific Antibodies That Cross the Blood-Brain Barrier", Science Translation Medicine, 5(183): 1-12 (2013).
Yu et al., "Therapeutic bispecific antibodies cross the blood-brain barrier in nonhuman primates", Science Translation Medicine, 6(261): 1-10 (2014).
Niewoehner et al., "Increased Brain Penetration and Potency of a Therapeutic Antibody Using a Monovalent Molecular Shuttle", Neuron, 81: 49-60 (2014).
Yue et al., Fluorescence-Labeled Immunomicelles: Preparation, in vivo Biodistribution, and Ability to Cross the Blood-Brain Barrier, Macromol. Biosci., 12: 1209-1219 (2012).
Partridge et al., "Reengineering Biopharmaceuticals for Targeted Delivery Across the Blood-Brain Barrier", Methods in Enzymology, 503: 269-292 (2012).
Boado et al., "Comparison of Blood-Brain Barrier Transport of Glial-Derived Neurotrophic Factor (GDNF) and an IgG-GDNF Fusion Protein in the Rhesus Monkey", Drug Metabolism and Disposition, 37(12): 2299-2304 (2009).
Boado et al., "Drug Targeting in Erythropoietin Across the Primate Blood-Brain Barrier with an IgG Molecular Trojan Horse", The Journal of Pharmacology and Experimental Therapeutics, 333(3): 961-969 (2010).
Boado et al., "IgG-Enzyme Fusion Protein: Pharmacokinetics and Anti-Drug Antibody Response in Rhesus Monkeys", Bioconjugate Chemistry, 24: 97-104 (2013).
Zhang et al., "Delivery of β-Galactosidase to Mouse Brain via the Blood-Brain Barrier Transferrin Receptor", The Journal of Pharmacology and Experimental Therapeutics, 313(3): 1075-1081 (2005).
Abulrob et al., "The blood-brain barrier transmigrating single domain antibody: mechanisms of transport and antigenic epitopes in human brain endothelial cells", Journal of Neurochemistry, 95: 1201-1214 (2005).
Farrington et al., "A novel platform for engineering blood-brain barrier-crossing bispecific biologics", The FASEB Journal, 28: 4764-4778 (2014).
Webster et al., "Brain penetration, target engagement, and disposition of the blood-brain barrier-crossing bispecific antibody antagonist of metabotropic glutamate receptor type 1", The FASEB Journal, 30: 1927-1940 (2016).
Zhang et al., "Mediated efflux of IgG molecules from brain to blood across the blood-brain barrier", Journal of Neuroimmunology, 114: 168-172 (2001).
Cooper et al., "Efflux of monoclonal antibodies from rat brain by neonatal Fc receptor, FcRn", Brain Research, 1534: 13-21 (2013).
Brunner et al., "Differential Ultrastructural Localization of Myelin Basic Protein, Myelin/Oligodendroglial Glycoprotein, and 2',3'-Cyclic Nucleotide 3'-Phosphodiesterase in the CNS of Adult Rats", Journal of Neurochemistry, 52(1): 296-304 (1989).
Pham-Dinh et al., "Myelin/oligodendrocyte glycoprotein is a member of a subset of the immunoglobulin superfamily encoded within the major histocompatibility complex", Proc. Natl. Acad. Sci. USA, 90: 7990-7994 (1993).
Gardiner et al., "Myelin/Oligodendrocyte Glycoprotein Is a Unique Member of the Immunoglobulin Superfamily", Journal of Neuroscience Research, 33: 177-187 (1992).
Urich et al., Autoantibody-mediated demyelination depends on complement activation but not activatory Fc-receptors, PNAS, 103(49): 18697-18702 (2006).
Reindl et al., "Antibodies against the myelin oligodendrocyte glycoprotein and the myelin basic protein in multiple sclerosis and other neurological diseases: a comparative study", Brain, 122: 2047-2056 (1999).
Shimizu et al., "Disruption of blood-brain barrier in multiple sclerosis and neuromyelitis optica", Nippon Rinsho, 72(11): 1949-1954 (2014).
Sinmaz et al., "Autoantibodies in movement and psychiatric disorders: updated concepts in detection methods, pathogenicity, and CNS entry", Annals of the New York Academy of Sciences, 1351: 22-38 (2015).
Quintana et al., "Antigen microarrays identify CNS-produced autoantibodies in RRMS", Neurology, 78: 532-539 (2012).
Gold et al., "Understanding pathogenesis and therapy of multiple sclerosis via animal models: 70 years of merits and culprits in experimental autoimmune encephalomyelitis research", Brain, 129: 1953-1971 (2006).
Morris-Downes et al., "Pathological and regulatory effects of anti-myelin antibodies in experimental allergic encephalomyelitis in mice", Journal of Neuroimmunology, 125: 114-124 (2002).
Locatelli et al., "Primary oligodendrocyte death does not elicit anti-CNS immunity", Nature Neuroscience, 15(4): 543-551 (2012).
Schluesener et al., "A monoclonal antibody against a myelin oligodendrocyte glycoprotein induces relapses and demyelination in central nervous system autoimmune disease", The Journal of Immunology, 139(12): 4016-4021 (1987).
Tokuhara et al., "N-type Calcium Channel in the Pathogenesis of Experimental Autoimmune Encephalomyelitis", Journal of Biological Chemistry, 285(43): 33294-33306 (2010).
International Search Report (ISR) and Written Opinion of the International Searching Authority, dated Mar. 27, 2018 in corresponding International Patent Application No. PCT/JP2017/046445, with English language translation of the ISR.
Extended European Search Report dated Nov. 25, 2020 in corresponding European Patent Application No. 17885914.6.
Von Budingen et al., "Molecular characterization of antibody specificities against myelin/oligodendrocyte glycoprotein in autoimmune demyelination", PNAS 99(12):8207-8212 (2002).
Urich et al., "Autoantibody-mediated demyelination depends on complement activation but not activatoly Fc-receptors", PNAS 103 (49):18697-18702 (2006).
Nakano et al., "A new technology for increasing therapeutic protein levels in the brain over extended periods", PLOS ONE 14(4): e0214404, pp. 1-16 (2019).

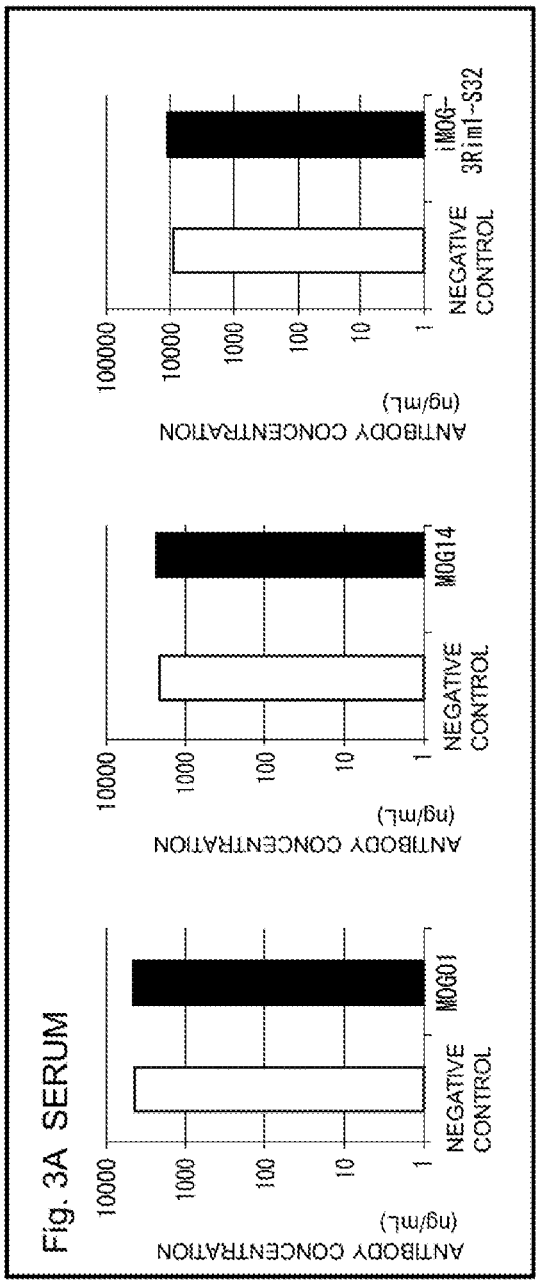
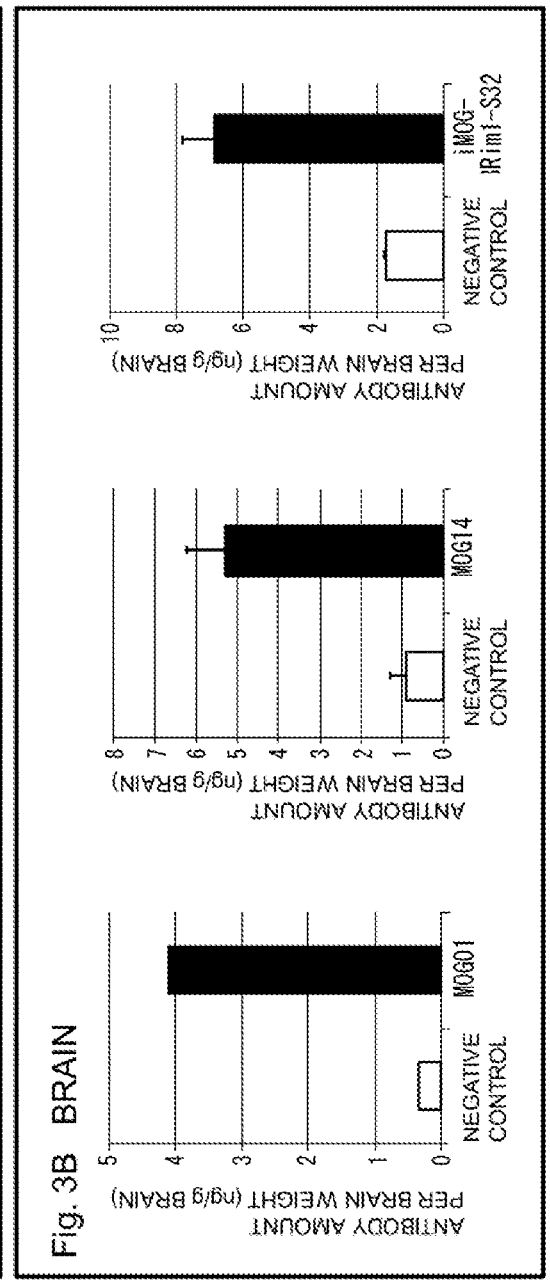

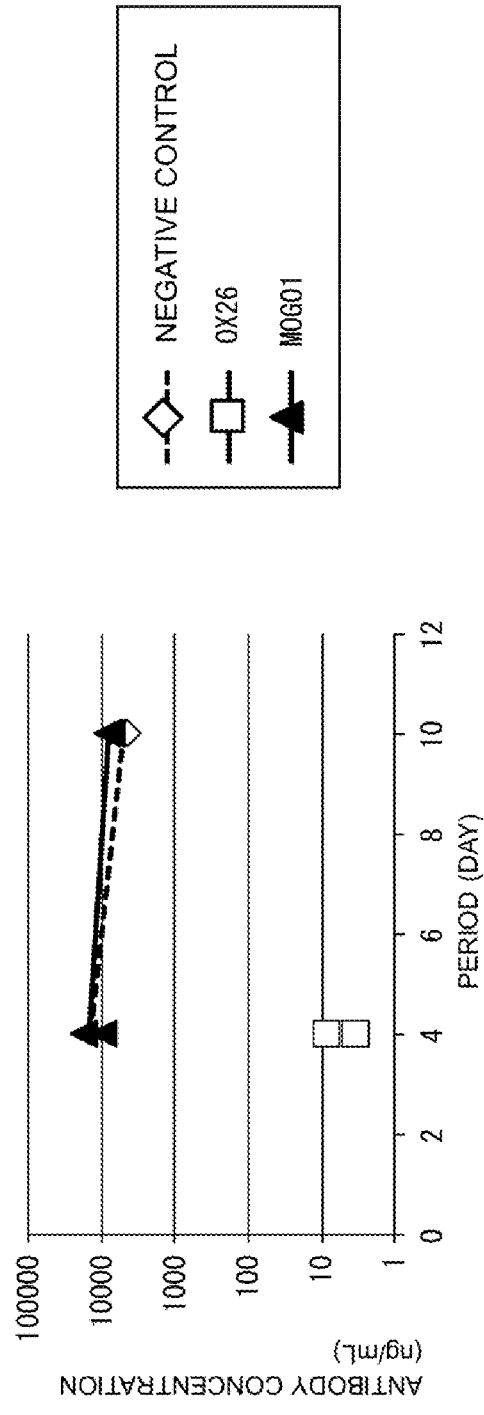
Fig. 4A SERUM
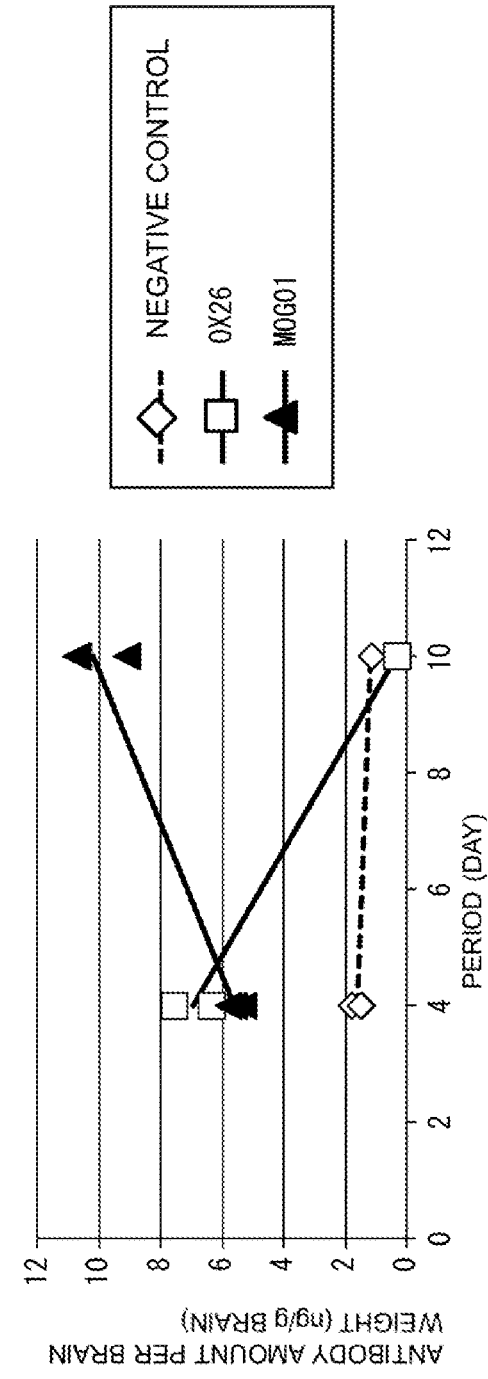
Fig. 4B BRAIN

SERUM

BRAIN

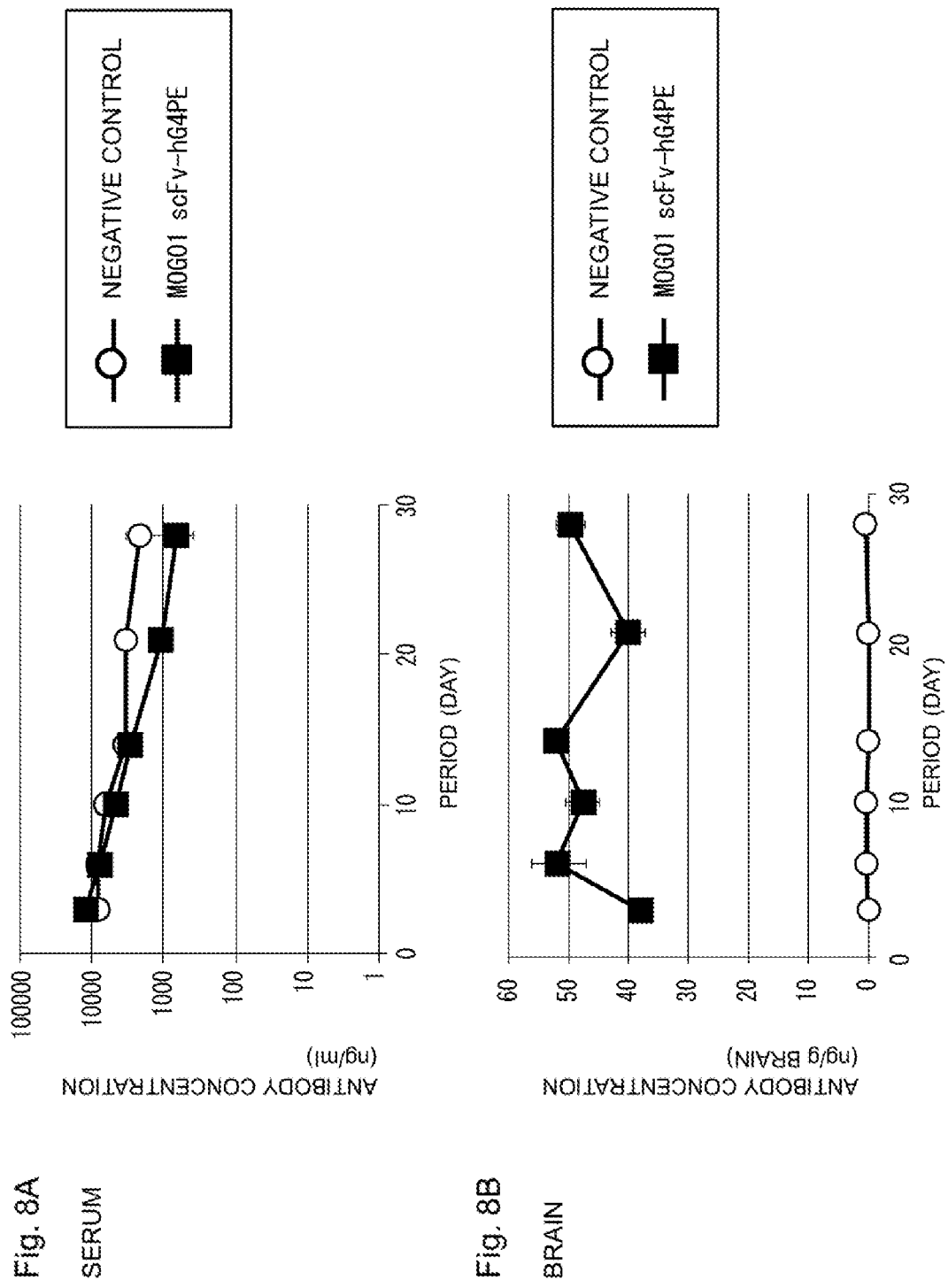
Fig. 8A SERUM
Fig. 8B BRAIN

AFTER 6 DAYS
AF488-AVM IgG4PE ANTIBODY
AF488-MOG01 IgG4PE ANTIBODY

AFTER 14 DAYS
AF488-AVM IgG4PE ANTIBODY
AF488-MOG01 IgG4PE ANTIBODY

Fig. 10A

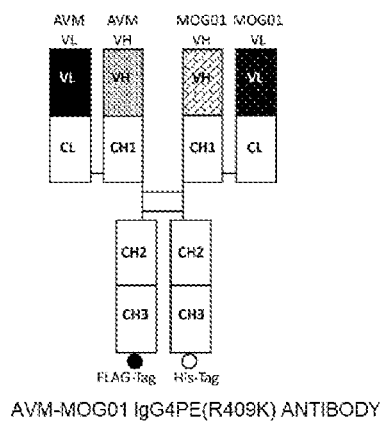

AVM-MOG01 IgG4PE(R409K) ANTIBODY

Fig. 10B

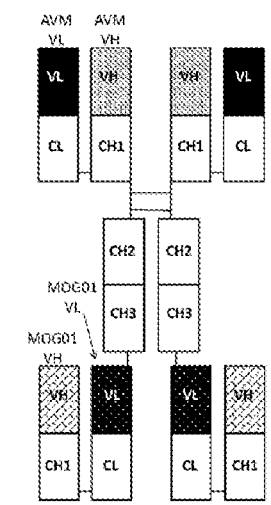

AVM IgG4PE(R409K)_MOG01 Fab ANTIBODY

Fig. 10C

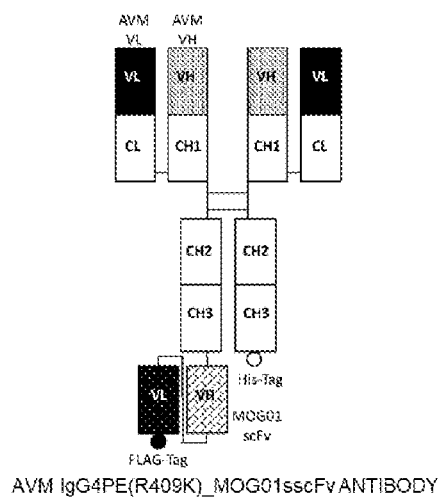

AVM IgG4PE(R409K)_MOG01sscFv ANTIBODY

Fig. 11A

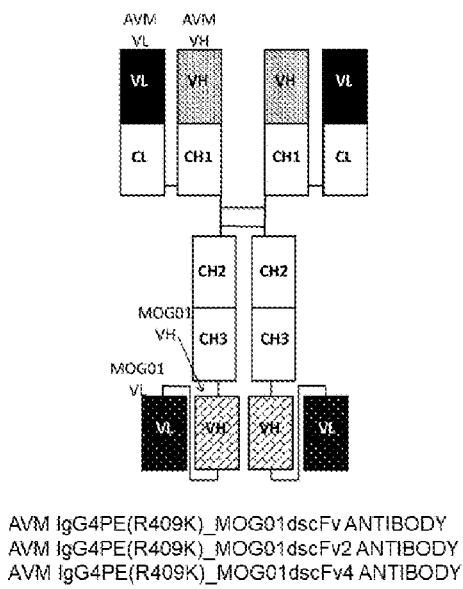

AVM IgG4PE(R409K)_MOG01dscFv ANTIBODY
AVM IgG4PE(R409K)_MOG01dscFv2 ANTIBODY
AVM IgG4PE(R409K)_MOG01dscFv4 ANTIBODY

Fig. 11B

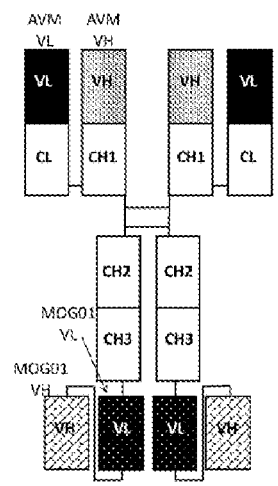

AVM IgG4PE(R409K)_MOG01dscFv3 ANTIBODY
AVM IgG4PE(R409K)_MOG01dscFv5 ANTIBODY
AVM IgG4PE(R409K)_MOG01dscFv6 ANTIBODY
AVM IgG4PE(R409K)_MOG01dscFv7 ANTIBODY
AVM IgG4PE(R409K)_MOG01dscFv8 ANTIBODY
AVM IgG4PE(R409K)_MOG01dscFv9 ANTIBODY
AVM IgG4PE(R409K)_MOG01dscFv10 ANTIBODY
AVM IgG4PE(R409K)_MOG01dscFv11 ANTIBODY

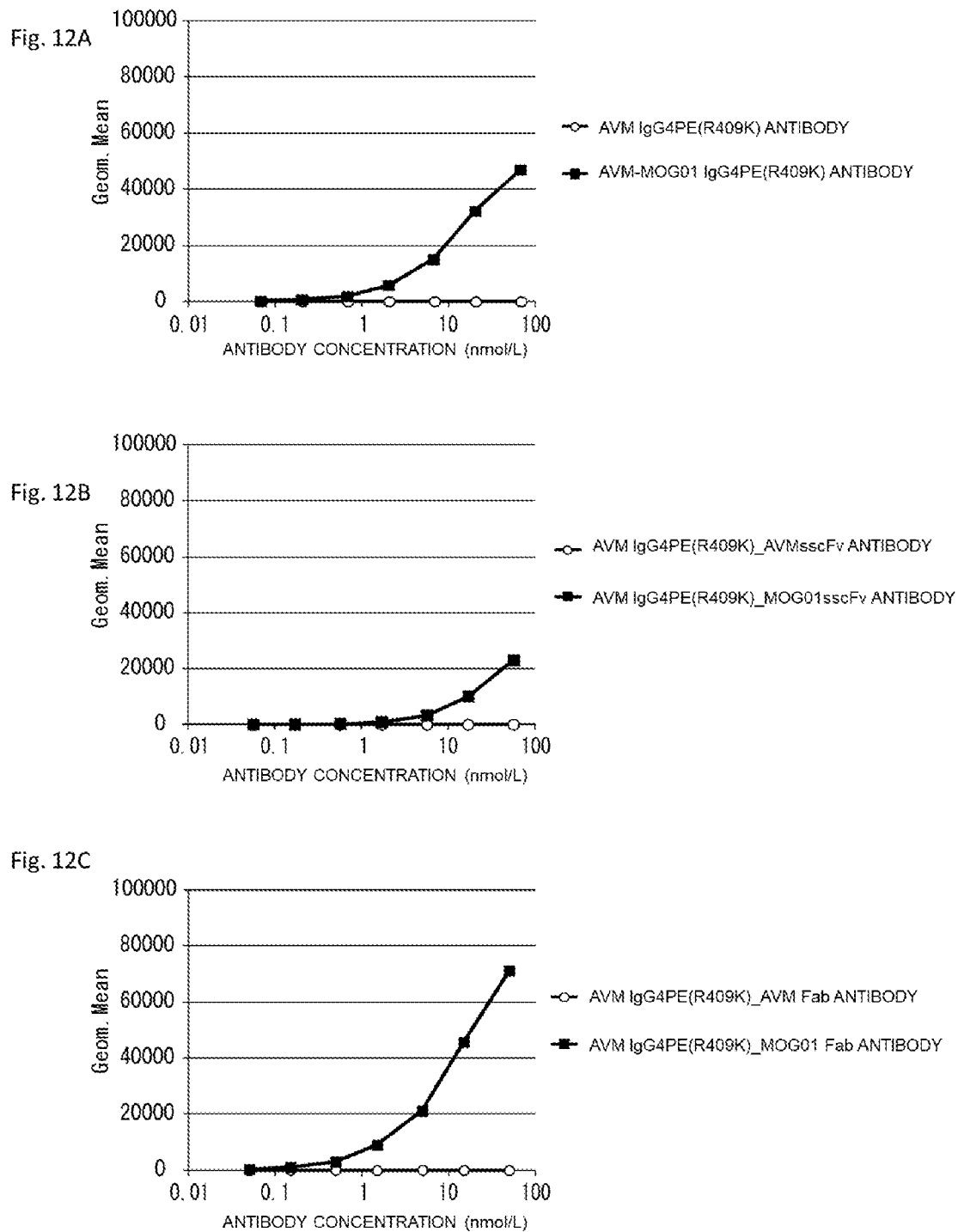

SERUM

BRAIN

SERUM

BRAIN

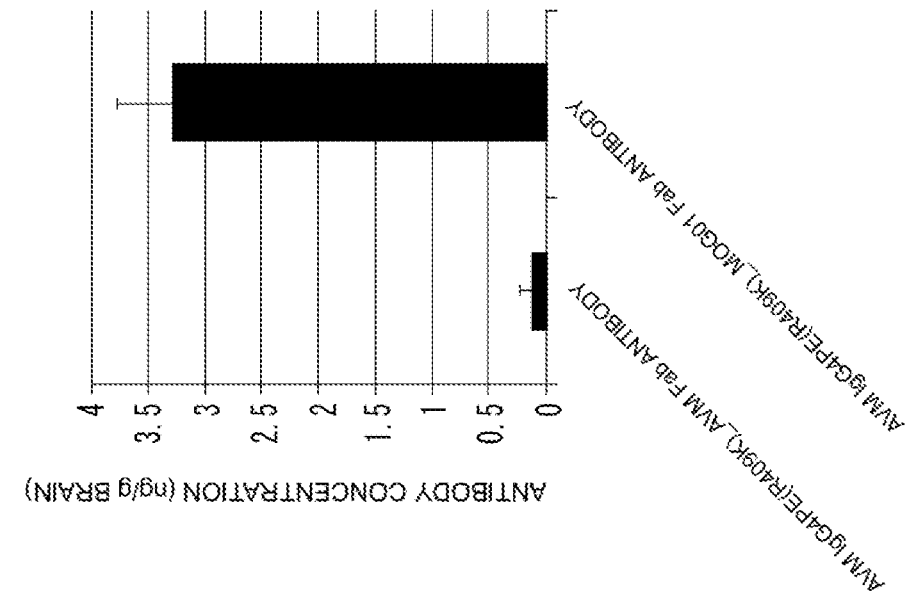
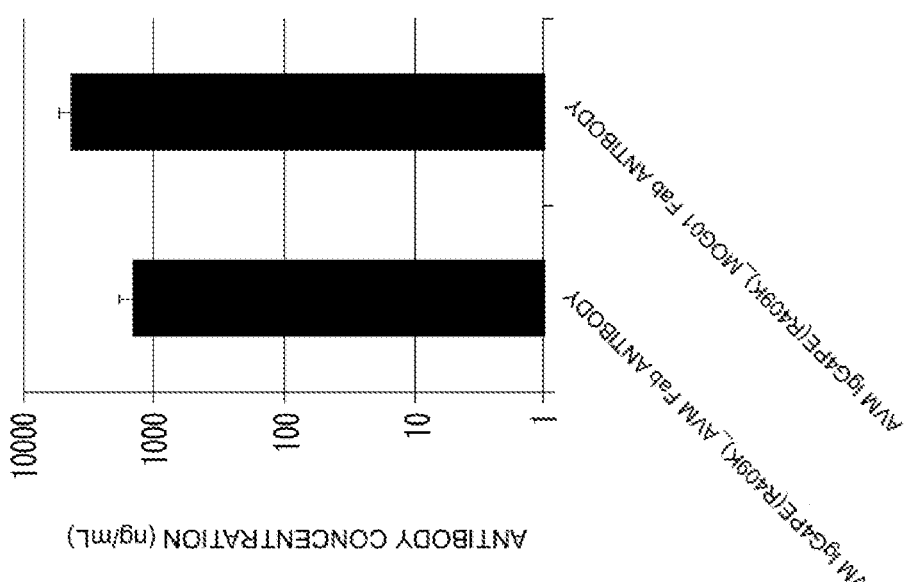

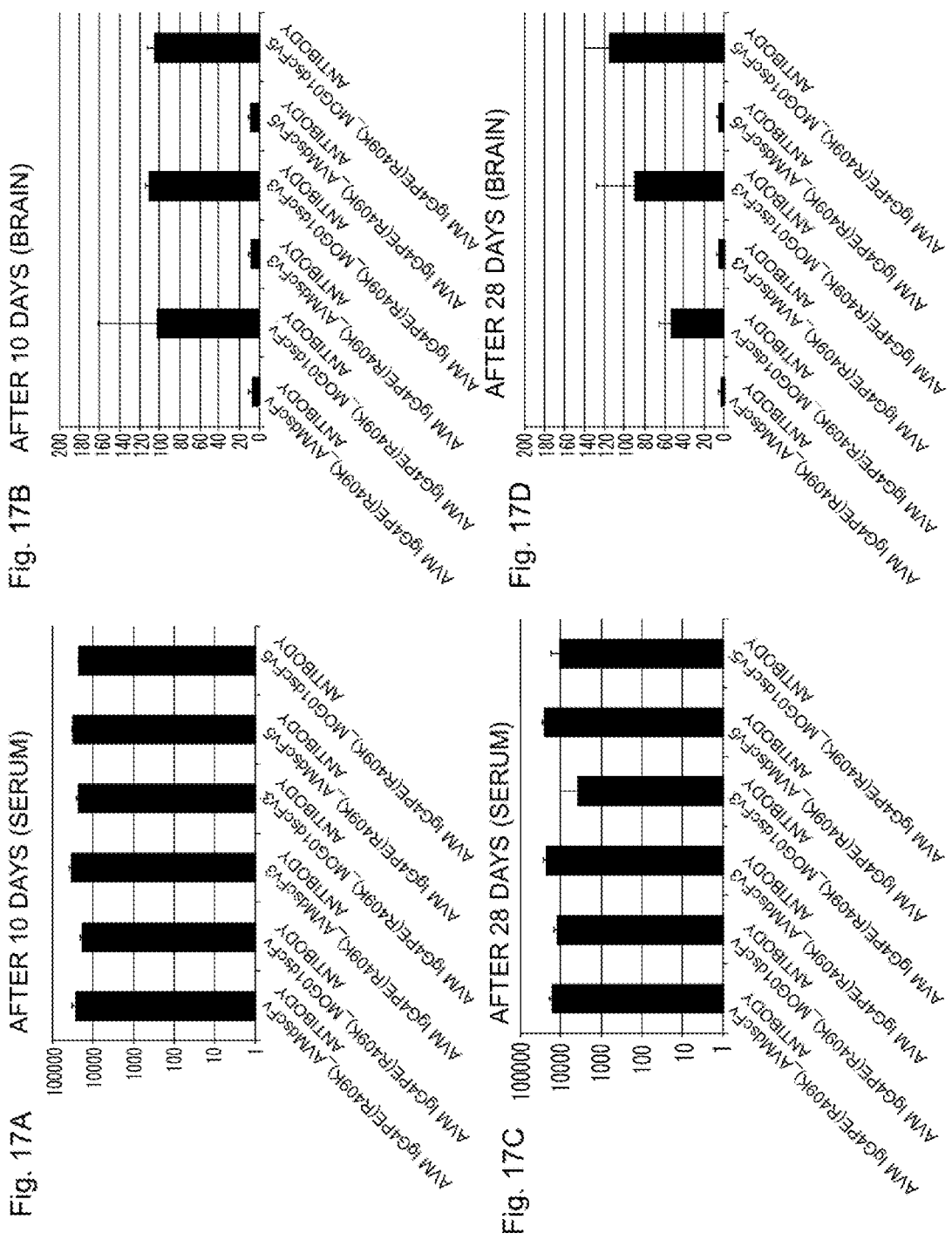

Fig. 18

CLONES SIMILAR TO MOG301 ANTIBODY

```
MOG#426  QVQLVQSGAEVKKPGASVKVSCKASGYSFNSYGINWVRQAPGQGLEWMGWISAYTGKTSY
MOG#428  EVQLVQSGAEVKKPGASVKVSCKASGYSFNSYGINWVRQAPGQGLEWMGWISAYTGKTSY
MOG#301  QVQLVQSGAEVKKPGASVKVSCKASGYSFTSYGINWVRQAPGQGLEWMGWISAYNGTTNY

MOG#426  AQKVQGRVTMTTDRSTSTAYMELRSLRSDDTAMYYCAREYDILTGYSDAFDTWGQGTMVT
MOG#428  AQKVQGRVTMTTDRSTSTAYMELRSLRSDDTAMYYCAREYDILTGYSDAFDTWGQGTMVT
MOG#301  AQKQGRVTMTRDSTRTAYMELRSLRSDDTAYYCAREYDILTGYSDAFDTWGQGTVT

MOG#426  VSSGGGGSGGRASGGGGSEIVLTQSPTLSLSPGERATLSCRASQSVSS-YLAWYQQKPG
MOG#428  VSSGGGGSGGRASGGGGSEIVLTQSPGTLSLSPGERATLSCRASQSVSSSYLAWYQQKPG
MOG#301  VSSGGGGSGGRASGGGGSEIVTQSPGTLSLSPGERATLSCRASQSVSSSYLAWYQQKPG

MOG#426  QAPRLLIYDASRATGIPARFSGSGSGTDFTLTISSLEPEDFAVYYCQQRGNWPLTFGGG
MOG#428  QAPRLLIYGASSRATGIPDRFSGSGSGTDFTLTISRLEPEDFAVYYCQQYGSSPRTFGCG
MOG#301  QAPRLLIYGASSRATGIPDRFSGSGSGTDFTLTISRLEPEDFAVYYCQQYGSSPLTFGGG

MOG#426  TKLEIK
MOG#428  TKLEIK
MOG#301  TKEIK
```

Fig. 19

CLONES SIMILAR TO MOG303 ANTIBODY

```
MOG#303  EVQLVESGGGLVQPGGSLRLSCAASGFTFSSYAMGWVRQAPGKGLEWVSAISGSGGSTYY
MOG#476  EVQLVESGGGLVQPGGSLRLSCAASGFTFSSYAMNWVRQAPGKGLEWVSAISYSGRSTYY
MOG#314  QVQLVESGGGLVQPGGSLRLSCAASGFTFSSYAMSWVRQAPGKGLEWVSAIGRGSSTYY
MOG#315  EVQLVESGGGLVQPGGSLRLSCAASGFTFSYAMSWVRQAPGKGLEWVSAISGSGVSTYY
MOG#313  QVQLVESGGGLVQPGGSLRLSCAASGFTFSSYAMSWVRQAPGKGLEWVSISGSGGSTYY
MOG#357  EVQLVEGGGLVQPGGSLRLSCAASGFTFSSYAMSWVRQAPGKGLEWVSINHSGGSTYY
MOG#331  EVQLVESGGGLVYPGGSLRLSCAASGFTFSSYAMSWVRQAPGKGLEWVSAISGSGGSTYY

MOG#303  ADSVKGRFTISRDNSKNTLYLQMNSLRAEDTAVYYCARGYDILTGYFDYWGQGTLVTV
MOG#476  ADSVKGRFTISRDNSKNTLYLQMNSLRAEDTAVYYCARGLYDILTGGCFDYWGQGTLVTV
MOG#314  ADSVKGRFTISRDNSKNTLYLQMNSLRAEDTAVYYCARAYYDILTGSFFDYWGQGTLVTV
MOG#315  ADSVKGRFTISRDNSKNTLYLQMNSLRAEDTAVYYCARAYYDILTGNFLDYWGQGTLVTV
MOG#313  ADSVKGRFTISRDNSKNTLYLQMNSLRAEDTAVYYCARAYYDILTGSLFDSWGQGTLVTV
MOG#357  ADSVKGRFTISRDNSKHTLYLQMNSLRAEDTAVYYCARDYYDILTGSFFDYWGQGTLVTV
MOG#331  ADSVKGRFTISRDNSKNTLYLQMNSLRAEDTAVYYCARAYYDILTGSFFDYWGQGTLVTV

MOG#303  SSGGGGSGGRASGGGGSAIQMTQSPSSLSASVGDRVTITCRASQGISSALAWYQQKPGKA
MOG#476  SSGGGGSGGRASGGGGSDIQMTQSPSSLSASVGDRVTITCRASQGISSALAWYQQKPGKA
MOG#314  SSGGGGSGGRASGGGGSDIQITQSPSSLSASVGDRVTITCRASQGISSALAWYQQKPGKA
MOG#315  SSGGGGSGGRASGGGGSAIQITQSPSSLSASVGDRVTITCRASQGISSALAWYQQKPGKA
MOG#313  SSGGGGSGGRASGGGGSDIVMTQSPSSLSASVGDRVTITCRASQGISSALAWYQQKPGKA
MOG#357  SSGGGGSGGRASGGGGSDIVMTQSPSSLSASVGDRVTITCRASQGISSALAWYQQKPGKA
MOG#331  SSGGGGSGGRASGGGGSIVMTQSPATLSLSPGERATCRASQSVSSYLAWYQQKPGRA

MOG#303  PKLLIYDASSLESGVPSRFSGSGSGTDFTLTISSLQPEDFATYYCQQFNSYPFTFGPGT
MOG#476  PKLLIYDASSLESGVPSRFSGSGSGTDFTLTISSLQPEDFATYYCQQFNSYPSTFGQGT
MOG#314  PKLLIYDASSLESGVPSRFSGSGSGTDFTLTISSLQPEDFATYYCQQFNSYPYTFGQGTK
MOG#315  PKLLIYDASSLESGVPSRFSGSGSGTDFTLTISSLQPEDFATYYCQQFNSYPLYFGQGTK
MOG#313  PKLLIYDASSLESGVPSRFSGSGSGTDFTLTISSLQPEDFATYYCQQFNSYPLTFGQGTK
MOG#357  PKLLIYDASSLESGVPSRFSGSGSGTDFTLTISSLQPEDFATYYCQQFNSYPWTFGQGTK
MOG#331  PKLLIYDASNRATGIPARFSGSGSGTDFTLTISRLEPEDFAVYYCQQCSSPLTFGQGTK

MOG#303  LEIK
MOG#476  LEIK
MOG#314  LEIK
MOG#315  VEIK
MOG#313  VEIK
MOG#357  VEIK
MOG#331  LEIK
```

Fig. 20

CLONES SIMILAR TO MOG307 ANTIBODY

```
MOG#307  R TLRESGPTLVKPTQTLTLTCTFSGFSLSTSGVGVGWIRQPPGKALEWLALIFWDDD H
MOG#323  RITLRESGPTLVKPTQTLTLTCTFSGFSLSTSGVGVGWIRQPPGKALEWLALIFWDDD H
MOG#341  RITL ESGPTLVKPTQTLTLTCTFSGFSLSTSGVGVGWIRQPPGKALEWLALI WDDD H
MOG#354  RITLRESGPTLVKPTQTLTLTCT S G L SLSTSGVGVGWIRQPPGKALEWLALIFWDDD H
MOG#355  RITLRESGPTLVKPTQTLTLTC T S G L SLSTSGVGVGWIRQPPGKALEWLALIFWDDD H

MOG#307  YSPSLKSRLTITKDTSKNQVVLTMTNMDPVDTATYYCARYYFGSGSYFPSYWYFDLWGRG
MOG#323  YSPSLKSRLTITKDTSKNQVVLTMTNMDPVDTATYYCARYYFGSGSYFPSYWYFDLWGRG
MOG#341  YSPSLKSRLTITKDTSKNQVVLTMTNMDPVDTATYYCARYYFGSGSY PSYWYFDLWGRG
MOG#354  YSPSLKSRLTITKDTSKNQVVLTMTNMDPVDTATYYCARYYFGSGSYFPSYWYFDLWGRG
MOG#355  YSPSLKSRLTITKDTSKNQVVLTMTNMDPVDTATYYCARYYFGSGSYFPSYWYFDLWGRG

MOG#307  TLVTVSSGGGGSGGRASGGGGSEIVMTQSPATLSLSPGERATLSCRASQSVSSYLAWYQQ
MOG#323  TLVTVSSGGGGSGGRASGGGGSEIVMTQSPATLSLSPGERATLSCRASQSVSSYLAWYQQ
MOG#341  TLVTVSSGGGGSGGRASGGGGSEI TQSPATLSLSPGERATLSCRASQSVSSYLAWYQQ
MOG#354  T VTVSSGGGGSGGRASGGGGSEIVMTQSPATLSLSPGERATLSCRASQSVSSYLAWYQQ
MOG#355  TLVTVSSGGGGSGGRASGGGGSEIV TQSPATLSLSPGERATLSCRASQSVSSYLAWYQQ

MOG#307  KPGQAPRLLIYDASNRATGIPARFSGSGSGTDFTLTISSLEPEDFAVYYCQQRSNWPPTF
MOG#323  KPGQAPRLLIYDASNRATGIPARFSGSGSGTDFTLTISSLEPEDFAVYYCQQRSNWPPTF
MOG#341  KPGQAPRLLIYDASNRATGIPARFSGSGSGTDFTLTISSLEPEDFAVYYCQQRSNWPPTF
MOG#354  KPGQAPRLLIYDASNRATGIPARFSGSGSGTDFTLTISSLEPEDFAVYYCQQRSNWP TF
MOG#355  KPGQAPRLLIYDASNRATGIPARFSGSGSGTDFTLTISSLEPEDFAVYYCQQRSNWP TF

MOG#307  G GTKVEIK
MOG#323  GGGTK EIK
MOG#341  GGGTKVEIK
MOG#354  GGGTKVEIK
MOG#355  GGGTK EIK
```

Fig. 21

CLONES SIMILAR TO MOG310 ANTIBODY

```
MOG#308  EVQLVQSGAEVKKPGSSVKVSCKASGGTFSRYAISWVRQAPGQGLEWMGGIIPMFSTINY
MOG#338  QVQLVQSGAEVKKPGSSVKVSCKASGGTFSRYAISWVRQAPGQGLEWMGGIIPMFNTANY
MOG#319  QVQLVQSGAEVKKPGSSVKVSCKASGGTFSRYAISWVRQAPGQGLEWMGGIIPMFSTANY
MOG#320  QVQLVQSGAEVKKPGSSVKVSCKASGGTFSRYAINWVRQAPGQGLEWMGGIIPMFSTANY
MOG#310  QVQLVQSGAEVKKPGSSVKVSCKASGGTFSRYAISWVRQAPGQGLEWMGGIIPMFSTANY
MOG#359  EVQLVQSGAEVKKPGSSVKVSCKASGGTFSRYAISWVRQAPGQGLEWMGGIIPMFNTANY
MOG#478  EVQLVQSGAEVKKPGSSVKVSCKASGGTFSRYAISWVRQAPGQGLEWMGGIIPMFATANY
MOG#316  EVQLVQSGAEVKKPGSSVKVSCKASGGTFSRYAISWVRQAPGQGLEWMGGIIPMFNTANY
MOG#352  EVQLVQSGAEVKKPGSSVKVSCKASGGTFSRYAINWVRQAPGQGLEWMGGIIPMFSTANY

MOG#308  AQKFQGRVTITADESTSTAYMELSSLRSEDTAVYYCARDWAVAGMGFAYWGQGTLVTVSS
MOG#338  AQKFQGRVTITADESTSTAYMELSSLRSEDTAVYYCARDWAVAGMGFDFWGQGTLVTVSS
MOG#319  AQKFQGRVTITADESTSTAYMELSSLRSEDTAVYYCARDWAVAGMGFNYWGQGTLVTVSS
MOG#320  AQKFQGRVTITADESTSTAYMELSSLRSEDTAVYYCARDWAVAGMGFDYWGQGTLVTVSS
MOG#310  AQKFQGRVTITADESTSTAYMELSSLRSEDTAVYYCARDWAVAGMGFNYWGQGTLVTVSS
MOG#359  AQKFQGRVTITADESTSTAYMELSSLRSEDTAVYYCARDWAVAGMGFNYWGQGTLVTVSS
MOG#478  AQKFQGRVTITADESTSTAYMELSSLRSEDTVYYCARDWAVAGMGFAHWGQGTLVTVSS
MOG#316  AQKFQGRVTITADESTSTAYMELSSLRSEDTAVYYCARDWAVAGMGFNYWGQGTLVTVSS
MOG#352  AQKFQGRVTITADESTSTAYMELSSLRSEDTAVYYCARDWAVAGMGFDYWGQGTLVTVSS

MOG#308  GGGGSGGRASGGGGSEIVLTQSPGTLSLSPGERATLSCRASQSVSS-YLAWYQQKPGQAP
MOG#338  GGGGSGGRASGGGGSEIVLTQSPGTLSLSPGERATLSCRASQSVSS-YLAWYQQKPGQAP
MOG#319  GGGGSGGRASGGGGSEIVLTQSPGTLSLSPGERATLSCRASQSVSSSYLAWYQQKPGQAP
MOG#320  GGGGSGGRASGGGGSEIVLTQSPGTLSLSPGERATLSCRASQSVSSSYLAWYQQKPGQAP
MOG#310  GGGGSGGRASGGGGSEIVLTQSPGTLSLSPGERATLSCRASQSVSSSYLAWYQQKPGQAP
MOG#359  GGGGSGGRASGGGGSEIVLTQSPGTLSLSPGERATLSCRASQSVSSSYLAWYQQKPGQAP
MOG#478  GGGGSGGRASGGGGSEIVLTQSPGTLSLSPGERATLSCRASQSVSSSYLAWYQQKPGQAP
MOG#316  GGGGSGGRASGGGGSTQSTQSPSLSASVGDRVTCRASQGNS-ALAWYQQKPGQAP
MOG#352  GGGGSGGRASGGGGSATQSTQSPSSSASVGDRVTCRASQGSS-YLAWYQHKPGQAP

MOG#308  RLLIYDASSRATGIPARFSGSGSGTDFTLTISSLEPEDFAVYYCQQRSNWPPTFGQGTKV
MOG#338  RLLIYDASSRATGIPARFSGSGSGTDFTLTISSLEPEDFAVYYCQQRNNWPPTFGGGTKV
MOG#319  RLLIYGASSRATGIPDRFSGSGSGTDFTLTISRLEPEDFAVYYCQQYGSSPFTFGPGTKV
MOG#320  RLLIYGASSRATGIPDRFSGSGSGTDFTLTISRLEPEDFAVYYCQQYGSSPFTFGPGTKV
MOG#310  RLLIYGASSRATGIPDRFSGSGSGTDFTLTISRLEPEDFAVYYCQQYGSSPFTFGQGTKV
MOG#359  RLLIYGASSRATGIPDRFSGSGSGTDFTLTISRLEPEDFAVYYCQQYGSSPFTFGGGTKV
MOG#478  RLLIYGASSRATGIPDRFSGSGSGTDFTLTISRLEPEDFAVYYCQQYGSSPFTFGQGTKV
MOG#316  RLLIYAASSLQSGVPSRFSGSGSGTDFTLTISSLQPEDFATYYCQQYNSYPFTFGQGTKV
MOG#352  KLLIYAASSLQSGVPSRFSGSGSGTDFTLTISSLQPEDFATYYCQQYNSYPFTFGGGTKV

MOG#308  EIK
MOG#338  EIK
MOG#319  EIK
MOG#320  EIK
MOG#310  EIK
MOG#359  EIK
MOG#478  EIK
MOG#316  EIK
MOG#352  EIK
```

Fig. 22A

CLONE SIMILAR TO MOG329 ANTIBODY

```
MOG#329  QVQLVESGGGLVQPGGSLRLSCAASGF E NYAMNWVRQAPGKGLEWVSAISGSGGSTYY
MOG#470  QVQLVESGGGLVQPGGSLRLSCAASGFT S SYAMNWVRQAPGKGLEWVSAISGSGGSTYY

MOG#329  ADSVKGRFTISRDNSKNTLYLQ NSLRAEDTAVYYCARDYGGISPFDYWGQGTLVTVSSG
MOG#470  ADSVKGRFTISRDNSKNTLYLQ NSLRAEDTAVYYCARDYGGISPFDYWGQGTLVTVSSG

MOG#329  GGGSGGRASGGGGS  Q  TQS S L AS VG  V  T CRASQG ISSA LAWYQQKPG AP L
MOG#470  GGGSGGRASGGGGS  IV TQS A L SLSPG RA T CRASQS VSSY LAWYQQKPG QAP L

MOG#329  LIYDAS SLE S  PSRFSGSGSGTDFTLTIS  Q PEDFA YYCQQ  NSYP TFGQGTK  I
MOG#470  LIYDAS NRA T  PARFSGSGSGTDFTLTISR  PEDFA YYCQQ  GSSP YTFGQGTK  I

MOG#329  R
MOG#470  R
```

Fig. 22B

CLONE SIMILAR TO MOG456 ANTIBODY

```
MOG#418  Q VYL V SGGGLVKPGGSLRLSCAASGFTFSSYSMHWVRQAPGKGLEWVSSI SH SSSYI SY
MOG#456  E VQL VE SGGGLVKPGGSLRLSCAASGFTFSSYSMHWVRQAPGKGLEWVSSI GS RS YI YY

MOG#418  ADSVKGRFTISRDNAKNSLYLQMNSLRAEDTAVYYCAKGYYDILTGSLFDYWGQGTLVTV
MOG#456  ADSVKGRFTISRDNAKNSLYLQMNSLRAEDTAVYYCAKGYYDILTGSLFDYWGQGTLVTV

MOG#418  SSGGGGSGGRASGGGGS IV TQSPA  LSLSPG RA T CRASQS  SSY LAWYQQKPG A
MOG#456  SSGGGGSGGRASGGGGS IV TQSPS  LSAS VG RV T CRASQG  SSA LAWYQQKPG KA

MOG#418  P LLIYDAS NRA T G PARFSGSGSGTDFTLTISR  PEDFA YYCQQ YGSSP TFG GTK
MOG#456  P LLIYDAS SLE G PSRFSGSGSGTDFTLTISS Q PEDFA YYCQQ  NSYP TFG QGTK

MOG#418  VQ IK
MOG#456  V  IK
```

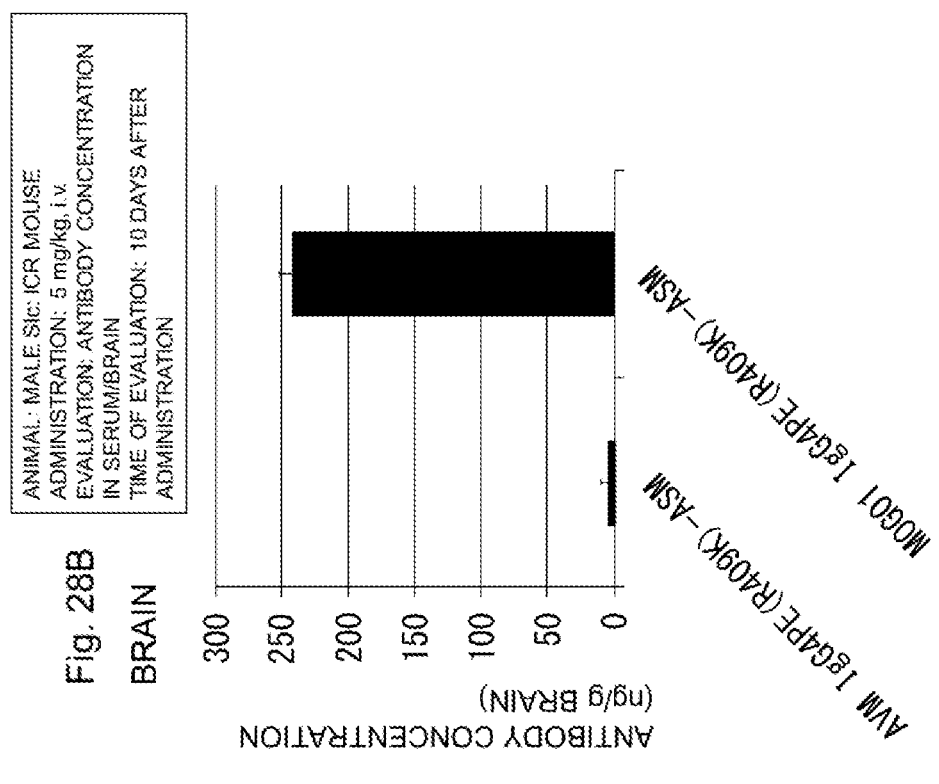
Fig. 28A SERUM
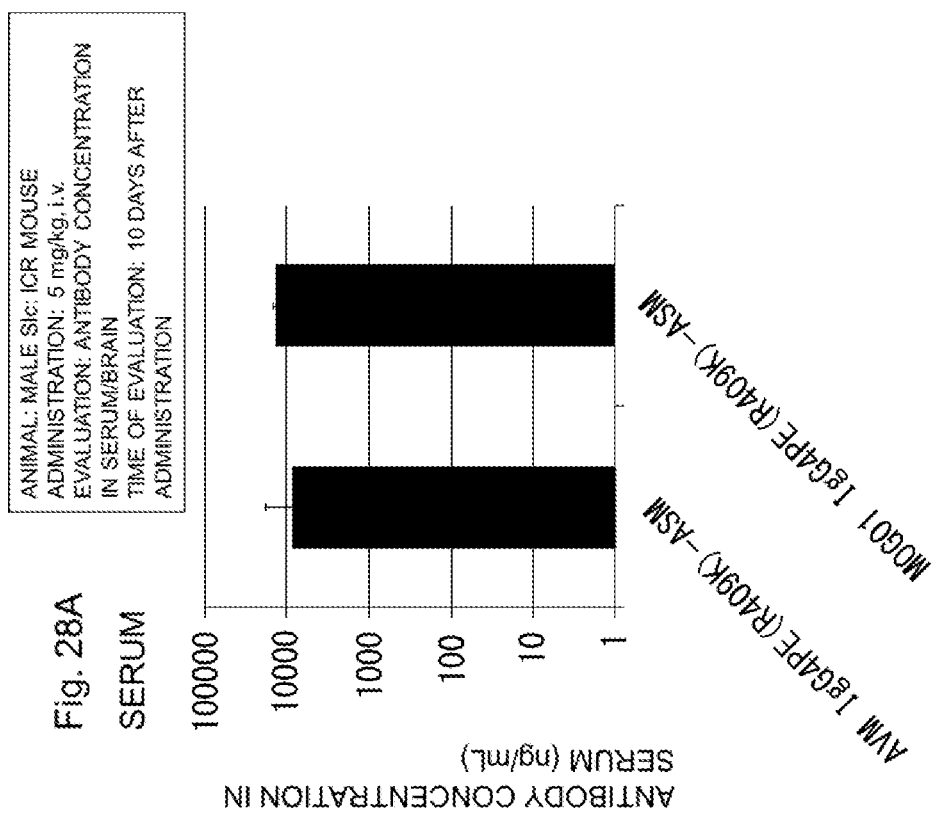
Fig. 28B BRAIN

ANTIBODY WHICH BINDS TO MYELIN OLIGODENDROCYTE GLYCOPROTEIN

TECHNICAL FIELD

The present invention relates to an antibody which binds to myelin oligodendrocyte glycoprotein (MOG), an antibody fragment thereof, a hybridoma which produces the antibody or the antibody fragment, a nucleic acid containing a nucleotide sequence which encodes the antibody or the antibody fragment, a transformant cell containing a vector containing the nucleic acid, a method for producing the antibody or the antibody fragment, a composition containing the antibody or the antibody fragment and a method for detecting or measuring an antigen that is present in the brain, a method for diagnosing or treating a brain disease, a method for improving the property of an antibody of accumulating in the brain and a method for increasing the amount of an antibody in the brain which use the antibody or the antibody fragment.

BACKGROUND ART

Since the approval of a mouse anti-CD3 antibody, muromonab-CD3 (OKT3) as the first antibody drug by FDA in 1986, many antibody drugs have been developed. In 1994, a chimeric antibody, abciximab, in which a variable region of a mouse antibody and a constant region of a human antibody are linked to reduce the antigenicity of the mouse antibody, has been approved.

To further reduce the antigenicity, humanized antibody technique in which a complementarity determining region (CDR below), which plays an important role in binding to an antigen, of a variable region of a mouse antibody is inserted to the frame work region (FR below) of a human antibody has been developed, and a humanized anti-CD20 antibody, dacizumab has been approved in 1997.

Moreover, phage display technique using a human antibody sequence library has been used, and a fully human anti-TNF α antibody, adalimumab, which is the first antibody using the phage display technique that has been approved, has been approved in 2002. Sixty or more antibody drugs targeting antigens such as CD20, CD52, TNF α, HER2 and EGFR have already been approved (NPL 1).

In this manner, antibodies are a widely recognized drug format. Most of the antibody drugs that have been approved so far are those for cancers and immune diseases, which account for about 75% or more of all the antibody drugs.

The importance of biologics such as antibodies is increasing also in the treatment of central nervous system diseases, and it is reported that a monoclonal antibody to amyloid β is studied in Alzheimer's disease and that neurotrophic factors (brain-derived neurotrophic factor BDNF and glial-derived neurotrophic factor GDNF) having neuroprotective effect exhibit neuroprotective effect in central nervous system diseases in an animal model (NPL 2).

However, when an antibody is peripherally administered, the amount sent to the central nervous system is lower than those to the other organs, and the antibody migration rate (the ratio of the concentration in the cerebrospinal fluid (CSF) to the serum concentration) is reported to be 0.1-0.3% (NPLs 3-5).

A reason why the drug delivery amount decreases in the central nervous system including the brain and the bone marrow is the mechanism which is called the blood brain barrier (BBB) and which limits the transportation of a substance between the tissue liquids of the blood and the brain. The blood brain barrier has a physical/nonspecific control mechanism due to the intercellular adhesion of the vascular endothelial cells and a substrate-specific efflux mechanism due to efflux transporters. The blood brain barrier protects the central nervous system from foreign matters or drugs and plays an important role in maintaining the homeostasis.

However, due to the existence of the blood brain barrier, the effective concentration of drug administration is not easily obtained in the central nervous system, and the drug development is difficult. For example, although enzyme replacement therapy is conducted by intravenously administering α-L-iduronidase to Hurler syndrome (mucopolysaccharidosis-I) or iduronate-2-sulfatase to Hunter syndrome (mucopolysaccharidosis-II), the enzymes do not pass through the blood brain barrier due to their high molecular weights, and no efficacy on conditions in the central nervous system has been found (NPLs 6-9). Moreover, it is reported that side effects such as production of a neutralizing antibody are caused because a certain amount of a recombinant enzyme is continuously administered regularly (NPL 10).

Moreover, attempts to directly administer biologics into the medullary cavity or the brain have been made to increase the concentration in the brain. For example, a method of administering iduronate-2-sulfatase into the brain of patients with Hunter syndrome (mucopolysaccharidosis-II) to prevent the progress of brain disorder of the patients is reported (PTL 1). However, direct administration into the medullary cavity or the brain is highly invasive (NPL 11).

Therefore, various delivery techniques have been studied to increase the concentrations of substances with high molecular weights such as biologics in the brain. For example, methods for allowing a substance with a high molecular weight to pass through the blood brain barrier through endocytosis by binding the substance and a membrane protein which is expressed in the brain vascular endothelial cells and by forming a complex of the substance with a high molecular weight and the membrane protein are reported.

Most of the reported techniques use receptor-mediated transcytosis (RMT below), and the target receptors expressed in the brain vascular endothelium are, for example, transferrin receptors, insulin receptors, insulin-like growth factor receptors and the low-density lipoprotein receptor family (LDLRf).

Techniques for passing the blood brain barrier through a transferrin receptor by producing a fused protein of an anti-transferrin receptor antibody and a nerve growth factor are reported. Reported techniques using an anti-transferrin receptor antibody are bispecific antibodies of an anti-transferrin receptor antibody and an anti-beta secretase (BACE1) antibody (PTLs 2 and 3 and NPLs 12 and 13) and fused antibodies obtained by fusing a monovalent anti-transferrin receptor antibody to the carboxyl terminus of an anti-amyloid β antibody (PTL 4 and NPL 14).

It is reported that, regarding the brain delivery using a bispecific antibody of an anti-transferrin receptor antibody and an anti-BACE1 antibody, the amount of the antibody taken into the brain increases to about four times the amount of the control when the antibody is administered to a mouse at 20 mg/kg body weight (NPL 13).

Furthermore, a technique for allowing a drug to pass through the blood brain barrier by encapsulating the drug with a liposome having an anti-transferrin receptor antibody on its surface is reported. It is reported that the amount taken into the rat brain increases to about two to five times when an anti-rat transferrin receptor antibody fused to immunomicelle is used (NPL 9).

Techniques for passing through the blood brain barrier through an insulin receptor by producing a fused protein of a neurotrophic factor, an enzyme or an anti-amyloid antibody fused to the carboxyl terminus of an anti-insulin receptor antibody are reported (NPLs 16-19).

It is reported that when a fused antibody of a labeled anti-human insulin receptor antibody and GDNF is administered to a rhesus monkey, the amount taken into the brain after two hours is about 15 times compared to that of GDNF (NPL 17).

However, because transferrin receptors and insulin receptors are expressed not only in the brain vascular endothelial cells but also in the whole body including the liver and the like, a drug is delivered also to the liver and the like as the amount of the drug delivered to the central nervous system increases in these techniques (NPL 20). Moreover, because the antigen is expressed in the whole body, the half-life of the antibody in the blood is short (NPL 12).

Moreover, it is reported that an antibody (Fc5) to TMEM30A, which is an antigen expressed in the brain vascular endothelial membrane, shows an RMT-like activity (PTL 5 and NPLs 21 and 22). Fc5 is an antibody of a variable domain of heavy chain of heavy chain antibody (VHH below) of a single domain derived from llama, and it is shown in an in vitro BBB model and in a rat in vivo model that the amount of Fc5 fused with human Fc delivered to the brain is higher than that of the control IgG.

It is reported that the CSF exposure of a Fc5-derived single chain antibody (scFv) fused with a metabotropic glutamate receptor type I (mGluRI below) antibody is higher than that of a control single chain antibody fused with a mGluRI antibody in a rat model, but the increase in the amount is around five times (NPL 23).

It is also reported that an IgG antibody is rapidly discharged from the brain to the circulating blood by neonatal Fc receptor (FcRn) (NPLs 24 and 25), and for example, the half-life of IgG in the brain after the administration into the brain is as short as 48 minutes in rats (NPL 24).

MOG is a protein belonging to the immunoglobulin superfamily and constitutes myelin. Whole human MOG consists of 218 amino acids, and human MOG is expressed in the outermost layer of myelin in the central nervous system and plays a role in the cell adhesion and the cell surface interaction (NPLs 26-28).

MOG is considered as a candidate of an autoantigen in inflammatory diseases in which the glial cells in the central nerves are attacked by the autoimmunity, such as multiple sclerosis (MS) (NPLs 29 and 30). It is reported that, although the concentrations of anti-MOG antibodies in the serum are low in MS patients, anti-MOG antibodies are detected also in the central nerves (NPL 29).

As a reason for this, it is reported that the blood brain barrier breaks due to leakage of humoral factors and entry of inflammatory cells in pathological conditions such as MS and that antibodies easily migrate to the central nervous system (NPLs 30 and 31). It is also reported that autoantibodies are produced locally in the central nervous system due to B cells and plasma cells infiltrated to the central nervous system (NPLs 30, 32 and 33).

Experimental autoimmune encephalomyelitis (EAE) and MS have many pathological conditions in common, and thus EAE is a model used for studying the pathological conditions of MS. It is reported that EAE can be induced by immunizing an animal with MOG protein or peptide (NPL 34).

It is also reported that the EAE score deteriorates when an anti-MOG antibody is administered to an animal in which EAE has been induced (NPLs 29 and 35). However, the EAE score reaches its peak one to two days (NPL 29) or four days (NPL 35) after the administration of the antibody, and the deterioration is temporal. On the other hand, it is also reported that EAE does not develop even when an anti-MOG antibody alone is administered to a normal animal (NPLs 36 and 37).

CITATION LIST

Patent Literature

PTL 1: International Publication No. 2012/023623
PTL 2: International Publication No. 2016/081640
PTL 3: International Publication No. 2016/081643
PTL 4: International Publication No. 2014/033074
PTL 5: Canadian Patent No. 2623841

Non Patent Literature

NPL 1: Kyla R R. and Richard C C., Biotechnol Adv, pii: S0734-9750 (16), 30091-X, 2016
NPL 2: Pardridge W M., Bioconjugate Chem., 19, 1327-1338, 2008
NPL 3: Wang W., et al., Clin. pharmacol. Ther., 84, 548-558, 2008
NPL 4: Garg A., et al., AAPSJ., 11, 553-557, 2009
NPL 5: Kaj B., et al., Arch. Neurol., 69 (8), 1002-1010, 2012
NPL 6: Wraith J E. et al., J. Pediatr. 144 (5), 581-588, 2004
NPL 7: Muenzer J. et al., Genet Med. 8 (8), 465-473, 2006
NPL 8: Document attached to intravenous infusion 2.9 mg of Aldurazyme® (July, 2016, 8th edition)
NPL 9: Document attached to intravenous infusion 6 mg of Elaprase® (July, 2016, 6th edition)
NPL 10: Brooks, D. A. et al., Trends Mol. Med. 9, 450-453, 2003
NPL 11: Sorrentino N C. et al., Pediatr Endocrinol Rev. 1, 630-638, 2016
NPL 12: Couch J A., et al., Science Translational Medicine, 5, 183ra57, 2013
NPL 13: Yu Y J., et al., Science Translational Medicine, 6, 261ra154, 2014
NPL 14: Niewoehner J., et al., Neuron. 81, 49-60, 2014
NPL 15: Jun Y, et al., Macromol. Biosci. 12, 1209-1219, 2012
NPL 16: Pardridge W M. and Boado R J., Methods in Enzymology, 503, 269-292, 2012
NPL 17: Boado R J., et al., Drug Metab. Dispos., 37 (12), 2299-2304, 2009
NPL 18: Boado R J., et al., J. Pharmacol. Exp. Ther., 333 (3), 961-969, 2010
NPL 19: Boado R J., et al., Bioconjugate Chem., 1, 97-104, 2012
NPL 20: Yun Zhang. et al., J. Pharmacol. Exp. Ther., 313 (3), 1075-1081, 2005
NPL 21: Abulrob A., et al., J. Neuyrochem., 95 (4), 1201-1214, 2005
NPL 22: Farrington G K., et al., FASEB J., 28, 4764-4778, 2014
NPL 23: Webster C I., et al., FASEB J., 30, 1927-1940, 2016
NPL 24: Zhang Y, et al., J. Neuroimmunol., 114(1-2), 168-172, 2001
NPL 25: Philip R C., et al., Brain Research, 1534, 13-21, 2013
NPL 26: Brunner C., et al., J. Neurochem, 52, 296-394, 1989
NPL 27: Pham-Dinh D., et al., Proc. Natl. Acad. Sci. USA, 90, 7990-7994, 1993

NPL 28: Gardinier M V, et al., J. Neurosci. Res., 33, 177-187, 1992
NPL 29: Eduard Urich, et al., PNAS, 103, 18697-18702, 2006
NPL 30: Markus Reindl, et al., Brain, 122, 2047-2056, 1999
NPL 31: Shimizu F., et al., Nihon Rinsho. 72(11), 1949-1954, 2014
NPL 32: Nese Sinmaz., et al., Ann. N.Y. Acad. Sci., 1351, 22-38, 2015
NPL 33: F. J. Quintana, Neurology, 78, 532-539, 2012
NPL 34: Ralf Gold., et al., Brain, 129, 1953-1971, 2006
NPL 35: Margaret M., et al., J. Neuroimmunology, 125, 114-124, 2002
NPL 36: G. Locatelli, et al., Nature Neuro Scienence, 15(4), 543-551, 2012
NPL 37: H J Schluesener, et al., J. Immunol., 139, 4016-4021, 1987

SUMMARY OF INVENTION

Technical Problem

Although it is disclosed in NPLs 29 and 35 that an anti-MOG antibody is detected in the brain when the antibody is administered to an EAE model, there is no report on an anti-MOG antibody which can be detected in the brain when the anti-MOG antibody is peripherally administered to a normal animal.

The invention relates to a myelin oligodendrocyte glycoprotein (MOG)-binding molecule which binds to MOG and methods using the molecule. Specifically, an object is to provide an antibody which binds to MOG, an antibody fragment thereof, a hybridoma which produces the antibody or the antibody fragment, a nucleic acid containing a nucleotide sequence which encodes the antibody or the antibody fragment, a transformant cell containing a vector containing the nucleic acid, a method for producing the antibody or the antibody fragment, a composition containing the antibody or the antibody fragment and a method for detecting or measuring an antigen that is present in the brain, a method for diagnosing or treating a brain disease, a method for improving the property of an antibody of accumulating in the brain and a method for increasing the amount of an antibody in the brain which use the antibody or the antibody fragment.

Solution to Problem

As means for solving the problems, the invention provides a MOG-binding molecule which binds to MOG and methods using the molecule and specifically provides an antibody or an antibody fragment thereof.

That is, the invention relates to (1) to (22) below.

(1) An antibody which binds to myelin oligodendrocyte glycoprotein (referred to as MOG below) or an antibody fragment thereof.

(2) The antibody or the antibody fragment according to (1), wherein the antibody has a property of accumulating in a brain.

(3) The antibody or the antibody fragment according to (1) or (2), wherein the antibody is selected from the group consisting of (a) to (r) below, (a) an antibody in which the amino acid sequences of complementarity determining regions (CDRs below) 1 to 3 of a heavy chain variable region (referred to as VH below) contain the amino acid sequences of SEQ ID NOs: 4, 5 and 6, respectively, and in which the amino acid sequences of CDRs 1 to 3 of a light chain variable region (VL) contain the amino acid sequences of SEQ ID NOs: 10, 11 and 12, respectively, (b) an antibody in which the amino acid sequences of CDRs 1 to 3 of VH contain the amino acid sequences of SEQ ID NOs: 16, 17 and 18, respectively, and in which the amino acid sequences of CDRs 1 to 3 of VL contain the amino acid sequences of SEQ ID NOs: 22, 23 and 24, respectively, (c) an antibody in which the amino acid sequences of CDRs 1 to 3 of VH contain the amino acid sequences of SEQ ID NOs: 28, 29 and 30, respectively, and in which the amino acid sequences of CDRs 1 to 3 of VL contain the amino acid sequences of SEQ ID NOs: 34, 35 and 36, respectively, (d) an antibody fragment in which the amino acid sequences of CDRs 1 to 3 of a heavy chain variable region of a heavy chain antibody (referred to as VHH below) contain the amino acid sequences of SEQ ID NOs: 40, 41 and 42, respectively, (e) an antibody in which the amino acid sequences of CDRs 1 to 3 of VH contain the amino acid sequences of SEQ ID NOs: 153, 154 and 155, respectively, and in which the amino acid sequences of CDRs 1 to 3 of VL contain the amino acid sequences of SEQ ID NOs: 158, 159 and 160, respectively, (f) an antibody in which the amino acid sequences of CDRs 1 to 3 of VH contain the amino acid sequences of SEQ ID NOs: 163, 164 and 165, respectively, and in which the amino acid sequences of CDRs 1 to 3 of VL contain the amino acid sequences of SEQ ID NOs: 168, 169 and 170, respectively, (g) an antibody in which the amino acid sequences of CDRs 1 to 3 of VH contain the amino acid sequences of SEQ ID NOs: 173, 174 and 175, respectively, and in which the amino acid sequences of CDRs 1 to 3 of VL contain the amino acid sequences of SEQ ID NOs: 178, 179 and 180, respectively, (h) an antibody in which the amino acid sequences of CDRs 1 to 3 of VH contain the amino acid sequences of SEQ ID NOs: 183, 184 and 185, respectively, and in which the amino acid sequences of CDRs 1 to 3 of VL contain the amino acid sequences of SEQ ID NOs: 188, 189 and 190, respectively, (i) an antibody in which the amino acid sequences of CDRs 1 to 3 of VH contain the amino acid sequences of SEQ ID NOs: 193, 194 and 195, respectively, and in which the amino acid sequences of CDRs 1 to 3 of VL contain the amino acid sequences of SEQ ID NOs: 198, 199 and 200, respectively, (j) an antibody in which the amino acid sequences of CDRs 1 to 3 of VH contain the amino acid sequences of SEQ ID NOs: 203, 204 and 205, respectively, and in which the amino acid sequences of CDRs 1 to 3 of VL contain the amino acid sequences of SEQ ID NOs: 208, 209 and 210, respectively, (k) an antibody in which the amino acid sequences of CDRs 1 to 3 of VH contain the amino acid sequences of SEQ ID NOs: 213, 214 and 215, respectively, and in which the amino acid sequences of CDRs 1 to 3 of VL contain the amino acid sequences of SEQ ID NOs: 218, 219 and 220, respectively, (l) an antibody in which the amino acid sequences of CDRs 1 to 3 of VH contain the amino acid sequences of SEQ ID NOs: 223, 224 and 225, respectively, and in which the amino acid sequences of CDRs 1 to 3 of VL contain the amino acid sequences of SEQ ID NOs: 228, 229 and 230, respectively, (m) an antibody in which the amino acid sequences of CDRs 1 to 3 of VH contain the amino acid sequences of SEQ ID NOs: 233, 234 and 235, respectively, and in which the amino acid sequences of CDRs 1 to 3 of VL contain the amino acid sequences of SEQ ID NOs: 238, 239 and 240, respectively, (n) an antibody in which the amino acid sequences of CDRs 1 to 3 of VH contain the amino acid sequences of SEQ ID NOs: 243, 244 and 245, respectively, and in which the amino acid sequences of CDRs 1 to 3 of VL contain the amino acid sequences of SEQ ID NOs: 248, 249 and 250, respectively, (o) an antibody which competes in binding to MOG with at least one of the antibodies described in (a) to (n), (p) an antibody which binds to an epitope containing an epitope to which any one of the antibodies described in (a) to (n) binds, (q) an antibody which binds to the same epitope as an epitope to which any one of the antibodies described in (a) to (n) binds and (r) an antibody which contains an amino acid sequence having homology of 85% or higher to the amino acid sequence of any one of the antibodies described in (a) to (n).

(4) The antibody or the antibody fragment according to any one of (1) to (3), wherein the antibody is selected from the group consisting of (a) to (n), (o1) to (o22) and (p) below, (a) an antibody in which the amino acid sequence of VH contains the amino acid sequence of SEQ ID NO: 3 and in which the amino acid sequence of VL contains the amino acid sequence of SEQ ID NO: 9, (b) an antibody in which the amino acid sequence of VH contains the amino acid sequence of SEQ ID NO: 15 and in which the amino acid sequence of VL contains the amino acid sequence of SEQ ID NO: 21, (c) an antibody in which the amino acid sequence of VH contains the amino acid sequence of SEQ ID NO: 27 and in which the amino acid sequence of VL contains the amino acid sequence of SEQ ID NO: 33, (d) an antibody fragment in which the amino acid sequence of VHH contains the amino acid sequence of SEQ ID NO: 39, (e) an antibody in which the amino acid sequence of VH contains the amino acid sequence of SEQ ID NO: 152 and in which the amino acid sequence of VL contains the amino acid sequence of SEQ ID NO: 157, (f) an antibody in which the amino acid sequence of VH contains the amino acid sequence of SEQ ID NO: 162 and in which the amino acid sequence of VL contains the amino acid sequence of SEQ ID NO: 167, (g) an antibody in which the amino acid sequence of VH contains the amino acid sequence of SEQ ID NO: 172 and in which the amino acid sequence of VL contains the amino acid sequence of SEQ ID NO: 177, (h) an antibody in which the amino acid sequence of VH contains the amino acid sequence of SEQ ID NO: 182 and in which the amino acid sequence of VL contains the amino acid sequence of SEQ ID NO: 187, (i) an antibody in which the amino acid sequence of VH contains the amino acid sequence of SEQ ID NO: 192 and in which the amino acid sequence of VL contains the amino acid sequence of SEQ ID NO: 197, (j) an antibody in which the amino acid sequence of VH contains the amino acid sequence of SEQ ID NO: 202 and in which the amino acid sequence of VL contains the amino acid sequence of SEQ ID NO: 207, (k) an antibody in which the amino acid sequence of VH contains the amino acid sequence of SEQ ID NO: 212 and in which the amino acid sequence of VL contains the amino acid sequence of SEQ ID NO: 217, (l) an antibody in which the amino acid sequence of VH contains the amino acid sequence of SEQ ID NO: 222 and in which the amino acid sequence of VL contains the amino acid sequence of SEQ ID NO: 227, (m) an antibody in which the amino acid sequence of VH contains the amino acid sequence of SEQ ID NO: 232 and in which the amino acid sequence of VL contains the amino acid sequence of SEQ ID NO: 237, (n) an antibody in which the amino acid sequence of VH contains the amino acid sequence of SEQ ID NO: 242 and in which the amino acid sequence of VL contains the amino acid sequence of SEQ ID NO: 247, (o1) an antibody in which the amino acid sequence of VH contains the amino acid sequence of SEQ ID NO: 252 and in which the amino acid sequence of VL contains the amino acid sequence of SEQ ID NO: 254, (o2) an antibody in which the amino acid sequence of VH contains the amino acid sequence of SEQ ID NO: 256 and in which the amino acid sequence of VL contains the amino acid sequence of SEQ ID NO: 258, (o3) an antibody in which the amino acid sequence of VH contains the amino acid sequence of SEQ ID NO: 260 and in which the amino acid sequence of VL contains the amino acid sequence of SEQ ID NO: 262, (o4) an antibody in which the amino acid sequence of VH contains the amino acid sequence of SEQ ID NO: 264 and in which the amino acid sequence of VL contains the amino acid sequence of SEQ ID NO: 266, (o5) an antibody in which the amino acid sequence of VH contains the amino acid sequence of SEQ ID NO: 268 and in which the amino acid sequence of VL contains the amino acid sequence of SEQ ID NO: 270, (o6) an antibody in which the amino acid sequence of VH contains the amino acid sequence of SEQ ID NO: 272 and in which the amino acid sequence of VL contains the amino acid sequence of SEQ ID NO: 274, (o7) an antibody in which the amino acid sequence of VH contains the amino acid sequence of SEQ ID NO: 276 and in which the amino acid sequence of VL contains the amino acid sequence of SEQ ID NO: 278, (o8) an antibody in which the amino acid sequence of VH contains the amino acid sequence of SEQ ID NO: 280 and in which the amino acid sequence of VL contains the amino acid sequence of SEQ ID NO: 282, (o9) an antibody in which the amino acid sequence of VH contains the amino acid sequence of SEQ ID NO: 284 and in which the amino acid sequence of VL contains the amino acid sequence of SEQ ID NO: 286, (o10) an antibody in which the amino acid sequence of VH contains the amino acid sequence of SEQ ID NO: 288 and in which the amino acid sequence of VL contains the amino acid sequence of SEQ ID NO: 290, (o11) an antibody in which the amino acid sequence of VH contains the amino acid sequence of SEQ ID NO: 292 and in which the amino acid sequence of VL contains the amino acid sequence of SEQ ID NO: 294, (o12) an antibody in which the amino acid sequence of VH contains the amino acid sequence of SEQ ID NO: 296 and in which the amino acid sequence of VL contains the amino acid sequence of SEQ ID NO: 298, (o13) an antibody in which the amino acid sequence of VH contains the amino acid sequence of SEQ ID NO: 300 and in which the amino acid sequence of VL contains the amino acid sequence of SEQ ID NO: 302, (o14) an antibody in which the amino acid sequence of VH contains the amino acid sequence of SEQ ID NO: 304 and in which the amino acid sequence of VL contains the amino acid sequence of SEQ ID NO: 306, (o15) an antibody in which the amino acid sequence of VH contains the amino acid sequence of SEQ ID NO: 308 and in which the amino acid sequence of VL contains the amino acid sequence of SEQ ID NO: 310, (o16) an antibody in which the amino acid sequence of VH contains the amino acid sequence of SEQ ID NO: 312 and in which the amino acid sequence of VL contains the amino acid sequence of SEQ ID NO: 314, (o17) an antibody in which the amino acid sequence of VH contains the amino acid sequence of SEQ ID NO: 316 and in which the amino acid sequence of VL contains the amino acid sequence of SEQ ID NO: 318, (o18) an antibody in which the amino acid sequence of VH contains the amino acid sequence of SEQ ID NO: 320 and in which the amino acid sequence of VL contains the amino acid sequence of SEQ ID NO: 322, (o19) an antibody in which the amino acid sequence of VH contains the amino acid sequence of SEQ ID NO: 324 and in which the amino acid sequence of VL contains the amino acid sequence of SEQ ID NO: 326, (o20) an antibody in which the amino acid sequence of VH contains the amino acid sequence of SEQ ID NO: 328 and in which the amino acid sequence of VL contains the amino acid sequence of SEQ ID NO: 330, (o21) an antibody in which the amino acid sequence of VH contains the amino acid sequence of SEQ ID NO: 332 and in which the amino acid sequence of VL contains the amino acid sequence of SEQ ID NO: 334, (o22) an antibody in which the amino acid sequence of VH contains the amino acid sequence of SEQ ID NO: 336 and in which the amino acid sequence of VL contains the amino acid sequence of SEQ ID NO: 338 and (p) an antibody which contains an amino acid sequence having homology of 85% or higher to the amino acid sequence of any one of the antibodies described in (a) to (n) and (o1) to (o22).

(5) The antibody or the antibody fragment according to any one of (1) to (4), wherein the antibody or the antibody fragment is a bispecific antibody.

(6) The bispecific antibody according to (5), wherein the bispecific antibody binds to MOG and an antigen that is present in a brain.

(7) The bispecific antibody according to (5) or (6), wherein the bispecific antibody contains an antigen binding site which binds to MOG and an antigen binding site which binds to an antigen that is present in a brain.

(8) The antibody fragment according to any one of (1) to (7) which is selected from the group consisting of Fab, Fab', F(ab')$_2$, a single chain antibody (scFv), a dimerized V region (diabody), a disulfide-stabilized V region (dsFv), VHH and, a peptide containing CDR.

(9) The antibody and the antibody fragment according to any one of (1) to (8), wherein the antibody is a genetically recombinant antibody.

(10) The antibody and the antibody fragment according to any one of (1) to (9), wherein the antibody is selected from the group consisting of a mouse antibody, a rat antibody, a rabbit antibody, an alpaca antibody, a camel antibody, a llama antibody, a chimeric antibody, a humanized antibody, and a human antibody.

(11) A fused antibody or a fused antibody fragment which is obtained by binding at least one selected from the group consisting of (a) to (c) below to the antibody which binds to MOG according to any one of (1) to (10) or the antibody fragment thereof, (a) a hydrophilic polymer,
(b) an amphipathic polymer, and
(c) a functional molecule.

(12) A hybridoma which produces the antibody according to any one of (1) to (11).

(13) A nucleic acid which contains a nucleotide sequence which encodes the antibody according to any one of (1) to (11).

(14) A transformant cell which contains a vector containing the nucleic acid according to (13).

(15) A method for producing the antibody or the antibody fragment according to any one of (1) to (11), including culturing the hybridoma according to (12) or the transformant cell according to (14) and collecting the antibody or the antibody fragment according to any one of (1) to (11) from a culture solution.

(16) A composition which contains the antibody or the antibody fragment according to any one of (1) to (11).

(17) The composition according to (16), wherein the composition is a composition for detecting or measuring an antigen that is present in a brain.

(18) The composition according to (16), wherein the composition is a composition for diagnosing or treating a brain disease.

(19) A method for detecting or measuring an antigen that is present in a brain using the antibody or the antibody fragment according to any one of (1) to (11) or the composition according to (16).

(20) A method for diagnosing or treating a brain disease using the antibody or the antibody fragment according to any one of (1) to (11) or the composition according to (16).

(21) A method for improving the property of accumulating in the brain of an antibody, an antibody fragment thereof, a fused antibody or a fused antibody fragment using the antibody, the antibody fragment, the fused antibody or the fused antibody fragment according to any one of (1) to (11) or the composition according to (16).

(22) A method for increasing the amount of an antibody, the amount of an antibody fragment thereof, the amount of a fused antibody or the amount of a fused antibody fragment in a brain using the antibody, the antibody fragment, the fused antibody or the fused antibody fragment according to any one of (1) to (11) or the composition according to (16).

Advantageous Effects of Invention

The MOG-binding molecule of the invention improves the property of the binding molecule itself of accumulating in the brain by specifically binding to MOG, and the MOG-binding molecule can also be applied to the treatment of brain diseases because another molecule which is modified by the MOG-binding molecule is delivered and kept in the brain. A specific MOG-binding molecule of the invention is an antibody. The antibody or the antibody fragment of the invention relates to an antibody which binds to MOG in the brain and thus has a property of accumulating in the brain. Accordingly, the antibody or the antibody fragment of the invention can be used for a composition for detecting or measuring an antigen that is present in the brain (MOG, or MOG and another antigen that is present in the brain), a composition for diagnosing a brain disease and a pharmaceutical composition for treating a brain disease.

BRIEF DESCRIPTION OF DRAWINGS

FIGS. 3A and 3B show the results of evaluation of the rat brain migration properties of anti-MOG antibodies. FIG. 3A shows the antibody concentrations in the serum four days after administering the antibodies to rats. The vertical axis shows the antibody concentration (ng/mL), and the horizontal axis shows the administered antibodies. FIG. 3B shows the antibody concentrations in the brain tissues four days after administering the antibodies to rats. The vertical axis shows the antibody amount per brain weight (ng/g brain), and the horizontal axis shows the administered antibodies. In both figures, the white bars show the results of an anti-AVM antibody used as a negative control, and the black bars show the results of the anti-MOG antibodies.

FIGS. 4A and 4B show the results of evaluation of the rat brain migration property of an anti-MOG antibody. FIG. 4A shows the antibody concentrations in the serum four days and 10 days after administering the antibodies to rats. The vertical axis shows the antibody concentration (ng/mL), and the horizontal axis shows the period (day) after the administration of the antibodies. FIG. 4B shows the antibody concentrations in the brain tissues four days and 10 days after administering the antibodies to rats. The vertical axis shows the antibody amount per brain weight (ng/g brain), and the horizontal axis shows the period (day) after the administration of the antibodies. In both figures, the plots with white diamond markers show the results of an anti-AVM antibody used as a negative control. The plots with white square markers show the results of an anti-transferrin receptor antibody, OX26 antibody, and the plots with black triangle markers show the results of the anti-MOG antibody, MOG01.

FIG. 7A shows the antibody concentrations in the serum 10 days after administering the antibodies to rats. The vertical axis shows the antibody concentration (ng/mL), and the horizontal axis shows the bispecific antibodies used. FIG. 7B shows the antibody concentrations in the brain tissues 10 days after administering the antibodies to rats. The vertical axis shows the antibody amount per brain weight (ng/g brain), and the horizontal axis shows the bispecific antibodies used.

FIGS. 8A and 8B show the results of evaluation of the mouse brain migration property of an anti-MOG01 antibody. FIG. 8A shows the antibody concentrations in the serum 3, 6, 10, 14, 21 and 28 days after administering the antibodies to mice. The vertical axis shows the antibody concentration (ng/mL), and the horizontal axis shows the time (day). FIG. 8B shows the antibody concentrations in the brain tissues 3, 6, 10, 14, 21 and 28 days after administering the antibodies to mice. The vertical axis shows the antibody concentration (ng/g brain), and the horizontal axis shows the time (day). In both figures, the plots with white circle markers show the results of an anti-AVM antibody used as a negative control, and the plots with black square markers show the results of MOG01 scFv-hG4PE.

FIG. 9A shows the measurement data of the fluorescence intensities in the brain six days after administering an Alexa FluorR 488-labeled anti-AVM antibody as a negative control and an Alexa FluorR 488-labeled anti-MOG01 antibody to mice, and FIG. 9B shows the measurement data of the fluorescence intensities in the brain after 14 days. FIG. 9C shows the values obtained by correcting the fluorescence amounts in the brain after six days and 14 days using the fluorescence intensities of the administered antibodies. The vertical axis shows the fluorescence amount in brain/fluorescence amount of administered antibody (%), and the horizontal axis shows the administered antibodies.

FIGS. 10A to 10C show the structures of bispecific antibodies which bind to AVM and MOG. FIG. 10A shows the structure of AVM-MOG01 IgG4PE(R409K) antibody, and FIG. 10B shows the structure of AVM IgG4PE (R409K)_ MOG01 Fab antibody. FIG. 10C shows the structure of AVM IgG4PE(R409K)_MOG01sscFv antibody.

FIGS. 11A and 11B show the structures of bispecific antibodies which bind to AVM and MOG. FIG. 11A shows the structure of AVM IgG4PE(R409K)_MOG01dscFv antibody, AVM IgG4PE(R409K)_MOG01dscFv2 antibody and AVM IgG4PE(R409K)_MOG01dscFv4 antibody, and FIG. 11B shows the structure of AVM IgG4PE(R409K)_ MOG01dscFv3 antibody and AVM IgG4PE(R409K)_ MOG01dscFv5 antibody to AVM IgG4PE(R409K)_ MOG01dscFv11 antibody.

FIGS. 12A to 12C show the results of analysis using a flow cytometer of the affinities of bispecific antibodies to human MOG/L929 cells. The vertical axis shows the average fluorescence intensity, and the horizontal axis shows the antibody concentration. In FIG. 12A, the plot with white circle markers shows the results of AVM IgG4PE(R409K) antibody (negative control), and the plot with black square markers shows the results of AVM-MOG01 IgG4PE (R409K) antibody. In FIG. 12B, the plot with white circle markers shows the results of AVM IgG4PE(R409K)_ AVMsscFv antibody (negative control), and the plot with black square markers shows the results of AVM IgG4PE (R409K)_MOG01sscFv antibody. In FIG. 12C, the plot with white circle markers shows the results of AVM IgG4PE (R409K)_AVM Fab antibody (negative control), and the plot with black square markers shows the results of AVM IgG4PE(R409K)_MOG01 Fab antibody.

In FIG. 13A, the plot with white square markers shows the results of AVM IgG4PE(R409K)_MOG01dscFv antibody, the plot with white circle markers shows the results of AVM IgG4PE(R409K)_MOG01dscFv2 antibody, and the plot with white triangle markers shows the results of AVM IgG4PE(R409K)_MOG01dscFv4 antibody. In FIG. 13B, the plot with white diamond markers shows the results of AVM IgG4PE(R409K)_MOG01dscFv3 antibody, the plot with black diamond markers shows the results of AVM IgG4PE(R409K)_MOG01dscFv5 antibody, the plot with white circle markers shows the results of AVM IgG4PE(R409K)_MOG01dscFv6 antibody, the plot with black circle markers shows the results of AVM IgG4PE(R409K)_MOG01dscFv7 antibody, the plot with white triangle markers shows the results of AVM IgG4PE(R409K)_MOG01dscFv8 antibody, the plot with black triangle markers shows the results of AVM IgG4PE(R409K)_MOG01dscFv9 antibody, the plot with white square markers shows the results of AVM IgG4PE(R409K)_MOG01dscFv10 antibody, and the plot with black square markers shows the results of AVM IgG4PE(R409K)_MOG1 dscFv11 antibody.

FIGS. 14A and 14B show the antibody concentrations in the serum and in the brain tissues, respectively, 10 days after the administration of AVM IgG4PE(R409K) antibody (negative control) and AVM-MOG01 IgG4PE(R409K) antibody.

FIGS. 15A and 15B show the antibody concentrations in the serum and in the brain tissues, respectively, 10 days after the administration of AVM IgG4PE(R409K)_AVMsscFv antibody (negative control) and AVM IgG4PE(R409K)_MOG01sscFv antibody.

FIGS. 16A and 16B show the results of evaluation of the mouse brain migration properties of bispecific antibodies. The vertical axis shows the antibody concentration, and the horizontal axis shows the bispecific antibodies used. FIGS. 16A and 16B show the antibody concentrations in the serum and in the brain tissues, respectively, 10 days after the administration of AVM IgG4PE(R409K)_AVM Fab antibody (negative control) and AVM IgG4PE(R409K)_MOG01 Fab antibody.

FIGS. 17A to 17D show the results of evaluation of the mouse brain migration properties of bispecific antibodies. The vertical axis shows the antibody concentration, and the horizontal axis shows the bispecific antibodies used. The negative control corresponding to AVM IgG4PE(R409K)_MOG01dscFv antibody is AVM IgG4PE(R409K)_AVMdscFv antibody, and the negative control corresponding to AVM IgG4PE(R409K)_MOG01dscFv3 antibody is AVM IgG4PE(R409K)_AVMdscFv3 antibody. The negative control corresponding to AVM IgG4PE(R409K)_MOG01dscFv5 antibody is AVM IgG4PE(R409K)_AVMdscFv5 antibody. FIG. 17A shows the antibody concentrations in the serum 10 days after the administration of the antibodies. FIG. 17B shows the antibody concentrations in the brain tissues 10 days after the administration of the antibodies. FIG. 17C shows the antibody concentrations in the serum 28 days after the administration of the antibodies. FIG. 17D shows the antibody concentrations in the brain tissues 28 days after the administration of the antibodies.

FIG. 18 shows the amino acid sequences of scFv of clones similar to a MOG antibody and shows clones similar to MOG301 antibody.

FIG. 19 shows the amino acid sequences of scFv of clones similar to a MOG antibody and shows clones similar to MOG303 antibody.

FIG. 20 shows the amino acid sequences of scFv of clones similar to a MOG antibody and shows clones similar to MOG307 antibody.

FIG. 21 shows the amino acid sequences of scFv of clones similar to a MOG antibody and shows clones similar to MOG310 antibody.

FIGS. 22A and 22B show the amino acid sequences of scFv of clones similar to MOG antibodies. FIG. 22A shows a clone similar to MOG329 antibody, and FIG. 22B shows a clone similar to MOG456 antibody.

FIGS. 28A and 28B show the results of evaluation of the mouse brain migration properties of enzyme-fused antibodies, MOG01 IgG4PE(R409K)-ASM and AVM IgG4PE(R409K)-ASM. The vertical axis shows the antibody concentration, and the horizontal axis shows the enzyme-fused antibodies used. FIG. 28A shows the antibody concentrations in the serum 10 days after the administration of the antibodies. FIG. 28B shows the antibody concentrations in the brain tissues 10 days after the administration of the antibodies.

DESCRIPTION OF EMBODIMENTS

Figure 1:
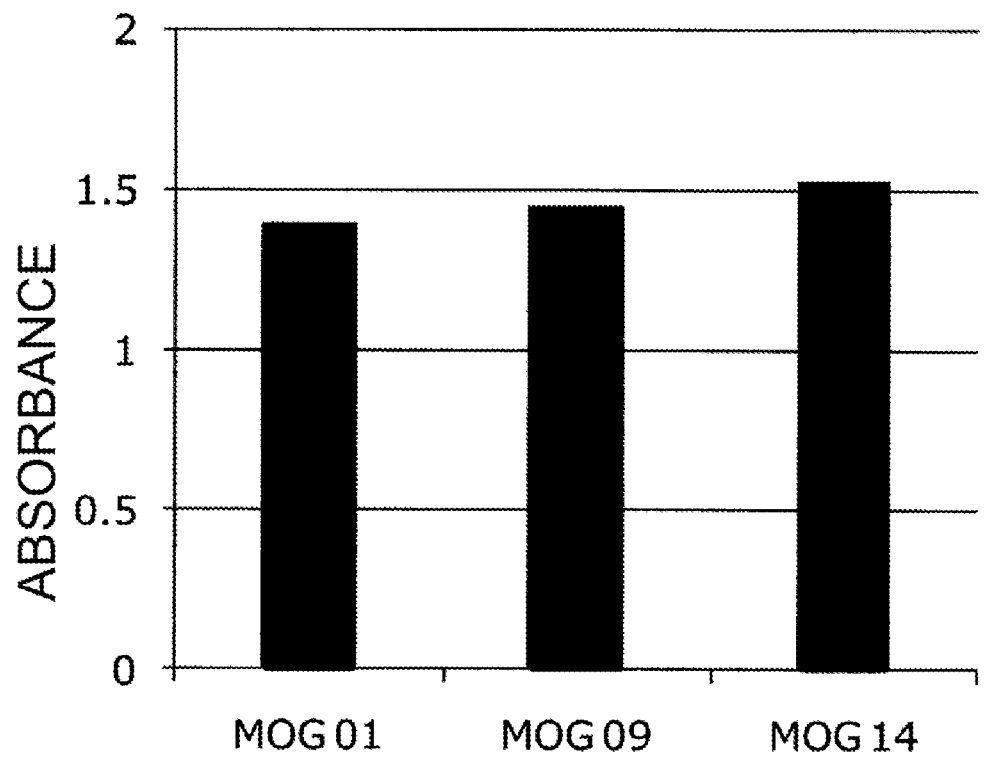
FIG. 1 shows the results of analysis by ELISA of the affinities to rMOG-FLAG_Fc of phage clones displaying scFv that binds to MOG. The vertical axis shows the absorbance relative to rMOG-FLAG_Fc, and the horizontal axis shows the names of the scFv antibodies displayed by the phage clones.

The invention relates to an antigen-binding molecule which binds to myelin-oligodendrocyte glycoprotein (referred to as MOG below). More specifically, the invention relates to an antibody which binds to MOG or an antibody fragment thereof.

The MOG-binding molecule of the invention may be a molecule of any state as long as the molecule specifically binds to MOG and accumulates in the brain, and the MOG-binding molecule may be any of molecules such as proteins, nucleic acids and synthetic organic low-molecular-weight compounds/high-molecular-weight compounds. Specifically, the MOG-binding molecule may be any of recombinant proteins, antibodies, aptamers, low-molecular-weight compounds obtained by screening low-molecular-weight molecules and the like, but an antibody and an antibody fragment thereof are preferable. The MOG-binding molecule is preferably a molecule which binds to an extracellular region of MOG.

MOG is a protein belonging to the immunoglobulin superfamily and constitutes myelin. Whole human MOG, for example, consists of 218 amino acids, and human MOG is expressed in the outermost layer of myelin in the central nervous system and plays a role in the cell adhesion and the cell surface interaction.

The kinds of animal of MOG to which the MOG-binding molecule of the invention binds are mouse, rat, cynomolgus monkey, human and/or the like but are not particularly limited to these kinds, and an appropriate animal kind can be selected depending on the use of the antibody. For example, when the antibody of the invention is used for a pharmaceutical use for humans, the antibody is preferably an antibody which binds to at least human MOG.

In the invention, human MOG is a polypeptide which contains the amino acid sequence of SEQ ID NO: 78 or the amino acid sequence of NCBI accession No. AAB08088, a polypeptide which has the amino acid sequence of SEQ ID NO: 78 or the amino acid sequence of NCBI accession No. AAB08088, wherein one or more amino acids are deleted, substituted or added, and which has a function of human MOG, a polypeptide which has an amino acid sequence having homology of 60% or higher, preferably 80% or higher, further preferably 90% or higher, most preferably 95% or higher to the amino acid sequence of SEQ ID NO: 78 or the amino acid sequence of NCBI accession No. AAB08088 and which has a function of human MOG or the like.

The polypeptide which has the amino acid sequence of SEQ ID NO: 78 or the amino acid sequence of NCBI accession No. AAB08088, wherein one or more amino acids are deleted, substituted or added, can be obtained by introducing a site-specific mutation for example to DNA that encodes a polypeptide containing the amino acid sequence of SEQ ID NO: 78 using the site-directed mutagenesis [Molecular Cloning, A Laboratory Manual, Second Edition, Cold Spring Harbor Laboratory Press (1989), Current Protocols in Molecular Biology, John Wiley & Sons (1987-1997), Nucleic acids Research, 10, 6487 (1982), Proc. Natl. Acad. Sci. USA, 79, 6409 (1982), Gene, 34, 315 (1985), Nucleic Acids Research, 13, 4431 (1985) and Proc. Natl. Acad. Sci. USA, 82, 488 (1985)] or the like.

The number of amino acids that are deleted, substituted or added is not particularly limited but is preferably one to tens, for example, 1 to 20, more preferably one to a few, for example, one to five amino acids.

The same applies to the amino acid sequence of mouse MOG [SEQ ID NO: 74 and NCBI accession No. NP_034944], the amino acid sequence of rat MOG [SEQ ID NO: 68 and NCBI accession No. AAA41628] and the amino acid sequence of cynomolgus monkey MOG [SEQ ID NO: 76 and NCBI accession No. NP_001271785].

Genes which encode human MOG are the nucleotide sequence of SEQ ID NO: 77 and the nucleotide sequence of NCBI accession No. U64564. A gene containing DNA which has the nucleotide sequence of SEQ ID NO: 77 or the nucleotide sequence of NCBI accession No. U64564, wherein one or more bases are deleted, substituted or added, and which encodes a polypeptide having a function of MOG, a gene containing DNA which has a nucleotide sequence having homology of at least 60% or higher to the nucleotide sequence of SEQ ID NO: 77 or the nucleotide sequence of NCBI accession No. U64564, preferably a nucleotide sequence having homology of 80% or higher or further preferably a nucleotide sequence having homology of 95% or higher and which encodes a polypeptide having a function of MOG, a gene which contains DNA that hybridizes with DNA containing the nucleotide sequence of SEQ ID NO: 77 or the nucleotide sequence of NCBI accession No. U64564 under stringent conditions and which encodes a polypeptide having a function of MOG and another gene are also included as the genes that encode MOG in the invention.

The DNA that hybridizes under stringent conditions means hybridizable DNA that is obtained by a colony hybridization method, a plaque hybridization method, a southern blot hybridization method, a DNA microarray method or the like using DNA containing the nucleotide sequence of SEQ ID NO: 77 or the nucleotide sequence of NCBI accession No. U64564 as a probe.

Specifically, it is possible to exemplify DNA that can be identified by washing a filter or a glass slide under the condition of 65° C. using a SSC solution of the concentration of 0.1 to 2 times (the composition of the SSC solution with the concentration of 1 time is 150 mmol/L sodium chloride and 15 mmol/L sodium citrate), after performing hybridization [Molecular Cloning, A Laboratory Manual, Second Edition, Cold Spring Harbor Laboratory Press (1989), Current Protocols in Molecular Biology, John Wiley & Sons (1987-1997) and DNA Cloning 1: Core Techniques, A Practical Approach, Second Edition, Oxford University, (1995)] at 65° C. in the presence of 0.7 to 1.0 mol/L sodium chloride using a filter or a glass slide on which DNA derived from a hybridized colony or plaque or a PCR product or DNA oligo having the sequence is fixed.

Examples of the hybridizable DNA include DNA having homology of at least 60% or higher to the nucleotide sequence of SEQ ID NO: 77 or the nucleotide sequence of NCBI accession No. U64564, preferably DNA having homology of 80% or higher and further preferably DNA having homology of 95% or higher.

The same applies to the nucleotide sequence of mouse MOG [SEQ ID NO: 73 and NCBI accession No. NM_010814], the nucleotide sequence of rat MOG [SEQ ID NO: 67 and NCBI accession No. M99485] and the nucleotide sequence of cynomolgus monkey MOG [SEQ ID NO: 75 and NCBI accession No. NM_001284856].

The function of MOG is involvement in the cell adhesion, the cell surface interaction and the like on myelin.

Genetic polymorphism is often recognized in a nucleotide sequence of a gene that encodes a protein of a eukaryote. The genes that encode MOG in the invention also include genes in which small scale mutations arise in the nucleotide sequences by such polymorphism in the genes used in the invention.

A value of homology in the invention may be a value calculated using a homology detection program known to those skilled in the art unless particularly specified. Regarding a nucleotide sequence, there are a value calculated using a default parameter of BLAST [J. Mol. Biol., 215, 403 (1990)] and the like. Regarding an amino acid sequence, there are a value calculated using a default parameter of BLAST2 [Nucleic Acids Res., 25, 3389 (1997), Genome Res., 7, 649 (1997) and http://www.ncbi.nlm.nih.gov/Education/BLASTinfo/information3.htmL] and the like.

Regarding the default parameters, G (Cost to open gap) is 5 for a nucleotide sequence and 11 for an amino acid sequence, −E (Cost to extend gap) is 2 for a nucleotide sequence and 1 for an amino acid sequence, −q (Penalty for nucleotide mismatch) is −3, −r (reward for nucleotide match) is 1, −e (expect value) is 10, −W (wordsize) is 11 residues for a nucleotide sequence and 3 residues for an amino acid sequence, −y [Dropoff (X) for blast extensions in bits] is 20 for the blastn and 7 for programs other than the blastn, −X (X dropoff value for gapped alignment in bits) is 15, and −Z (final X dropoff value for gapped alignment in bits) is 50 for the blastn and 25 for programs other than the blastn (http://www.ncbi.nlm.nih.gov/blast/htmL/blastcgi-help.htmL).

A polypeptide containing a partial sequence of the amino acid sequence of any of the MOG kinds can be produced by a method known to those skilled in the art. Specifically, the polypeptide can be produced by deleting a part of DNA that encodes the amino acid sequence of any of the MOG kinds and culturing a transformant into which an expression vector including the DNA has been introduced. In addition, a polypeptide having the amino acid sequence of any of the MOG kinds in which one or more amino acids are deleted, substituted or added can be obtained by the same method as above.

Furthermore, a polypeptide that has the amino acid sequence of any of the MOG kinds or a polypeptide having the amino acid sequence of any of the MOG kinds in which one or more amino acids are deleted, substituted or added can be produced also using a chemical synthesis method such as a fluorenylmethyloxycarbonyl (Fmoc) method or a t-butyloxycarbonyl (tBoc) method.

In the invention, the extracellular region of human MOG is the amino acid sequence of from position 30 to position 154 or from position 232 to position 247 in the amino acid sequence of SEQ ID NO: 78 or NCBI accession No. AAB08088 and is preferably the amino acid sequence of from position 30 to position 154.

The extracellular region of mouse MOG is the amino acid sequence of from position 30 to position 157 or from position 232 to position 247 in the amino acid sequence of SEQ ID NO: 74 or NCBI accession No. NP_034944 and is preferably the amino acid sequence of from position 30 to position 157. The extracellular region of rat MOG is the amino acid sequence of from position 28 to position 155 or from position 230 to 245 in the amino acid sequence of SEQ ID NO: 68 or NCBI accession No. AAA41628 and is preferably the amino acid sequence of from position 28 to position 155.

The extracellular region of cynomolgus monkey MOG is the amino acid sequence of from position 30 to position 154 or from position 232 to position 247 in the amino acid sequence of SEQ ID NO: 76 or NCBI accession No. NP_001271785 and is preferably the amino acid sequence of from position 30 to position 154.

That the antibody of the invention binds to an extracellular region of MOG can be confirmed by measuring the affinity of the antibody of the invention to MOG-expressing cells or a recombinant MOG protein using ELISA, flow cytometry, surface plasmon resonance method or the like. Moreover, binding of the antibody can be confirmed also using a combination of known immunological detection methods [Monoclonal Antibodies-Principles and practice, Third edition, Academic Press (1996), Antibodies-A Laboratory Manual, Cold Spring Harbor Laboratory (1988) and A manual for monoclonal antibody experiments, Kodansha scientific books (1987)] and the like.

The MOG-binding molecule of the invention is a molecule which specifically binds to MOG in the brain and which thus has a property of accumulating in the brain, and for example, the antibody is an antibody which binds to MOG in the brain and which thus has a property of accumulating in the brain. Moreover, the antibody of the invention is an antibody which passes through the blood brain barrier in the brain from the peripheral part, migrates to the brain and binds to MOG in the brain when peripherally administered to an animal and which thus has a property of accumulating in the brain. The antibody of the invention is preferably an antibody having an excellent property of accumulating in the brain or an antibody having an improved property of accumulating in the brain.

In the invention, the property of accumulating in the brain is a property of a subject of accumulating in the brain when the subject is administered to an animal to be tested. That is, the property means that the concentration in the brain (or the amount in the brain) of the subject increases or that the subject exists at a certain detectable concentration due to at least any one cause selected from an increase in the migration into the brain, an increase in the accumulation in the brain, a decrease in the migration to outside from the brain, a decrease in the discharge to outside from the brain and a decrease in the decomposition in the brain.

In the invention, that the property of accumulating in the brain is excellent, that the property of accumulating in the brain is high or that the property of accumulating in the brain is improved means that the concentration in the brain (or the amount in the brain) of the subject increases or that the subject exists in the brain at a certain concentration (amount) which is detectable for a long time when the subject is administered to an animal to be tested, as compared to a control after a same period (day) after the administration.

The phenomena are caused by at least any one of an increase in the migration of the subject into the brain, an increase in the accumulation in the brain, a decrease in the migration to outside from the brain, a decrease in the discharge to outside from the brain and a decrease in the decomposition in the brain as compared to a control.

In the invention, that the property of accumulating in the brain is excellent, that the property of accumulating in the brain is high or that the property of accumulating in the brain is improved means, for example, that, when the subject is administered to an animal to be tested, the concentration (amount) of the subject in the brain is higher than that of a control 1 to 10 days after the administration, preferably 2 to 10 days or 3 to 10 days, more preferably 4 to 10 days after the administration or that the peak of the concentration in the brain (or the amount in the brain) of the subject is seen on day 4 or later after the administration, preferably on day 5 or later, day 6 or later, day 7 or later, day 8 or later or day 9 or later, more preferably on day 10 or later after the administration.

The antibody having an excellent property of accumulating in the brain, the antibody having a high property of accumulating in the brain or the antibody having an improved property of accumulating in the brain may be any antibody as long as the antibody is an antibody whose antibody concentration (antibody amount) in the brain is higher than that of a control antibody or an antibody having the characteristic of existing in the brain for a long time.

Examples include antibodies having the characteristic that the migration rate to the brain and/or the accumulation rate in the brain are higher than those of a control antibody, the characteristic that the migration rate to outside from the brain, the discharge rate and/or the decomposition rate in the brain are lower and the characteristic that the migration rate to the brain and/or the accumulation rate in the brain are higher than the migration rate to outside from the brain, the discharge rate and/or the decomposition rate in the brain.

Accordingly, the antibody or the antibody fragment of the invention is, for example an antibody or an antibody fragment thereof whose antibody concentration (or the antibody amount) in the brain is higher than that of a control antibody after a same period (day) after the administration when the antibody or the antibody fragment is administered to an animal or an antibody or an antibody fragment thereof which can exist in the brain for a long time.

The change in the antibody concentration (or the antibody amount) in the brain may be any change, and examples include a case in which the antibody concentration gradually decreases after the antibody concentration in the brain once reaches its peak during the measurement period, a case in which after the antibody concentration in the brain reaches its peak, the antibody concentration is maintained, a case in which the antibody concentration in the brain continues to increase after the administration of the antibody or another case.

The antibody or the antibody fragment of the invention is, for example, an antibody whose antibody concentration or antibody amount in the brain is higher than that of a control antibody on day 4 or day 10 after the administration to a rat, an antibody whose antibody concentration or antibody amount in the brain is maintained or increases from day 4 to day 10 after the administration to a rat, an antibody whose existence in the brain can be clearly confirmed on day 10 or later after the administration to a rat or another antibody but is not limited to these examples.

The control antibody may be any antibody as long as the control antibody is an antibody of the same species or subclass as that of the antibody to be tested, but for example, an anti-avermectin (AVM) antibody and the like can be used.

In the invention, the term "in the brain" is, for example, in the brain parenchyma, in a cerebral ventricle, in the cerebrospinal fluid or the like but is not limited to these examples.

In the invention, the method for administering an antibody to an animal is, for example, intravenous administration, intraventricular administration, intraperitoneal administration, subcutaneous administration, intradermal administration, nasal administration, intrathecal administration or the like but is not limited to these methods.

In the invention, the method for measuring the property of an antibody of accumulating in the brain is, for example, a method of collecting brain tissues several days after administering the antibody to an animal, measuring the antibody concentration of the supernatant obtained after homogenization and centrifugation and calculating the antibody amount per unit brain weight, a method of detecting the antibody using a known immunological method using the collected brain tissues, a method of administering the antibody which has been labeled to an animal and detecting the antibody by an in vivo imaging system sequentially or another method.

The antibody of the invention may be an antibody selected from the group consisting of (a) to (q) below, (a) an antibody in which the amino acid sequences of CDRs 1 to 3 of VH are the amino acid sequences of SEQ ID NOs: 4, 5 and 6, respectively, and in which the amino acid sequences of CDRs 1 to 3 of VL contain the amino acid sequences of SEQ ID NOs: 10, 11 and 12, respectively, (b) an antibody in which the amino acid sequences of CDRs 1 to 3 of VH are the amino acid sequences of SEQ ID NOs: 16, 17 and 18, respectively, and in which the amino acid sequences of CDRs 1 to 3 of VL contain the amino acid sequences of SEQ ID NOs: 22, 23 and 24, respectively, (c) an antibody in which the amino acid sequences of CDRs 1 to 3 of VH are the amino acid sequences of SEQ ID NOs: 28, 29 and 30, respectively, and in which the amino acid sequences of CDRs 1 to 3 of VL contain the amino acid sequences of SEQ ID NOs: 34, 35 and 36, respectively, (d) an antibody fragment in which the amino acid sequences of CDRs 1 to 3 of VHH contain the amino acid sequences of SEQ ID NOs: 40, 41 and 42, respectively, (e) an antibody in which the amino acid sequences of CDRs 1 to 3 of VH contain the amino acid sequences of SEQ ID NOs: 153, 154 and 155, respectively, and in which the amino acid sequences of CDRs 1 to 3 of VL contain the amino acid sequences of SEQ ID NOs: 158, 159 and 160, respectively, (f) an antibody in which the amino acid sequences of CDRs 1 to 3 of VH contain the amino acid sequences of SEQ ID NOs: 163, 164 and 165, respectively, and in which the amino acid sequences of CDRs 1 to 3 of VL contain the amino acid sequences of SEQ ID NOs: 168, 169 and 170, respectively, (g) an antibody in which the amino acid sequences of CDRs 1 to 3 of VH contain the amino acid sequences of SEQ ID NOs: 173, 174 and 175, respectively, and in which the amino acid sequences of CDRs 1 to 3 of VL contain the amino acid sequences of SEQ ID NOs: 178, 179 and 180, respectively, (h) an antibody in which the amino acid sequences of CDRs 1 to 3 of VH contain the amino acid sequences of SEQ ID NOs: 183, 184 and 185, respectively, and in which the amino acid sequences of CDRs 1 to 3 of VL contain the amino acid sequences of SEQ ID NOs: 188, 189 and 190, respectively, (i) an antibody in which the amino acid sequences of CDRs 1 to 3 of VH contain the amino acid sequences of SEQ ID NOs: 193, 194 and 195, respectively, and in which the amino acid sequences of CDRs 1 to 3 of VL contain the amino acid sequences of SEQ ID NOs: 198, 199 and 200, respectively, (j) an antibody in which the amino acid sequences of CDRs 1 to 3 of VH contain the amino acid sequences of SEQ ID NOs: 203, 204 and 205, respectively, and in which the amino acid sequences of CDRs 1 to 3 of VL contain the amino acid sequences of SEQ ID NOs: 208, 209 and 210, respectively, (k) an antibody in which the amino acid sequences of CDRs 1 to 3 of VH contain the amino acid sequences of SEQ ID NOs: 213, 214 and 215, respectively, and in which the amino acid sequences of CDRs 1 to 3 of VL contain the amino acid sequences of SEQ ID NOs: 218, 219 and 220, respectively, (l) an antibody in which the amino acid sequences of CDRs 1 to 3 of VH contain the amino acid sequences of SEQ ID NOs: 223, 224 and 225, respectively, and in which the amino acid sequences of CDRs 1 to 3 of VL contain the amino acid sequences of SEQ ID NOs: 228, 229 and 230, respectively, (m) an antibody in which the amino acid sequences of CDRs 1 to 3 of VH contain the amino acid sequences of SEQ ID NOs: 233, 234 and 235, respectively, and in which the amino acid sequences of CDRs 1 to 3 of VL contain the amino acid sequences of SEQ ID NOs: 238, 239 and 240, respectively, (n) an antibody in which the amino acid sequences of CDRs 1 to 3 of VH contain the amino acid sequences of SEQ ID NOs: 243, 244 and 245, respectively, and in which the amino acid sequences of CDRs 1 to 3 of VL contain the amino acid sequences of SEQ ID NOs: 248, 249 and 250, respectively, (o) an antibody which competes in binding to MOG with at least one of the antibodies described in (a) to (n), (p) an antibody which binds to an epitope containing an epitope to which any one of the antibodies described in (a) to (n) binds and (q) an antibody which binds to the same epitope as an epitope to which any one of the antibodies described in (a) to (n) binds.

As the antibody of the invention, an antibody having amino acid sequences of CDRs 1 to 3 of VH and CDRs 1 to 3 of VL of an antibody having homology of 85% or higher, preferably 90% or higher to the amino acid sequences of CDRs 1 to 3 of VH and CDRs 1 to 3 of VL of any one of the antibodies described in (a) to (n) is included. The homology of 90% or higher is more preferably homology of 91%, 92%, 93%, 94%, 95%, 96%, 97%, 98% or 99% or the like.

In the invention, embodiments of the antibodies described in (a) to (n) include human anti-MOG monoclonal antibodies, MOG01 antibody, MOG09 antibody and MOG14 antibody and an alpaca anti-MOG monoclonal VHH antibody, iMOG-3Rim1-S32 antibody. In addition, embodiments include a human chimeric antibody of iMOG-3Rim1-S32, a humanized antibody of iMOG-3Rim1-S32 and the like.

In the invention, the antibody of (o) is a second antibody which inhibits binding of a first antibody and MOG, wherein the antibody described in any of (a) to (n) is the first antibody.

In the invention, the antibody of (p) is a second antibody which binds to a second epitope containing a first epitope, wherein the antibody described in any of (a) to (n) is a first antibody, and the epitope to which the first antibody binds is the first epitope.

Moreover, the antibody of (q) of the invention is a second antibody which binds to a first epitope, wherein the antibody described in any of (a) to (n) is a first antibody, and the epitope to which the first antibody binds is the first epitope.

Furthermore, the antibody of the invention may be specifically an antibody selected from the group consisting of (a) to (n) and (o1) to (o22) below, (a) an antibody in which the amino acid sequence of VH is the amino acid sequence of SEQ ID NO: 3 and in which the amino acid sequence of VL contains the amino acid sequence of SEQ ID NO: 9, (b) an antibody in which the amino acid sequence of VH is the amino acid sequence of SEQ ID NO: 15 and in which the amino acid sequence of VL contains the amino acid sequence of SEQ ID NO: 21, (c) an antibody in which the amino acid sequence of VH is the amino acid sequence of SEQ ID NO: 27 and in which the amino acid sequence of VL contains the amino acid sequence of SEQ ID NO: 33, (d) an antibody fragment in which the amino acid sequence of VHH contains the amino acid sequence of SEQ ID NO: 39, (e) an antibody in which the amino acid sequence of VH contains the amino acid sequence of SEQ ID NO: 152 and in which the amino acid sequence of VL contains the amino acid sequence of SEQ ID NO: 157, (f) an antibody in which the amino acid sequence of VH contains the amino acid sequence of SEQ ID NO: 162 and in which the amino acid sequence of VL contains the amino acid sequence of SEQ ID NO: 167, (g) an antibody in which the amino acid sequence of VH contains the amino acid sequence of SEQ ID NO: 172 and in which the amino acid sequence of VL contains the amino acid sequence of SEQ ID NO: 177, (h) an antibody in which the amino acid sequence of VH contains the amino acid sequence of SEQ ID NO: 182 and in which the amino acid sequence of VL contains the amino acid sequence of SEQ ID NO: 187, (i) an antibody in which the amino acid sequence of VH contains the amino acid sequence of SEQ ID NO: 192 and in which the amino acid sequence of VL contains the amino acid sequence of SEQ ID NO: 197, (j) an antibody in which the amino acid sequence of VH contains the amino acid sequence of SEQ ID NO: 202 and in which the amino acid sequence of VL contains the amino acid sequence of SEQ ID NO: 207, (k) an antibody in which the amino acid sequence of VH contains the amino acid sequence of SEQ ID NO: 212 and in which the amino acid sequence of VL contains the amino acid sequence of SEQ ID NO: 217, (l) an antibody in which the amino acid sequence of VH contains the amino acid sequence of SEQ ID NO: 222 and in which the amino acid sequence of VL contains the amino acid sequence of SEQ ID NO: 227, (m) an antibody in which the amino acid sequence of VH contains the amino acid sequence of SEQ ID NO: 232 and in which the amino acid sequence of VL contains the amino acid sequence of SEQ ID NO: 237, (n) an antibody in which the amino acid sequence of VH contains the amino acid sequence of SEQ ID NO: 242 and in which the amino acid sequence of VL contains the amino acid sequence of SEQ ID NO: 247, (o1) an antibody in which the amino acid sequence of VH contains the amino acid sequence of SEQ ID NO: 252 and in which the amino acid sequence of VL contains the amino acid sequence of SEQ ID NO: 254, (o2) an antibody in which the amino acid sequence of VH contains the amino acid sequence of SEQ ID NO: 256 and in which the amino acid sequence of VL contains the amino acid sequence of SEQ ID NO: 258, (o3) an antibody in which the amino acid sequence of VH contains the amino acid sequence of SEQ ID NO: 260 and in which the amino acid sequence of VL contains the amino acid sequence of SEQ ID NO: 262, (o4) an antibody in which the amino acid sequence of VH contains the amino acid sequence of SEQ ID NO: 264 and in which the amino acid sequence of VL contains the amino acid sequence of SEQ ID NO: 266, (o5) an antibody in which the amino acid sequence of VH contains the amino acid sequence of SEQ ID NO: 268 and in which the amino acid sequence of VL contains the amino acid sequence of SEQ ID NO: 270, (o6) an antibody in which the amino acid sequence of VH contains the amino acid sequence of SEQ ID NO: 272 and in which the amino acid sequence of VL contains the amino acid sequence of SEQ ID NO: 274, (o7) an antibody in which the amino acid sequence of VH contains the amino acid sequence of SEQ ID NO: 276 and in which the amino acid sequence of VL contains the amino acid sequence of SEQ ID NO: 278, (o8) an antibody in which the amino acid sequence of VH contains the amino acid sequence of SEQ ID NO: 280 and in which the amino acid sequence of VL contains the amino acid sequence of SEQ ID NO: 282, (o9) an antibody in which the amino acid sequence of VH contains the amino acid sequence of SEQ ID NO: 284 and in which the amino acid sequence of VL contains the amino acid sequence of SEQ ID NO: 286, (o10) an antibody in which the amino acid sequence of VH contains the amino acid sequence of SEQ ID NO: 288 and in which the amino acid sequence of VL contains the amino acid sequence of SEQ ID NO: 290, (o11) an antibody in which the amino acid sequence of VH contains the amino acid sequence of SEQ ID NO: 292 and in which the amino acid sequence of VL contains the amino acid sequence of SEQ ID NO: 294, (o12) an antibody in which the amino acid sequence of VH contains the amino acid sequence of SEQ ID NO: 296 and in which the amino acid sequence of VL contains the amino acid sequence of SEQ ID NO: 298, (o13) an antibody in which the amino acid sequence of VH contains the amino acid sequence of SEQ ID NO: 300 and in which the amino acid sequence of VL contains the amino acid sequence of SEQ ID NO: 302, (o14) an antibody in which the amino acid sequence of VH contains the amino acid sequence of SEQ ID NO: 304 and in which the amino acid sequence of VL contains the amino acid sequence of SEQ ID NO: 306, (o15) an antibody in which the amino acid sequence of VH contains the amino acid sequence of SEQ ID NO: 308 and in which the amino acid sequence of VL contains the amino acid sequence of SEQ ID NO: 310, (o16) an antibody in which the amino acid sequence of VH contains the amino acid sequence of SEQ ID NO: 312 and in which the amino acid sequence of VL contains the amino acid sequence of SEQ ID NO: 314, (o17) an antibody in which the amino acid sequence of VH contains the amino acid sequence of SEQ ID NO: 316 and in which the amino acid sequence of VL contains the amino acid sequence of SEQ ID NO: 318, (o18) an antibody in which the amino acid sequence of VH contains the amino acid sequence of SEQ ID NO: 320 and in which the amino acid sequence of VL contains the amino acid sequence of SEQ ID NO: 322, (o19) an antibody in which the amino acid sequence of VH contains the amino acid sequence of SEQ ID NO: 324 and in which the amino acid sequence of VL contains the amino acid sequence of SEQ ID NO: 326, (o20) an antibody in which the amino acid sequence of VH contains the amino acid sequence of SEQ ID NO: 328 and in which the amino acid sequence of VL contains the amino acid sequence of SEQ ID NO: 330, (o21) an antibody in which the amino acid sequence of VH contains the amino acid sequence of SEQ ID NO: 332 and in which the amino acid sequence of VL contains the amino acid sequence of SEQ ID NO: 334 and (o22) an antibody in which the amino acid sequence of VH contains the amino acid sequence of SEQ ID NO: 336 and in which the amino acid sequence of VL contains the amino acid sequence of SEQ ID NO: 338.

As the antibody of the invention, an antibody having amino acid sequences of VH and VL of an antibody having homology of 85% or higher, preferably 90% or higher to the amino acid sequences of VH and VL of any one of the antibodies described in (a) to (n) and (o1) to (o22) is included. The homology of 90% or higher is more preferably homology of 91%, 92%, 93%, 94%, 95%, 96%, 97%, 98% or 99% or the like.

In the invention, embodiments of the antibodies described in (a) to (n) and (o1) to (o22) include human anti-MOG monoclonal antibodies, MOG01 antibody, MOG09 antibody and MOG14 antibody and an alpaca anti-MOG monoclonal VHH antibody, iMOG-3Rim1-S32 antibody. In addition, embodiments include an iMOG-3Rim1-S32 human chimeric antibody, an iMOG-3Rim1-S32 humanized antibody and the like.

In the invention, the EU index refers to the position of an amino acid residue according to Sequences of Proteins of Immunological Interest, Fifth edition (1991). The positions of the amino acid residues shown below are all the positions of the amino acid residues according to the EU index unless particularly described.

An antibody molecule is also called an immunoglobulin (referred to as Ig below), and its basic structure is a tetramer having two polypeptides called heavy chains (referred to as H chains below) and two polypeptides called light chains (referred to as L chains below).

Each H chain is composed of a H chain variable region (also referred to as VH) and a H chain constant region (also referred to as CH) from the N-terminus side, and each L chain is composed of a L chain variable region (also referred to as VL) and a L chain constant region (also referred to as CL) from the N-terminus side.

For CH, $\alpha$, $\delta$, $\epsilon$, $\gamma$ and $\mu$ chains are known for each subclass. CH is further composed of a CH1 domain, a hinge domain, a CH2 domain and a CH3 domain from the N-terminus side.

A domain is a functional structural unit which constitutes a polypeptide of an antibody molecule. The CH2 domain and the CH3 domain are together called a Fc (Fragment, crystallizable) region or simply Fc. For CL, $C_\lambda$ chain and $C_\kappa$ chain are known.

The subclasses of antibody in which CH is $\alpha$, $\delta$, $\epsilon$, $\gamma$ and $\mu$ chains are called IgA, IgD, IgE, IgG and IgM, respectively. There are sometimes isotypes for a subclass of an antibody depending on the animal. In human, there are isotypes IgA1 and IgA2 for IgA, and there are isotypes IgG1, IgG2, IgG3 and IgG4 for IgG.

The CH1 domain, the hinge domain, the CH2 domain, the CH3 domain and the Fc region in the invention can be identified by the positions of the amino acid residues from the N-terminus according to the EU index.

Specifically, CH1 is identified as the amino acid sequence of from position 118 to position 215 according to the EU index, and the hinge is identified as the amino acid sequence of from position 216 to position 230 according to the EU index. CH2 is identified as the amino acid sequence of from position 231 to position 340 according to the EU index, and CH3 is identified as the amino acid sequence of from position 341 to position 447 according to the EU index. The Fc region is identified as the amino acid sequence of from position 231 to position 447 according to the EU index.

As the antibody of the invention, a polyclonal antibody, a monoclonal antibody and an oligoclonal antibody are all included. A polyclonal antibody is a group of antibody molecules that are secreted by antibody-producing cells of different clones. A monoclonal antibody is an antibody that is secreted by antibody-producing cells of a single clone and recognizes only one epitope (also called an antigenic determinant). The amino acid sequences (primary sequences) of same monoclonal antibodies are the same. An oligoclonal antibody is a group of antibody molecules in which different monoclonal antibodies are mixed.

The monoclonal antibody of the invention may be an antibody that is produced from a hybridoma or a genetically recombinant antibody that is produced by a transformant transformed with an expression vector containing the antibody genes.

The epitope may be a single amino acid sequence, a three-dimensional structure made of an amino acid sequence, an amino acid sequence modified after translation, a three-dimensional structure made of an amino acid sequence modified after translation which the monoclonal antibody recognizes and binds to or the like.

The amino acid sequence modified after translation may be an O-linked glycan in which sugar chains are attached to Tyr and Ser having OH substituents, an N-linked glycan in which sugar chains are attached to Gln and Asn having $NH_2$ substituents or a tyrosine sulfated amino acid sequence in which a sulfuric acid molecule is attached to Tyr having OH substituents.

The epitope of MOG to which the antibody of the invention binds can be identified by an antibody-binding test using a deletion variant of MOG in which some domains are lost, a mutant in which some domains are replaced with domains derived from another protein, a partial peptide fragment of MOG or the like. The antibody-binding test can also be conducted using cells expressing the deletion variant or the mutant.

Alternatively, the epitope of MOG to which the antibody of the invention binds can also be identified by adding the antibody of the invention to peptide fragments of MOG obtained by decomposition using a protease and conducting epitope mapping using a known mass spectrometry.

As the antibody of the invention, genetically recombinant antibodies of a mouse antibody, a rat antibody, a hamster antibody, a rabbit antibody, a llama antibody, a camel antibody, an alpaca antibody, a chimeric antibody, a humanized antibody (also called a "Complementarity Determining Region (CDR)-inserted antibody"), a human antibody and the like are also included.

In the invention, the chimeric antibody is an antibody in which VH and VL are derived from a different animal kind from that of CH and CL. An antibody composed of VH and VL of an antibody of an animal other than human (a non-human animal) and CH and CL of a human antibody is called a human chimeric antibody, and an antibody composed of VH and VL of an antibody of an animal other than mouse and CH and CL of a mouse antibody is called a mouse chimeric antibody. Other chimeric antibodies are named in the same manner.

As the non-human animal, any animal such as mouse, rat, hamster, rabbit, llama, camel or alpaca can be used as long as a hybridoma can be produced or an antibody phage library can be produced.

A hybridoma is a cell which is obtained by cell fusion of a B cell obtained by immunizing a non-human animal with an antigen and a myeloma cell derived from a mouse or the like and which produces a monoclonal antibody having a desired antigen specificity.

An antibody phage library is a library produced by cloning the genes of immunoglobulin variable regions to a phage and expressing an antigen-binding molecule on its surface. The phages used are M13 phage and the like but are not particularly limited.

The antigen-binding molecule which is displayed on a phage may be in any form but is preferably an antibody fragment such as scFv, Fab or VHH.

In the invention, the antibody phage library may be any library of an immune library, a naive library and a synthetic library.

An immune library is an antibody phage library which is constructed based on the antibody genes derived from lymphocytes of an animal immunized with an antigen or a patient. A naive library is an antibody phage library which is constructed based on the antibody genes derived from lymphocytes of a normal animal or a healthy human. A synthetic library is a library in which CDRs of a V gene in genome DNA or a reconstructed functional V gene are replaced with oligonucleotides that encode any amino acid sequences of appropriate lengths.

As a method for producing a chimeric antibody, a method for producing a human chimeric antibody is described below. Other chimeric antibodies can also be produced by the same method.

A human chimeric antibody can be produced by obtaining cDNAs that encode VH and VL from a hybridoma derived from a non-human animal cell producing a monoclonal antibody, inserting the cDNAs into an expression vector for animal cells having DNA that encodes CH and CL of a human antibody, thereby constructing a human chimeric antibody expression vector, introducing the vector to an animal cell and expressing the antibody.

A human chimeric antibody can also be produced by cloning the genes that encode VH and VL from an antibody phage library derived from a non-human animal, inserting the genes into an expression vector for animal cells having DNA that encodes CH and CL of a human antibody, thereby constructing a human chimeric antibody expression vector, introducing the vector to an animal cell and expressing the antibody.

A humanized antibody is an antibody in which the amino acid sequences of CDRs of VH and VL of an antibody of a non-human animal are implanted to the corresponding CDRs of VH and VL of a human antibody. The region other than the CDRs of VH and VL is called a framework region (referred to as FR below).

A humanized antibody can be produced by constructing cDNA that encodes the amino acid sequence of VH formed from the amino acid sequences of CDRs of VH of an antibody of a non-human animal and the amino acid sequence of FR of VH of any human antibody and cDNA that encodes the amino acid sequence of VL formed from the amino acid sequences of CDRs of VL of an antibody of a non-human animal and the amino acid sequence of FR of VL of any human antibody, inserting the cDNAs to an expression vector for animal cells having DNA that encodes CH and CL of a human antibody, thereby constructing a humanized antibody expression vector, introducing the vector to an animal cell and expressing the antibody.

A human antibody is originally an antibody that naturally exists in the human body, but antibodies obtained from a human antibody phage library and a human antibody-producing transgenic animal and the like are also included.

A human antibody can be obtained by immunizing a mouse having a human immunoglobulin gene (Tomizuka K. et al., Proc Natl Acad Sci USA. 97, 722-7, 2000.) with a desired antigen. A human antibody can be obtained also without immunization by selecting a human antibody having a desired binding activity using a phage display library obtained by amplifying antibody genes from human-derived B cells (Winter G. et al., Annu Rev Immunol. 12:433-55. 1994).

Moreover, a human antibody can be obtained by producing cells which produce a human antibody having a desired binding activity by immortalizing human B cells using EB virus (Rosen A. et al., Nature 267, 52-54.1977).

A human antibody phage library is a library in which antibody fragments such as Fab, scFv and VHH are expressed on the surface of phages by inserting an antibody gene produced from lymphocytes of a human (a healthy individual or a patient) to phage genes. It is possible to collect phages on which antibody fragments having a desired antigen binding activity are expressed using binding activity to a substrate to which an antigen is fixed as an index from the library. The antibody fragments can be further converted to a human antibody molecule formed from two whole H chains and two whole L chains using the genetic engineering technique.

A human antibody-producing transgenic animal is an animal in which a human antibody gene is incorporated into the chromosomes of the host animal. Specifically, a human antibody-producing transgenic animal can be produced by introducing a human antibody gene to mouse ES cells, implanting the ES cells to an early embryo of another mouse and then causing development.

A human antibody can be produced from a human antibody-producing transgenic animal by culturing a human antibody-producing hybridoma obtained by a general hybridoma production method performed for mammals other than human, producing and accumulating the human antibody in the culture and purifying the antibody from the culture.

The antibody of the invention includes a heavy chain antibody composed of heavy chains only. Heavy chain antibodies are an antibody obtained from a Camelidae animal such as llama, camel and alpaca and a genetically recombinant antibody produced based on the antibody.

In the invention, the antibody fragment is a fragment of an antibody which has an antigen binding activity. Examples include Fab, Fab', F(ab')$_2$, single chain Fv (scFv), diabody, dsFv, a peptide containing CDRs, VHH and the like. The antibody fragment of the invention also includes any antibody fragment as long as the antibody fragment contains a partial fragment of an antibody and has a MOG binding activity, such as an antibody fragment obtained by fusing the whole or a part of a constant region or Fc of an antibody to the antibody fragment or an antibody fragment containing a constant region or Fc.

Fab is an antibody fragment which has an antigen binding activity and a molecular weight of approximately fifty thousand and in which about a half of the H chain in the N-terminus side and the entire L chain are linked to each other through disulfide bonds (S—S bonds) (cleaved at the 224th amino acid residue in the H chain), of the fragments obtained by treating IgG antibody with a protease, papain.

F(ab')$_2$ is an antibody fragment which has an antigen binding activity and a molecular weight of approximately hundred thousand and which is slightly larger than the one in which Fabs are bound through the S—S bond in the hinge region (cleaved at the 234th amino acid residue in the H chain), of the fragments obtained by treating IgG with a protease, pepsin.

Fab' is an antibody fragment which has an antigen binding activity and a molecular weight of approximately fifty thousand and in which the S—S bond in the hinge region of the above F(ab')$_2$ is cleaved.

scFv is a VH-P-VL or VL-P-VH polypeptide in which one VH and one VL are linked using an appropriate peptide linker (P) such as a linker peptide of any number of connected linkers each having four Gly residues and one Ser residue (G4S) and is an antibody fragment having an antigen binding activity.

Diabody is an antibody fragment in which scFvs having same or different antigen binding specificities form a dimer and is an antibody fragment having a divalent antigen binding activity to a same antigen or specific antigen binding activities to different antigens.

dsFv is a fragment in which polypeptides obtained by substituting one amino acid residue in VH and that in VL with cysteine residues are bound through the S—S bond between the cysteine residues.

A peptide containing CDR is composed of and contains at least one or more regions of CDRs of VH or VL. In a peptide containing CDRs, the CDRs can be bound directly or through an appropriate peptide linker.

Production can be performed by constructing DNA that encodes CDRs of VH and VL of the antibody of the invention, inserting the DNA into an expression vector for a prokaryote or an expression vector for a eukaryote and introducing the expression vector into a prokaryote or a eukaryote for expression. In addition, a peptide containing CDR can also be produced by a chemical synthesis method such as the Fmoc method or the tBoc method.

VHH is a variable region of a heavy chain antibody and is also called a nanobody.

The antibody fragment of the invention includes any antibody fragment as long as the antibody fragment contains any of the antibody fragments described above or a partial fragment thereof and has a MOG binding activity.

In the invention, an antibody having one antigen binding site or an antibody fragment thereof is called a monovalent antibody. The formats of a monovalent antibody are the formats of an antibody having one antigen binding site or an antibody fragment thereof described in International Publication No. 2014/054804, International Publication No. 2011/090754, International Publication No. 2007/048037, International Publication No. 2012/116927 and the like and other formats.

In the invention, an antibody of one molecule which binds to three or more different antigens or epitopes or an antibody fragment thereof is called a multispecific antibody. In the invention, an antibody of one molecule which binds to two different antigens or epitopes or an antibody fragment thereof is called a bispecific antibody.

The formats of a multispecific antibody or a bispecific antibody are the formats described in International Publication No. 2009/131239, International Publication No. 2014/054804, International Publication No. 01/077342, US Patent Application Publication No. 2007/0071675, International Publication No. 2007/024715, Wu et al., [Nature Biotechnology, 2007, 25(11), p. 1290-1297], Labrijn et al., [PNAS 2013, vol. 110, no. 13, p 5145-5150], Jong et al., [http://dx.doi.org/10.1371/journal.pbio.1002344], Kontermann et al., [mAbs 2012, vol. 4, issue 2, p 182-197], Spiess et al., [Molecular Immunology 67 (2015) 95-106], Ridgway et al., [Protein engineering, 1996 vol. 9 no. 7 pp 617-621, International Publication No. 2009/080251, International Publication No. 2010/151792, International Publication No. 2014/033074 and the like and other formats.

The bispecific antibody may be specifically any of the bispecific antibodies described below and the like.

(1) A bispecific antibody in which amino acid modifications S354C/T366W are introduced to CH3 of one of the two heavy chains of an antibody (heavy chain A) and in which amino acid modifications Y349C/T366S/L368A/Y407V are introduced to CH3 of the other heavy chain (heavy chain B).

(2) A bispecific antibody in which an antibody fragment is fused to a C-terminus of an antibody.

(3) A bispecific antibody in which an antibody fragment is fused to a N-terminus of an antibody.

The bispecific antibody described in (1) may be a bispecific antibody in which the antigen binding site containing VH of heavy chain A binds to MOG and in which the antigen binding site containing VH of heavy chain B binds to an antigen that is present in the brain or one in which the bindings are the other way around.

The bispecific antibody described in (2) may be any bispecific antibody of a bispecific antibody in which an antibody fragment is bound to the C-terminus of one of the two heavy chains constituting the antibody and a bispecific antibody in which antibody fragments are bound to both of the two heavy chains. Moreover, an appropriate linker may be between the C-terminus of the heavy chain of the antibody and the antibody fragment.

The antibody fragment(s) that the bispecific antibody described in (2) has is preferably scFv, Fab, VHH or the like but is not particularly limited to these fragments.

The bispecific antibody described in (2) may be a bispecific antibody in which the antigen binding site at the N-terminus binds to MOG and in which the antigen binding site at the C-terminus binds to an antigen that is present in the brain or one in which the bindings are the other way around.

The bispecific antibody described in (3) is a bispecific antibody in which an antibody fragment is bound to the N-terminus of at least any one of the two heavy chains or the light chains constituting the antibody. Moreover, an appropriate linker may be between the N-terminus of the heavy chain and/or the light chain of the antibody and the antibody fragment. The antibody fragment that the bispecific antibody described in (3) has is preferably scFv, Fab, VHH or the like but is not particularly limited to these fragments.

The bispecific antibody described in (3) is a bispecific antibody having a structure $VH_1$-CH1-$VH_2$-CH1-hinge-CH2-CH3 from the N-terminus of a heavy chain, a bispecific antibody which has the heavy chain structure and in which $VH_1$ and $VH_2$ each form an antigen binding site with VL or the like. The VLs with which $VH_1$ and $VH_2$ form antigen binding sites may have a same amino acid sequence or different amino acid sequences.

In the invention, the multispecific antibody or the bispecific antibody may be any antibody as long as the antibody is a multispecific antibody or a bispecific antibody which binds to MOG. Of such antibodies, a multispecific antibody or a bispecific antibody which binds to MOG and an antigen that is present in the brain is preferable, and a multispecific antibody or a bispecific antibody containing an antigen binding site which binds to MOG and an antigen binding site which binds to an antigen that is present in the brain is more preferable.

In the invention, the antigen that is present in the brain is a protein, a sugar chain, a lipid or the like and is preferably a protein of these antigens.

Examples of the protein that is present in the brain include MOG, Prion, 5T4, AFP, ADAM-10, ADAM-12, ADAM17, AFP, AXL, BSG, C5, C5R, CA9, CA72-4, CCL11, CCL2, CCR1, CCR4, CCR5, CCR6, CD2, CD3E, CD4, CD5, CD6, CD8, CD11, CD18, CD19, CD20, CD22, CD24, CD25, CD29, CD30, CD32B, CD33, CD37, CD38, CD40, CD40LG, CD44, CD47, CD52, CD55SC1, CD56, CD66E, CD71, CD72, CD74, CD79a, CD79b, CD80, CD86, CD95, CD98, CD137, CD147, CD138, CD168, CD200, CD248, CD254, CD257, CDH3, CEA, CEACAM1, CEACAM5, CEACAM6, CEACAM8, Claudin3, Claudin4, c-Met, CS-1, CSF2RA, CSPG-4, CTLA4, CRF-1, Cripto, CXCR4, CXCR5, DLL4, DR4, DR5, ED-B, EFNA2, EGFR, EGFRvIII, ETBR, ENPP3, EPCAM, EphA2, ERBB2, ERBB3, ERBB4, FAPα, FAS, FcγRI, FCER2, FGFR1, FGFR2, FGFR3, FGFR4, FLT1, FOLH1, FOLR1, GDF2, GFR, GLP1R, glypican-3, GPNMB, GRP78, HB-EGF, HGF, HLA-DRβ, ICAM1, IFNA1, IFNA1, IgE, IgE-Fc, IGF1R, IL10, IL12B, IL13, IL15, IL17A, IL1A, IL1B, IL2RA, IL4, IL5, IL5RA, IL6, IL6R, IL9, IL2Rα, IL2Rβ, IL2Rγ, INSR, ITGA2, ITGA2B2, ITGB3, ITGA4, ITGB7, ITGA5, ITGAL, ITGAV, ITGB3, ITGB2, KDR, L1CAM, mesothelin, MMP14, MMP15, MST1R, MSTN, MUC1, MUC4, MUC16, MUC5AC, myostatin, NECTIN4, NGF, NOTCH, NRG1, NRP, OX40, OX40L, PDGFA, PDGFB, PDGFRA, PDGFRB, PD1, PDL1, PSCA, SLAM7, SLC44A4, TAG-72, TCR, TGFB1, TGFB2, TGFBR, TNF, TNFR, TNFRSF10A, TNFRSF10B, TNFRSF12A, TNFSF13, TNFSF14, TNFSF2, TNFSF7, TRAILR2, TRKA, TRKB, TRKC, VEGF, VEGFR, VLA-4, CGRP, alpha-synuclein, TDP-43, Tau, FUS, Amyloid-beta (Aβ), APP, BACE1, Presenilin, LINGO-1, Nogo, polyQ, androgen receptor, huntingtin, ataxin 1, ataxin 2, RGMA, Phospho-Tau, Phospho-alpha-synuclein and the like, but the protein is not limited to these proteins.

Examples of the sugar chain that is present in the brain include Lewis-x, Lewis-y, CD15 and the like, but the sugar chain is not limited to these sugar chain.

Examples of the lipid that is present in the brain include GD1a, GD2, GD3, GM1, GM2, GM3, phosphatidylserine and the like, but the lipid is not limited to these lipids.

The antibody or the antibody fragment of the invention also includes an antibody containing any amino acid that is modified after translation. Examples of the modification after translation include deletion of the lysine residue at the C-terminus of a H chain (lysine clipping), conversion of the glutamine residue at the N-terminus of a polypeptide into pyroglutamine (puroGlu) and the like [Beck et al, Analytical Chemistry, 85, 715-736(2013)].

An amino acid residue in the Fc region of the antibody or the antibody fragment of the invention may be modified. Examples of the amino acid modification in the Fc region include amino acid modification for stabilizing the antibody or regulating the half-life in the blood and the like. Specific examples of the amino acid modification in the Fc region include those in International Publication No. 2006/033386, International Publication No. 2006/075668, International Publication No. 2011/122011, International Publication No. 2009/125825 and the like.

The antibody or the antibody fragment of the invention also includes a fused antibody or a fused antibody fragment in which an antibody or an antibody fragment is modified. The method for modifying an antibody is not particularly limited, and any method which can modify a desired amino acid residue and a sugar chain can be used.

Examples include chemical modification using chemical reaction [Introduction to Antibody Engineering, Chijinshokan Co., Ltd. (1994); and Kolb et al., Angew Chem Int Ed Engl. 40. 2004-21, 2001], modification by the genetic engineering technique in which a recombinant protein expression vector is introduced to an appropriate host cell for expression using genetic recombination technology and the like.

In the invention, examples of the molecule which modifies the antibody or the antibody fragment include a hydrophilic polymer, an amphipathic polymer, a functional molecule and the like. Examples of the hydrophilic polymer and the amphipathic polymer include a polyoxyalkylene, a molecule containing a polyol or a polysaccharide and the like.

Examples of the polyoxyalkylene include linear or branched chain polyethylene glycol (referred to as PEG below), polypropylene glycol, polypropylene ethylene glycol and the like.

Examples of the molecule containing a polyol or a polysaccharide include homo- or hetero-polysaccharides such as amylose, dextran, pullulan or glycogen composed of linear or branched chain polyglycerol and the like.

The molecular weight of the molecule containing a hydrophilic polymer or an amphipathic polymer is not particularly limited but is preferably 100 Da or more, preferably for example 100 Da to 100 kDa.

Examples of the functional molecule include an antigen-binding molecule, a fragment thereof, a drug, a bioactive peptide, a bioactive protein, a nucleic acid, a radiolabeling compound, a sugar chain, a lipid, a fluorescent compound and the like. A molecule which has double specificity as a result of modification with a functional molecule such as an antigen-binding molecule is a bispecific antibody.

Examples of the antigen-binding molecule include an antibody, a receptor, a ligand and the like.

The fragment of the antigen-binding molecule may be any fragment as long as the fragment is a fragment of the antigen-binding molecule and has an antigen binding activity.

Examples of the drug include anti-cancer drugs such as alkylating agents, nitrosoureas, antimetabolites, antiviral agents, antibiotics, plant alkaloids, topoisomerase inhibitors, tubulin polymerization inhibitors, hormonal therapy agents, hormone antagonists, aromatase inhibitors, P-glycoprotein inhibitors, platinum complex derivatives, M cycle inhibitor or kinase inhibitors [Clinical oncology, Cancer and chemotherapy (1996)], anti-inflammatory agents such as steroids such as hydrocortisone or prednisone, nonsteroidal drugs such as aspirin or indomethacin, immune modulating drugs such as gold thiomalate or penicillamine, immunosuppressive drugs such as cyclophosphamide or azathioprine, antihistamine drugs such as chlorpheniramine maleate or clemastine [Inflammation and anti-inflammatory therapy, Ishiyaku Pub, Inc. (1982)] and the like.

Examples of the anti-cancer drugs include mertansine, emtansine, amifostine (Ethyol), cisplatin, dacarbazine (DTIC), dactinomycin, mechlorethamine (nitrogen mustard), streptozocin, cyclophosphamide, ifosfamide, carmustine (BCNU), lomustine (CCNU), doxorubicin (Adriamycin), epirubicin, gemcitabine (Gemzar), daunorubicin, procarbazine, mitomycin, cytarabine, etoposide, 5-fluorouracil, fluorouracil, vinblastine, vincristine, bleomycin, daunomycin, peplomycin, estramustine, paclitaxel (Taxol), docetaxel (Taxotere), Aldesleukin, asparaginase, busulfan, carboplatin, oxaliplatin, nedaplatin, cladribine, camptothecin, 7-ethyl-10-hydroxycamptothecin (SN38), floxuridine, fludarabine, hydroxyurea, idarubicin, mesna, irinotecan (CPT-11), nogitecan, mitoxantrone, topotecan, leuprolide, megestrol, melphalan, mercaptopurine, hydroxycarbamide, plicamycin, mitotane, pegaspargase, pentostatin, pipobroman, streptozocin, tamoxifen, goserelin, leuprorelin, flutamide, teniposide, testolactone, thioguanine, thiotepa, uracil mustard, vinorelbine, chlorambucil, hydrocortisone, prednisolone, methylprednisolone, vindesine, nimustine, semustine, capecitabine, Tomudex, azacitidine, UFT, oxaloplatin, gefitinib (Iressa), imatinib (STI571), erlotinib, FMS-like tyrosine kinase 3 (Flt3) inhibitor, vascular endothelial growth factor receptor (VEGFR) inhibitor, fibroblast growth factor receptor (FGFR) inhibitor, epidermal growth factor receptor (EGFR) inhibitor such as Tarceva, radicicol, 17-allylamino-17-demethoxygeldanamycin, rapamycin, amsacrine, all-trans retinoic acid, thalidomide, lenalidomide, anastrozole, fadrozole, letrozole, exemestane, gold thiomalate, D-penicillamine, bucillamine, azathioprine, mizoribine, cyclosporine, rapamycin, hydrocortisone, bexarotene (Targretin), tamoxifen, dexamethasone, progestins, estrogens, anastrozole (Arimidex), Leuplin, Aspirin, indomethacin, celecoxib, azathioprine, penicillamine, gold thiomalate, chlorpheniramine maleate, chlorpheniramine, clemastine, tretinoin, bexarotene, arsenic, bortezomib, allopurinol, calicheamicin, ibritumomab tiuxetan, targretin, ozogamine, clarithromycin, leucovorin, ketoconazole, aminoglutethimide, suramin, methotrexate, maytansinoid, derivatives thereof and the like.

Examples of the method for binding the drug and the antibody or the antibody fragment include a method of binding the drug to an amino group of the antibody through glutaraldehyde, a method of binding an amino group of the drug to a carboxyl group of the antibody through water-soluble carbodiimide and the like in addition to the above method.

Examples of the bioactive peptide or the bioactive protein include interferon (referred to as IFN below)-α, IFN-β, IFN-γ, interleukin (referred to as IL below)-2, IL-12, IL-15, IL-18, IL-21, IL-23, granulocyte colony stimulating factor (G-CSF), granulocyte-macrophage colony stimulating factor (GM-CSF), macrophage colony stimulating factor (M-CSF), cytokines or growth factors which activate immunocompetent cells such as NK cells, macrophages or neutrophils, proteases such as hydrase, lyase and isomerase, enzymes such as acid sphingomyelinase, toxins including bacterial toxins and phytotoxins such as ricin, diphtheria toxin or ONTAK, antimicrobial peptides having cytomembrane-damaging activity, peptides having cytomembrane-binding affinity or permeability to cytomembrane, derivatives thereof and the like.

The nucleic acid may be any molecule as long as it is a molecule in which nucleotides or molecules having equivalent function to that of nucleotides are polymerized, and examples include siRNA, microRNA, antisense RNA, DNA aptamers and the like.

The radiolabeling compound may be any nuclide that is used for applications for diagnoses or treatment, and examples include $^{3}$H, $^{14}$C, $^{32}$P, $^{33}$P, $^{35}$S, $^{51}$Cr, $^{57}$CO, $^{18}$F, $^{153}$Gd, $^{159}$Gd, $^{64}$Cu, $^{68}$Ge, $^{166}$Ho, $^{115}$In, $^{113}$In, $^{112}$In, $^{111}$In, $^{131}$I, $^{125}$I, $^{123}$I, $^{121}$I, $^{140}$La, $^{177}$Lu, $^{54}$Mn, $^{99}$Mo, $^{103}$Pd, $^{142}$Pr, $^{149}$Pm, $^{186}$Re, $^{188}$Re, $^{211}$At, $^{105}$Rh, $^{97}$Ru, $^{153}$Sm, $^{47}$Sc, $^{75}$Se, $^{85}$Sr, $^{99}$Tc, $^{201}$Ti, $^{113}$Sn, $^{117}$Sn, $^{133}$Xe, $^{169}$Yb, $^{175}$Yb, $^{90}$Y, $^{65}$Zn and compounds containing the nuclides.

The radiolabeling compound can be directly bound to the antibody by the chloramine T method or the like. In addition, a substance that chelates the radiolabeling compound may be bound to the antibody. Examples of the chelating agent include DOTA, PA-DOTA, TRITA, DTPA and the like, and an antibody modified with the chelating agent and a modified antibody which is labeled with the radiolabeling compound through the chelating agent are also included in the antibody of the invention.

Examples of the sugar chain include monosaccharides, disaccharides or oligosaccharides such as fucose, mannose, glucose, allose, aldose, gulose, idose, galactose, talose, ribose, arabinose, xylose, lyxose, erythose, erythrose, threose, cellobiose, maltose, isomaltose, lactose, lipoarabinomannan, Lewis X trisaccharide and sialyl-Lewis X tetrasaccharide and the like. Moreover, the sugar chain may be a natural product containing a sugar chain known as immunoadjuvant and may be $\beta(1\rightarrow 3)$ glucan (lentinan or schizophyllan), $\alpha$-galactosylceramide (KRN7000) or the like.

Examples of the lipid include simple lipids (neutral lipids), which are esters of fatty acids and alcohols and analogues thereof. Examples include fats (for example, triacylglycerol), wax (for example, fatty acid esters of higher alcohols), sterol esters, cholesterol esters, fatty acid esters and the like of vitamins, complex lipids having a polar group such as phosphoric acid, saccharide, sulfuric acid or amine in addition to a fatty acid and an alcohol such as phospholipids (for example, glycerophospholipids, sphingophospholipids and the like) and glycolipids (for example, glyceroglycolipids, sphingoglycolipids and the like), derived lipids which are lipid-soluble compounds of compounds produced by hydrolysis of simple lipids and complex lipids such as fatty acids, higher alcohols, lipid-soluble vitamins, steroids and carbohydrates and the like.

Examples of the fluorescent compound include fluorescent dyes such as fluorescein series like fluorescein isothiocyanate (FITC), rhodamine series, Cy3, Cy5, eosine series, Alexa Fluor series and NBD series, light-emitting substances such as acridinium esters or lophine, fluorescent proteins such as green fluorescent protein (GFP) and the like.

The antibody or the antibody fragment of the invention can be bound to the hydrophilic polymer, the amphipathic polymer or the functional molecule directly or through an appropriate linker. Examples of the linker include esters, disulfides, hydrazones, dipeptides and the like.

When a fused antibody or a fused antibody fragment is produced by modifying the antibody or the antibody fragment of the invention by the genetic engineering technique, a fused antibody or a fused antibody fragment can be produced by linking cDNA encoding a protein to cDNA encoding an antibody to construct DNA that encodes the fused antibody or the fused antibody fragment, inserting the DNA into an expression vector for a prokaryote or a eukaryote, introducing the expression vector into a prokaryote or a eukaryote and expressing the fused antibody or the fused antibody fragment.

The composition of the invention may be any composition as long as the composition contains the antibody or the antibody fragment of the invention. The composition may contain an appropriate carrier or an additive such as a stabilizing agent in addition to the antibody or the antibody fragment.

Examples of the composition of the invention includes a composition for detection or measurement containing the antibody or the antibody fragment of the invention and the like. Examples of the composition of the invention include a pharmaceutical composition (a therapeutic agent) containing the antibody or the antibody fragment of the invention as an active ingredient and the like, and pharmaceutical formulation with a desired dosage form is prepared together with a pharmacologically acceptable carrier.

In the invention, the composition for detection or measurement may be any composition as long as the composition contains the antibody or the antibody fragment of the invention and can detect or measure an antigen to which the antibody or the antibody fragment of the invention specifically binds. The antigen to which the antibody or the antibody fragment of the invention specifically binds is MOG, MOG and an antigen that is present in the brain or the like.

The antibody or the antibody fragment of the invention has a property of binding to MOG in the brain and accumulating in the brain when administered to an animal. Therefore, when the composition for detection or measurement containing the antibody or the antibody fragment is used, the antibody can be maintained in the brain, or the antibody concentration in the brain can be improved. Thus, MOG or MOG and an antigen that is present in the brain can be detected or measured for a long time, and/or MOG or MOG and an antigen that is present in the brain can also be detected or measured with high sensitivity.

For example, when the composition for detection or measurement is a composition containing a bispecific antibody which binds to MOG and an antigen that is present in the brain, MOG and the antigen in the brain, to which the bispecific antibody binds, can be detected or measured for a long time, and/or MOG and the antigen that is present in the brain can be detected or measured with high sensitivity.

Moreover, for example, when the composition for detection or measurement is a composition containing a fused antibody or a fused antibody fragment which is labeled with a radiolabeling compound or a fluorescent dye and which binds to MOG, MOG can be detected or measured for a long time, and/or MOG can be detected or measured with high sensitivity.

The pharmaceutical composition (therapeutic agent) containing the antibody of the invention may be a therapeutic agent for any disease as long as the antigen to which the antibody or the antibody fragment of the invention specifically binds is expressed in the disease but is preferably a therapeutic agent for a brain disease.

Examples of the brain disease include Alzheimer's disease, the prodromal stage of Alzheimer's disease, Huntington disease, Parkinson's disease, brain tumors, multiple sclerosis, muscular dystrophy, amyotrophic lateral sclerosis, multiple system atrophy, progressive supranuclear palsy, nigrostriatal degeneration, olivopontocerebellar atrophy, bulbospinal muscular atrophy, spinocerebellar degeneration, cerebrovascular disease, epilepsy, migraine, hyperactivity disorder, Creutzfeldt-Jakob disease, corticobasal degeneration, lysosomal storage disease, depression, dystonia and the like.

The antibody of the invention has a property of binding to MOG in the brain and accumulating in the brain when administered to an animal. Therefore, when the therapeutic agent containing the antibody or the antibody fragment is used, the antibody or the antibody fragment can be maintained in the brain for a long time, and the antibody concentration in the brain can be improved. Thus, therapeutic effects on the diseases can be exhibited.

For example, when the therapeutic agent is a therapeutic agent containing a bispecific antibody which binds to MOG and an antigen that is present in the brain, a therapeutic effect on a brain disease related to the antigen in the brain, to which the bispecific antibody binds, can be exhibited.

Moreover, for example, when the therapeutic agent is a fused antibody or a fused antibody fragment which is modified with a low molecular weight drug and which binds to MOG, a therapeutic effect on a brain disease targeted by the low molecular weight drug can be exhibited. At this point, the therapeutic effect is preferably higher when the therapeutic agent of the invention is used compared to the effect of the low molecular weight drug alone.

The therapeutic agent containing the antibody or the antibody fragment of the invention may be an agent that contains only the antibody or the antibody fragment as an active ingredient, but the agent is generally desirably mixed with one or more pharmacologically acceptable carriers and provided as medicinal formulation that is produced by any method known in the technical field of pharmaceutical science.

As the route of administration, it is preferable to use the most effective route for the treatment, and examples include oral administration or parenteral administration such as intraoral, airway, intrarectal, subcutaneous, intradermal, intramuscular, intraventricular, intraspinal cord, intranasal, intraperitoneal or intravenous administration. Intravenous or intraventricular administration or the like is particularly preferable. Examples of the form of administration include a spray, a capsule, a tablet, a powder, a granule, a syrup, an emulsion, a suppository, an injection, an ointment, a tape and the like.

The dose or the frequency of administration varies according to the desired therapeutic effect, administration method, treatment period, age, body weight and the like but is usually 10 µg/kg to 20 mg/kg per day for adult.

The invention also includes a method for keeping an antibody in the brain, a method for improving the property of an antibody of accumulating in the brain and a method for increasing the antibody concentration (or the antibody amount) in the brain which use the antibody or the antibody fragment of the invention.

The invention also relates to a peptide which binds to MOG, a nucleic acid containing a nucleotide sequence which encodes the peptide, a transformant cell which contains a vector containing the nucleic acid, a method for producing the peptide including culturing the transformant cell and collecting the peptide from the culture solution, a composition containing the peptide or a method for detecting or measuring an antigen that is present in the brain, a method for diagnosing or treating a brain disease, a method for improving the property of a peptide of accumulating in the brain or a method for increasing the peptide amount in the brain that uses the peptide or the composition.

The peptide of the invention includes a fused peptide obtained by modifying a peptide.

The definitions of the terms related to the peptide which binds to MOG and the like are the same as the definitions of the terms described for the antibody which binds to MOG and the like above unless particularly described.

The method for producing the antibody or the antibody fragment of the invention, the method for treating a disease, the method for diagnosing a disease and the like are specifically explained below.

1. Production Method of Antibody
(1) Preparation of Antigen

MOG as an antigen or a MOG-expressing cell can be obtained by introducing an expression vector containing cDNA that encodes the full length of MOG or a partial length thereof to *E. coli*, yeast, insect cells, animal cells or the like. In addition, MOG can also be obtained by purifying MOG from an animal cell line, an animal cell or an animal tissue of various kinds and the like in which MOG is expressed in a large amount.

In addition, the animal cell line, the animal cell, the animal tissue and the like can also be used as they are as an antigen. Furthermore, a synthetic peptide having a partial sequence of MOG can be prepared using a chemical synthesis method such as the Fmoc method or the tBoc method and used as an antigen.

A known tag such as FLAG or His may be added to the C-terminus or the N-terminus of MOG or the synthetic peptide having a partial sequence of MOG.

MOG used in the invention can be produced using the method described in Molecular Cloning, A Laboratory Manual, Second Edition, Cold Spring Harbor Laboratory Press (1989), Current Protocols In Molecular Biology, John Wiley & Sons (1987-1997) or the like or another method by expressing DNA that encodes MOG in a host cell for example by the following method.

First, a recombinant vector is produced by inserting the full-length cDNA containing the part that encodes MOG into downstream of a promoter in an appropriate expression vector. A DNA fragment of an appropriate length which contains the part that encodes the polypeptide and which is prepared based on the full-length cDNA may be used in place of the full-length cDNA. Next, a transformant that produces the polypeptide can be obtained by introducing the obtained recombinant vector into a host cell suitable for the expression vector.

As the expression vector, any vector can be used as long as it can replicate autonomously or can be inserted into a chromosome in a host cell to be used and which contains a suitable promoter in the position that enables the transcription of DNA that encodes the polypeptide. As the host cell, any cell, such as a microorganism belonging to the genus *Escherichia* such as *E. coli*, yeast, an insect cell or an animal cell, can be used as long as it enables the expression of a target gene.

In a case where a prokaryote such as *E. coli* is used as a host cell, the expression vector is preferably a vector that can replicate autonomously in the prokaryote and that contains a promoter, a ribosomal binding sequence, DNA containing the part encoding human MOG and a transcription termination sequence. In addition, the transcription termination sequence is not essentially needed for the expression vector, but the transcription termination sequence is preferably placed immediately after the structural gene. Furthermore, the recombinant vector may contain a gene controlling the promoter.

As the expression vector, it is preferable to use a plasmid in which the distance between the Shine-Dalgarno sequence (also called SD sequence) that is a ribosomal binding sequence and the initiation codon is appropriately adjusted (to, for example, 6 to 18 nucleotides).

In addition, regarding the nucleotide sequence of DNA that encodes MOG, a nucleotide can be substituted in a manner that the codon becomes optimum for the expression in a host, which enables the enhancement in the production rate of target MOG.

As the expression vector, any vector can be used as long as it can exhibit its function in a host cell to be used. Examples thereof include pBTrp2, pBTac1 and pBTac2 (manufactured by Roche Diagnostics K.K.), pKK233-2 (manufactured by Pharmacia), pSE280 (manufactured by Invitrogen), pGEMEX-1 (manufactured by Promega Corporation), pQE-8 (manufactured by QIAGEN), pKYP10 (JP-A-S58-110600), pKYP200 [Agricultural Biological Chemistry, 48, 669 (1984)], pLSA1 [Agric. Biol. Chem., 53, 277 (1989)], pGEL1 [Proc. Natl. Acad. Sci. USA, 82, 4306 (1985)], pBluescript II SK(−) (manufactured by Stratagene Corporation), pTrs30 [prepared from *Escherichia coli* JM109/pTrS30 (FERM BP-5407)], pTrs32 [prepared from *Escherichia coli* JM109/pTrS32 (FERM BP-5408)], pGHA2 [prepared from *Escherichia coli* IGHA2 (FERM BP-400), JP-A-S60-221091], pGKA2 [prepared from *Escherichia coli* IGKA2 (FERM BP-6798), JP-A-S60-221091], pTerm2 (U.S. Pat. Nos. 4,686,191, 4,939,094 and 160,735), pSupex, pUB110, pTP5, pC194, pEG400 [J. Bacteriol., 172, 2392 (1990)], pGEX (manufactured by Pharmacia), pET System (manufactured by Novagen), pME18SFL3 and the like.

As the promoter, any promoter may be used as long as it can exhibit its function in a host cell to be used. Examples thereof include promoters such as a trp promoter (Ptrp), a lac promoter, a PL promoter, a PR promoter or a T7 promoter, which are derived from *E. coli*, a phage or the like. In addition, examples thereof also include promoters such as a tandem promoter with two tandemly arrayed Ptrps, a tac promoter, a lacT7 promoter or a let I promoter, which are artificially designed and altered.

Examples of the host cell include *E. coli* XL1-Blue, *E. coli* XL2-Blue, *E. coli* DH1, *E. coli* MC1000, *E. coli* KY3276, *E. coli* W1485, *E. coli* JM109, *E. coli* HB101, *E. coli* No. 49, *E. coli* W3110, *E. coli* NY49, *E. coli* DH5α and the like.

As a method for introducing a recombinant vector into a host cell, any method can be used as long as it is a method by which DNA is introduced into a host cell to be used. Examples thereof include a method using calcium ions [Proc. Natl. Acad. Sci. USA, 69, 2110 (1972), Gene, 17, 107 (1982) and Molecular & General Genetics, 168, 111 (1979)].

In a case of using an animal cell as a host, as the expression vector, any vector can be used as long as it can exhibit its function in the animal cell. Examples thereof include pcDNAI, pCDM8 (manufactured by Funakoshi Co., Ltd.), pAGE107 [JP-A-H3-22979; and Cytotechnology, 3, 133 (1990)], pAS3-3 (JP-A-H2-227075), pCDM8 [Nature, 329, 840 (1987)], pcDNAI/Amp (manufactured by Invitrogen), pcDNA3.1 (manufactured by Invitrogen), pREP4 (manufactured by Invitrogen), pAGE103 [J. Biochemistry, 101, 1307 (1987)], pAGE210, pME18SFL3, pKANTEX93 (International Publication No. 97/10354), N5KG1val (U.S. Pat. No. 6,001,358), INPEP4 (manufactured by Biogen-IDEC), pCI (manufactured by Promega Corporation), a transposon vector (International Publication No. 2010/143698) and the like.

As the promoter, any promoter can be used as long as it can exhibit its function in the animal cell. Examples thereof include a promoter of cytomegalovirus (CMV) immediate early (IE) gene, an early promoter of SV40, a retroviral promoter, a metallothionein promoter, a heat-shock promoter, a SRα promoter, a promoter of Moloney murine leukemia virus or an enhancer. In addition, an enhancer of human CMV IE gene may be used together with the promoter.

Examples of the host cell include a human leukemia cell Namalwa, a monkey cell COS, a Chinese hamster ovary cell CHO [Journal of Experimental Medicine, 108, 945 (1958); Proc. Natl. Acad. Sci. USA, 60, 1275 (1968); Genetics, 55, 513 (1968); Chromosoma, 41, 129 (1973); Methods in Cell Science, 18, 115 (1996); Radiation Research, 148, 260 (1997); Proc. Natl. Acad. Sci. USA, 77, 4216 (1980); Proc. Natl. Acad. Sci., 60, 1275 (1968); Cell, 6, 121 (1975); and Molecular Cell Genetics, Appendix I, II (pp. 883-900)]; a CHO cell which lacks dihydrofolate reductase gene (referred to as dhfr below) (CHO/DG44 cell) [Proc. Natl. Acad. Sci. USA, 77, 4216(1980)], CHO-K1 (ATCC CCL-61), DUkXB11 (ATCC CCL-9096), Pro-5 (ATCC CCL-1781), CHO-S (Life Technologies, Cat #11619), Pro-3, a rat myeloma cell YB2/3HL.P2.G11.16Ag.20 (also called YB2/0), a mouse myeloma cell NS0, a mouse myeloma cell SP2/0-Ag14, a Syrian hamster cell BHK, HBT5637 (JP-A-S63-000299) and the like.

As a method for introducing an expression vector into a host cell, any method can be used as long as it is a method by which DNA is introduced into an animal cell. Examples thereof include the electroporation [Cytotechnology, 3, 133 (1990)], the calcium phosphate transfection method (JP-A-H2-227075), the lipofection [Proc. Natl. Acad. Sci. USA, 84, 7413 (1987)] and the like.

MOG can be produced by culturing a transformant derived from a microorganism, an animal cell or the like having the expression vector into which DNA that encodes MOG has been introduced and which is obtained as above in a medium, generating and accumulating MOG in the culture solution and then collecting MOG from the culture solution. A method of culturing the transformant in a medium can be performed according to a usual method used for a host culture.

In a case of expression in the cells derived from a eukaryote, MOG added with sugars or sugar chains can be obtained.

When culturing a microorganism that has been transformed by an expression vector using an inducible promoter, an inducer may be added to the medium if necessary. For example, isopropyl-β-D-thiogalactopyranoside or the like may be added to the medium for a case of culturing a microorganism that has been transformed by an expression vector using a lac promoter, and indoleacrylic acid or the like may be added to the medium for a case of culturing a microorganism that has been transformed by an expression vector using a trp promoter.

Examples of the medium in which the transfectant obtained using an animal cell as a host is cultured include RPMI 1640 Medium [The Journal of the American Medical Association, 199, 519 (1967)], Eagle's MEM Medium [Science, 122, 501 (1952)], Dulbecco's Modified MEM Medium [Virology, 8, 396 (1959)], Medium 199 [Proc. Soc. Exp. Biol. Med., 73, 1 (1950)], Iscove's Modified Dulbecco's Medium (IMDM), which are generally used, or a medium in which fetal bovine serum (FBS) or the like is added to such a medium. Culture is usually performed under the conditions of pH 6 to 8 and 30 to 40° C. in the presence of 5% $CO_2$ for 1 to 7 days. In addition, during the culture, antibiotics such as kanamycin or penicillin may be added to the medium, if necessary.

Examples of the method for expressing a gene that encodes MOG include a method such as secretory production or fused protein expression [Molecular Cloning, A Laboratory Manual, Second Edition, Cold Spring Harbor Laboratory Press (1989)] in addition to direct expression.

Examples of the method for producing MOG include a method of producing in a host cell, a method of secretion out of a host cell and a method of producing on the outer membrane of a host cell. An appropriate method can be selected by changing the host cell to be used or the structure of MOG to be produced.

In a case where MOG is produced in a host cell or on the outer membrane of a host cell, MOG can be actively secreted outside the host cell using the method by Paulson et al. [J. Biol. Chem., 264, 17619 (1989)], the method by Lowe et al. [Proc. Natl. Acad. Sci., USA, 86, 8227 (1989) and Genes Develop., 4, 1288 (1990)] or the method described in JP-A-H05-336963, International Publication No. 94/23021 or the like. In addition, the amount of production of MOG can also be increased using the gene amplification using dihydrofolate reductase gene or the like (JP-A-H2-227075).

Obtained MOG can be isolated and purified as follows for example. In a case where MOG is expressed in the cells in a dissolved state, the cells are collected by centrifugation after completing culture and suspended in an aquatic buffer solution, followed by crushing of the cells using an ultrasonic crusher, a French press, a Manton Gaulin homogenizer, a Dyno mill or the like, and therefore cell-free extract is obtained. A purified sample can be obtained from a supernatant obtained by centrifugation of the cell-free extract using a method such as a general method for isolation and purification of proteins, that is, a solvent extraction method, a salting-out method using ammonium sulfate or the like, a desalting method, a precipitation method using an organic solvent, anion-exchange chromatography using a resin such as Diethylaminoethyl (DEAE)-Sepharose or DIAION HPA-75 (manufactured by Mitsubishi Chemical Corporation), cation-exchange chromatography using a resin such as S-Sepharose FF (manufactured by Pharmacia), hydrophobic interaction chromatography method using a resin such as Butyl Sepharose or Phenyl Sepharose, a gel filtration method using molecular decoration, affinity chromatography, a chromatofocusing method, electrophoresis such as isoelectric focusing electrophoresis and the like alone or in combination.

In a case where MOG forms an insoluble complex and expressed in the cells, the cells are collected and then crushed in the same manner as above, followed by centrifugation, and then an insoluble complex of MOG is collected as a precipitated fraction. The collected insoluble complex of MOG is solubilized with a protein denaturant. A purified sample of the polypeptide can be obtained by the same method for isolation and purification as above, after returning MOG back to the normal three-dimensional structure through dilution or dialysis of the solubilized solution.

In a case where MOG or a derivative thereof such as a sugar-modified complex is extracellularly secreted, MOG or the derivative thereof such as a sugar-modified complex can be collected in a culture supernatant. By subjecting the culture to procedures using a method such as centrifugation as in the same manner as above, thereby obtaining a soluble fraction, and then using the same method for isolation and purification as above, a purified sample can be obtained from the soluble fraction.

In addition, MOG used in the invention can be produced also by a chemical synthesis method such as the Fmoc method or the tBoc method. MOG can be also chemically synthesized using a peptide synthesizer manufactured by Advanced Chemtech, PerkinElmer, Inc., Pharmacia, Protein Technology Instrument, Inc., Shinseserubega Co., Perceptive, Shimadzu Corporation or the like.

(2) Immunization of Animal and Preparation of Antibody-Producing Cell for Fusion By immunizing a 3- to 20-week old animal such as a mouse, a rat, a rabbit or a hamster with the antigen obtained in (1), antibody-producing cells are collected from the spleen, lymph nodes or peripheral blood of the animal. In addition, an animal such as a llama, an alpaca or a camel can also be used as the animal to be immunized.

Immunization is performed by administering the antigen for example together with an appropriate adjuvant such as Freund's complete adjuvant, aluminum hydroxide gel or *Bordetella pertussis* vaccine subcutaneously, intravenously or intraperitoneally to the animal. In a case where the antigen is a partial peptide, a conjugate of the antigen with a carrier protein such as BSA (bovine serum albumin) or KLH (Keyhole Limpet hemocyanin) is produced and used as an immunogen.

When a mouse or a rat is immunized, the administration of the antigen is performed 5 to 10 times every 1 to 2 weeks after the first administration. On the $3^{rd}$ to $7^{th}$ day after each administration, the blood is collected from a venous plexus of the fundus of the eye, and the antibody valency of the serum is measured using an enzyme immunoassay method [Antibodies—A Laboratory Manual, Cold Spring Harbor Laboratory (1988)] or the like. An animal in which the serum exhibited sufficient antibody valency with respect to the antigen used for the immunization is used as a supply source for the antibody-producing cells for fusion.

On the $3^{rd}$ to $7^{th}$ day after a final administration of the antigen, tissues including the antibody-producing cells such as the spleen are extracted from the immunized animal, and the antibody-producing cells are collected. In a case of using the spleen cells, the spleen is shredded and loosened, followed by centrifugation, and then erythrocytes are removed. The antibody-producing cells for fusion are thus obtained.

Other animals to be immunized can also be immunized by the same method, and antibody-producing cells can be obtained. Appropriate conditions for the interval of immunizations and the period between the final immunization and the collection of the tissues can be determined depending on the kind of the animal to be immunized.

(3) Preparation of Myeloma Cells

As the myeloma cells, established cells obtained from a mouse are used, and for example, a 8-azaguanine resistant mouse (BALB/c derived) myeloma cell line, P3-X63Ag8-U1 (P3-U1) [Current Topics in Microbiology and Immunology, 18, 1 (1978)], P3-NS1/1-Ag41 (NS-1) [European J. Immunology, 6, 511 (1976)], SP2/0-Ag14(SP-2) [Nature, 276, 269 (1978)], P3-X63-Ag8653 (653) [J. Immunology, 123, 1548 (1979)], P3-X63-Ag8(X63) [Nature, 256, 495 (1975)] or the like is used.

The myeloma cells are subjected to subculturing with a normal medium [RPMI1640 medium supplemented with glutamine, 2-mercaptoethanol, gentamicin, FBS and 8-azaguanine] and subjected to subculturing with a normal medium 3 to 4 days before the cell fusion, and $2 \times 10^7$ or more cells are acquired on the day of the fusion.

(4) Cell Fusion and Preparation of Monoclonal Antibody-Producing Hybridoma

The antibody-producing cells for fusion obtained in (2) and the myeloma cells obtained in (3) are thoroughly washed with the Minimum Essential Medium (MEM) or PBS (disodium phosphate 1.83 g, monopotassium phosphate 0.21 g, salt 7.65 g, distilled water 1 liter, pH 7.2), mixed at cell numbers of antibody-producing cells for fusion:myeloma cells of 5:1 to 10:1 and centrifuged, and then the supernatant is removed.

After the precipitated cell clusters are loosened thoroughly, a mixture of polyethylene glycol-1000 (PEG-1000), MEM and dimethylsulfoxide is added thereto while stirring at 37° C. Furthermore, 1 to 2 mL of MEM is added thereto every 1 to 2 minutes for several times, and then MEM is added so that the total amount becomes 50 mL.

After centrifugation, the supernatant is removed. The precipitated cell clusters are loosened gently, and then the cells are suspended gently in the HAT medium [normal medium supplemented with hypoxanthine, thymidine and aminopterin]. This suspension is cultured in a 5% $CO_2$ incubator at 37° C. for 7 to 14 days.

After culturing, a part of the culture supernatant is taken, and cell clusters which react with MOG and which do not react with antigens other than MOG are selected by a method for selecting a hybridoma such as the binding assay described below. Next, after cloning by the limiting dilution method, a hybridoma which stably shows potent antibody valency is selected as a monoclonal antibody-producing hybridoma.

(5) Preparation of Purified Monoclonal Antibody

The monoclonal antibody-producing hybridoma obtained in (4) is intraperitoneally injected into an 8- to 10-week old mouse or nude mouse which has been treated by pristane treatment [by intraperitoneally administering 2,6,10,14-tetramethylpentadecane (Pristane) 0.5 mL and breeding for 2 weeks]. In 10 to 21 days, the hybridoma becomes an ascites tumor.

The ascites are collected from this mouse, and the solid is removed by centrifugation. Then, by salting out with 40 to 50% ammonium sulfate and purifying by caprylic acid precipitation method, a DEAE-Sepharose column, a protein A-column or a gel filtration column, an IgG or IgM fraction is collected to obtain a purified monoclonal antibody.

Moreover, the monoclonal antibody-producing hybridoma obtained in (4) is cultured in RPMI1640 medium supplemented with 10% FBS or the like, and then the supernatant is removed by centrifugation. The hybridoma is suspended in Hybridoma SFM medium and cultured for 3 to 7 days.

A purified monoclonal antibody can also be obtained by centrifuging the obtained cell suspension, purifying from the obtained supernatant by a protein A-column or a protein G-column and collecting an IgG fraction. In this regard, 5% Daigo's GF21 can be added to Hybridoma SFM medium.

The subclass of the antibody is determined by the enzyme immunoassay method using a subclass typing kit. The protein mass is determined by the Lowry method or by calculating from the absorbance at 280 nm.

(6) Selection of Antibody

The antibody is selected for example by measuring the affinity of the antibody to MOG-expressing cells using flow cytometry as shown below. The MOG-expressing cells may be any cells as long as MOG is expressed on the cell surface, and examples include animal cells, an animal cell line, the MOG forcibly-expressing cell line obtained in (1) and the like.

After dispensing the MOG-expressing cells to a plate such as a 96-well plate, the substances to be tested such as serum, culture supernatants of hybridomas or purified antibodies are dispensed as the first antibodies and reacted. The cells after the reaction are thoroughly washed with PBS containing 1 to 10% bovine serum albumin (BSA) (referred to as BSA-PBS below) or the like, and an anti-immunoglobulin antibody labeled with a fluorescent reagent or the like is then dispensed as the second antibody and reacted. After thoroughly washing with BSA-PBS or the like, the fluorescence amounts of the labeled antibody are measured using a flow cytometer, and an antibody which specifically reacts with the MOG-expressing cells is thus selected.

Moreover, the antibody can also be selected by measuring the affinity of the monoclonal antibody to MOG-expressing cells, a MOG protein or the like using ELISA or surface plasmon resonance described below. The MOG protein may be a protein composed of some domains of MOG or a protein to which a tag such as GST is added.

In ELISA, after dispensing the MOG-expressing cells or the MOG protein to a plate such as a 96-well plate, the wells are blocked with BSA-PBS, and the substances to be tested such as serum, culture supernatants of hybridomas or purified antibodies are dispensed as the first antibodies and reacted. Next, after thoroughly washing with PBS or the like, an anti-immunoglobulin antibody labeled with a fluorescent reagent or the like is dispensed as the second antibody and reacted.

Then, after thoroughly washing with PBS or the like, a chromogenic reagent is added. At the end, the chromogenic reaction is stopped with a solution for stopping the reaction, and the absorbances of the wells are measured with a microplate reader. An antibody which specifically reacts with the MOG-expressing cells or the MOG protein is thus selected.

In surface plasmon resonance, using a known protocol, the affinity of an antibody which binds to MOG can be measured by immobilizing the antibody on an appropriate sensor chip and using a MOG protein as the analyte.

Using the affinity of the antibody obtained, an antibody having desired affinity to a MOG protein can be selected. The affinity of an antibody which binds to MOG can also be measured by immobilizing a MOG protein on a sensor chip and using the antibody as the analyte.

In addition, an antibody which competes in binding to MOG with the antibody of the invention can be obtained by adding an antibody to be tested to the assay system using flow cytometry or ELISA described above and reacting. That is, by selecting an antibody which inhibits binding of the antibody of the invention and MOG when the antibody to be tested is added by screening, an antibody that competes with the antibody of the invention in binding to the amino acid sequence of MOG or the three-dimensional structure thereof can be obtained.

An antibody which binds to an epitope containing the epitope to which the antibody of the invention binds can be obtained by identifying the epitope of an antibody obtained by the screening method described above by a known method, producing a synthetic peptide containing the identified epitope, a synthetic peptide which mimics the three-dimensional structure of the epitope or the like and immunizing.

An antibody which binds to the same epitope as the epitope to which the antibody of the invention binds can be obtained by identifying the epitope of an antibody obtained by the screening method described above, producing a partial synthetic peptide of the identified epitope, a synthetic peptide which mimics the three-dimensional structure of the epitope or the like and immunizing.

(7) Acquisition of Antibody by Phage Display Method (7-1) Production Method of Antibody Phage Library In the invention, as the antibody phage library, an immune library, a naive library and a synthetic library can be used. The methods for producing the libraries are described below.

Lymphocytes derived from an animal immunized by the same method as that of (1) or a patient are collected for an immune library, and lymphocytes derived from a normal animal or a healthy human are collected for a naive library. RNA is extracted from the lymphocytes, and cDNA is synthesized by reverse transcription reaction.

A fragment of an antibody gene amplified by PCR using the cDNA as a template is inserted to a phagemid vector, and *E. coli* is transformed by the phagemid vector. When the obtained transformant is infected with a helper phage, an antibody phage library of the antibody gene can be obtained.

With respect to a synthetic library, CDR of a V gene in the genome DNA or a reconstructed functional V gene is substituted with an oligonucleotide that encodes any amino acid sequence of an appropriate length, and *E. coli* is transformed by a phagemid vector into which the V gene has been inserted. When the obtained transformant is infected with a helper phage, an antibody phage library can be obtained.

As the cDNA derived from lymphocytes and the antibody phage library, those which are commercially available can also be used.

As the phagemid vector, pCANTAB 5E (Amersham Pharmacia Biotech Inc.), pUC118/pUC119 vector (TaKaRa), pBlueScript II Phagemid Vector (Agilent Technologies), pKSTV-02 (Miyazaki et al, J. Biochem. 2015; 1) and the like can be used.

As the helper phage, M13K07 helper phage (Invitrogen), VCSM13 Interference Resistant Helper Phage (Agilent Technologies), R408 Interference Resistant Helper Phage (Agilent Technologies) and the like can be used.

A phage vector can also be used for phage display. There are a peptide phage library in which filamentous bacteriophage g3p is a displayed molecule (manufactured by New England Biolabs and the like), a method in which g7p, g8p or g9p is a displayed molecule and the like.

Moreover, phage display using T7 phage can also be used. A display system for T7 phage is T7 Select vector (Novagen) or the like.

(7-2) Selection of Antibody Phage Clone

An antibody phage clone can be selected from the antibody phage libraries produced in (7-1) using the ELISA method shown below.

MOG is immobilized in an immuno tube, and the tube is blocked with a blocking buffer. The antibody phage libraries produced in (7-1) are added to the wells of the tube and reacted. Next, the wells are washed, and a fluorescently labeled anti-phage antibody is added and reacted. Then, the wells are washed again, and a chromogenic solution is added. Then, the chromogenic reaction is stopped with a solution for stopping the reaction, and the absorbances of the wells are measured with a microplate reader. In this manner, an antibody phage clone which binds to MOG is selected.

2. Production of Genetically Recombinant Antibody

As examples for producing a genetically recombinant antibody, methods for producing a human chimeric antibody and a humanized antibody are described below. Genetically recombinant mouse antibody, rat antibody, rabbit antibody, hamster antibody, camel antibody, llama antibody, alpaca antibody and human antibody, chimeric antibodies, a heavy chain antibody and the like can also be produced by the same method.

(1) Construction of Expression Vector for Genetically Recombinant Antibody

An expression vector for a genetically recombinant antibody is an expression vector for animal cells in which DNA that encodes CH and CL of a human antibody has been incorporated and can be constructed by cloning DNAs that encode CH and CL of a human antibody into an expression vector for animal cells.

As the C region of a human antibody, CH and CL of any human antibody can be used. For example, CH of γ1 subclass and CL of κ class of a human antibody and the like are used. As the DNAs that encode CH and CL of the human antibody, cDNA is used, but chromosomal DNA consisting of exons and introns can also be used.

As the expression vector for animal cells, any vector can be used as long as it is capable of incorporating and expressing a gene that encodes the C region of a human antibody. For example, pAGE107 [Cytotechnol., 3, 133 (1990)], pAGE103 [J. Biochem., 101, 1307 (1987)], pHSG274 [Gene, 27, 223 (1984)], pKCR [Proc. Natl. Acad. Sci. USA, 78, 1527 (1981)], pSG1bd2-4 [Cytotechnol., 4, 173 (1990)], pSE1UK1Sed1-3 [Cytotechnol., 13, 79 (1993)] and the like are used.

The promoter and the enhancer of the expression vector for animal cells are the early promoter of SV40 [J. Biochem., 101, 1307 (1987)], the Moloney murine leukemia virus LTR [Biochem. Biophys. Res. Commun., 149, 960 (1987)] or the promoter of immunoglobulin H chain [Cell, 41, 479 (1985)] and the enhancer [Cell, 33, 717 (1983)] or the like.

As the expression vector for the genetically recombinant antibody, an expression vector for a genetically recombinant antibody of a type in which the antibody H chains and L chains are on the same vector (tandem type) [J. Immunol. Methods, 167, 271 (1994)] is used from the viewpoints of ease of construction of the expression vector for the genetically recombinant antibody, ease of introduction into animal cells, balanced expression levels of the antibody H chains and L chains in animal cells and the like, but a type in which the antibody H chains and L chains are on different vectors can also be used. As the tandem type expression vector for a genetically recombinant antibody, pKANTEX93 (International Publication No. 97/10354), pEE18 [Hybridoma, 17, 559 (1998)] and the like are used.

(2) Acquisition of cDNA Encoding V Region of Antibody Derived from Animal Other than Human and Analysis of Amino Acid Sequence cDNA that encodes VH and VL of a non-human antibody can be obtained, and the amino acid sequence can be analyzed as follows.

(2-1) When Antibody is Obtained by Hybridoma Method mRNA is extracted from hybridoma cells producing a non-human antibody, and cDNA is synthesized. The synthesized cDNA is cloned into a vector such as a phage or a plasmid to produce a cDNA library.

Recombinant phages or recombinant plasmids having cDNAs that encode VH or VL are isolated from the libraries using DNAs that encode the C region and the V region of the non-human antibody as probes. The entire nucleotide sequences of VH or VL of the target non-human antibody on the recombinant phages or the recombinant plasmids are determined, and then the entire amino acid sequences of VH or VL are deduced from the nucleotide sequences.

As the animal other than human which produces the hybridoma cells producing the non-human antibody, a mouse, a rat, a hamster, a rabbit, a llama, a camel, an alpaca or the like is used, but any animal can be used as long as hybridoma cells can be produced.

For the preparation of total RNA from hybridoma cells, the guanidine thiocyanate-cesium trifluoroacetate method [Methods in Enzymol., 154, 3 (1987)], a kit such as RNA easy Kit (manufactured by QIAGEN) or the like is used.

To prepare mRNA from total RNA, oligo (dT) immobilized cellulose column chromatography [Molecular Cloning, A Laboratory Manual, Second Edition, Cold Spring Harbor Laboratory Press (1989)], a kit such as Oligo-dT30 <Super> mRNA Purification (registered trademark) Kit (manufactured by Takara Bio Inc.) or the like is used. Furthermore, mRNA can also be prepared from hybridoma cells using a kit such as Fast Track mRNA Isolation (registered trademark) Kit (manufactured by Invitrogen) or QuickPrep mRNA Purification (registered trademark) Kit (manufactured by Pharmacia).

For the synthesis of cDNA and the production of a cDNA library, a known method [Molecular Cloning, A Laboratory Manual, Second Edition, Cold Spring Harbor Laboratory Press (1989) and Current Protocols in Molecular Biology, Supplement 1, John Wiley & Sons (1987-1997)], a kit such as SuperScript Plasmid System for cDNA Synthesis and Plasmid Cloning (manufactured by Invitrogen) or ZAP-cDNA Synthesis (registered trademark) Kit (manufactured by Stratagene) or the like is used.

When a cDNA library is produced, any vector capable of incorporating the cDNA can be used as a vector into which the cDNA synthesized using mRNA extracted from the hybridoma cells as a template is incorporated. For example, ZAP Express [Strategies, 5, 58 (1992)], pBluescript II SK (+) [Nucleic Acids Research, 17, 9494 (1989)], λZAPII (manufactured by Stratagene), λgt 10 and λgt 11 [DNA Cloning: A Practical Approach, I, 49 (1985)], Lambda Blue Mid (manufactured by Clontech Laboratories, Inc.), λExCell, pT7T3-18U (manufactured by Pharmacia), pCD2 [Mol. Cell. Biol., 3, 280 (1983)], pUC18 [Gene, 33, 103 (1985)] or the like is used.

Any *Escherichia coli* can be used as *Escherichia coli* into which a cDNA library constructed by a phage or a plasmid vector is introduced as long as the cDNA library can be introduced, expressed and maintained. For example, XL1-Blue MRF' [Strategies, 5, 81 (1992)], C600 [Genetics, 39, 440 (1954)], Y1088, Y1090 [Science, 222, 778 (1983)], NM522 [J. Mol. Biol., 166, 1 (1983)], K802 [J. Mol. Biol., 16, 118 (1966)], JM105 [Gene, 38, 275 (1985)] or the like is used.

For the selection of the cDNA clone that encodes VH or VL of the non-human antibody from the cDNA libraries, a colony hybridization method using an isotope- or fluorescently labeled probe, the plaque hybridization method [Molecular Cloning, A Laboratory Manual, Second Edition, Cold Spring Harbor Laboratory Press (1989)] or the like is used.

In addition, the cDNA that encodes VH or VL can also be prepared by preparing primers and performing the polymerase chain reaction method [referred to as PCR method below, Molecular Cloning, A Laboratory Manual, Second Edition, Cold Spring Harbor Laboratory Press (1989) and Current Protocols in Molecular Biology, Supplement 1, John Wiley & Sons (1987-1997)] using the cDNA synthesized from mRNA or a cDNA library as a template.

The selected cDNA is cleaved with an appropriate restriction enzyme or the like and then cloned into a plasmid such as pBluescript SK (−) (manufactured by Stratagene), and the nucleotide sequence of the cDNA is determined by a commonly used nucleotide sequence analysis method or the like. For the nucleotide sequence analysis method, for example, after performing a reaction such as the dideoxy method [Proc. Natl. Acad. Sci. USA, 74, 5463 (1977)], an automatic nucleotide sequence analyzer such as ABI PRISM3700 (manufactured by PE Biosystems) or A.L.F. DNA sequencer (manufactured by Pharmacia) or the like is used.

(2-2) When Antibody is Obtained by Phage Display Method

The entire nucleotide sequences of VH or VL are determined from the plasmid vectors of the selected phage clones using DNAs that encode the vector region or the V region as probes, and then the entire amino acid sequences of VH or VL can be deduced from the nucleotide sequences.

In both of the hybridoma method and the phage display method, by deducing the entire amino acid sequences of VH and VL from the determined nucleotide sequences and comparing with the entire amino acid sequences of VH and VL of a known antibody [Sequences of Proteins of Immunological Interest, US Dept. Health and Human Services (1991)], it is confirmed whether the obtained cDNA encodes the complete amino acid sequences of VH and VL of an antibody containing a secretion signal sequence.

Regarding the complete amino acid sequences of VH and VL of the antibody containing a secretion signal sequence, by comparing with the entire amino acid sequences of VH and VL of a known antibody [Sequences of Proteins of Immunological Interest, US Dept. Health and Human Services (1991)], the length of the secretion signal sequence and the N-terminus amino acid sequence can be deduced, and the subgroup to which they belong can be found.

In addition, the amino acid sequences of the CDRs of VH and VL can also be determined by comparing with the amino acid sequences of VH and VL of a known antibody [Sequences of Proteins of Immunological Interest, US Dept. Health and Human Services (1991)].

Furthermore, using the obtained complete amino acid sequences of VH and VL, it is possible to confirm whether the complete amino acid sequences of VH and VL are new by carrying out homology search by the BLAST method [J. Mol. Biol., 215, 403 (1990)] or the like using any database such as SWISS-PROT or PIR-Protein.

(3) Construction of Human Chimeric Antibody Expression Vector

By cloning cDNAs that encode VH and VL of a non-human antibody in the upstream of the respective genes that encode CH and CL of a human antibody in the expression vector for a genetically recombinant antibody obtained in (1), a human chimeric antibody expression vector can be constructed.

In order to link the 3' terminus sides of the cDNAs that encode VH or VL of the non-human antibody with the respective 5' terminus sides of CH or CL of the human antibody, cDNAs of VH and VL in which the nucleotide sequences of the linking parts are designed to encode an appropriate amino acid and to become an appropriate restriction enzyme recognition sequence are produced.

The produced cDNAs of VH and VL are cloned in the upstream of the respective genes that encode CH or CL of the human antibody in the expression vector for a genetically recombinant antibody obtained in (1) in a manner that they are expressed in an appropriate form, and therefore a human chimeric antibody expression vector is constructed.

In addition, each of the cDNAs that encode VH or VL of the non-human antibody can be amplified by the PCR method using synthetic DNA having an appropriate restriction enzyme recognition sequence at both ends and cloned into the expression vector for a genetically recombinant antibody obtained in (1).

(4) Construction of cDNA Encoding V Region of Humanized Antibody

A cDNA that encodes VH or VL of a humanized antibody can be constructed as follows.

Amino acid sequences of the FRs of VH and VL of a human antibody for the insertion of the amino acid sequences of the CDRs of VH and VL of a non-human antibody are selected. Any amino acid sequences derived from a human antibody can be used as the selected amino acid sequences of the FRs.

For example, an amino acid sequence of FR of a human antibody registered in a database such as Protein Data Bank, a common amino acid sequence of the subgroups of FR of a human antibody [Sequences of Proteins of Immunological Interest, US Dept. Health and Human Services (1991)] or the like is used. In order to suppress a decrease in binding activity of the antibody, an amino acid sequence of FR having as high homology (at least 60% or more) as possible to the amino acid sequence of the FR of VH or VL of the original antibody is selected.

Next, the amino acid sequences of the CDRs of the original antibody are inserted to the respective selected amino acid sequences of the FRs of VH and VL of the human antibody, and the amino acid sequences of VH and VL of a humanized antibody are designed. By converting the designed amino acid sequences into DNA sequences in consideration of the use frequency of codons found in the nucleotide sequences of the antibody genes [Sequences of Proteins of Immunological Interest, US Dept. Health and Human Services (1991)], DNA sequences encoding the amino acid sequences of VH and VL of a humanized antibody are designed.

Based on the designed DNA sequences, several synthetic DNAs having lengths of around 100 bases are synthesized, and the PCR reaction is carried out using the DNAs. In this case, due to the reaction efficiency of the PCR reaction and the synthesizable lengths of DNAs, 6 synthetic DNAs are preferably designed for each of the VH and VL.

Furthermore, by introducing an appropriate restriction enzyme recognition sequence at the 5' or 3' terminus of the synthetic DNAs located at both ends, cDNA that encodes VH or VL of a humanized antibody can be easily cloned into the expression vector for a genetically recombinant antibody obtained in (1).

After the PCR reaction, the amplified products are each cloned into a plasmid such as pBluescript SK (−) (manufactured by Stratagene), and the nucleotide sequences are determined by the same method as the method described in (2). A plasmid having the DNA sequence that encodes the amino acid sequence of VH or VL of a desired humanized antibody is thus obtained.

Alternatively, the entire VH and the entire VL each synthesized as a long chain DNA based on the designed DNA sequences can also be used instead of the PCR amplified products. Moreover, by introducing an appropriate restriction enzyme recognition sequence at both ends of the synthesized long chain DNAs, cDNAs that encode VH and VL of the humanized antibody can be easily cloned into the expression vector for a genetically recombinant antibody obtained in (1).

(5) Modification of Amino Acid Sequence of V Region of Humanized Antibody

When only the CDRs of VH and VL of a non-human antibody are merely inserted into the FRs of VH and VL of a human antibody, the antigen binding activity of the humanized antibody is lower than that of the original non-human antibody [BIO/TECHNOLOGY, 9, 266 (1991)].

In a humanized antibody, by identifying the amino acid residues directly related to antigen binding, the amino acid residues interacting with the amino acid residues of the CDRs and the amino acid residues which maintain the three-dimensional structure of the antibody and which are indirectly related to antigen binding, in the amino acid sequences of the FRs of VH and VL of a human antibody, and by substituting these amino acid residues with the amino acid residues of the original non-human antibody, the lowered antigen binding activity can be increased.

In order to identify the amino acid residues of FR related to the antigen binding activity, the three-dimensional structure of the antibody can be constructed and analyzed using X-ray crystallography [J. Mol. Biol., 112, 535 (1977)], computer modeling [Protein Engineering, 7, 1501 (1994)] or the like. Furthermore, a humanized antibody having necessary antigen binding activity can be obtained by producing various types of variants for each antibody and repeatedly examining their correlation with the antigen binding activities and through trial and error.

Amino acid residues of the FRs of VH and VL of a human antibody can be modified by carrying out the PCR reaction described in (4) using synthetic DNA for the modification. The nucleotide sequence of the amplified product after the PCR reaction is determined, and whether the intended modification has been carried out is confirmed by the method described in (2).

(6) Construction of Expression Vector for Humanized Antibody

By cloning the cDNAs that encode VH and VL of the constructed genetically recombinant antibody in the upstream of the respective genes that encode CH and CL of the human antibody in the expression vector for a genetically recombinant antibody obtained in (1), an expression vector for a humanized antibody can be constructed.

For example, the cDNAs are cloned in the upstream of the respective genes that encode CH and CL of the human antibody in the expression vector for a genetically recombinant antibody obtained in (1) in a manner that the cDNAs are expressed in an appropriate form by introducing an appropriate restriction enzyme recognition sequence at the 5' or 3' terminus of the synthetic DNAs located at both ends of the synthetic DNAs used for constructing the VH and VL of the humanized antibody obtained in (4) and (5).

(7) Transient Expression of Genetically Recombinant Antibody

By transiently expressing genetically recombinant antibodies using the expression vectors of a genetically recombinant antibody obtained in (3) and (6) or modified expression vectors thereof, the antigen binding activities of the produced various human chimeric antibodies and humanized antibodies can be efficiently evaluated.

As a host cell into which an expression vector is introduced, any cell can be used as long as it is a host cell capable of expressing a genetically recombinant antibody, but for example, COS-7 cells [American Type Culture Collection (ATCC) number: CRL1651] are used [Methods in Nucleic Acids Res., CRC press, 283 (1991)].

For introduction of an expression vector into COS-7 cells, the DEAE-dextran method [Methods in Nucleic Acids Res., CRC press (1991)], the lipofection method [Proc. Natl. Acad. Sci. USA, 84, 7413 (1987)] or the like is used.

After the introduction of the expression vector, the expression level and the antigen binding activity of the genetically recombinant antibody in a culture supernatant are measured using the enzyme immunoassay method [Monoclonal Antibodies-Principles and practice, Third edition, Academic Press (1996), Antibodies-A Laboratory Manual, Cold Spring Harbor Laboratory (1988) and A manual for monoclonal antibody experiments, Kodansha scientific books (1987)] or the like.

(8) Acquisition of Stable Expression Transformant of Genetically Recombinant Antibody and Preparation of Genetically Recombinant Antibody By introducing the expression vector for a genetically recombinant antibody obtained in (3) or (6) into an appropriate host cell, a transformant stably expressing the genetically recombinant antibody can be obtained.

For the introduction of the expression vector into a host cell, the electroporation method [JP-A-H2-257891 and Cytotechnology, 3, 133 (1990)] or the like is used.

As the host cell into which the expression vector for a genetically recombinant antibody is introduced, any cell can be used as long as it is a host cell capable of expressing the genetically recombinant antibody. For example, CHO-K1 (ATCC CCL-61), DUKXB11 (ATCC CCL-9096), Pro-5 (ATCC CCL-1781), CHO-S (Life Technologies, Cat

11619), rat myeloma cells YB2/3HL.P2.G11.16Ag.20 (ATCC No. CRL1662, also called YB2/0), mouse myeloma cells NS0, mouse myeloma cells SP2/0-Ag14 (ATCC No. CRL1581), mouse P3X63-Ag8.653 cells (ATCC No. CRL1580), CHO cells in which the dihydrofolate reductase gene (referred to as dhfr below) is deficient (CHO/DG44 cells) [Proc. Natl. Acad. Sci. USA, 77, 4216 (1980)] and the like are used.

In addition, a host cell in which the activity of a protein such as enzymes related to intracellular synthesis of sugar nucleotide GDP-fucose, a protein such as enzymes related to glycosylation modification in which the 1-position of fucose is α-bonded to the 6-position of N-acetylglucosamine at the reducing terminus of a N-glycoside-linked complex type sugar chain, a protein related to intracellular transport of sugar nucleotide GDP-fucose to the Golgi body or the like is reduced or lost, for example, CHO cells in which the α1,6-fucosyltransferase gene is deficient (International Publication No. 2005/035586 and International Publication No. 02/31140), Lec13 having lectin resistance [Somatic Cell and Molecular genetics, 12, 55 (1986)] and the like can also be used.

After the introduction of the expression vector, a transformant stably expressing a genetically recombinant antibody is selected by culturing the transformant in a medium for animal cell culture containing a drug such as G418 sulfate (referred to as G418 below) (JP-A-H2-257891).

As the medium for animal cell culture, RPMI 1640 medium (manufactured by Invitrogen), GIT medium (manufactured by Nippon Pharmaceutical Co., Ltd.), EX-CELL 301 medium (manufactured by Jay Earl H., Inc.), IMDM medium (manufactured by Invitrogen), Hybridoma-SFM medium (manufactured by Invitrogen), a medium in which various additives such as FBS are added to any of these media or the like is used.

A genetically recombinant antibody is expressed and accumulated in a culture supernatant by culturing the obtained transformant in the medium. The expression level and the antigen binding activity of the genetically recombinant antibody in the culture supernatant can be measured by the ELISA method or the like. In addition, the expression level of the genetically recombinant antibody produced by the transformant can be increased using the dhfr gene amplification system (JP-A-H2-257891) or the like.

The genetically recombinant antibody is purified using a protein A-column from the culture supernatant of the transformant [Monoclonal Antibodies—Principles and practice, Third edition, Academic Press (1996) and Antibodies—A Laboratory Manual, Cold Spring Harbor Laboratory (1988)]. In addition, a method used for purifying proteins, such as gel filtration, ion exchange chromatography and ultrafiltration, can also be combined.

The molecular weights of the H chains, the L chains or the whole antibody molecule of the purified genetically recombinant antibody can be measured using polyacrylamide gel electrophoresis [Nature, 227, 680 (1970)], western blotting method [Monoclonal Antibodies—Principles and practice, Third edition, Academic Press (1996) and Antibodies—A Laboratory Manual, Cold Spring Harbor Laboratory (1988)] or the like.

(9) Production Method of Antibody Fragment

The antibody fragment of the invention can be produced according to a known method. The antibody fragment of the invention may be produced by cleaving an antibody produced according to the method described in (1) to (8) using an enzyme or the like or may be produced by the genetic engineering technique after preparing a nucleotide sequence which encodes a desired antibody fragment.

(10) Production Method of Monovalent Antibody

In the invention, a monovalent antibody can be produced by the method described in International Publication No. 2014/054804, International Publication No. 2011/090754, International Publication No. 2007/048037, International Publication No. 2012/116927 or the like or another method.

(11) Production Method of Bispecific Antibody or Multispecific Antibody

The bispecific antibody or the multispecific antibody of the invention can be produced according to the production method of the antibody described above. For example, the bispecific antibody or the multispecific antibody can be produced using the method described in International Publication No. 2009/131239, International Publication No. 2014/054804, International Publication No. 01/077342, US Patent Application Publication No. 2007/0071675, International Publication No. 2007/024715, Wu et al., [Nature Biotechnology, 2007, 25(11), p. 1290-1297], Labrijn et al., [PNAS 2013, vol. 110, no. 13, p 5145-5150], Jong et al., [http://dx.doi.org/10.1371/journal.pbio.1002344], Kontermann et al., [mAbs 2012, vol. 4, issue 2, p 182-197], Spiess et al., [Molecular Immunology 67 (2015) 95-106], Ridgway et al., [Protein engineering, 1996 vol. 9 no. 7 pp 617-621, International Publication No. 2009/080251, International Publication No. 2010/151792, International Publication No. 2014/033074 or the like.

For example, an expression vector of a bispecific antibody in which scFv that binds to MOG is fused to the C-terminus of an IgG antibody that binds to an antigen that is present in the brain can be produced by the method described below, and the bispecific antibody can be produced according to the expression method of the antibody and the purification method of the antibody described above. In addition, a bispecific antibody in which an antibody fragment is fused to the C-terminus of an antibody can also be produced by the same methods.

A gene fragment of a CH1-Hinge-CH2-CH3-linker domain is amplified by the PCR method using a synthetic gene of a heavy chain constant region of an IgG antibody which binds to an antigen that is present in the brain as a template. Next, using the nucleotide sequence of an antibody which binds to MOG as a template, the nucleotide sequence of a scFv domain in which VH and VL of the antibody are linked with an appropriate linker is prepared using the PCR method or the like. The two domains are linked by the PCR method or the like, and the obtained gene fragment is inserted to an appropriate vector such as pCI vector.

Moreover, a gene fragment of a light chain domain (VL and CL) of an IgG antibody which binds to an antigen that is present in the brain and a gene fragment of VH of the antibody are amplified by the PCR method using appropriate templates and are inserted into the appropriate position of the vector.

In addition, the bispecific antibody of the invention can also be produced by binding an antigen binding site containing an antibody fragment to an IgG antibody by a chemical method.

3. Evaluation of Activity of Antibody or Antibody Fragment Thereof

In the invention, the activity of an antibody or an antibody fragment thereof can be evaluated as follows.

(1) Binding Activity to MOG

The binding activity of the antibody or the antibody fragment of the invention to MOG is measured using flow cytometry, ELISA or surface plasmon resonance detection described in 1-(6) above or the like. Moreover, the binding activity can also be measured using a fluorescent antibody method [Cancer Immunol. Immunother., 36, 373 (1993)].

Also when the antibody or the antibody fragment of the invention is a monovalent antibody which binds to MOG, the binding activity of the monovalent antibody to MOG can be measured by the same method. Also when the antibody or the antibody fragment of the invention is a bispecific antibody or a multispecific antibody which binds to MOG and an antigen that is present in the brain, the binding activity of the bispecific antibody or the multispecific antibody to MOG or the antigen that is present in the brain can be measured by the same method.

(2) Measurement Method of Property of Accumulating in Brain

The property of the antibody or the antibody fragment of the invention of accumulating in the brain can be measured by the method described below.

A method of collecting brain tissues several days after administering the antibody or the antibody fragment to an animal, homogenizing the brain tissues, measuring the concentration of the antibody or the antibody fragment in the supernatant after centrifugation and calculating the amount of the antibody or the antibody fragment per unit brain weight, a method of detecting the presence of the antibody or the antibody fragment by a known immunological method using the collected brain tissues or the like is used. Moreover, a method of administering the antibody or the antibody fragment to which a pharmacologically acceptable label has been attached to an animal and detecting the presence of the antibody or the antibody fragment by in vivo imaging system sequentially or the like is used.

As the animal used, an animal suitable for the use of the antibody or the antibody fragment of the invention can be selected.

(3) Measurement Method of ADCC and CDC

The CDC or the ADCC of the antibody or the antibody fragment of the invention to human MOG-expressing cells or cells in which MOG and the antigen that is present in the brain are expressed can be measured by a known measurement method [Cancer Immunol. Immunother., 36, 373 (1993); and Current protocols in Immunology, Chapter 7. Immunologic studies in humans, Editor, John E, Coligan et al., John Wiley & Sons, Inc., (1993)].

4. Method for Controlling Effector Activity of Antibody or Antibody Fragment

As the method for controlling the effector activity of the antibody or the antibody fragment of the invention, a method for controlling the amount of α1,6-fucose (also called a core fucose) binding to N-acetylglucosamine (GlcNAc) present on the reducing terminal of the N-linked complex sugar chain that bind to the $297^{th}$ asparagine (Asn) in the Fc region of the antibody or the antibody fragment containing Fc (International Publication No. 2005/035586, International Publication No. 2002/31140 and International Publication No. 00/61739), a method for controlling by modifying an amino acid residue in the Fc region of the antibody or the antibody fragment and the like are known. The effector activity of the antibody or the antibody fragment of the invention can be controlled using any of the methods.

The effector activity refers to the antibody-dependent activity that is caused through the Fc region of the antibody or the antibody fragment, and ADCC, CDC, Antibody-dependent phagocytosis (ADP) that is caused by phagocytes such as macrophages or dendritic cells and the like are known.

As the method for measuring the effector activity, for example, the effector activity can be measured by mixing the target cells, human peripheral blood mononuclear cells (PBMCs) as the effector and a target cell-specific antibody or an antibody fragment thereof, incubating the mixture for around four hours and then measuring the released lactate dehydrogenase (LDH) as an index of the cytotoxicity. In addition, the effector activity can also be measured by $^{51}$Cr-release method, flow cytometry method or the like.

The effector activity of an antibody or an antibody fragment containing Fc can be increased or decreased by controlling the core fucose content of the N-linked complex sugar chain of Fc of the antibody. Regarding the method for reducing the amount of fucose that binds to the N-linked complex sugar chain binding to Fc of the antibody or the antibody fragment, an antibody or an antibody fragment thereof to which fucose is not bound can be obtained by expressing the antibody or the antibody fragment using CHO cells in which the α1,6-fucosyltransferase gene is deficient. An antibody or an antibody fragment thereof to which fucose is not bound has high ADCC.

On the other hand, as the method for increasing the amount of fucose that binds to the N-linked complex sugar chain binding to Fc of the antibody or the antibody fragment, an antibody or an antibody fragment thereof to which fucose is bound can be obtained by expressing the antibody or the antibody fragment using host cells into which the α1,6-fucosyltransferase gene has been introduced. An antibody or an antibody fragment thereof to which fucose is bound has lower ADCC than that of an antibody or an antibody fragment thereof to which fucose is not bound.

Moreover, by modifying an amino acid residue in the Fc region of the antibody or the antibody fragment, the ADCC or the CDC can be increased or reduced. For example, the CDC of the antibody or the antibody fragment can be increased using the amino acid sequence of the Fc region described in US Patent Application Publication No. 2007/0148165.

Furthermore, the ADCC or the CDC can be increased or decreased by the amino acid modifications described in U.S. Pat. No. 6,737,056, 7,297,775 or 7,317,091.

The antibody or the antibody fragment of the invention also includes an antibody or an antibody fragment thereof whose half-life in the blood is controlled by controlling the reactivity with Fc receptor, for example through the amino acid modifications described in JP-A-2013-165716, JP-A-2012-021004 or the like in accordance with the amino acid modifications or the sugar chain modifications in the constant region contained in the antibody or the antibody fragment.

Moreover, when a combination of the above methods is applied to one antibody or an antibody fragment thereof, an antibody or an antibody fragment thereof whose effector activity and the half-life in the blood are controlled can be obtained.

5. Method for Treating Disease Using Antibody or Antibody Fragment of Invention

The antibody or the antibody fragment of the invention can be used for treating a brain disease of an animal in which MOG is expressed in the brain.

Examples of the brain disease include Alzheimer's disease, the prodromal stage of Alzheimer's disease, Huntington disease, Parkinson's disease, brain tumors, multiple sclerosis, muscular dystrophy, amyotrophic lateral sclerosis, multiple system atrophy, progressive supranuclear palsy, nigrostriatal degeneration, olivopontocerebellar atrophy, bulbospinal muscular atrophy, spinocerebellar degeneration, cerebrovascular disease, epilepsy, migraine, hyperactivity disorder, Creutzfeldt-Jakob disease, corticobasal degeneration, lysosomal storage disease, depression, dystonia and the like.

The brain disease that the antibody or the antibody fragment of the invention can treat differs with the antigen to which the antibody or the antibody fragment of the invention binds, the kind of the molecule which modifies the antibody or the antibody fragment in the fused antibody or the fused antibody fragment of the invention and the like.

The therapeutic agent containing the antibody or the antibody fragment of the invention may contain only the antibody or the antibody fragment as an active ingredient, but the agent is generally mixed with one or more pharmacologically acceptable carriers and provided as medicinal formulation that is produced by a method known in the technical field of pharmaceutical science.

Examples of the route of administration include oral administration or parenteral administration such as intraoral, airway, intrarectal, subcutaneous, intramuscular, intraventricular, intraperitoneal, intradermal, intranasal, intrathecal or intravenous administration. Examples of the form of administration include a spray, a capsule, a tablet, a powder, a granule, a syrup, an emulsion, a suppository, an injection, an ointment, a tape and the like.

Formulations suitable for oral administration are emulsions, syrups, capsules, tablets, powders, granules and the like.

Liquid preparations such as emulsions or syrups are produced using water, sugars such as sucrose, sorbitol or fructose, glycols such as polyethylene glycol or propylene glycol, oils such as sesame oil, olive oil or soybean oil, preservatives such as p-hydroxybenzoic acid esters, flavors such as strawberry flavor or peppermint or the like as an additive.

The capsules, the tablets, the powders, the granules and the like are produced using excipients such as lactose, glucose, sucrose or mannitol, disintegrating agents such as starch or sodium alginate, lubricants such as magnesium stearate or talc, binders such as polyvinyl alcohol, hydroxypropyl cellulose or gelatin, surfactants such as a fatty acid ester, plasticizers such as glycerin or the like as an additive.

Formulations suitable for parenteral administration are injections, suppositories, sprays and the like. The injections are produced using a salt solution, a glucose solution, a carrier formed of a mixture of these solutions or the like. The suppositories are produced using carriers such as cocoa butter, hydrogenated fats or carboxylic acids.

The sprays are produced using a carrier which does not stimulate the oral and respiratory mucosa of a recipient and which enables dispersion of the antibody or the antibody fragment of the invention as fine particles and easy absorption or the like. As the carrier, for example, lactose, glycerin or the like is used. In addition, it can also be produced as an aerosol or a dry powder. Furthermore, also for the above parenteral preparations, the components exemplified as the additives for the formulations suitable for oral administration can also be added.

6. Method for Detecting or Measuring Antigen Present in Brain or Method for Diagnosing Disease Using Antibody or Antibody Fragment of Invention Using the antibody or the antibody fragment of the invention, MOG or MOG and an antigen that is present in the brain can be detected or measured. Moreover, by detecting or measuring MOG or MOG and an antigen that is present in the brain, a brain disease of an animal in which MOG is expressed in the brain can be diagnosed.

Examples of the brain disease include Alzheimer's disease, the prodromal stage of Alzheimer's disease, Huntington disease, Parkinson's disease, brain tumors, multiple sclerosis, muscular dystrophy, amyotrophic lateral sclerosis, multiple system atrophy, progressive supranuclear palsy, nigrostriatal degeneration, olivopontocerebellar atrophy, bulbospinal muscular atrophy, spinocerebellar degeneration, cerebrovascular disease, epilepsy, migraine, hyperactivity disorder, Creutzfeldt-Jakob disease, corticobasal degeneration, lysosomal storage disease, depression, dystonia and the like. The brain disease that the antibody or the antibody fragment of the invention can diagnose differs with the antigen to which the antibody or the antibody fragment of the invention binds, the kind of the molecule which modifies the antibody or the antibody fragment in the fused antibody or the fused antibody fragment of the invention and the like.

The brain disease of an animal in which MOG is expressed in the brain can be diagnosed for example by detecting or measuring MOG that is present in the brain of the patient or the patient animal by an immunological method. Moreover, the brain disease can be diagnosed by detecting MOG that is expressed or present in the cells in the brain of the patient or the patient animal using an immunological method such as flow cytometry.

When a monovalent antibody which binds to MOG is used as the antibody or the antibody fragment of the invention, MOG in the brain can be measured by the same method as that described above. When a bispecific antibody or a multispecific antibody which binds to MOG and an antigen that is present in the brain is used as the antibody or the antibody fragment of the invention, MOG in the brain or the antigen that is present in the brain can be detected or measured by the same method as that described above.

The immunological method is a method of detecting or measuring the amount of an antibody or the amount of an antigen using a labeled antigen, antibody or the like. For example, the radioactive material labeled immune antibody method, the enzyme immunoassay method, the fluorescence immunoassay method, the luminescence immunoassay method, the western blotting method, the physicochemical method or the like is used.

In the radioactive material labeled immune antibody method, for example, the antibody or the antibody fragment of the invention is reacted with an antigen, cells expressing an antigen or the like and then reacted with an anti-immunoglobulin antibody or an antibody fragment thereof subjected to radiolabeling, followed by measurement with a scintillation counter or the like.

In the enzyme immunoassay method, for example, the antibody or the antibody fragment of the invention is reacted with an antigen, cells expressing an antigen or the like and then reacted with an anti-immunoglobulin antibody or an antibody fragment thereof subjected to labeling with an enzyme or the like, followed by addition of a substrate and measurement of the absorbance of the reaction solution with an absorptiometer. For example, a sandwich ELISA method or the like is used. As a labeling substance used in the enzyme immunoassay method, a known [Enzyme Immunoassay Method, Igaku-Shoin Ltd. (1987)] enzyme label can be used.

For example, alkaline phosphatase label, peroxidase label, luciferase label, biotin label or the like is used. The sandwich ELISA method is a method in which after binding an antibody to a solid phase, a target antigen to be detected or to be measured is trapped, and then a second antibody is reacted with the trapped antigen.

In the ELISA method, two kinds of antibodies which recognize the antigen to be detected or measured and which have different antigen recognition sites are prepared, and among these, a first antibody is adsorbed on a plate (for example, a 96-well plate) in advance, followed by labeling the second antibody with a fluorescent substance such as FITC, an enzyme such as peroxidase, biotin or the like.

The plate on which the first antibody is adsorbed is allowed to react with cells or a lysate thereof, tissues or a lysate thereof, a cell culture supernatant, serum, pleural effusion, ascites, intraocular fluid or the like separated from the living body and then to react with the second antibody, followed by the detection reaction according to the labeling material. From a calibration curve prepared by serially diluting the antigen of a known concentration, the antigen concentration in the test sample is calculated.

As the antibodies used in the sandwich ELISA method, either a polyclonal antibody or a monoclonal antibody may be used. Antibody fragments such as Fab, Fab' and $F(ab)_2$ may be used instead of the antibodies. The combination of the two kinds of antibodies used in the sandwich ELISA method may be a combination of monoclonal antibodies or antibody fragments thereof which recognize different epitopes or may be a combination of a polyclonal antibody, a monoclonal antibody and antibody fragments thereof.

In the fluorescence immunoassay method, measurement is carried out by the method described in documents [Monoclonal Antibodies-Principles and practice, Third edition, Academic Press (1996) and A manual for monoclonal antibody experiments, Kodansha scientific books (1987)] or the like. As the labeling substance used in the fluorescence immunoassay method, a known [Fluorescent Antibody Method, Soft Science (1983)] fluorescent label can be used. For example, FITC, RITC or the like is used.

In the luminescence immunoassay method, measurement is carried out by the method described in a document [Bioluminescence and Chemiluminescence, Clinical Test 42, Hirokawa-Shoten Ltd. (1998)] or the like. As the labeling substance used in the luminescence immunoassay method, a known luminescent label is used, and an acridinium ester, a lophine or the like is used.

In the western blotting method, measurement is carried out by after fractionating antigens, cells expressing an antigen or the like by SDS (sodium dodecyl sulfate)—PAGE (polyacrylamide gel) [Antibodies—A Laboratory Manual Cold Spring Harbor Laboratory (1988)], blotting the gel on a polyvinylidene fluoride (PVDF) membrane or a nitrocellulose membrane, reacting an antibody or an antibody fragment that recognizes the antigen with the membrane, further reacting it with an anti-mouse IgG antibody or a binding fragment subjected to labeling with a fluorescent substance such as FITC, labeling with an enzyme such as peroxidase, biotin labeling or the like and then visualizing the label. An example is shown below.

Cells or tissues expressing a polypeptide having the amino acid sequence of MOG are lysed, and 0.1 to 30 µg as a protein amount per lane is subjected to electrophoresis by the SDS-PAGE method under reducing conditions. The electrophoresed proteins are transferred to a PVDF membrane and reacted with PBS containing 1 to 10% BSA (referred to as BSA-PBS below) for 30 minutes at room temperature to perform blocking operation.

The antibody or the antibody fragment of the invention is reacted therewith, and the membrane is washed with PBS containing 0.05 to 0.1% Tween-20 (referred to as Tween-PBS below) and reacted with a goat anti-mouse IgG labeled with peroxidase for 2 hours at room temperature.

By washing with Tween-PBS and detecting a band to which the antibody or the antibody fragment of the invention is bound using ECL Western Blotting Detection Reagents (manufactured by Amersham) or the like, the polypeptide having the amino acid sequence of MOG is detected.

As the antibody or the antibody fragment used for detection by western blotting, an antibody or an antibody fragment thereof capable of binding to a polypeptide that does not retain the natural three-dimensional structure is used.

The physicochemical method is carried out, for example, by binding MOG, which is the antigen, with the antibody or the antibody fragment of the invention to form an aggregate and detecting the aggregate. As another physicochemical method, a capillary tube method, a one-dimensional immunodiffusion method, an immunoturbidimetric method, a latex immunoturbidimetric method [Outline of Clinical Examination Method, KANEHARA & Co., LTD. (1998)] or the like can also be used.

In the latex immunoturbidimetric method, when a carrier such as a polystyrene latex having a particle size of approximately 0.1 to 1 µm sensitized with an antibody or an antigen is used to cause the antigen-antibody reaction with a corresponding antigen or antibody, the scattered light is increased in a reaction solution, and the transmitted light is decreased. The antigen concentration and the like in the test sample are measured by detecting this change as absorbance or integrating sphere turbidity.

For detection or measurement of cells expressing MOG, a known immunological detection method can be used, but of known methods, the immunoprecipitation method, the immunocytostaining method, the immunohistochemical staining method, the fluorescent antibody staining method or the like is preferably used.

In the immunoprecipitation method, after reacting cells expressing MOG or the like with the antibody or the antibody fragment of the invention, a carrier having specific binding ability to an immunoglobulin such as Protein G-Sepharose is added thereto, and therefore an antigen-antibody complex is precipitated. Alternatively, the method can also be carried out by the following method.

The antibody or the antibody fragment of the invention described above is immobilized on a 96-well plate for ELISA and then blocked with BSA-PBS. When the antibody is an antibody which is not purified such as a hybridoma culture supernatant for example, the hybridoma culture supernatant is dispensed and bound after immobilizing anti-mouse immunoglobulin, anti-rat immunoglobulin, protein-A, protein-G or the like on a 96-well plate for ELISA in advance and blocking the plate with BSA-PBS.

Next, after discarding BSA-PBS and thoroughly washing with PBS, lysates of cells or tissues expressing human MOG are reacted therewith. Immunoprecipitates are extracted from the plate after thoroughly washing with a sample buffer for SDS-PAGE and detected by the above western blotting.

The immunocytostaining method or the immunohistochemical staining method is a method in which cells, tissues or the like expressing an antigen are treated with a surfactant, methanol or the like in order to improve passing of the antibody in some cases, then reacted with the antibody of the invention and further reacted with an anti-immunoglobulin antibody or a binding fragment thereof subjected to fluorescent labeling with FITC or the like, labeling with an enzyme such as peroxidase, biotin labeling or the like and in which the label is then visualized and observed with a microscope.

In addition, detection can be carried out by the fluorescent antibody staining method in which a fluorescently-labeled antibody is reacted with cells and analyzed with a flow cytometer [Monoclonal Antibodies—Principles and practice, Third edition, Academic Press (1996) and A manual for monoclonal antibody experiments, Kodansha scientific books (1987)]. In particular, the antibody or the antibody fragment of the invention can detect cells in which the antigen is expressed and retains the natural three-dimensional structure by the fluorescent antibody staining method.

In addition, when the FMAT 8100 HTS system (manufactured by Applied Biosystems) or the like of the fluorescent antibody staining methods is used, the amount of an antigen or the amount of an antibody can be measured without separating the formed antibody-antigen complex from the free antibody or antigen that is not involved in formation of the antibody-antigen complex.

Hereinafter, the invention will be explained in more detail by Examples, but the invention is not limited to the following Examples.

EXAMPLES

[Example 1] Acquisition of Anti-MOG Antibodies (1) Acquisition of Antibodies Using Human Antibody Phage Libraries A VH gene fragment and a VL gene fragment were amplified from human PBMC-derived cDNA by PCR. The VH gene fragment and the VL gene fragment were inserted to a phagemid vector pCANTAB 5E (manufactured by Amersham Pharmacia Biotech), and a plasmid was obtained by transforming *Escherichia coli* TG1 (manufactured by Lucigen).

The obtained plasmid was infected with M13KO7 Helper Phage (manufactured by Invitrogen), and a human antibody M13 phage library of the VH gene and the VL gene was thus obtained.

Using the human antibody M13 phage libraries, anti-rat MOG (rMOG) monoclonal antibodies were obtained using the phage display method described below. rMOG-FLAG_Fc of Example 4 described below was immobilized on a MAXISORP STARTUBE (manufactured by NUNC), and the sites to which rMOG-FLAG_Fc was not bound were blocked using SuperBlock Blocking Buffer (manufactured by Thermo Fisher Scientific Inc.).

A human antibody M13 phage library was reacted with the tube at room temperature for an hour, and the phage was eluted with 0.1 M Gly-HCl (pH 2.2) after washing with PBS or PBS containing 0.1% Tween 20 (referred to as PBS-T below). The eluate was neutralized by adding Tris-HCl (pH 8.5). TG1 competent cells were infected with the eluted phage, and the phage was amplified.

Then, the reaction with rMOG-FLAG_Fc immobilized on a MAXISORP STARTUBE was conducted again, and washing and elution were conducted. This procedure was repeated, and phages displaying scFv which specifically binds to rMOG-FLAG_Fc were concentrated. The concentrated phages were monocloned, and three clones having affinity to rMOG-FLAG_Fc were selected by ELISA.

In ELISA, rMOG-FLAG_Fc was immobilized on MAXISORP (manufactured by NUNC), and the sites to which rMOG-FLAG_Fc was not bound were blocked using SuperBlock Blocking Buffer (manufactured by Thermo Fisher Scientific Inc.). As the negative control, a plate in which FLAG_Fc was immobilized was also prepared.

The phage clones were added to separate wells and reacted at room temperature for 30 minutes, and then the wells were washed with PBS-T. Subsequently, a solution obtained by diluting horseradish peroxidase-labeled anti-M13 antibody (manufactured by GE Healthcare) with PBS-T containing 10% Block Ace (manufactured by Dainippon Pharma Co., Ltd.) was added to the wells, and the plates were incubated at room temperature for 30 minutes.

After washing the microplates three times with PBS-T, a TMB chromogenic substrate solution (manufactured by DAKO) was added, and the plates were incubated at room temperature. The chromogenic reaction was stopped by adding 0.5 M sulfuric acid to the wells, and the absorbances at the wavelength of 450 nm (reference wavelength of 570 nm) were measured with a microplate reader (manufactured by Molecular Devices). The results obtained are shown in FIG. 1.

As shown in FIG. 1, it could be confirmed that the three phage clones all bind to rMOG-FLAG Fc. On the other hand, none of the phage clones bound to FLAG Fc (data not shown).

The sequences of the clones which bound to rMOG-FLAG_Fc were analyzed, and anti-MOG antibody phagemid vectors, pCANTAB_MOG01, pCANTAB_MOG09 and pCANTAB_MOG14 were obtained.

In the following paragraphs, the names of the anti-MOG scFv antibodies displayed by the phages expressed using pCANTAB_MOG01, pCANTAB_MOG09 and pCANTAB_MOG14 are referred to as MOG01 antibody, MOG09 antibody and MOG14 antibody, respectively. The nucleotide sequences which encode VH or VL of the anti-MOG scFv antibodies, and the amino acid sequences deduced from the nucleotide sequences are shown in Table 1.

TABLE 1

Sequence Information of Anti-MOG scFv Antibodies (MOG01 Antibody, MOG09 Antibody and MOG14 Antibody)

| Clone Name | MOG01 | MOG09 | MOG14 |
|---|---|---|---|
| Nucleotide sequence encoding VH (including signal sequence) | SEQ ID NO: 1 | SEQ ID NO: 13 | SEQ ID NO: 25 |
| Amino acid sequence of VH (including signal sequence) | SEQ ID NO: 2 | SEQ ID NO: 14 | SEQ ID NO: 26 |
| Amino acid sequence of VH (excluding signal sequence) | SEQ ID NO: 3 | SEQ ID NO: 15 | SEQ ID NO: 27 |
| Amino acid sequence of HCDR1 | SEQ ID NO: 4 | SEQ ID NO: 16 | SEQ ID NO: 28 |
| Amino acid sequence of HCDR2 | SEQ ID NO: 5 | SEQ ID NO: 17 | SEQ ID NO: 29 |
| Amino acid sequence of HCDR3 | SEQ ID NO: 6 | SEQ ID NO: 18 | SEQ ID NO: 30 |
| Nucleotide sequence encoding VL (including signal sequence) | SEQ ID NO: 7 | SEQ ID NO: 19 | SEQ ID NO: 31 |
| Amino acid sequence of VL (including signal sequence) | SEQ ID NO: 8 | SEQ ID NO: 20 | SEQ ID NO: 32 |

TABLE 1-continued

Sequence Information of Anti-MOG scFv Antibodies (MOG01 Antibody, MOG09 Antibody and MOG14 Antibody)

| Clone Name | MOG01 | MOG09 | MOG14 |
|---|---|---|---|
| Amino acid sequence of VL (excluding signal sequence) | SEQ ID NO: 9 | SEQ ID NO: 21 | SEQ ID NO: 33 |
| Amino acid sequence of LCDR1 | SEQ ID NO: 10 | SEQ ID NO: 22 | SEQ ID NO: 34 |
| Amino acid sequence of LCDR2 | SEQ ID NO: 11 | SEQ ID NO: 23 | SEQ ID NO: 35 |
| Amino acid sequence of LCDR3 | SEQ ID NO: 12 | SEQ ID NO: 24 | SEQ ID NO: 36 |

(2) Acquisition of Antibodies Using Alpaca Antibody Libraries

An emulsion of rMOG-FLAG_Fc and complete adjuvant for the first immunization and an emulsion of rMOG-FLAG_Fc and incomplete adjuvant for the second and third immunization were produced as immunogens, and an alpaca was immunized.

Lymphocytes ($2 \times 10^7$ cells) were collected from the blood (50 mL) of the immunized alpaca, and RNA was extracted from the obtained cells using RNA IsoPlus (manufactured by TAKARA). After synthesizing cDNA by reverse transcription reaction using SuperScript (registered trademark) III First-Strand Synthesis System for RT-PC (manufactured by Invitrogen), VHH gene was amplified using primers specific to alpaca IgG2 (Short hinge-heavy chain antibody) and IgG3 (Long hinge-heavy chain antibody).

The VHH gene fragment was inserted to a phagemid vector pKSTV-02 (described in Miyazaki et al, J. Biochem. 2015; 1), and *Escherichia coli* TG1 was transformed by electroporation using a MicroPulser electroporator (manufactured by BioRad) (the IgG2 titer of the transformant was $2.6 \times 10^7$, and the IgG3 titer was $3.2 \times 10^7$).

The obtained transformant was infected with M13KO7 Helper Phage (manufactured by Invitrogen), and an alpaca antibody M13 phage library of the VHH gene was thus obtained.

Using the alpaca antibody M13 phage libraries, anti-MOG antibodies were obtained using the biopanning method described below. rMOG-GST (4 µg/2 mL) was immobilized on an immuno tube, and the sites to which rMOG-GST was not bound were blocked using 0.5% BSA.

The alpaca antibody M13 phage library was reacted with the tube at room temperature for an hour, and the phage was eluted with 0.1 M Gly-HCl (pH 2.7) after washing with PBS-T. The eluant was neutralized by adding Tris-HCl (pH 9.1). *Escherichia coli* TG1 was infected with the eluted phage, and then the phage was amplified. Then, the reaction with rMOG-GST immobilized on an immuno tube was conducted again, and washing and elution were conducted.

The procedure was repeated three times for IgG2 and twice for IgG3, and phages displaying VHH which specifically binds to rMOG-GST were concentrated. From the concentrated phages, 96 phage clones displaying VHH of IgG2 and 96 phage clones displaying VHH of IgG3 were monocloned, and clones having affinity to rMOG-GST were selected by ELISA.

In ELISA, rMOG-GST was immobilized (50 ng/50 µL) on MAXISORP (manufactured by NUNC), and the sites to which rMOG-GST was not bound were blocked using 0.5% BSA. The phage clones were added to separate wells and reacted at room temperature for an hour, and then the wells were washed five times with PBS-T.

Subsequently, 50 µL of a biotinylated anti-M13 phage antibody (manufactured by Abcam) and horseradish peroxidase-labeled streptavidin (manufactured by Vector) were added to the wells, and the plate was incubated at room temperature for an hour.

After washing the microplate with PBS-T, a TMB chromogenic substrate solution (manufactured by CALBIOCHEM) was added to the wells, and the plate was incubated at room temperature. The chromogenic reaction was stopped by adding 1 M hydrochloric acid to the wells, and the absorbances at the wavelength of 450 nm (reference wavelength of 570 nm) were measured with a microplate reader (Model 680XR, manufactured by BioRad).

The sequences of the clones which bound to rMOG-GST were analyzed, and an anti-MOG VHH antibody, iMOG-3Rim1-S32 antibody was obtained. The nucleotide sequence encoding VHH of iMOG-3Rim1-S32 antibody and the amino acid sequence deduced from the nucleotide sequence are shown in Table 2.

TABLE 2

Sequence Information of Anti-MOG VHH Antibody (iMOG-3Rim1-S32 Antibody)

| Clone Name | iMOG-3Rim1-S32 |
|---|---|
| Nucleotide sequence encoding VHH (including signal sequence) | SEQ ID NO: 37 |
| Amino acid sequence of VHH (including signal sequence) | SEQ ID NO: 38 |
| Amino acid sequence of VHH (excluding signal sequence) | SEQ ID NO: 39 |
| Amino acid sequence of CDR1 | SEQ ID NO: 40 |
| Amino acid sequence of CDR2 | SEQ ID NO: 41 |
| Amino acid sequence of CDR3 | SEQ ID NO: 42 |

[Example 2] Construction of Antibody Expression Vectors (1) Construction of Anti-MOG Antibody Expression Vectors To produce anti-MOG antibodies of human IgG type, expression vectors for anti-MOG antibodies in which the DNA sequences encoding the amino acid sequences of the variable regions of the human antibody phage library-derived anti-MOG scFv antibodies obtained in Example 1 were incorporated into a nucleotide sequence encoding the amino acid sequence of a constant region of human IgG antibody were produced by the method described below.

A nucleotide sequence encoding the lambda chain constant region of human IgG was synthesized and inserted to the BglII-EcoRI site of N5KG4PE vector (described in International Publication No. 2002/088186), and N5LG4PE vector was thus produced.

Expression vectors obtained by inserting nucleotide sequences encoding the amino acid sequences of VH and VL of MOG01 antibody and MOG09 antibody into N5LG4PE were named N5LG4PE_MOG01 and N5LG4PE_MOG09, respectively. Moreover, an expression vector obtained by inserting nucleotide sequences encoding the amino acid sequences of VH and VL of MOG14 antibody into N5KG4PE vector was named N5KG4PE_MOG14.

(1-1) MOG01 Antibody Expression Vector N5LG4PE_MOG01

Using phagemid vector pCANTAB_MOG01 as a template and using primer 1 (SEQ ID NO: 43) and primer 2 (SEQ ID NO: 44) and KOD plus DNA Polymerase (manufactured by Toyobo Co., Ltd.), a gene fragment of the VL region was amplified by PCR. In the PCR, 30 cycles of reaction of 30 seconds at 94° C., 30 seconds at 58° C. and 45 seconds at 68° C. were conducted. The PCR described in Example 2 was conducted under the conditions unless particularly described.

Using the PCR product as a template and using primer 3 (SEQ ID NO: 45) and primer 2 (SEQ ID NO: 44) and KOD plus DNA Polymerase (manufactured by Toyobo Co., Ltd.), a signal sequence was added to the gene fragment of the VL region by PCR.

The obtained gene fragment was inserted to the BglII-BlpI site of N5LG4PE vector, and N5LG4PE_MOG01VL was obtained. Next, using pCANTAB_MOG01 as a template and using primer 4 (SEQ ID NO: 46) and primer 5 (SEQ ID NO: 47) and KOD plus DNA Polymerase (manufactured by Toyobo Co., Ltd.), a gene fragment of the VH region was amplified by PCR.

Using the PCR product as a template and using primer 6 (SEQ ID NO: 48) and primer 5 (SEQ ID NO: 47) and KOD plus DNA Polymerase (manufactured by Toyobo Co., Ltd.), a signal sequence was added to the gene fragment of the VH region by PCR. The obtained gene fragment was inserted to the SalI-NheI site of N5LG4PE_MOG01VL vector, and N5LG4PE_MOG01 was obtained.

(1-2) MOG09 Antibody Expression Vector N5LG4PE_MOG09

N5LG4PE_MOG09 was produced by the same method as that of (1-1). A phagemid vector pCANTAB_MOG09 was used as a template. Primer 7 (SEQ ID NO: 49) and primer 8 (SEQ ID NO: 50) were used to amplify a gene fragment of the VL region, and primer 3 (SEQ ID NO: 45) and primer 8 (SEQ ID NO: 50) were used to add a signal sequence to the gene fragment of the VL region. Primer 9 (SEQ ID NO: 51) and primer 10 (SEQ ID NO: 52) were used to amplify a gene fragment of the VH region, and primer 6 (SEQ ID NO: 48) and primer 10 (SEQ ID NO: 52) were used to add a signal sequence to the gene fragment of the VH region.

(1-3) MOG14 Antibody Expression Vector N5KG4PE_MOG14

N5KG4PE_MOG14 was produced by the same method as that of (1-1). A phagemid vector pCANTAB_MOG14 was used as a template. Primer 11 (SEQ ID NO: 53) and primer 12 (SEQ ID NO: 54) were used to amplify a gene fragment of the VL region, and primer 3 (SEQ ID NO: 45) and primer 12 (SEQ ID NO: 54) were used to add a signal sequence to the gene fragment of the VL region. The obtained gene fragment of the VL region to which the signal sequence was added was inserted to the BglII-BsiWI site of N5KG4PE vector, and N5KG4PE_MOG14VL was obtained.

Next, pCANTAB_MOG14 was used as a template. Primer 13 (SEQ ID NO: 55) and primer 14 (SEQ ID NO: 56) were used to amplify a gene fragment of the VH region, and primer 6 (SEQ ID NO: 48) and primer 14 (SEQ ID NO: 56) were used to add a signal sequence to the gene fragment of the VH region. The obtained gene fragment of the VH region to which the signal sequence was added was inserted to the SalI-NheI site of N5KG4PE_MOG14VL, and N5KG4PE_MOG14 was obtained.

(1-4) iMOG-3Rim1-S32 Antibody Expression Vector N5G4PEFc_iMOG-3Rim1-S32

A sequence obtained by adding a signal sequence to the gene encoding the Fc region of human IgG4PE was synthesized, and a gene fragment of human Fc region was amplified by PCR using primer 25 (SEQ ID NO: 79) and primer 26 (SEQ ID NO: 80) and KOD plus DNA Polymerase (manufactured by Toyobo Co., Ltd.).

In the PCR, 30 cycles of reaction of 30 seconds at 94° C., 30 seconds at 58° C. and 60 seconds at 68° C. were conducted. The obtained Fc gene fragment was inserted to the BglII-BamHI site of N5KG4PE vector, and N5G4PEFc vector was produced.

An expression vector obtained by inserting a nucleotide sequence encoding the amino acid sequence of VHH of iMOG-3Rim1-S32 to N5G4PEFc was named N5G4PEFc_iMOG-3Rim1-S32. The VHH-Fc expression vector was produced by the method described below.

The nucleotide sequence of VHH of iMOG-3Rim1-S32 was synthesized, and a gene fragment of the VHH region was amplified by PCR using primer 15 (SEQ ID NO: 57) and primer 16 (SEQ ID NO: 58) and KOD plus DNA Polymerase (manufactured by Toyobo Co., Ltd.). In the PCR, 30 cycles of reaction of 30 seconds at 94° C., 30 seconds at 58° C. and 60 seconds at 68° C. were conducted. The obtained VHH gene fragment was inserted to the EcoRI-BglII site of N5G4PEFc vector, and N5G4PEFc_iMOG-3Rim1-S32 was obtained.

(2) Anti-Avermectin Antibody Expression Vector N5LG4PE_AVM

As a negative control antibody, a chimeric anti-Avermectin (AVM) antibody was produced by the same method as that of (1-1). An expression vector obtained by inserting nucleotide sequences encoding the amino acid sequences of VH and VL of an AVM antibody to N5LG4PE was named N5LG4PE_AVM.

An SD rat was immunized with AVM, and an anti-AVM antibody-producing hybridoma was established by a general method. The variable region of the anti-AVM antibody derived from the hybridoma was used as a template. Primer 29 (SEQ ID NO: 83) and primer 30 (SEQ ID NO: 84) were used to amplify a gene fragment of the VL region, and primer 3 (SEQ ID NO: 45) and primer 30 (SEQ ID NO: 84) were used to add a signal sequence to the gene fragment of the VL region.

Primer 31 (SEQ ID NO: 85) and primer 32 (SEQ ID NO: 86) were used to amplify a gene fragment of the VH region, and primer 6 (SEQ ID NO: 48) and primer 32 (SEQ ID NO: 86) were used to add a signal sequence to the gene fragment of the VH region.

(3) Anti-Rat Transferrin Receptor Antibody OX26 Antibody Expression Vector N5KG4PE(R409K)_OX26

As a positive control antibody of an anti-rat transferrin receptor antibody, the anti-rat transferrin receptor antibody, OX26 antibody described in [Protein Engineering, 12, 787-796, 1999] was produced. An expression vector obtained by inserting nucleotide sequences encoding the amino acid sequences of VH and VL of OX26 antibody to N5KG4PE (R409K) (described in International Publication No. 2002/088186) was produced by the same method as that of (1-1) and named N5KG4PE(R409K)_OX26.

The gene encoding the amino acid sequence of VL of OX26 antibody was synthesized and used as a template. Primer 40 (SEQ ID NO: 94) and primer 41 (SEQ ID NO: 95) were used to amplify a gene fragment of the VL region, and primer 42 (SEQ ID NO: 96) and primer 43 (SEQ ID NO: 97) were used to amplify a gene fragment of the VH region.

[Example 3] Construction of Bispecific Antibody Expression Vectors (1) Production of Vector Expressing Bispecific Antibody Binding to Her2 and MOG A vector expressing a bispecific antibody binding to HER2 and MOG, pCI-Trastuzumab-hKG4PE(R409K)_MOG01scFv was produced by the following method. In the bispecific antibody, scFv of an anti-MOG antibody is fused to the C-terminuses of the two H chains of IgG of an anti-HER2 antibody.

Using a synthetic gene of the heavy chain constant region as a template and using primer 17 (SEQ ID NO: 59) and primer 18 (SEQ ID NO: 60) and KOD plus DNA Polymerase (manufactured by Toyobo Co., Ltd.), a gene fragment of the CH1-Hinge-CH2-CH3-linker region was amplified by PCR.

In the PCR, 30 cycles of reaction of 30 seconds at 94° C., 30 seconds at 58° C. and two minutes at 68° C. were conducted. Using a phagemid vector pCANTAB_MOG01 as a template and using primer 19 (SEQ ID NO: 61) and primer 20 (SEQ ID NO: 62) and KOD plus DNA Polymerase (manufactured by Toyobo Co., Ltd.), a gene fragment of the scFv region (referred to as MOG01scFv below) was amplified by PCR.

In the PCR, 30 cycles of reaction of 30 seconds at 94° C., 30 seconds at 58° C. and 90 seconds at 68° C. were conducted. Next, using the CH1-Hinge-CH2-CH3 region and the MOG01scFv region as templates and using primer 17 (SEQ ID NO: 59) and primer 20 (SEQ ID NO: 62) and KOD plus DNA Polymerase (manufactured by Toyobo Co., Ltd.), CH1-Hinge-CH2-CH3-MOG01scFv was amplified.

In the PCR, 30 cycles of reaction of 30 seconds at 94° C., 30 seconds at 58° C. and two minutes at 68° C. were conducted. The obtained gene fragment was inserted to pCI vector (manufactured by Promega Corporation), and pCI-hG4PE(R409K)_MOG01scFv vector was produced.

The gene encoding the amino acid sequence of VL of an anti-HER2 antibody (Trastuzumab) (described in International Publication No. 1999/57134) was synthesized and used as a template, and a gene fragment of the VL region was amplified by PCR using primer 21 (SEQ ID NO: 63) and primer 22 (SEQ ID NO: 64) and KOD plus DNA Polymerase (manufactured by Toyobo Co., Ltd.).

In the PCR, 30 cycles of reaction of 30 seconds at 94° C., 30 seconds at 58° C. and 45 seconds at 68° C. were conducted. Using N5KG4PE vector (described in International Publication No. 2002/088186) as a template and using primer 27 (SEQ ID NO: 81) and primer 28 (SEQ ID NO: 82) and KOD plus DNA Polymerase (manufactured by Toyobo Co., Ltd.), a gene fragment of the CL region was amplified by PCR.

In the PCR, 30 cycles of reaction of 30 seconds at 94° C., 30 seconds at 58° C. and 45 seconds at 68° C. were conducted. Using the obtained gene fragments VL and CL as templates and using primer 21 (SEQ ID NO: 63) and primer 28 (SEQ ID NO: 82) and KOD plus DNA Polymerase (manufactured by Toyobo Co., Ltd.), a gene fragment was amplified by PCR.

In the PCR, 30 cycles of reaction of 30 seconds at 94° C., 30 seconds at 58° C. and 90 seconds at 68° C. were conducted. The obtained gene fragment was inserted to pCI-hG4PE(R409K)_MOG01scFv, and pCI-TrastuzumabVL-hKG4PE(R409K)_MOG01scFv was obtained.

Next, the gene encoding the amino acid sequence of VH of Trastuzumab was synthesized and used as a template, and a gene fragment of the VH region was amplified by PCR using primer 23 (SEQ ID NO: 65) and primer 24 (SEQ ID NO: 66) and KOD plus DNA Polymerase (manufactured by Toyobo Co., Ltd.). In the PCR, 30 cycles of reaction of 30 seconds at 94° C., 30 seconds at 58° C. and 45 seconds at 68° C. were conducted.

The obtained gene fragment was inserted to pCI-TrastuzumabVL-hKG4PE(R409K)_MOG01scFv, and pCI-Trastuzumab-hKG4PE(R409K)_MOG01scFv was obtained.

(2) Production of Vector Expressing Bispecific Antibody Binding to AVM and MOG

Moreover, a vector expressing a bispecific antibody binding to AVM and MOG, pCI-AVM-hLG4PE(R409K)_MOG01scFv was produced by the method described below. In the bispecific antibody, scFv of an anti-MOG antibody is fused to the C-terminus of IgG of an anti-AVM antibody.

Using N5LG4PE_AVM as a template and using primer 33 (SEQ ID NO: 87) and primer 34 (SEQ ID NO: 88) and KOD plus DNA Polymerase (manufactured by Toyobo Co., Ltd.), a gene fragment of the AVM light chain region was amplified by PCR. In the PCR, 30 cycles of reaction of 30 seconds at 94° C., 30 seconds at 58° C. and 60 seconds at 68° C. were conducted.

Using N5LG4PE_AVM as a template and using primer 35 (SEQ ID NO: 89) and primer 32 (SEQ ID NO: 86) and KOD plus DNA Polymerase (manufactured by Toyobo Co., Ltd.), a gene fragment of the AVM VH region was amplified by PCR.

In the PCR, 30 cycles of reaction of 30 seconds at 94° C., 30 seconds at 58° C. and 45 seconds at 68° C. were conducted. The obtained gene fragment was inserted to pCI-hG4PE(R409K)_MOG01scFv produced above, and pCI-AVM-hLG4PE(R409K)_MOG01scFv was obtained.

(3) Production of Vector Expressing Antibody in which scFv of Anti-AVM Antibody is Fused to C-Terminus of IgG of Anti-AVM Antibody As a negative control antibody, a vector expressing an antibody in which scFv of an anti-AVM antibody is fused to the C-terminus of IgG of an anti-AVM antibody was named pCI-AVM-hLG4PE(R409K)_AVM scFv.

Using a synthetic gene of the heavy chain constant region as a template and using primer 36 (SEQ ID NO: 90) and primer 37 (SEQ ID NO: 91) and KOD plus DNA Polymerase (manufactured by Toyobo Co., Ltd.), a gene fragment of the CH1-Hinge-CH2-CH3-linker region was amplified by PCR.

In the PCR, 30 cycles of reaction of 30 seconds at 94° C., 30 seconds at 58° C. and two minutes at 68° C. were conducted. Using a synthetic gene of AVM scFv as a template and using primer 38 (SEQ ID NO: 92) and primer 39 (SEQ ID NO: 93) and KOD plus DNA Polymerase (manufactured by Toyobo Co., Ltd.), a gene fragment of the scFv region was amplified by PCR.

In the PCR, 30 cycles of reaction of 30 seconds at 94° C., 30 seconds at 58° C. and 90 seconds at 68° C. were conducted. Next, using the CH1-Hinge-CH2-CH3 region and the AVM scFv region as templates and using primer 36 (SEQ ID NO: 90) and primer 39 (SEQ ID NO: 93) and KOD plus DNA Polymerase (manufactured by Toyobo Co., Ltd.), CH1-Hinge-CH2-CH3-AVM scFv was amplified. In the PCR, 30 cycles of reaction of 30 seconds at 94° C., 30 seconds at 58° C. and two minutes at 68° C. were conducted.

The obtained gene fragment was inserted to the NheI-BamHI site of pCI-AVM-hLG4PE(R409K)_MOG01scFv, and pCI-AVM-hLG4PE(R409K)_AVM scFv was obtained.

Example 4

Production of Soluble MOG Antigen and Soluble HER2 Antigen (1) Production of Extracellular Domain Protein of Rat MOG to which FLAG-Fc is Bound As a soluble antigen of rat MOG, an extracellular domain protein of MOG to which FLAG-Fc was added at the C-terminus was produced by the method described below. The nucleotide sequence encoding rMOG is shown in SEQ ID NO: 67, and the amino acid sequence deduced from the nucleotide sequence is shown in SEQ ID NO: 68.

A gene sequence of the extracellular domain of MOG was synthesized and inserted to the BglII-XbaI site of INPEP4 (manufactured by IDEC) vector to which FLAG-Fc had been inserted, and a plasmid vector INPEP4_rMOG-FLAG-Fc expressing the extracellular domain of MOG to which FLAG-Fc was added at the C-terminus was thus produced. The nucleotide sequence of rMOG-FLAG-Fc is shown in SEQ ID NO: 69, and the amino acid sequence deduced from the nucleotide sequence is shown in SEQ ID NO: 70.

INPEP4_rMOG-FLAG-Fc was introduced to suspension 293 cells using Expi293 (trademark) Expression System (manufactured by Thermo Fisher Scientific Inc.), and the cells were cultured to express the protein in a transient expression system. The culture supernatant was collected four days after the introduction of the vector and filtered through a membrane filter having a pore size of 0.22 μm (manufactured by Millipore Corporation.).

The MOG-FLAG-Fc protein in the culture supernatant was affinity-purified using Protein A resin (MabSelect SuRe, manufactured by GE Healthcare BioSciences). A phosphate buffer solution was used as a washing solution.

The protein adsorbed on the Protein A was eluted with 20 mM sodium citrate and 50 mM NaCl buffer solution (pH 3.4) and collected in a tube containing 1 M Tris-HCl Buffer Solution (pH 8.0).

Next, the solvent of the eluate was replaced with PBS by ultrafiltration using VIVASPIN (manufactured by Sartrius stealin) and a NAP column (manufactured by GE Healthcare BioSciences), and then filtration sterilization with a membrane filter having a pore size of 0.22 μm (Millex-GV, manufactured by Millipore Corporation) was conducted. The concentration of the purified MOG-FLAG-Fc protein in the solution was measured from the absorbance at 280 nm.

(2) Production of Extracellular Domain Protein of MOG to which GST is Bound

As a soluble antigen of rat MOG, an extracellular domain protein of MOG to which GST was added at the C-terminus was produced by the method described below.

A gene sequence of the extracellular domain of MOG was synthesized and inserted to the BglII-KpnI site of N5 vector (manufactured by IDEC) to which GST had been inserted, and a plasmid vector N5_rMOG-GST expressing the extracellular domain of MOG to which GST was added at the C-terminus was thus produced. The nucleotide sequence of rMOG-GST is shown in SEQ ID NO: 71, and the amino acid sequence deduced from the nucleotide sequence is shown in SEQ ID NO: 72.

As a soluble antigen of human HER2, an extracellular domain protein of HER2 to which GST was added at the C-terminus was produced by the method described below. A gene sequence of the extracellular domain of HER2 was synthesized and inserted to the BglII-KpnI site of N5 vector (manufactured by IDEC) to which GST had been inserted, and a plasmid vector N5_hHER2-GST expressing the extracellular domain of HER2 to which GST was added at the C-terminus was thus produced. The nucleotide sequence of hHER2-GST is shown in SEQ ID NO: 71, and the amino acid sequence deduced from the nucleotide sequence is shown in SEQ ID NO: 72.

N5_rMOG-GST and N5_hHER2-GST were introduced to suspension 293 cells using Expi293 (trademark) Expression System (manufactured by Thermo Fisher Scientific Inc.), and the cells were cultured to express the proteins in a transient expression system. The culture supernatants were collected four days after the introduction of the vectors and filtered through a membrane filter having a pore size of 0.22 μm (manufactured by Millipore Corporation).

The proteins in the culture supernatants were affinity-purified using Glutathione Sepharose 4B (manufactured by GE Healthcare BioSciences). A phosphate buffer solution was used as a washing solution. The proteins adsorbed on the Glutathione Sepharose 4B were eluted with 50 mM Tris-HCl and 10 mM reduced glutatione (pH 8.0).

Next, the solvents of the solutions were replaced with PBS by ultrafiltration using VIVASPIN (manufactured by Sartrius stealin) and a NAP column (manufactured by GE Healthcare BioSciences), and then filtration sterilization with a membrane filter having a pore size of 0.22 μm (Millex-GV, manufactured by Millipore Corporation) was conducted. The concentrations of the purified rMOG-GST protein and the hHER2-GST protein in the solutions were measured from the absorbances at 280 nm.

[Example 5] Production of Membrane MOG Antigen Expression Vectors

The entire gene sequences of rat MOG (rMOG), mouse MOG (mMOG), monkey MOG (cMOG) and human MOG (hMOG) were synthesized, and the gene sequences were each inserted to the BamHI-NotI site of pEF6/V5-His (manufactured by Thermo Fisher Scientific Inc.) vector. Plasmid vectors for expressing MOG in the membrane, pEF6_rMOG, pEF6_mMOG, pEF6_cMOG and pEF6_hMOG were thus produced.

The nucleotide sequence encoding mMOG is shown in SEQ ID NO: 73, and the amino acid sequence deduced from the nucleotide sequence is shown in SEQ ID NO: 74. The nucleotide sequence encoding cMOG is shown in SEQ ID NO: 75, and the amino acid sequence deduced from the nucleotide sequence is shown in SEQ ID NO: 76. The nucleotide sequence encoding hMOG is shown in SEQ ID NO: 77, and the amino acid sequence deduced from the nucleotide sequence is shown in SEQ ID NO: 78.

[Example 6] Preparation of Antibodies

The antibody expression plasmid vectors produced in Example 2 and Example 3 were introduced to suspension 293 cells using Expi293™ Expression System (manufactured by Thermo Fisher Scientific Inc.), and the cells were cultured to express the antibodies in a transient expression system.

The culture supernatants were collected four days after the introduction of the vectors and filtered through a membrane filter having a pore size of 0.22 μm (manufactured by Millipore Corporation). The proteins in the culture supernatants were affinity-purified using Protein A resin (MabSelect SuRe, manufactured by GE Healthcare BioSciences). A phosphate buffer solution was used as a washing solution. The antibodies adsorbed on the Protein A were eluted with 20 mM sodium citrate and 50 mM NaCl buffer solution (pH 3.4) and collected in tubes containing 1 M Tris-HCl Buffer Solution (pH 8.0).

Next, the solvents of the eluates were replaced with PBS by ultrafiltration using VIVASPIN (manufactured by Sartrius stealin) and a NAP column (manufactured by GE Healthcare BioSciences), and then filtration sterilization with a membrane filter having a pore size of 0.22 μm (Millex-GV, manufactured by Millipore Corporation) was conducted. The absorbances of the antibody solutions at 280 nm were measured, and the concentrations of the purified antibodies were calculated by converting the concentration 1 mg/mL to 1.40 Optimal density.

The anti-MOG human IgG antibodies expressed using the anti-MOG antibody expression vectors, N5LG4PE_MOG01, N5LG4PE_MOG09, N5KG4PE_MOG14 and N5G4PEFc_iMOG-3Rim1-S32 described in Example 2 are referred to as MOG01 antibody, MOG09 antibody, MOG14 antibody and iMOG-3Rim1-S32 antibody, respectively.

The antibodies obtained by expressing using the bispecific antibody expression vectors, pCI-AVM-hLG4PE(R409K)_AVM scFv, pCI-AVM-hLG4PE(R409K)_MOG01scFv and pCI-Trastuzumab-hKG4PE(R409K)_MOG01scFv produced in Example 3 were named AVM IgG4PE(R409K)_AVM dscFv antibody, AVM IgG4PE(R409K)_MOG01dscFv antibody and Trastuzumab IgG4PE(R409K)_MOG01scFv antibody, respectively.

[Example 7] Evaluation of Affinities of Anti-MOG Antibodies to MOG Using Flow Cytometer Binding of the anti-MOG antibodies, MOG01 antibody, MOG09 antibody, MOG14 antibody and iMOG-3Rim1-S32 antibody obtained in Example 6 to MOG were evaluated by the fluorescence activated cell sorting (FACS) method according to the following procedures.

The membrane MOG antigen expression vectors produced in Example 5 were introduced to suspension 293 cells using FreeStyle (trademark) 293 Expression System (manufactured by Thermo Fisher Scientific Inc.), and the cells were cultured to express the membrane antigens in a transient expression system. Using the cells, the reactivities of the anti-MOG antibodies were analyzed by the method described below.

rMOG/HEK293F, mMOG/HEK293F, cMOG/HEK293 and hMOG/HEK293 cells were suspended in a Staining Buffer (SB) of PBS containing 0.1% NaN$_3$ and 1% FBS each at a concentration of 5×10$^5$ cells/mL and dispensed to a round-bottom 96-well plate (manufactured by Becton Dickinson).

After centrifugation (2000 rpm, 4° C., two minutes), the supernatants were removed, and the antibodies obtained in Example 6 at 10 μg/mL were added to the pellets. After suspending the pellets, the plate was left to stand at ice temperature for 30 minutes. The supernatants were removed after further centrifugation (2000 rpm, 4° C., two minutes), and the pellets were washed with SB. Then, 1 μg/mL RPE fluorescently labeled goat anti-human antibody (manufactured by Southern Bioblot) was added, and the plate was incubated at ice temperature for 30 minutes.

Figure 2:
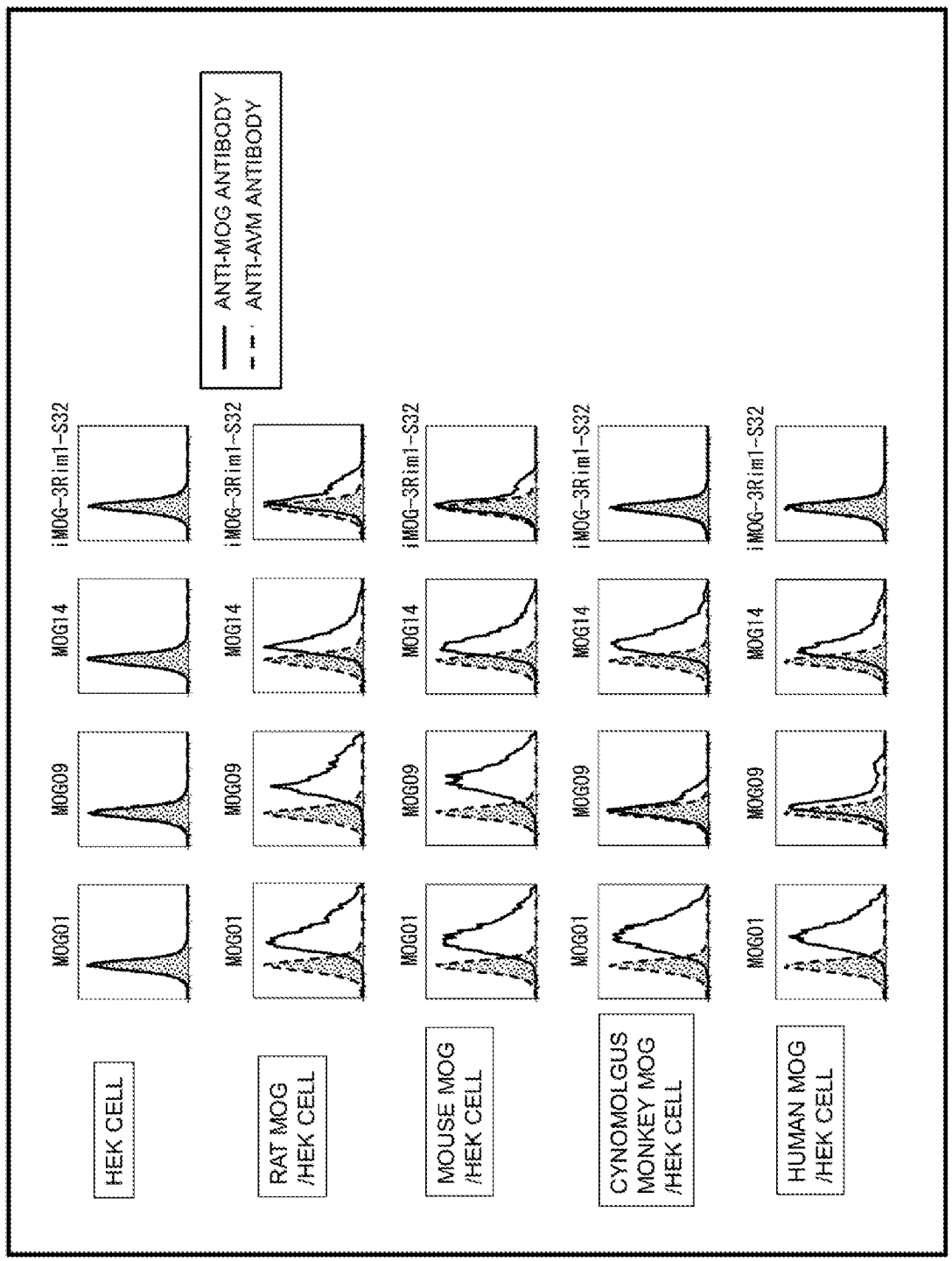
FIG. 2 shows the results of analysis using a flow cytometer of the affinities of anti-MOG antibodies to HEK cells, rat MOG/HEK cells, mouse MOG/HEK cells, cynomolgus monkey MOG/HEK cells or human MOG/HEK cells. The vertical axis shows the number of cells, and the horizontal axis shows the fluorescence intensity. A dotted line indicates a histogram of the affinity of an anti-AVM antibody used as a negative control, and a solid line indicates a histogram of the affinity of a MOG antibody.

After washing with SB, the cells were suspended in SB, and the fluorescence intensities of the cells were measured using a flow cytometer FACS CANTO II (manufactured by Becton Dickinson). The results obtained are shown in FIG. 2. As the negative control, an anti-AVM antibody was used.

As shown in FIG. 2, MOG01 antibody, MOG09 antibody, MOG14 antibody and iMOG-3Rim1-S32 antibody, which are anti-MOG antibodies, all showed binding activity to rMOG/HEK293F cells and mMOG/HEK293F cells. Moreover, MOG01 antibody and MOG14 antibody both showed binding activity also to cMOG/HEK293 cells and hMOG/HEK293 cells.

Accordingly, it was elucidated that anti-MOG human IgG antibodies, MOG01 and MOG14 recognize and bind to not only rat and mouse MOG but also cynomolgus monkey and human MOG.

[Example 8] Evaluation of Affinities of Anti-MOG Antibodies to MOG by Surface Plasmon Resonance Detection The affinities of the anti-MOG antibodies, MOG01 antibody, MOG09 antibody, MOG14 antibody and iMOG-3Rim1-S32 antibody obtained in Example 6 to rat MOG were measured using Biacore T-100 (GE Healthcare).

The antibodies were immobilized on CM5 sensor chips using a Human antibody Capture kit, and the binding abilities were evaluated using rMOG-GST produced in Example 4 as an analyte. The obtained sensorgrams were analyzed with BIA evaluation software, and the dissociation constants (KD values) were thus calculated. The results obtained are shown in Table 3.

TABLE 3

|  | ka (1/Ms) | kd (1/s) | KD (M) |
| --- | --- | --- | --- |
| MOG01 | 1.4E+05 | 9.5E−04 | 6.6E−09 |
| MOG09 | 9.0E+03 | 1.9E−07 | 2.1E−11 |
| MOG14 | 4.7E+03 | 1.9E−04 | 4.0E−08 |
| iMOG-3Rim1-S32 | 1.4E+06 | 8.4E−04 | 6.2E−10 |

As shown in Table 3, the dissociation constants (KD values) of the anti-MOG antibodies were $2.1 \times 10^{-11}$ (M) to $4.0 \times 10^{-8}$ (M), and it was elucidated that all the antibodies show excellent affinity. The dissociation rate constant kd of MOG09 antibody was outside the measurement range of the device, and the KD value could not be determined as a unique value.

[Example 9] Evaluation of Rat Brain Migration Properties of Anti-MOG Antibodies

An antibody was administered to the tail vein (i.v.) of a rat, and then blood was collected from the tail vein. On the same day of the blood collection, the brain tissues were collected after whole body perfusion under anesthesia with pentobarbital, and the weight was measured. A buffer solution was added to the collected brain tissues, and the brain tissues were homogenized. After centrifugation, the antibody solution eluted in the supernatant was collected. While the volume was measured, the antibody concentration was measured with AlphaLISA (manufactured by PerkinElmer, Inc.). The antibody amount per unit brain weight was calculated.

With respect to the anti-MOG antibodies, MOG01 antibody, MOG14 antibody and iMOG-3Rim1-S32 antibody and the anti-AVM antibody as a negative control, MOG01 antibody and MOG14 antibody were administered at an amount of 1 mg/kg body weight, and iMOG-3Rim1-S32 antibody was administered at an amount of 5 mg/kg body weight. The antibody concentrations in the serum and the antibody amounts per unit brain weight in the brain tissues four days after the administration of the antibodies are shown in FIGS. 3A and 3B.

As shown in FIGS. 3A and 3B, it was shown that the antibody concentrations in the serum of all the anti-MOG antibodies did not change as compared to that of the negative control (AVM) but that the antibody amounts in the brain increased to 5-10 times.

With respect to the anti-MOG antibody, MOG01 antibody, the anti-transferrin receptor antibody, OX26 antibody and the anti-AVM antibody as a negative control, the antibody concentrations in the serum and the antibody amounts per unit brain weight in the brain tissues four days and 10 days after the administration of the antibodies at an amount of 5 mg/kg body weight are shown in FIGS. 4A and 4B.

As shown in FIG. 4A, the antibody concentration of OX26 antibody in the serum was the lowest of the evaluated antibodies after four days and was equal to or lower than the detection sensitivity after 10 days, and thus the dynamics of the antibody in the blood was poor. The antibody concentration in the serum of MOG01 antibody, which is an anti-MOG antibody, did not change largely four days and 10 days after the administration, and the antibody concentration was equivalent to that of the negative control. This suggests that the half-life of MOG01 antibody in the blood is equivalent to that of the negative control.

Moreover, as shown in FIG. 4B, with respect to the antibody amounts in the brain, the antibody amount of the negative control was the lowest of the evaluated antibodies four days after the administration, and the antibody amount further decreased after 10 days although it was a slight decrease.

The antibody amount of OX26 antibody rapidly decreased between four days and 10 days after the administration, and the antibody amount 10 days after the administration was not higher than that of the negative control. On the other hand, the antibody amount of MOG01 antibody increased between four days and 10 days after the administration. The antibody amount four days after the administration was about 2.5 times the amount of the negative control, and the antibody amount 10 days after the administration was about 10 times the amount of the negative control.

The above results show that, while the anti-MOG antibody, MOG01 antibody shows an antibody concentration equal to that of the negative control in the serum, MOG01 antibody can increase its amount in the brain to about 2.5 times the amount of the negative control four days after the administration and to about 10 times the amounts of the negative control and OX26 antibody 10 days after the administration.

[Example 10] Evaluation of Affinities of Bispecific Antibodies of MOG to MOG or HER2 Using Flow Cytometer Binding to MOG or HER2 of the bispecific antibody binding to MOG and Her2, Trastuzumab IgG4PE(R409K)_MOG01dscFv antibody, the bispecific antibody binding to MOG and AVM, AVM IgG4PE(R409K)_MOG01dscFv antibody and the antibody binding to AVM, AVM IgG4PE(R409K)_AVM dscFv antibody obtained in Example 6 was evaluated by the fluorescence activated cell sorting (FACS) method according to the following procedures.

The membrane MOG antigen expression vectors produced in Example 5 were introduced to suspension 293 cells using FreeStyle (trademark) 293Expression System (manufactured by Thermo Fisher Scientific Inc.), and the cells were cultured to express the membrane antigens in a transient expression system.

HEK293F cells, rMOG/HEK293F cells, hMOG/HEK293F cells and human breast cancer cell line SK-BR-3 cells were suspended in a Staining Buffer (SB) of PBS containing 0.1% $NaN_3$ and 1% FBS each at a concentration of $5 \times 10^5$ cells/mL and dispensed to a round-bottom 96-well plate (manufactured by Becton Dickinson).

After centrifugation (2000 rpm, 4° C., two minutes), the supernatants were removed, and the antibodies obtained in Example 6 at 10 μg/mL were added to the pellets. After suspending the pellets, the plate was left to stand at ice temperature for 30 minutes. The supernatants were removed after further centrifugation (2000 rpm, 4° C., two minutes), and the pellets were washed with SB. Then, 1 μg/mL RPE fluorescently labeled goat anti-human antibody (manufactured by Southern Bioblot) was added, and the plate was incubated at ice temperature for 30 minutes.

After washing with SB, the cells were suspended in SB, and the fluorescence intensities of the cells were measured with a flow cytometer FACS CANTO II (manufactured by Becton Dickinson). As the negative control, 10 μg/mL anti-AVM antibody was used. The results of the analysis of the affinities to HEK293F cells, rMOG/HEK293F cells and hMOG/HEK293 cells are shown in FIG. 5.

Figure 5:
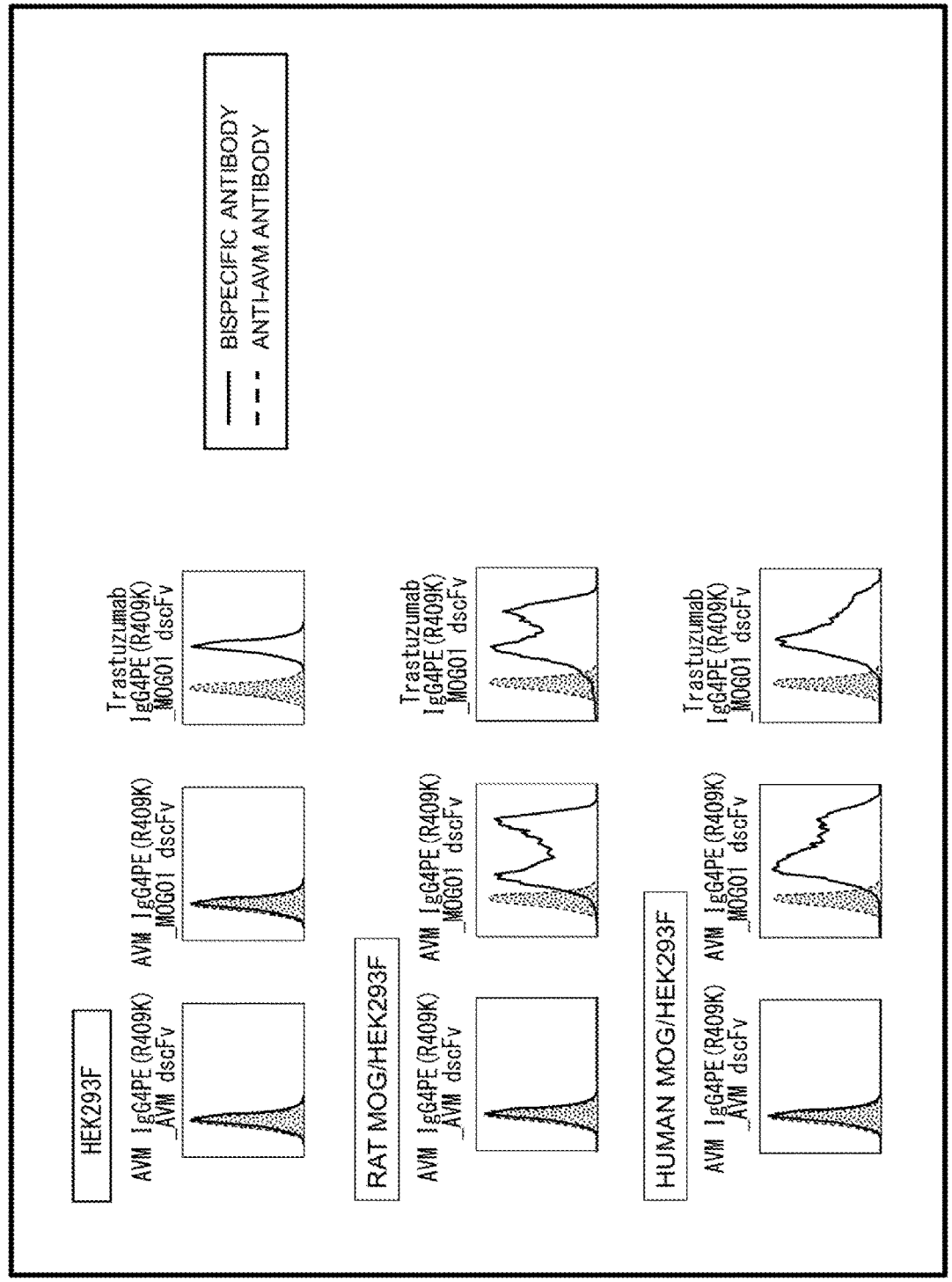
FIG. 5 shows the results of analysis using a flow cytometer of the affinities of bispecific antibodies to HEK293F cells, rat MOG/HEK293F cells or human MOG/HEK293F cells. The vertical axis shows the number of cells, and the horizontal axis shows the fluorescence intensity. A dotted line indicates a histogram of the affinity of an anti-AVM antibody used as a negative control, and a solid line indicates a histogram of the affinity of a bispecific antibody.

From FIG. 5, binding of AVM IgG4PE(R409K)_MOG01dscFv antibody and Trastuzumab IgG4PE(R409K)_MOG01dscFv antibody to rMOG/HEK293F cells and hMOG/HEK293 cells can be observed. Thus, it was shown that the antibodies maintain the affinities to rat MOG and human MOG also in the form of bispecific antibody.

Figure 6:
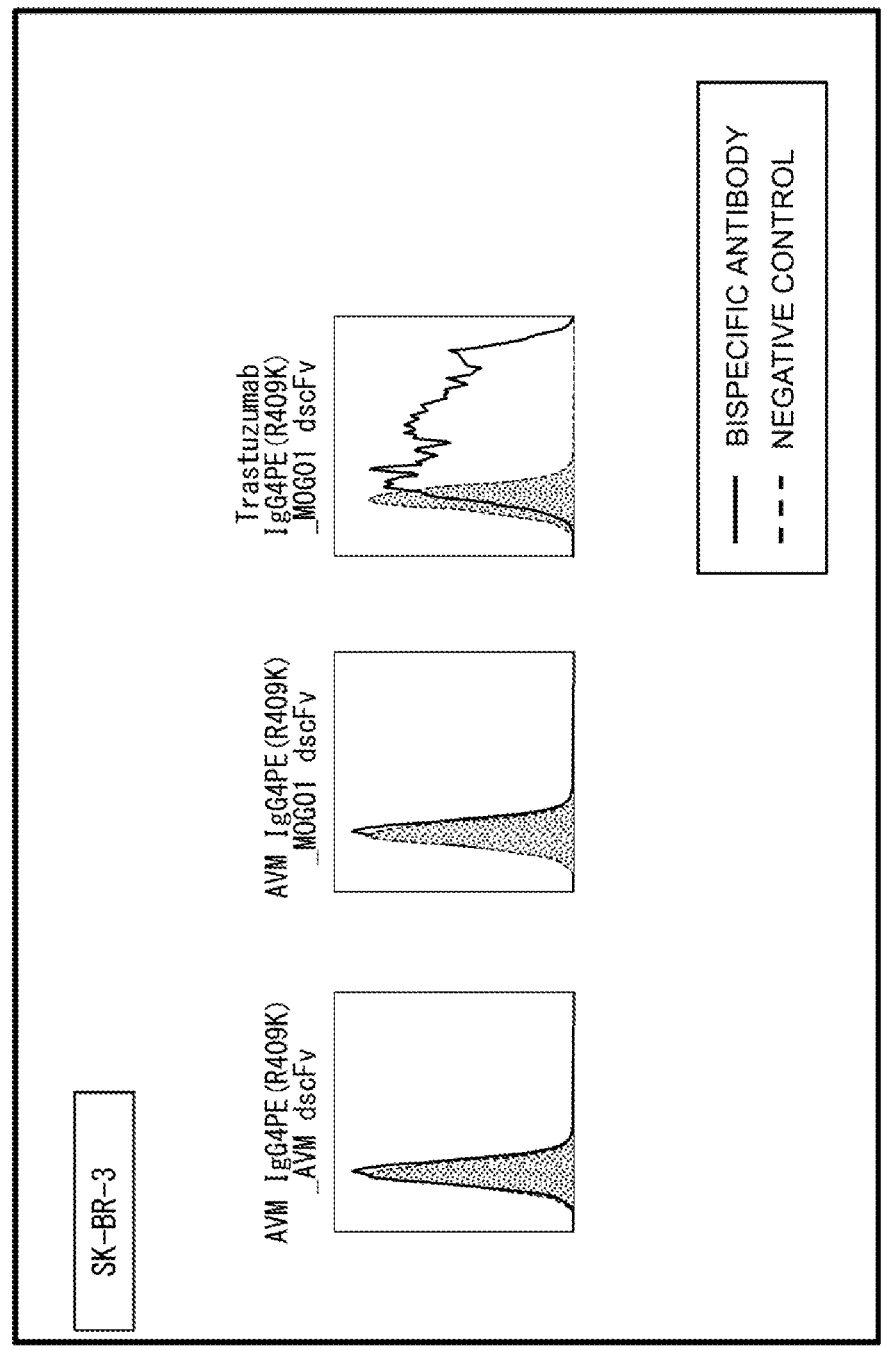
FIG. 6 shows the results of analysis using a flow cytometer of the affinities of bispecific antibodies to human breast cancer cell line, SK-BR-3. The vertical axis shows the number of cells, and the horizontal axis shows the fluorescence intensity. A dotted line indicates a histogram of the affinity of an anti-AVM antibody used as a negative control, and a solid line indicates a histogram of the affinity of a bispecific antibody.

The results of the analysis of the affinities to human breast cancer cell line SK-BR-3 cells are shown in FIG. 6. It is known that HER2 is expressed in the cells.

From FIG. 6, it was shown that Trastuzumab IgG4PE(R409K)_MOG01dscFv antibody maintains the affinity to HER2 also in the form of bispecific antibody.

[Example 11] Evaluation of Affinities of Bispecific Antibodies of MOG to MOG by Surface Plasmon Resonance Detection The affinities of the bispecific antibodies of MOG to MOG were measured by the same method as that of Example 8, and the results are shown in Table 4.

TABLE 4

| Antibody Name | ka (1/Ms) | kd (1/s) | KD (M) |
| --- | --- | --- | --- |
| AVM IgG4PE(R409K)_MOG01 dscFv | 2.3E+04 | 4.6E−03 | 2.0E−07 |
| Trastuzumab IgG4PE(R409K)_MOG01 dscFv | 2.4E+08 | 2.5E+01 | 1.0E−07 |

As shown in Table 4, the dissociation constant (KD value) of the bispecific antibody, AVM IgG4PE(R409K)_MOG01dscFv antibody was $2.0 \times 10^{-7}$ (M), and that of Trastuzumab IgG4PE(R409K)_MOG01dscFv antibody was $1.0 \times 10^{-7}$ (M). It was elucidated that both bispecific antibodies of MOG show excellent affinity.

The association rate constant ka and the dissociation rate constant kd of Trastuzumab IgG4PE(R409K)_MOG01dscFv antibody were outside the measurement ranges of the device, and the KD value could not be determined as a unique value.

[Example 12] Evaluation of Affinity of Bispecific Antibody of MOG to HER2 by Surface Plasmon Resonance Detection The affinity of the bispecific antibody binding to MOG and HER2, Trastuzumab IgG4PE(R409K)_MOG01dscFv antibody to HER2 was measured using Biacore T-100 (GE Healthcare).

The antibody was immobilized on a CM5 sensor chip using a Human antibody Capture kit, and the binding ability of the MOG-Her2 bispecific antibody was evaluated using HER2-GST produced in Example 4 as an analyte. The obtained sensorgram was analyzed with BIA evaluation software, and the dissociation constant (KD value) was thus calculated. The results are shown in Table 5.

TABLE 5

| Antibody Name | ka (1/Ms) | kd (1/s) | KD (M) |
| --- | --- | --- | --- |
| Trastuzumab IgG4PE(R409K)_MOG01 dscFv | 4.7E+04 | 1.8E−04 | 3.7E−09 |

As shown in Table 5, the dissociation constant (KD value) of Trastuzumab IgG4PE(R409K)_MOG01dscFv antibody to HER2 was $3.7 \times 10^{-9}$ (M), and it was elucidated that this is an antibody showing excellent affinity.

[Example 13] Evaluation of Rat Brain Migration Properties of Bispecific Antibodies of MOG The rat brain migration properties of the bispecific antibodies, AVM IgG4PE(R409K)_MOG01dscFv antibody, Trastuzumab IgG4PE(R409K)_MOG01dscFv antibody and AVM IgG4PE(R409K)_AVM dscFv antibody was evaluated by the same method as that of Example 9. The antibody concentrations in the serum and the antibody amounts per unit brain weight in the brain tissues 10 days after the administration of the antibodies at an amount of 5 mg/kg body weight are shown in FIGS. 7A and 7B.

Figure 7A:
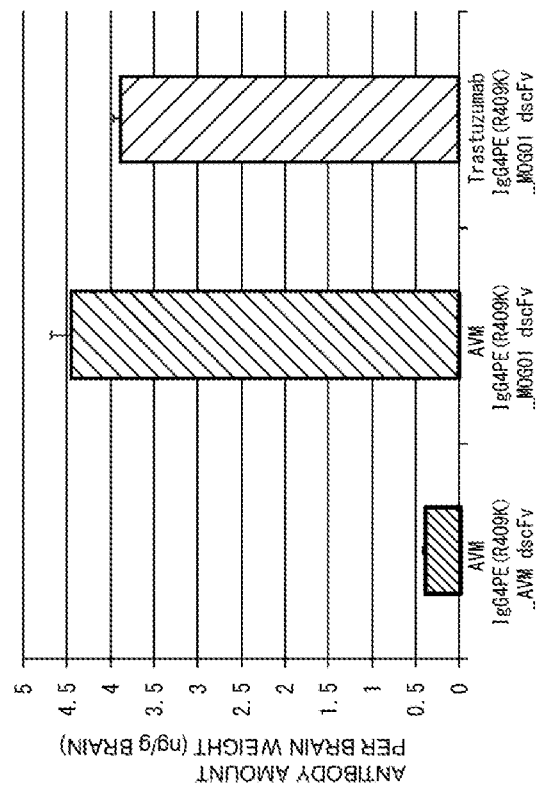
FIGS. 7A and 7B show the results of evaluation of the rat brain migration properties of bispecific antibodies which bind to MOG.

As shown in FIG. 7A, as compared to AVM IgG4PE(R409K)_AVM dscFv antibody, which is the negative control of the bispecific antibodies, the antibody concentrations in the serum of AVM IgG4PE(R409K)_MOG01dscFv antibody and Trastuzumab IgG4PE(R409K)_MOG01dscFv antibody were not different.

Figure 7B:
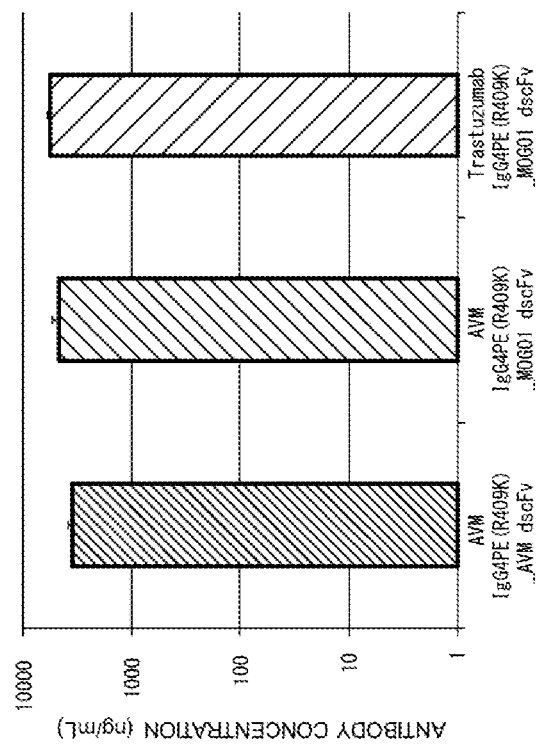

On the other hand, as shown in FIG. 7B, it was shown that, as compared to AVM IgG4PE(R409K)_AVM dscFv antibody, which is the negative control of the bispecific antibodies, the antibody amounts of AVM IgG4PE(R409K)_MOG01dscFv antibody and Trastuzumab IgG4PE(R409K)_MOG01dscFv antibody in the brain increased to about 10 times.

The above results show that while the bispecific antibodies which bind to MOG can increase the antibody amount in the brain to about 10 times the value of the bispecific antibody which does not bind to MOG, the half-lives in the blood do not change.

[Example 14] Evaluation of Mouse Brain Migration Property of Anti-MOG01 Antibody (1) Measurement of Antibody Amount Several days after administering the antibody to the tail vein (i.v.) of a mouse at 35 nmol/kg, blood was collected from the tail vein. On the same day of the blood collection, the brain tissues were collected after whole body perfusion under anesthesia with pentobarbital, and the weight was measured. A buffer solution was added to the collected brain tissues, and the brain tissues were homogenized. After centrifugation, the antibody solution eluted in the supernatant was collected. While the volume was measured, the antibody concentration was measured with AlphaLISA (manufactured by PerkinElmer, Inc.). The antibody amount per unit brain weight was calculated.

With respect to the anti-MOG01 human IgG antibody and an anti-AVM human IgG antibody as the negative control, the antibody concentrations in the serum and the antibody amounts per unit brain weight in the brain tissues 3, 6, 10, 14, 21 and 28 days after the administration of the antibodies are shown in FIGS. 8A and 8B, respectively.

As shown in FIG. 8A, the antibody concentrations of the anti-MOG01 human IgG antibody in the serum were not different from those of the negative control. On the other hand, as shown in FIG. 8B, it was shown that the antibody amount in the brain can be increased to several ten times over 28 days.

(2) Imaging Analysis

The anti-MOG01 human IgG antibody and the anti-AVM human IgG antibody as the negative control were labeled with Alexa FluorR 488 Protein Labeling Kit (manufactured by Molecular Probes). The labeled antibodies are referred to as AF488-MOG01 IgG4PE antibody and AF488-AVM IgG4PE antibody.

Several days after administering the labeled antibodies to the tail veins (i.v.) of mice at 10 mg/kg, Tomato lectin was administered, and the blood was collected from the cheeks of the mice. The brain tissues were collected after the blood collection and after whole body perfusion under anesthesia with pentobarbital, and the fluorescence intensities were measured with IVIS Spectrum (manufactured by PerkinElmer, Inc.). The brain images after six days are shown in FIG. 9A, and the brain images after 14 days are shown in FIG. 9B. The fluorescence amounts in the brain corrected with the fluorescence intensities of the administered antibodies are shown in FIG. 9C.

Figure 9C:
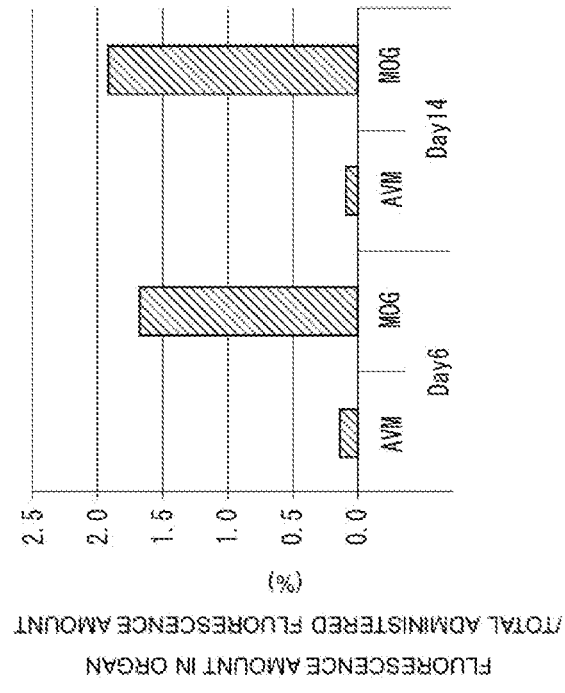
FIGS. 9A to 9C show the results of evaluation of the mouse brain migration property imaging of an anti-MOG01 antibody.
Figure 9A:
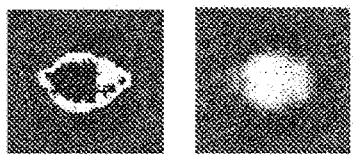
Figure 9B:
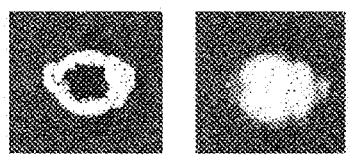
Figure 13A:
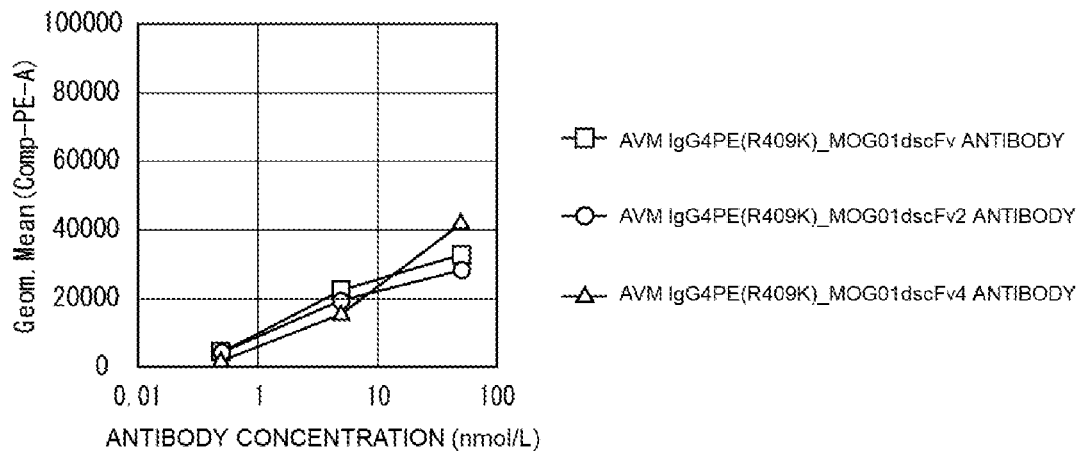
FIGS. 13A and 13B show the results of analysis using a flow cytometer of the affinities of bispecific antibodies to human MOG/L929 cells. The vertical axis shows the average fluorescence intensity, and the horizontal axis shows the antibody concentration.
Figure 13B:
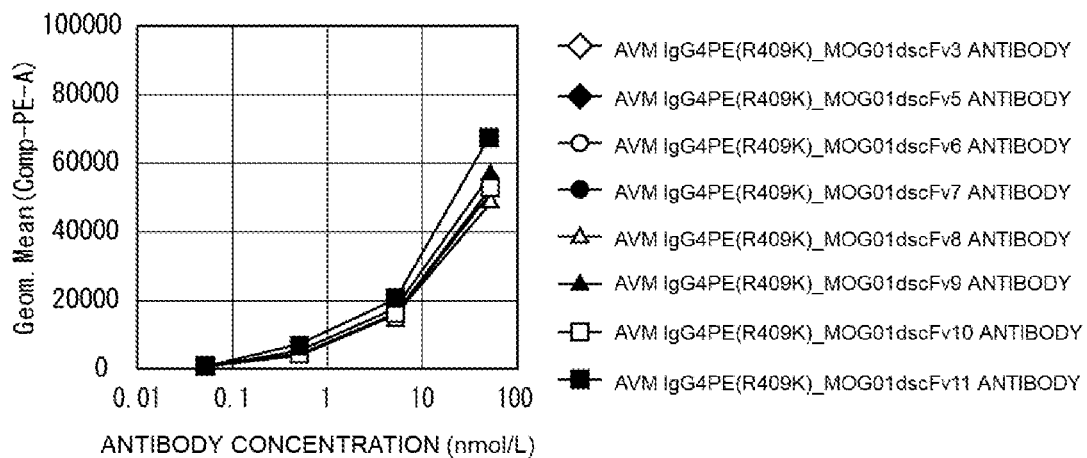

As shown in FIGS. 9A to 9C, it was shown that the anti-MOG01 antibody can increase the antibody amount to several ten times over the entire brain as compared to the negative control.

[Example 15] Construction of Bispecific Antibody Expression Vectors

Vectors expressing bispecific antibodies which have any of the structures described in FIGS. 10A to 10C and FIGS.

11A and 11B and which bind to AVM and MOG were produced by the following method. The names of the bispecific antibodies and the names of the antibody expression vectors are shown in Table 6, and the names of the antibody expression vectors, the nucleotide sequences of the antibodies and the amino acid sequences deduced from the nucleotide sequences are shown in Table 7.

a gene fragment of the MOG01 light chain region and a gene fragment of the MOG01 VH region were amplified by PCR using N5LG4PE_MOG01 as a template. The obtained gene fragments were inserted to pCI vector (manufactured by Promega Corporation), and pCI-MOG01-hLG4PE(R409K/Y349C/T366S/L368A/Y407V)-His tag vector was produced.

TABLE 6

| Name of Bispecific Antibody | Name of Antibody Expression Vector |
|---|---|
| AVM-MOG01 IgG4PE(R409K) antibody | pCI-AVM-hLG4PE(R409K/S354C/T366W)-FLAG tag |
|  | pCI-MOG01-hLG4PE(R409K/Y349C/T366S/L368A/Y407V)-His tag |
| AVM IgG4PE(R409K)_MOG01 Fab antibody | pCI-AVM-hLG4PE(R409K)-linker-MOG01VL-CL |
|  | pCI-MOG01VH-CH |
| AVM IgG4PE(R409K)_MOG01 sscFv antibody | pCI-AVM-hLG4PE(R409K/S354C/T366W)-linker-MOG01scFv-FLAG tag |
|  | pCI-AVM-hLG4PE(R409K/Y349C/T366S/L368A/Y407V)-His tag |
| AVM IgG4PE(R409K)_MOG01dscFv2 antibody | pCI-AVM-hLG4PE(R409K)_MOG01scFv2 |
| AVM IgG4PE(R409K)_MOG01dscFv3 antibody | pCI-AVM-hLG4PE(R409K)_MOG01scFv3 |
| AVM IgG4PE(R409K)_MOG01dscFv4 antibody | pCI-AVM-hLG4PE(R409K)_MOG01scFv4 |
| AVM IgG4PE(R409K)_MOG01dscFv5 antibody | pCI-AVM-hLG4PE(R409K)_MOG01scFv5 |
| AVM IgG4PE(R409K)_MOG01dscFv6 antibody | pCI-AVM-hLG4PE(R409K)_MOG01scFv6 |
| AVM IgG4PE(R409K)_MOG01dscFv7 antibody | pCI-AVM-hLG4PE(R409K)_MOG01scFv7 |
| AVM IgG4PE(R409K)_MOG01dscFv8 antibody | pCI-AVM-hLG4PE(R409K)_MOG01scFv8 |
| AVM IgG4PE(R409K)_MOG01dscFv9 antibody | pCI-AVM-hLG4PE(R409K)_MOG01scFv9 |
| AVM IgG4PE(R409K)_MOG01dscFv10 antibody | pCI-AVM-hLG4PE(R409K)_MOG01scFv10 |
| AVM IgG4PE(R409K)_MOG01dscFv11 antibody | pCI-AVM-hLG4PE(R409K)_MOG01scFv11 |

TABLE 7

| Name of Antibody Expression Vector | Light Chain Antibody Sequence | Nucleotide Sequence of Heavy Chain Antibody Sequence (excluding signal sequence) | Amino Acid Sequence of Heavy Chain Antibody Sequence (excluding signal sequence) |
|---|---|---|---|
| pCI-AVM-hLG4PE(R409K/S354C/T366W)-FLAG tag | AVM | SEQ ID NO: 108 | SEQ ID NO: 109 |
| pCI-MOG01-hLG4PE(R409K/Y349C/T366S/L368A/Y407V)-His tag | MOG01 | SEQ ID NO: 110 | SEQ ID NO: 111 |
| pCI-AVM-hLG4PE(R409K)-linker-MOG01VL-CL | AVM | SEQ ID NO: 112 | SEQ ID NO: 113 |
| pCI-MOG01VH-CH | None | SEQ ID NO: 114 | SEQ ID NO: 115 |
| pCI-AVM-hLG4PE(R409K/S354C/T366W)-linker-MOG01scFv-FLAG | AVM | SEQ ID NO: 116 | SEQ ID NO: 117 |
| pCI-AVM-hLG4PE(R409K/Y349C/T366S/L368A/Y407V)-His tag | AVM | SEQ ID NO: 118 | SEQ ID NO: 119 |
| pCI-AVM-hLG4PE(R409K)_MOG01scFv2 | AVM | SEQ ID NO: 120 | SEQ ID NO: 121 |
| pCI-AVM-hLG4PE(R409K)_MOG01scFv3 | AVM | SEQ ID NO: 122 | SEQ ID NO: 123 |
| pCI-AVM-hLG4PE(R409K)_MOG01scFv4 | AVM | SEQ ID NO: 124 | SEQ ID NO: 125 |
| pCI-AVM-hLG4PE(R409K)_MOG01scFv5 | AVM | SEQ ID NO: 126 | SEQ ID NO: 127 |
| pCI-AVM-hLG4PE(R409K)_MOG01scFv6 | AVM | SEQ ID NO: 128 | SEQ ID NO: 129 |
| pCI-AVM-hLG4PE(R409K)_MOG01scFv7 | AVM | SEQ ID NO: 130 | SEQ ID NO: 131 |
| pCI-AVM-hLG4PE(R409K)_MOG01scFv8 | AVM | SEQ ID NO: 132 | SEQ ID NO: 133 |
| pCI-AVM-hLG4PE(R409K)_MOG01scFv9 | AVM | SEQ ID NO: 134 | SEQ ID NO: 135 |
| pCI-AVM-hLG4PE(R409K)_MOG01scFv10 | AVM | SEQ ID NO: 136 | SEQ ID NO: 137 |
| pCI-AVM-hLG4PE(R409K)_MOG01scFv11 | AVM | SEQ ID NO: 138 | SEQ ID NO: 139 |

(1) Construction of Bispecific Antibody Expression Vectors Related to Structure in FIG. 10A (1-1) Construction of pCI-AVM-hLG4PE(R409K/S354C/T366W)-FLAG Tag Vector A gene fragment of the CH1-Hinge-CH2-CH3(R409K/S354C/T366W) region was amplified by PCR using a synthetic gene as a template and inserted to the NheI-BamHI site of pCI-AVM-hLG4PE(R409K)_AVMscFv, and pCI-AVM-hLG4PE(R409K/S354C/T366W)-FLAG tag vector was produced.

(1-2) Construction of pCI-MOG01-hLG4PE(R409K/Y349C/T366S/L368A/Y407V)-His Tag Vector A gene fragment of the CH1-Hinge-CH2-CH3(R409K/Y349C/T366S/L368A/Y407V)-His tag region was amplified by PCR using a synthetic gene as a template. Moreover, (2) Construction of Bispecific Antibody Expression Vectors Related to Structure in FIG. 10B (2-1) Construction of pCI-AVM-hLG4PE(R409K)-Linker-MOG01VL-CL Vector A gene fragment of the CH1-Hinge-CH2-CH3-linker-MOG01VL-CL region was amplified by PCR using a synthetic gene as a template and inserted to the NheI-BamHI site of pCI-AVM-hLG4PE(R409K)_AVMscFv, and pCI-AVM-hLG4PE(R409K)-linker-MOG01VL-CL vector was produced.

(2-2) Construction of pCI-MOG01VH-CH Vector

A gene fragment of the MOG01VH-CH region was amplified by PCR using a synthetic gene as a template and inserted to pCI vector (manufactured by Promega Corporation), and pCI-MOG01VH-CH vector was produced.

(3) Construction of Bispecific Antibody Expression Vectors Related to Structure in FIG. 10C
(3-1) Construction of pCI-AVM-hLG4PE(R409K/S354C/T366W)-linker-MOG01scFv-FLAG Tag Vector A gene fragment of the CH1-Hinge-CH2-CH3(R409K/S354C/T366W)-linker region was amplified by PCR using a synthetic gene as a template. Moreover, a gene fragment of the linker-MOG01scFv region was amplified by PCR using MOG01scFv as a template. Furthermore, a gene fragment of the linker-MOG01scFv-FLAG tag region was amplified by PCR using the PCR product as a template. The gene fragments of the CH1-Hinge-CH2-CH3(R409K/S354C/T366W)-linker region and the linker-MOG01scFv-FLAG tag region were inserted to the NheI-BamHI site of pCI-AVM-hLG4PE(R409K)_AVM scFv, and pCI-AVM-hLG4PE(R409K/S354C/T366W)-linker-MOG01scFv-FLAG tag vector was produced.

In the same manner, pCI-AVM-hLG4PE(R409K)_MOG01scFv3 vector, pCI-AVM-hLG4PE(R409K)_MOG01scFv4 vector, pCI-AVM-hLG4PE(R409K)_MOG01scFv5 vector, pCI-AVM-hLG4PE(R409K)_MOG01scFv6 vector, pCI-AVM-hLG4PE(R409K)_MOG01scFv7 vector, pCI-AVM-hLG4PE(R409K)_MOG01scFv8 vector, pCI-AVM-hLG4PE(R409K)_MOG01scFv9 vector, pCI-AVM-hLG4PE(R409K)_MOG01scFv10 vector and pCI-AVM-hLG4PE(R409K)_MOG01scFv11 vector were produced.

(5) Construction of Vectors Expressing Antibodies as Negative Controls

The antibodies as the negative controls were produced by the following method. The names of the antibodies and the names of the antibody expression vectors are shown in Table 8, and the names of the antibody expression vectors, the nucleotide sequences of the antibodies and the amino acid sequences deduced from the nucleotide sequences are shown in Table 9.

TABLE 8

| Name of Negative Control Antibody | Name of Antibody Expression Vector |
| --- | --- |
| AVM IgG4PE(R409K) antibody | pCI-AVM-hLG4PE(R409K) |
| AVM IgG4PE(R409K)_AVM Fab antibody | pCI-AVM-hLG4PE(R409K)-linker-AVMVL-CL<br>pCI-AVMVH-CH |
| AVM IgG4PE(R409K)_AVMscFv antibody | pCI-AVM-hLG4PE(R409K/S354C/T366W)-linker-AVMscFv-FLAG tag<br>pCI-AVM-hLG4PE(R409K/Y349C/T366S/L368A/Y407V)-His tag |
| AVM IgG4PE(R409K)_AVMdscFv3 antibody | pCI-AVM-hLG4PE(R409K)_AVMscFv3 |
| AVM IgG4PE(R409K)_AVMdscFv5 antibody | pCI-AVM-hLG4PE(R409K)_AVMscFv5 |

TABLE 9

| Name of Antibody Expression Vector | Light Chain Antibody Sequence | Nucleotide Sequence of Heavy Chain Antibody Sequence (excluding signal sequence) | Amino Acid Sequence of Heavy Chain Antibody Sequence (excluding signal sequence) |
| --- | --- | --- | --- |
| pCI-AVM-hLG4PE(R409K)-linker-AVMVL-CL | AVM | SEQ ID NO: 140 | SEQ ID NO: 141 |
| pCI-AVMVH-CH | None | SEQ ID NO: 142 | SEQ ID NO: 143 |
| pCI-AVM-hLG4PE(R409K/S354C/T366W)-linker-AVMscFv-FLAG tag | AVM | SEQ ID NO: 144 | SEQ ID NO: 145 |
| pCI-AVM-hLG4PE(R409K)_AVMscFv3 | AVM | SEQ ID NO: 146 | SEQ ID NO: 147 |
| pCI-AVM-hLG4PE(R409K)_AVMscFv5 | AVM | SEQ ID NO: 148 | SEQ ID NO: 149 |

(3-2) Construction of pCI-AVM-hLG4PE(R409K/Y349C/T366 S/L368A/Y407V)-His Tag Vector A gene fragment of the CH1-Hinge-CH2-CH3(R409K/Y349C/T366S/L368A/Y407V)-His tag region was amplified by PCR using a synthetic gene as a template and inserted to the NheI-BamHI site of pCI-AVM-hLG4PE(R409K)_AVMscFv, and pCI-AVM-hLG4PE(R409K/Y349C/T366 S/L368A/Y407V)-His tag vector was produced.

(4) Construction of Vectors Expressing Bispecific Antibodies Having Structures in FIGS. 11A and 11B
(4-1) Construction of pCI-AVM-hLG4PE(R409K)_MOG01scFv Vector A gene fragment of the CH1-Hinge-CH2-CH3-linker region was amplified by PCR using a synthetic gene as a template. Moreover, a gene fragment of the VH region and the VL region of MOG01 was amplified by PCR using MOG01scFv as a template. The gene fragment of the CH1-Hinge-CH2-CH3-linker region and the gene fragment of the VH region and the VL region of MOG01 were inserted to the NheI-BamHI site of pCI-AVM-hLG4PE(R409K)_AVMscFv, and pCI-AVM-hLG4PE(R409K)_MOG01scFv2 vector was produced.

(2-1) Production of pCI-AVM-hLG4PE(R409K) Vector

A gene fragment of the VH region, the VL region and the antibody constant region of AVM was amplified by PCR using a synthetic gene as a template and inserted to pCI vector (manufactured by Promega Corporation), and pCI-AVM-hLG4PE(R409K) vector was produced.

(2-2) Production of pCI-AVM-hLG4PE(R409K)-linker-AVMVL-CL Vector

A gene fragment of the CH1-Hinge-CH2-CH3-linker-AVMVL-CL region was amplified by PCR using a synthetic gene as a template and inserted to the NheI-BamHI site of pCI-AVM-hLG4PE(R409K)_AVM scFv, and pCI-AVM-hLG4PE(R409K)-linker-AVMVL-CL vector was produced.

(2-3) Construction of pCI-AVMVH-CH Vector

A gene fragment of the AVMVH-CH region was amplified by PCR using a synthetic gene as a template and inserted to pCI vector (manufactured by Promega Corporation), and pCI-AVMVH-CH vector was produced.

(2-4) Construction of pCI-AVM-hLG4PE(R409K/S354C/T366W)-Linker-AVMscFv-FLAG Tag Vector A gene fragment of the CH1-Hinge-CH2-CH3(R409K/S354C/T366W)-linker region was amplified by PCR using a synthetic gene as a template. Moreover, a gene fragment of the linker-AVMscFv-FLAG tag region was amplified by PCR using N5LG4PE_AVM as a template. The gene fragments of the CH1-Hinge-CH2-CH3(R409K/S354C/T366W)-linker region and the linker-AVMscFv-FLAG tag region were inserted to the NheI-BamHI site of pCI-AVM-hLG4PE(R409K)_AVM scFv, and pCI-AVM-hLG4PE(R409K/S354C/T366W)-linker-AVMscFv-FLAG tag vector was produced.

(2-5) Construction of pCI-AVM-hLG4PE(R409K)_AVMscFv Vector

A gene fragment of the CH1-Hinge-CH2-CH3-linker region was amplified by PCR using a synthetic gene as a template. Moreover, a gene fragment of the VH region and the VL region of AVM was amplified by PCR using N5LG4PE_AVM as a template. The gene fragment of the CH1-Hinge-CH2-CH3-linker region and the gene fragment of the VH region and the VL region of AVM were inserted to the NheI-BamHI site of pCI-AVM-hLG4PE(R409K)_AVMscFv, and pCI-AVM-hLG4PE(R409K)_AVMscFv3 vector and pCI-AVM-hLG4PE(R409K)_AVMscFv5 vector were produced.

[Example 16] Preparation of Bispecific Antibodies

By the method described in Example 6, AVM IgG4PE(R409K)_MOG01 Fab antibody, AVM IgG4PE(R409K)_MOG01dscFv2 antibody, AVM IgG4PE(R409K)_MOG01dscFv3 antibody, AVM IgG4PE(R409K)_MOG01dscFv4 antibody, AVM IgG4PE(R409K)_MOG01dscFv5 antibody, AVM IgG4PE(R409K)_MOG01dscFv6 antibody, AVM IgG4PE(R409K)_MOG01dscFv7 antibody, AVM IgG4PE(R409K)_MOG01dscFv8 antibody, AVM IgG4PE(R409K)_MOG01dscFv9 antibody, AVM IgG4PE(R409K)_MOG01dscFv10 antibody, AVM IgG4PE(R409K)_MOG01dscFv11 antibody, AVM IgG4PE(R409K)_AVM Fab antibody, AVM IgG4PE(R409K)_AVMdscFv3 antibody and AVM IgG4PE(R409K)_AVMdscFv5 antibody were prepared.

AVM-MOG01 IgG4PE(R409K) antibody, AVM IgG4PE(R409K)_MOG01sscFv antibody and AVM IgG4PE(R409K)_AVMsscFv antibody were prepared by the method described below. The antibody expression plasmid vectors were introduced to suspension 293 cells using Expi293 (trademark) Expression System (manufactured by Thermo Fisher Scientific Inc.), and the cells were cultured to express the antibodies in a transient expression system.

The culture supernatants were collected four days after the introduction of the vectors and filtered through a membrane filter having a pore size of 0.22 µm (manufactured by Millipore Corporation). The proteins in the culture supernatants were affinity-purified with His tag using Ni Sepharose resin (manufactured by GE Healthcare BioSciences). A 20 mM Imidazole-phosphate buffer solution was used as a washing solution.

The antibodies adsorbed on the Ni Sepharose resin were eluted with a 500 mM Imidazole-phosphate buffer solution. Next, the solvents of the eluates were replaced with PBS by ultrafiltration using VIVASPIN (manufactured by Sartrius stealin) and a NAP column (manufactured by GE Healthcare BioSciences).

The proteins after the His tag purification were affinity-purified using FLAG antibody affinity gel (manufactured by Sigma-Aldrich Co. LLC.). A phosphate buffer solution was used as a washing solution. The antibodies adsorbed on the FLAG antibody affinity gel were eluted with 20 mM sodium citrate and 50 mM NaCl buffer solution (pH 3.4) and collected in tubes containing 1 M Tris-HCl Buffer Solution (pH 8.0).

Next, the solvents of the eluates were replaced with PBS by ultrafiltration using VIVASPIN (manufactured by Sartrius stealin) and a NAP column (manufactured by GE Healthcare BioSciences), and then filtration sterilization with a membrane filter having a pore size of 0.22 µm (Millex-GV, manufactured by Millipore Corporation) was conducted. The absorbances of the antibody solutions at 280 nm were measured, and the concentrations of the purified antibodies were calculated.

[Example 17] Evaluation of Affinities of Bispecific Antibodies to MOG Using Flow Cytometer Binding of the bispecific antibodies and the negative control antibodies obtained in Example 6 and Example 16 to MOG was evaluated by the fluorescence activated cell sorting (FACS) method according to the following procedures.

pEF6_hMOG obtained in Example 5 was introduced to mouse connective tissue-derived fibroblast L929 cells [American Type Culture Collection (ATCC) No.: CCL-1] using HilyMax (manufactured by Dojindo Laboratories). The gene-transfected cells were selected using an antibiotic substance, Blasticidin (manufactured by Invitrogen) and then cloned by the limiting dilution method. Using the L929 cells expressing hMOG on the cell surface (abbreviated as hMOG/L929 below), the reactivities of the bispecific antibodies were analyzed by the method described below.

The hMOG/L929 cells were suspended in a Staining Buffer (SB) of PBS containing 0.1% $NaN_3$ and 1% FBS and dispensed to a round-bottom 96-well plate (manufactured by Becton Dickinson). After centrifugation (2000 rpm, 4° C., two minutes), the supernatants were removed, and the MOG01 bispecific antibodies obtained in Example 6 and Example 16 were added to the pellets. After suspending the pellets, the plate was left to stand at ice temperature for 30 minutes. The supernatants were removed after further centrifugation (2000 rpm, 4° C., two minutes), and the pellets were washed with SB. Then, 1 µg/mL RPE fluorescently labeled goat anti-human antibody (manufactured by Southern Biotech) was added, and the plate was incubated at ice temperature for 30 minutes. After washing with SB, the cells were suspended in SB, and the fluorescence intensities of the cells were measured with a flow cytometer FACS CANTO II (manufactured by Becton Dickinson). The results are shown in FIGS. 12A to 12C and FIGS. 13A and 13B.

As shown in FIGS. 12A to 12C and FIGS. 13A and 13B, it was confirmed that all the bispecific antibodies have affinity to MOG. In particular, it was elucidated that the affinities of AVM IgG4PE(R409K)_MOG01Fab antibody [FIG. 10B and FIG. 12C], AVM IgG4PE(R409K)_MOG01dscFv3 antibody, AVM IgG4PE(R409K)_MOG01dscFv5 antibody, AVM IgG4PE(R409K)_MOG01dscFv6 antibody, AVM IgG4PE(R409K)_MOG01dscFv7 antibody, AVM IgG4PE(R409K)_MOG01dscFv8 antibody, AVM IgG4PE(R409K)_MOG01dscFv9 antibody, AVM IgG4PE(R409K)_MOG01dscFv10 antibody and AVM IgG4PE(R409K)_MOG01dscFv11 antibody [FIG. 11B and FIG. 13B] are high.

[Example 18] Evaluation of Affinities of Bispecific Antibodies to MOG by Surface Plasmon Resonance Detection Binding of the bispecific antibodies obtained in Example 6 and Example 16 to MOG was evaluated by the same method as that of Example 8. The results obtained are shown in Table 10 and Table 11.

TABLE 10

| Antibody Name | ka (1/Ms) | kd (1/s) | KD (M) |
|---|---|---|---|
| AVM-MOG01 IgG4PE(R409K) antibody | 1.3E+05 | 1.6E−03 | 1.2E−08 |
| AVM IgG4PE(R409K)_MOG01sscFv antibody | 5.1E+04 | 1.0E−02 | 2.0E−07 |
| AVM IgG4PE(R409K)_MOG01 Fab antibody | 1.0E+05 | 3.5E−03 | 3.4E−08 |

TABLE 11

| Antibody Name | ka (1/Ms) | kd (1/s) | KD (M) |
|---|---|---|---|
| AVM IgG4PE(R409K)_MOG01dscFv antibody | 2.4E+04 | 4.9E−03 | 2.0E−07 |
| AVM IgG4PE(R409K)_MOG01dscFv3 antibody | 1.7E+05 | 2.2E−03 | 1.3E−08 |
| AVM IgG4PE(R409K)_MOG01dscFv5 antibody | 2.0E+05 | 4.8E−03 | 2.4E−08 |

As shown in Table 10 and Table 11, the dissociation constants (KD values) of the bispecific antibodies of MOG were $1.2 \times 10^{-8}$ (M) to $2.0 \times 10^{-7}$ (M), and it was elucidated that all the antibodies show excellent affinity.

In particular, it was elucidated that the affinities of AVM-MOG01 IgG4PE(R409K) antibody [FIG. 10A], AVM IgG4PE(R409K)_MOG01Fab antibody [FIG. 10B], AVM IgG4PE(R409K)_MOG01dscFv3 antibody and AVM IgG4PE(R409K)_MOG01dscFv5 antibody [FIG. 11B] are high.

[Example 19] Evaluation of Mouse Brain Migration Properties of Bispecific Antibodies The mouse brain migration properties of the bispecific antibodies and the negative control antibodies obtained in Example 6 and Example 16 were evaluated by the method of Example 14.

AVM-MOG01 IgG4PE(R409K) antibody, AVM IgG4PE (R409K)_MOG01sscFv antibody and AVM IgG4PE (R409K)_MOG01 Fab antibody were administered at 5 mg/kg, and the antibody concentrations in the serum and the antibody amounts per unit brain weight in the brain tissues after 10 days are shown in FIG. 14A to FIG. 16B.

Figure 14A:
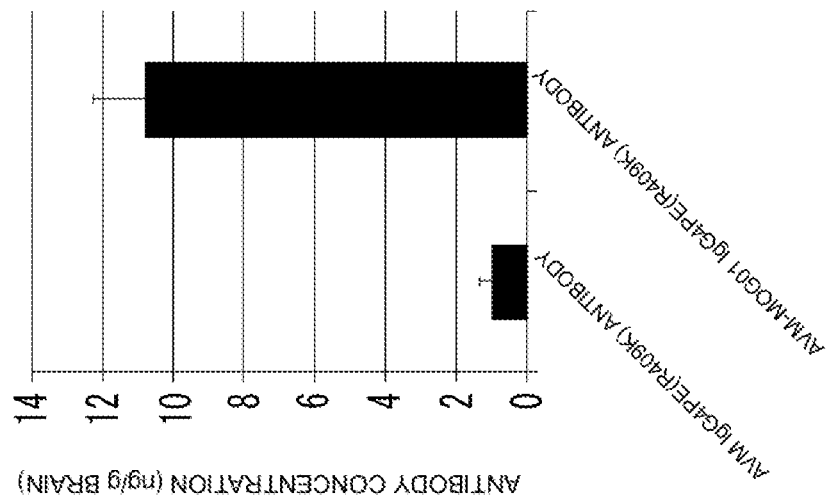
FIGS. 14A and 14B show the results of evaluation of the mouse brain migration properties of bispecific antibodies. The vertical axis shows the antibody concentration, and the horizontal axis shows the bispecific antibodies used.
Figure 14B:
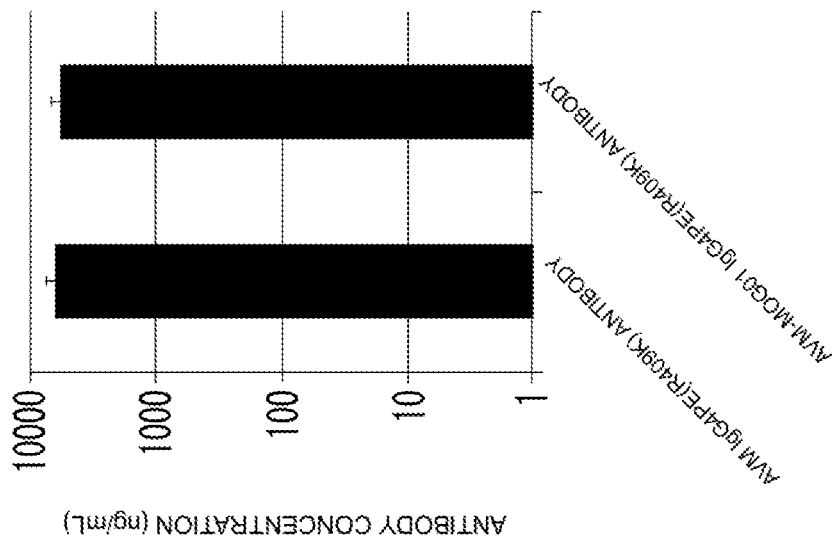
Figure 15A:
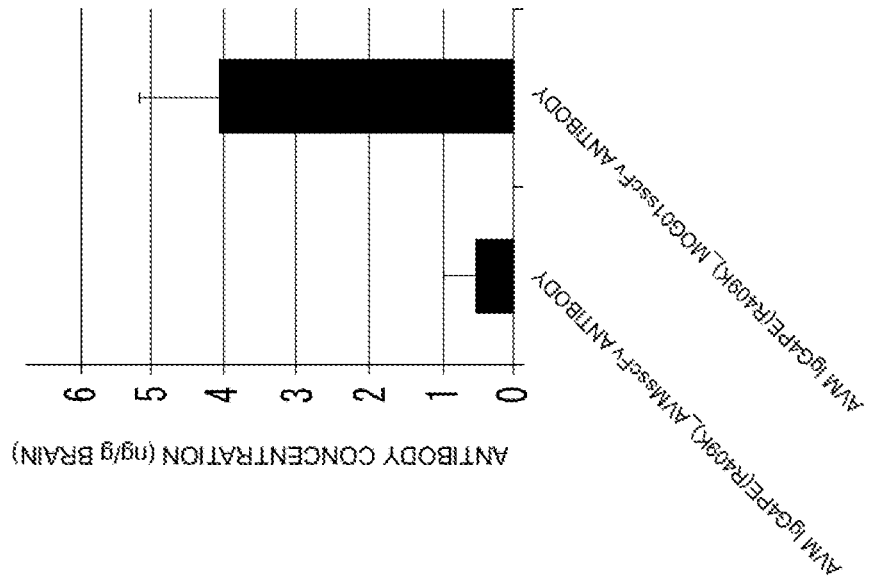
FIGS. 15A and 15B show the results of evaluation of the mouse brain migration properties of bispecific antibodies. The vertical axis shows the antibody concentration, and the horizontal axis shows the bispecific antibodies used.
Figure 15B:
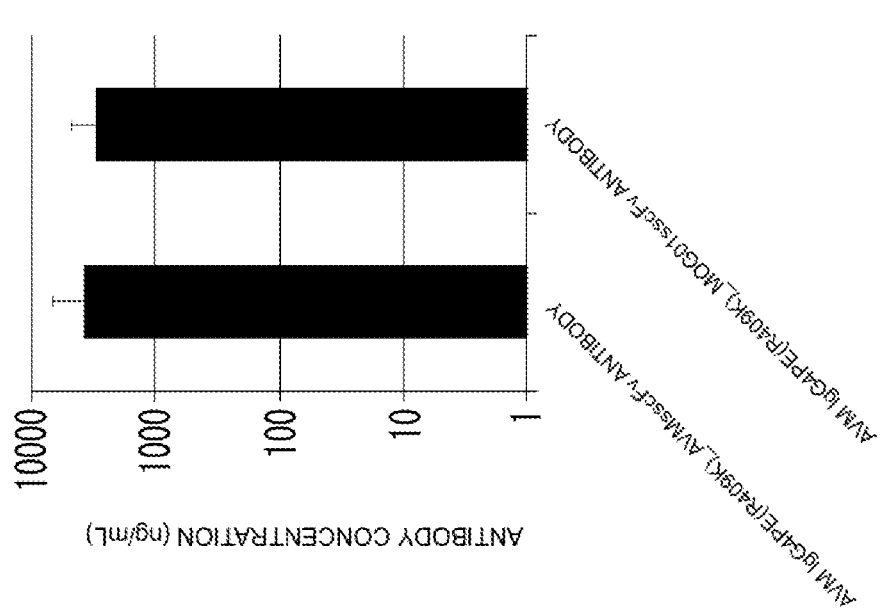

As shown in FIG. 14A, FIG. 15A and FIG. 16A, the antibody concentrations of all the MOG01 modified antibodies in the serum were not different from those of the negative controls. On the other hand, as shown in FIG. 14B, FIG. 15B and FIG. 16B, it was shown that the antibody amounts in the brain increase to about eight times in the case of AVM-MOG01 IgG4PE(R409K) antibody, about 12 times in the case of AVM IgG4PE(R409K)_MOG01sscFv antibody and about 30 times in the case of AVM IgG4PE (R409K)_MOG01 Fab antibody as compared to those of the negative controls.

The above results show that while the bispecific antibodies which bind to MOG can increase the antibody amount in the brain as compared to those of the negative control antibodies which do not bind to MOG, the half-lives in the blood do not change.

AVM IgG4PE(R409K)_MOG01dscFv antibody, AVM IgG4PE(R409K)_MOG01dscFv3 antibody and AVM IgG4PE(R409K)_MOG01dscFv5 antibody were administered at 5 mg/kg, and the antibody concentrations in the serum and the antibody amounts per unit brain weight in the brain tissues after 10 days and after 28 days are shown in FIGS. 17A to 17D.

As shown in FIGS. 17A and 17C, the antibody concentrations of all the bispecific antibodies in the serum were not different from those of the negative controls. On the other hand, as shown in FIGS. 17B and 17D, it was shown that the antibody amounts in the brain of AVM IgG4PE(R409K)_ MOG01dscFv antibody, AVM IgG4PE(R409K)_ MOG01dscFv3 antibody and AVM IgG4PE(R409K)_ MOG01dscFv5 antibody can be increased to several ten times over 28 days. Moreover, as shown in FIG. 17D, when the antibody amounts in the brain were high after 28 days, the affinities of the bispecific antibodies to MOG were also high (Table 11). It was elucidated that there is a correlation between the MOG binding activity and the antibody amount in the brain.

[Example 20] Acquisition of Novel MOG Antibodies Showing Higher Affinity to MOG than Anti-MOG01 Antibody (1) Production of Extracellular Domain Proteins of Soluble Human MOG Antigen and Soluble Mouse MOG Antigen to which FLAG-Fc is Bound Plasmid vectors, INPEP4_hMOG-FLAG-Fc and INPEP4_mMOG-FLAG-Fc, which each express an extracellular domain protein of MOG to which FLAG-Fc was added at the C-terminus, as soluble antigens of human MOG and mouse MOG were produced by the method described in Example 4. The nucleotide sequence of hMOG-FLAG-Fc is shown in SEQ ID NO: 100, and the amino acid sequence deduced from the nucleotide sequence is shown in SEQ ID NO: 101. The nucleotide sequence of mMOG-FLAG-Fc is shown in SEQ ID NO: 102, and the amino acid sequence deduced from the nucleotide sequence is shown in SEQ ID NO: 103. The extracellular domain proteins of MOG to which FLAG-Fc was bound were obtained by transiently expressing and purifying the proteins by the method described in Example 4.

(2) Production of Extracellular Domain Proteins of MOG to which GST is Bound

Plasmid vectors, N5_hMOG-GST and N5_mMOG-GST, which each express an extracellular domain protein of MOG to which GST was added at the C-terminus, as soluble antigens of human MOG and mouse MOG were produced by the method described in Example 4. The nucleotide sequence of hMOG-GST is shown in SEQ ID NO: 104, and the amino acid sequence deduced from the nucleotide sequence is shown in SEQ ID NO: 105. The nucleotide sequence of mMOG-GST is shown in SEQ ID NO: 106, and the amino acid sequence deduced from the nucleotide sequence is shown in SEQ ID NO: 107. The extracellular domain proteins of MOG to which GST was bound were obtained by transiently expressing and purifying the proteins by the method described in Example 4.

(3) Acquisition of Anti-MOG Antibodies from Human Antibody-Producing Mice hMOG-GST and mMOG-GST were mixed with pertussis vaccine and Alumgel and intraperitoneally or intradermally administered to human antibody-producing mice (Ishida & Lonberg, IBC's 11th Antibody Engineering, Abstract 2000; Ishida, I. et al., Cloning & Stem Cells 4, 85-96 (2002) and Ishida Isao (2002) Experimental Medicine 20, 6, 846-851).

After the first immunization, the mice were immunized with hMOG-GST and mMOG-GST three times. The individuals immunized by intraperitoneal administration were dissected four days after the final immunization, and the spleens were taken. After removing the red blood cells using a reagent for removing red blood cells (manufactured by Sigma Co. LLC.), the spleens were frozen with CELL-BANKER 1 (manufactured by Nippon Zenyaku Kogyo Co., Ltd.). The individuals immunized by intradermal administration were dissected, and the axillary lymph nodes were taken. After removing the red blood cells using a reagent for removing red blood cells, the axillary lymph nodes were frozen with CELLBANKER 1. RNAs were extracted from the obtained spleen cells and the cells of the axillary lymph nodes using an RNeasy Plus Mini kit (manufactured by QIAGEN), and cDNAs were synthesized with a SMARTer RACE cDNA amplification kit (manufactured by Clontech Laboratories, Inc.). Human antibody-producing mouse-derived phage libraries were produced using the synthesized cDNAs by the method described in Example 1.

Anti-human MOG monoclonal antibodies were obtained using the human antibody-producing mouse-derived phage libraries by the phage display method. The phage display method and cloning ELISA were conducted using hMOG-FLAG_Fc and mMOG-FLAG_Fc by the methods described in Example 1.

The sequences of the clones which bound to hMOG-FLAG_Fc, mMOG-FLAG_Fc and hMOG/Expi293F cells were analyzed, and anti-MOG antibody phagemid vectors, pCANTAB_MOG301, pCANTAB_MOG303, pCANTAB_MOG307, pCANTAB_MOG310, pCANTAB_MOG312, pCANTAB_MOG326, pCANTAB_MOG329, pCANTAB_MOG446, pCANTAB_MOG456 and pCANTAB_MOG473 were obtained.

In the following paragraphs, the names of the anti-MOG scFv antibodies displayed by the phages expressed using pCANTAB_MOG301, pCANTAB_MOG303, pCANTAB_MOG307, pCANTAB_MOG310, pCANTAB_MOG312, pCANTAB_MOG326, pCANTAB_MOG329, pCANTAB_MOG446, pCANTAB_MOG456 and pCANTAB_MOG473 are referred to as MOG301 antibody, MOG303 antibody, MOG307 antibody, MOG310 antibody, MOG312 antibody, MOG326 antibody, MOG329 antibody, MOG446 antibody, MOG456 antibody and MOG473 antibody, respectively.

The nucleotide sequences which encode VH or VL of the anti-MOG antibodies and the amino acid sequences deduced from the nucleotide sequences are shown in Table 12.

TABLE 12

| Clone Name | MOG301 | MOG303 | MOG307 | MOG310 | MOG312 | MOG326 | MOG329 | MOG446 | MOG456 | MOG473 |
|---|---|---|---|---|---|---|---|---|---|---|
| Nucleotide sequence encoding VH (excluding signal sequence) | SEQ ID NO: 151 | SEQ ID NO: 161 | SEQ ID NO: 171 | SEQ ID NO: 181 | SEQ ID NO: 191 | SEQ ID NO: 201 | SEQ ID NO: 211 | SEQ ID NO: 221 | SEQ ID NO: 231 | SEQ ID NO: 241 |
| Amino acid sequence of VH (excluding signal sequence) | SEQ ID NO: 152 | SEQ ID NO: 162 | SEQ ID NO: 172 | SEQ ID NO: 182 | SEQ ID NO: 192 | SEQ ID NO: 202 | SEQ ID NO: 212 | SEQ ID NO: 222 | SEQ ID NO: 232 | SEQ ID NO: 242 |
| Amino acid sequence of HCDR1 | SEQ ID NO: 153 | SEQ ID NO: 163 | SEQ ID NO: 173 | SEQ ID NO: 183 | SEQ ID NO: 193 | SEQ ID NO: 203 | SEQ ID NO: 213 | SEQ ID NO: 223 | SEQ ID NO: 233 | SEQ ID NO: 243 |
| Amino acid sequence of HCDR2 | SEQ ID NO: 154 | SEQ ID NO: 164 | SEQ ID NO: 174 | SEQ ID NO: 184 | SEQ ID NO: 194 | SEQ ID NO: 204 | SEQ ID NO: 214 | SEQ ID NO: 224 | SEQ ID NO: 234 | SEQ ID NO: 244 |
| Amino acid sequence of HCDR3 | SEQ ID NO: 155 | SEQ ID NO: 165 | SEQ ID NO: 175 | SEQ ID NO: 185 | SEQ ID NO: 195 | SEQ ID NO: 205 | SEQ ID NO: 215 | SEQ ID NO: 225 | SEQ ID NO: 235 | SEQ ID NO: 245 |
| Nucleotide sequence encoding VL (excluding signal sequence) | SEQ ID NO: 156 | SEQ ID NO: 166 | SEQ ID NO: 176 | SEQ ID NO: 186 | SEQ ID NO: 196 | SEQ ID NO: 206 | SEQ ID NO: 216 | SEQ ID NO: 226 | SEQ ID NO: 236 | SEQ ID NO: 246 |
| Amino acid sequence of VL (excluding signal sequence) | SEQ ID NO: 157 | SEQ ID NO: 167 | SEQ ID NO: 177 | SEQ ID NO: 187 | SEQ ID NO: 197 | SEQ ID NO: 207 | SEQ ID NO: 217 | SEQ ID NO: 227 | SEQ ID NO: 237 | SEQ ID NO: 247 |
| Amino acid sequence of LCDR1 | SEQ ID NO: 158 | SEQ ID NO: 168 | SEQ ID NO: 178 | SEQ ID NO: 188 | SEQ ID NO: 198 | SEQ ID NO: 208 | SEQ ID NO: 218 | SEQ ID NO: 228 | SEQ ID NO: 238 | SEQ ID NO: 248 |
| Amino acid sequence of LCDR2 | SEQ ID NO: 159 | SEQ ID NO: 169 | SEQ ID NO: 179 | SEQ ID NO: 189 | SEQ ID NO: 199 | SEQ ID NO: 209 | SEQ ID NO: 219 | SEQ ID NO: 229 | SEQ ID NO: 239 | SEQ ID NO: 249 |
| Amino acid sequence of LCDR3 | SEQ ID NO: 160 | SEQ ID NO: 170 | SEQ ID NO: 180 | SEQ ID NO: 190 | SEQ ID NO: 200 | SEQ ID NO: 210 | SEQ ID NO: 220 | SEQ ID NO: 230 | SEQ ID NO: 240 | SEQ ID NO: 250 |

Moreover, clones having similar sequences having homology of 91 to 93% to that of MOG301 antibody (MOG426 and MOG428), clones having similar sequences having homology of 85 to 95% to that of MOG303 antibody (MOG313, MOG314, MOG315, MOG331, MOG357 and MOG476), clones having similar sequences having homology of 97 to 99% to that of MOG307 antibody (MOG323, MOG341, MOG354 and MOG355), clones having similar sequences having homology of 85 to 98% to that of MOG310 antibody (MOG308, MOG316, MOG319, MOG320, MOG338, MOG352, MOG359 and MOG478), a clone having a similar sequence having homology of 85% to that of MOG329 antibody (MOG470) and a clone having a similar sequence having homology of 84% to that of MOG456 antibody (MOG418) were obtained by the phage display method using MOG affinity as an index. Because it was confirmed that these similar clones bind to hMOG-FLAG_Fc, mMOG-FLAG_Fc and hMOG/Expi293F cells, it was elucidated that antibody clones having high homology to the amino acid sequences of the antibody clones are also antibodies having MOG binding activity.

The nucleotide sequences which encode VH or VL of the similar clones and the amino acid sequences deduced from the nucleotide sequences are shown in Table 13, and comparisons of the amino acid sequences of the similar clones are shown in FIG. 18 to FIG. 22B.

The produced anti-MOG antibody expression vectors were prepared by the method described in Example 6. Antibodies were expressed using the anti-MOG antibody expression vectors, pCI-MOG301 scFv-hG4PE(R409K), pCI-MOG303 scFv-hG4PE(R409K), pCI-MOG307 scFv-hG4PE(R409K), pCI-MOG310 scFv-hG4PE(R409K), pCI-MOG312 scFv-hG4PE(R409K), pCI-MOG326 scFv-hG4PE(R409K), pCI-MOG329 scFv-hG4PE(R409K), pCI-MOG446 scFv-hG4PE(R409K), pCI-MOG456 scFv-hG4PE(R409K) and pCI-MOG473 scFv-hG4PE(R409K), and MOG301 scFv-hG4PE(R409K) antibody, MOG303 scFv-hG4PE(R409K) antibody, MOG307 scFv-hG4PE(R409K) antibody, MOG310 scFv-hG4PE(R409K) anti-

TABLE 13

| Name of Representative Clone | Name of Similar Clone | Nucleotide sequence encoding VH (excluding signal sequence) | Amino acid sequence of VH (excluding signal sequence) | Nucleotide sequence encoding VL (excluding signal sequence) | Amino acid sequence of VL (excluding signal sequence) |
|---|---|---|---|---|---|
| MOG301 | MOG426 | SEQ ID NO: 251 | SEQ ID NO: 252 | SEQ ID NO: 253 | SEQ ID NO: 254 |
|  | MOG428 | SEQ ID NO: 255 | SEQ ID NO: 256 | SEQ ID NO: 257 | SEQ ID NO: 258 |
| MOG303 | MOG313 | SEQ ID NO: 259 | SEQ ID NO: 260 | SEQ ID NO: 261 | SEQ ID NO: 262 |
|  | MOG314 | SEQ ID NO: 263 | SEQ ID NO: 264 | SEQ ID NO: 265 | SEQ ID NO: 266 |
|  | MOG315 | SEQ ID NO: 267 | SEQ ID NO: 268 | SEQ ID NO: 269 | SEQ ID NO: 270 |
|  | MOG331 | SEQ ID NO: 271 | SEQ ID NO: 272 | SEQ ID NO: 273 | SEQ ID NO: 274 |
|  | MOG357 | SEQ ID NO: 275 | SEQ ID NO: 276 | SEQ ID NO: 277 | SEQ ID NO: 278 |
|  | MOG476 | SEQ ID NO: 279 | SEQ ID NO: 280 | SEQ ID NO: 281 | SEQ ID NO: 282 |
| MOG307 | MOG323 | SEQ ID NO: 283 | SEQ ID NO: 284 | SEQ ID NO: 285 | SEQ ID NO: 286 |
|  | MOG341 | SEQ ID NO: 287 | SEQ ID NO: 288 | SEQ ID NO: 289 | SEQ ID NO: 290 |
|  | MOG354 | SEQ ID NO: 291 | SEQ ID NO: 292 | SEQ ID NO: 293 | SEQ ID NO: 294 |
|  | MOG355 | SEQ ID NO: 295 | SEQ ID NO: 296 | SEQ ID NO: 297 | SEQ ID NO: 298 |
| MOG310 | MOG308 | SEQ ID NO: 299 | SEQ ID NO: 300 | SEQ ID NO: 301 | SEQ ID NO: 302 |
|  | MOG316 | SEQ ID NO: 303 | SEQ ID NO: 304 | SEQ ID NO: 305 | SEQ ID NO: 306 |
|  | MOG319 | SEQ ID NO: 307 | SEQ ID NO: 308 | SEQ ID NO: 309 | SEQ ID NO: 310 |
|  | MOG320 | SEQ ID NO: 311 | SEQ ID NO: 312 | SEQ ID NO: 313 | SEQ ID NO: 314 |
|  | MOG338 | SEQ ID NO: 315 | SEQ ID NO: 316 | SEQ ID NO: 317 | SEQ ID NO: 318 |
|  | MOG352 | SEQ ID NO: 319 | SEQ ID NO: 320 | SEQ ID NO: 321 | SEQ ID NO: 322 |
|  | MOG359 | SEQ ID NO: 323 | SEQ ID NO: 324 | SEQ ID NO: 325 | SEQ ID NO: 326 |
|  | MOG478 | SEQ ID NO: 327 | SEQ ID NO: 328 | SEQ ID NO: 329 | SEQ ID NO: 330 |
| MOG329 | MOG470 | SEQ ID NO: 331 | SEQ ID NO: 332 | SEQ ID NO: 333 | SEQ ID NO: 334 |
| MOG456 | MOG418 | SEQ ID NO: 335 | SEQ ID NO: 336 | SEQ ID NO: 337 | SEQ ID NO: 338 |

[Example 21] Production of Anti-MOG scFv-Fc Antibodies

A gene fragment of the scFv region was amplified by PCR using a phagemid vector pCANTAB_MOG01 as a template. A gene fragment of the Hinge-CH2-CH3 region was amplified by PCR using a synthetic gene of the heavy chain constant region as a template. The obtained gene fragments were inserted to N5KG4PE vector (described in International Publication No. 2002/088186), and N5-MOG01scFv-hG4PE vector was produced.

A gene fragment of the scFv region was amplified by PCR using a phagemid vector pCANTAB_MOG301 as a template. A gene fragment of the Hinge-CH2-CH3 region was amplified by PCR using a synthetic gene of the heavy chain constant region as a template. The obtained gene fragments were inserted to pCI vector (manufactured by Promega Corporation), and pCI-MOG301 scFv-hG4PE(R409K) vector was produced.

By the same method, antibody expression vectors to which gene fragments of the scFv regions of the anti-MOG antibodies shown in Table 12 were inserted were produced and named pCI-MOG303 scFv-hG4PE(R409K), pCI-MOG307 scFv-hG4PE(R409K), pCI-MOG310 scFv-hG4PE(R409K), pCI-MOG312 scFv-hG4PE(R409K), pCI-MOG326 scFv-hG4PE(R409K), pCI-MOG446 scFv-hG4PE(R409K), pCI-MOG456 scFv-hG4PE(R409K) and pCI-MOG473 scFv-hG4PE(R409K).

body, MOG312 scFv-hG4PE(R409K) antibody, MOG326 scFv-hG4PE(R409K) antibody, MOG329 scFv-hG4PE(R409K) antibody, MOG446 scFv-hG4PE(R409K) antibody, MOG456 scFv-hG4PE(R409K) antibody and MOG473 scFv-hG4PE(R409K) antibody were obtained, respectively.

[Example 22] Evaluation of Affinities of Anti-MOG Antibodies to MOG Using Flow Cytometer Binding of the anti-MOG antibodies obtained in Example 21 to MOG was evaluated by the same method as that of Example 7. The results are shown in FIGS. 23 to 25.

Figure 23:
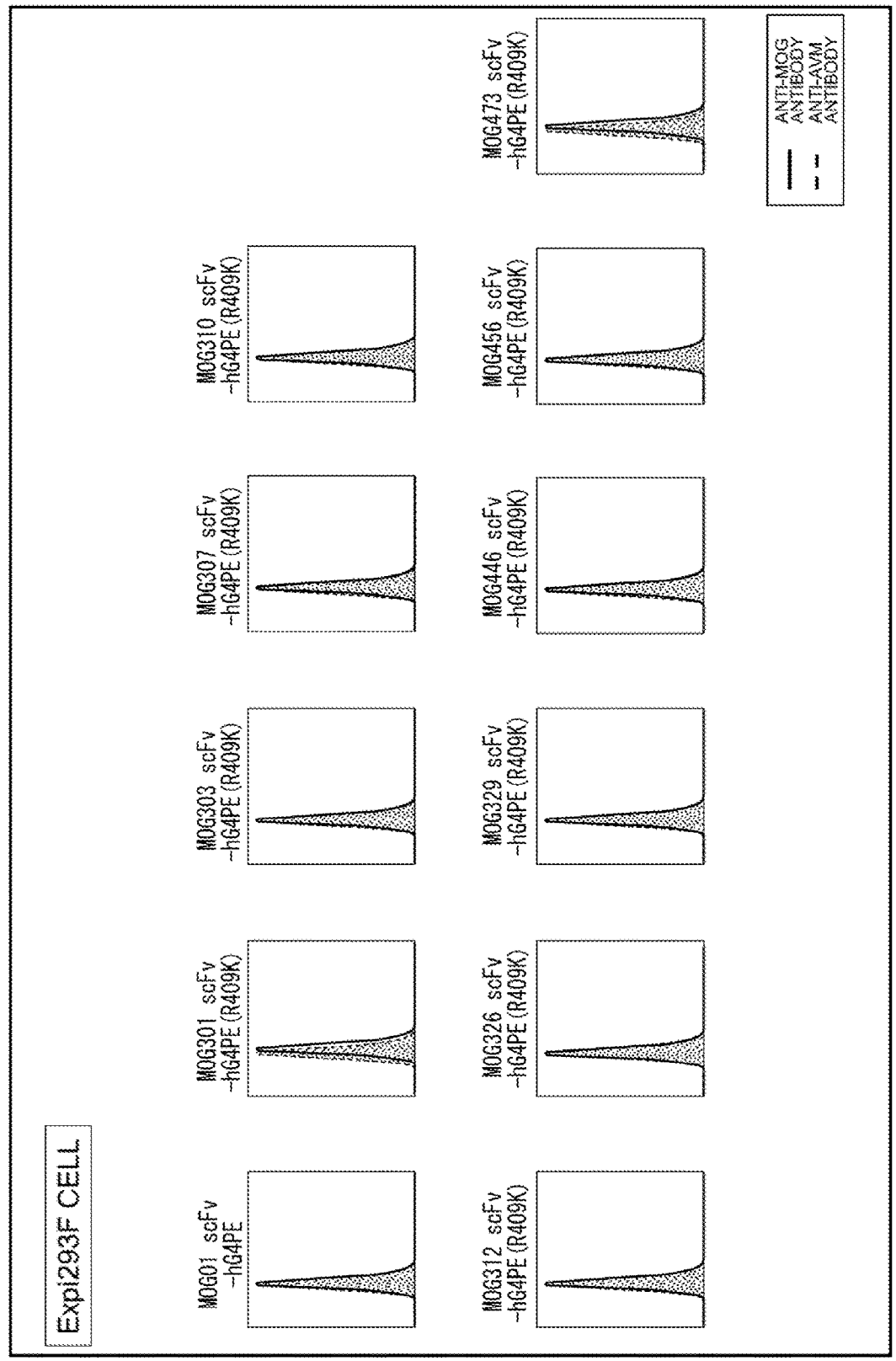
FIG. 23 shows the results of analysis using a flow cytometer of the affinities of anti-MOG antibodies to Expi293F cells. The vertical axis shows the number of cells, and the horizontal axis shows the fluorescence intensity. A dotted line indicates a histogram of the affinity of an anti-AVM antibody used as a negative control, and a solid line indicates a histogram of the affinity of a MOG antibody.
Figure 24:
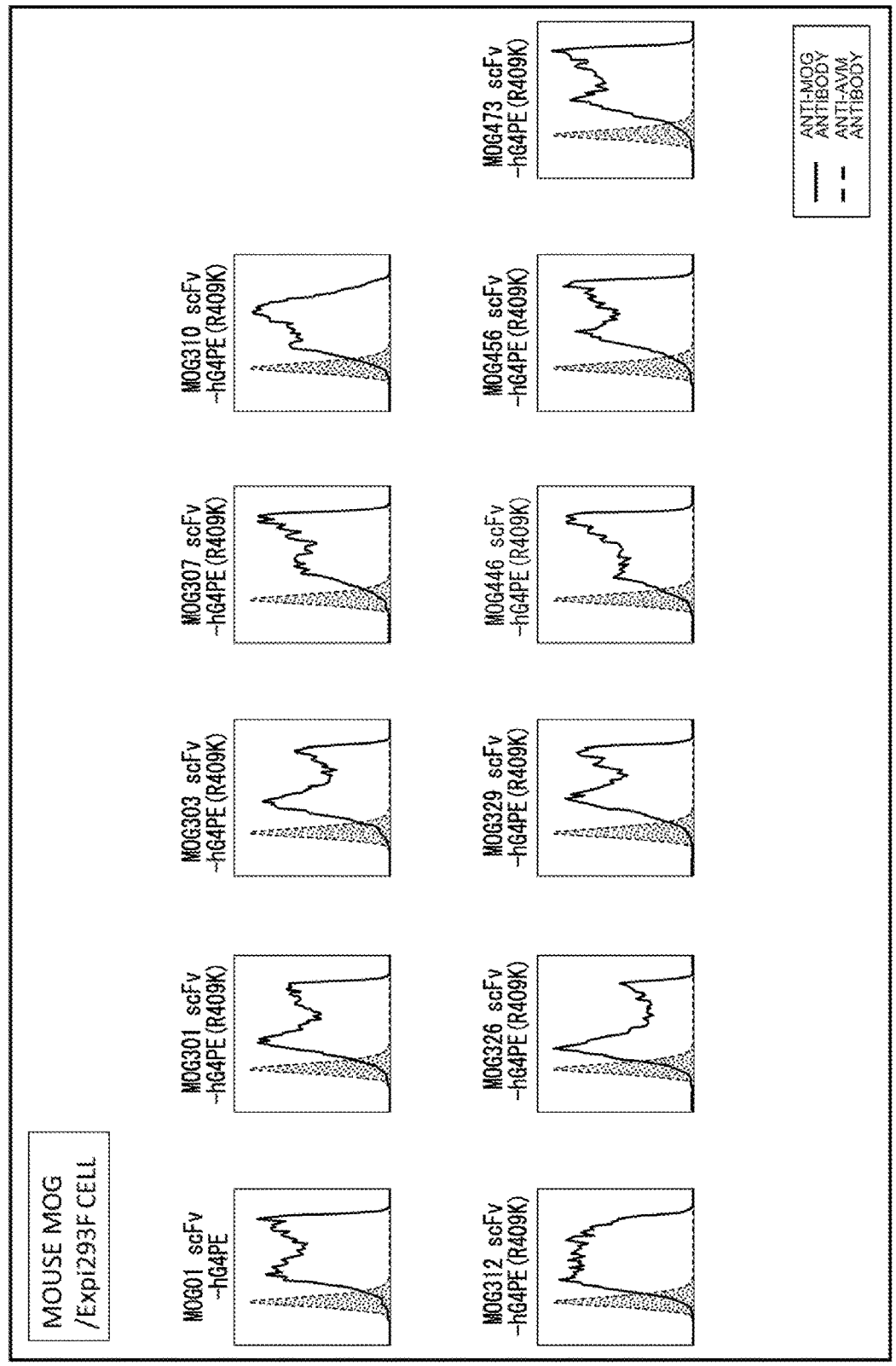
FIG. 24 shows the results of analysis using a flow cytometer of the affinities of anti-MOG antibodies to mouse MOG/Expi293F cells. The vertical axis shows the number of cells, and the horizontal axis shows the fluorescence intensity. A dotted line indicates a histogram of the affinity of an anti-AVM antibody used as a negative control, and a solid line indicates a histogram of the affinity of a MOG antibody.
Figure 25:
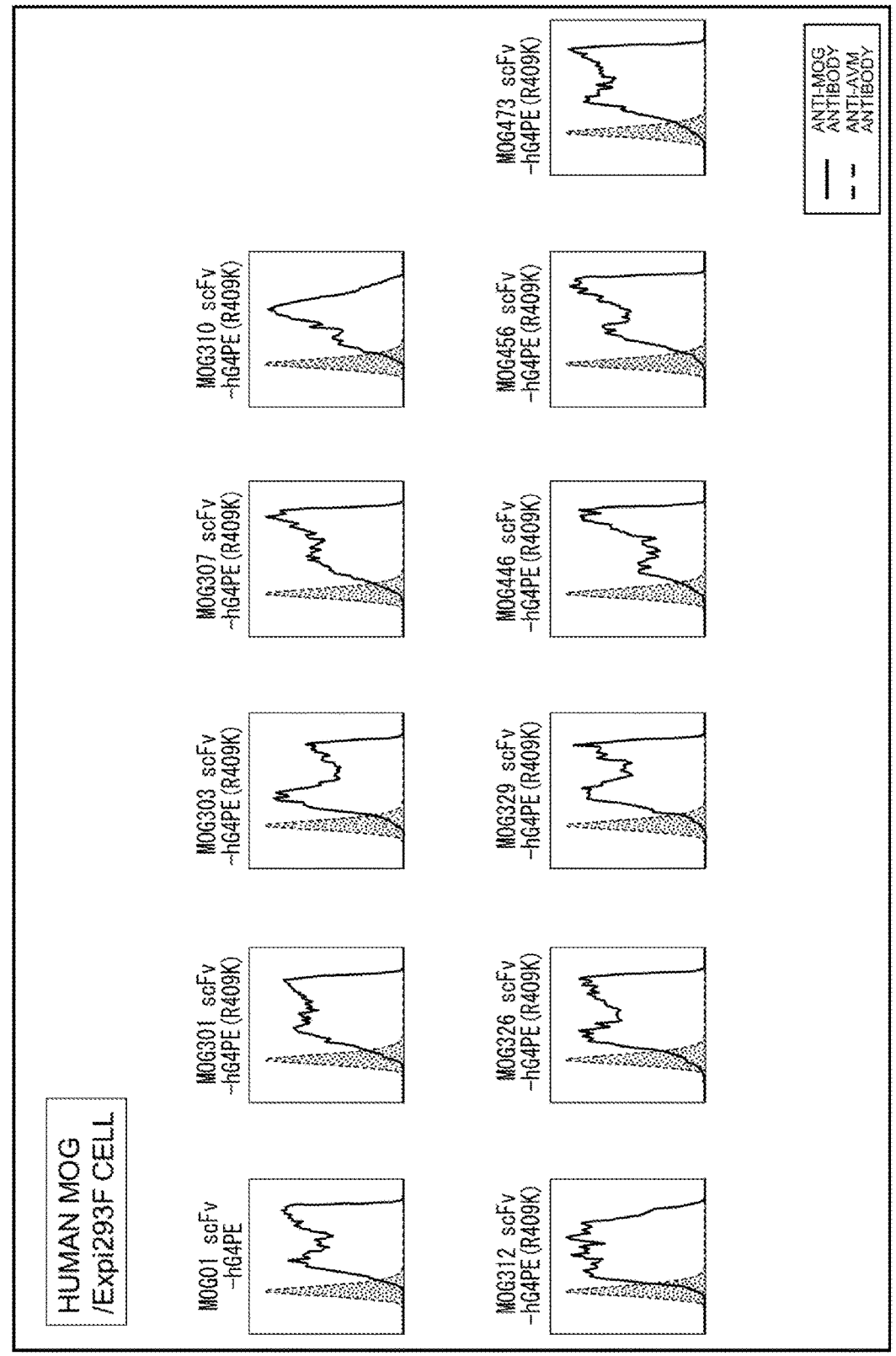
FIG. 25 shows the results of analysis using a flow cytometer of the affinities of anti-MOG antibodies to human MOG/Expi293F cells. The vertical axis shows the number of cells, and the horizontal axis shows the fluorescence intensity. A dotted line indicates a histogram of the affinity of an anti-AVM antibody used as a negative control, and a solid line indicates a histogram of the affinity of a MOG antibody.

As shown in FIGS. 23 to 25, MOG01 scFv-hG4PE, MOG301 scFv-hG4PE(R409K), MOG303 scFv-hG4PE(R409K), MOG307 scFv-hG4PE(R409K), MOG310 scFv-hG4PE(R409K), MOG312 scFv-hG4PE(R409K), MOG326 scFv-hG4PE(R409K), MOG329 scFv-hG4PE(R409K), MOG446 scFv-hG4PE(R409K), MOG456 scFv-hG4PE(R409K) and MOG473 scFv-hG4PE(R409K) all showed binding activity to hMOG/Expi293F cells and mMOG/Expi293F cells.

[Example 23] Evaluation of Affinities of Anti-MOG Antibodies to MOG by Surface Plasmon Resonance Detection Binding of MOG01 scFv-hG4PE, MOG301 scFv-hG4PE(R409K), MOG303 scFv-hG4PE(R409K), MOG307 scFvhG4PE(R409K), MOG329 scFv-hG4PE(R409K), MOG446 scFv-hG4PE(R409K), MOG456 scFv-hG4PE(R409K) and MOG473 scFv-hG4PE(R409K) obtained in Example 21 to human MOG and mouse MOG was evaluated by the same method as that of Example 8. hMOG-GST and mMOG-GST were used as analytes. The results of evaluation of the affinities to human MOG are shown in Table 14, and the results of evaluation of the affinities to mouse MOG are shown in Table 15.

TABLE 14

Reactivity to human MOG

| Antibody Name | ka (1/Ms) | kd (1/s) | KD (M) |
|---|---|---|---|
| MOG01 scFv-hG4PE | 4.1E+06 | 1.5E−02 | 3.6E−09 |
| MOG301 scFv-hG4PE(R409K) | 1.1E+06 | 1.8E−04 | 1.8E−10 |
| MOG303 scFv-hG4PE(R409K) | 9.1E+05 | 1.6E−04 | 1.7E−10 |
| MOG307 scFv-hG4PE(R409K) | 1.6E+05 | 1.4E−04 | 8.9E−10 |
| MOG329 scFv-hG4PE(R409K) | 1.6E+06 | 2.1E−04 | 1.3E−10 |
| MOG446 scFv-hG4PE(R409K) | 1.9E+05 | 1.7E−04 | 8.7E−10 |
| MOG456 scFv-hG4PE(R409K) | 1.0E+06 | 2.6E−04 | 2.5E−10 |
| MOG473 scFv-hG4PE(R409K) | 1.5E+06 | 1.5E−04 | 1.0E−10 | ka of MOG01 was outside the measurement range.

TABLE 15

Reactivity to mouse MOG

| Antibody Name | ka (1/Ms) | kd (1/s) | KD (M) |
|---|---|---|---|
| MOG01 scFv-hG4PE | 5.9E+06 | 4.0E−02 | 6.9E−09 |
| MOG301 scFv-hG4PE(R409K) | 4.9E+05 | 2.1E−04 | 4.3E−10 |
| MOG303 scFv-hG4PE(R409K) | 1.1E+06 | 2.1E−04 | 1.9E−10 |
| MOG307 scFv-hG4PE(R409K) | 1.6E+05 | 1.5E−04 | 9.6E−10 |
| MOG329 scFv-hG4PE(R409K) | 1.1E+06 | 2.3E−04 | 2.2E−10 |
| MOG446 scFv-hG4PE(R409K) | 1.2E+05 | 3.7E−04 | 3.2E−09 |
| MOG456 scFv-hG4PE(R409K) | 7.6E+05 | 3.9E−04 | 5.2E−10 |
| MOG473 scFv-hG4PE(R409K) | 7.6E+05 | 3.7E−04 | 4.9E−10 |

As shown in Table 14 and Table 15, the dissociation constants (KD values) of the anti-MOG antibodies to human MOG were $1.0 \times 10^{-10}$ (M) to $3.6 \times 10^{-9}$ (M), and the dissociation constants (KD values) to mouse MOG were $1.9 \times 10^{-10}$ (M) to $6.9 \times 10^{-9}$ (M). It was thus elucidated that all the antibodies show excellent affinity. The association rate constant ka of MOG01 scFv-hG4PE was outside the measurement range of the device, and the KD value could not be determined as a unique value.

[Example 24] Production of Enzyme-Fused Antibodies

Enzyme-fused antibodies in which acid sphingomyelinase (ASM) was fused to the C-terminus of anti-MOG01IgG antibody or anti-AVMIgG antibody were produced by the method described below. The vector expressing the antibody in which ASM was fused to the C-terminus of anti-MOG01IgG antibody was named pCI-MOG01-hLG4PE(R409K)_ASM, and the vector expressing the antibody in which ASM was fused to the C-terminus of anti-AVMIgG antibody was named pCI-AVM-hLG4PE(R409K)_ASM.

A gene fragment of the linker-ASM region was amplified by PCR using a synthetic gene of ASM shown in SEQ ID NO: 150 as a template. Moreover, a gene fragment of the CH1-Hinge-CH2-CH3(R409K) region was synthesized by PCR using a synthetic gene as a template. A gene fragment of the MOG01 light chain region and a gene fragment of the MOG01 VH region were amplified by PCR using N5LG4PE_MOG01 as a template.

The obtained gene fragments were inserted to pCI vector (manufactured by Promega Corporation), and pCI-MOG01-hLG4PE(R409K)_ASM vector was produced. A gene fragment of the CH2-CH3 region was amplified by PCR using a synthetic gene as a template. The gene fragments of the CH2-CH3 region and the linker-ASM region were inserted to the PmlI-BamHI site of pCI-AVM-hLG4PE(R409K) vector, and pCI-AVM-hLG4PE(R409K)_ASM was produced.

pCI-MOG01-hLG4PE(R409K)_ASM and pCI-AVM-hLG4PE(R409K)_ASM were expressed and purified by the method shown in Example 6. The antibody obtained by expression using pCI-MOG01-hLG4PE(R409K)_ASM was named MOG01 IgG4PE(R409K)-ASM, and the antibody obtained by expression using pCI-AVM-hLG4PE(R409K)_ASM was named AVM IgG4PE(R409K)-ASM.

[Example 25] Evaluation of Activities of Enzyme-Fused Antibodies

Figure 26:
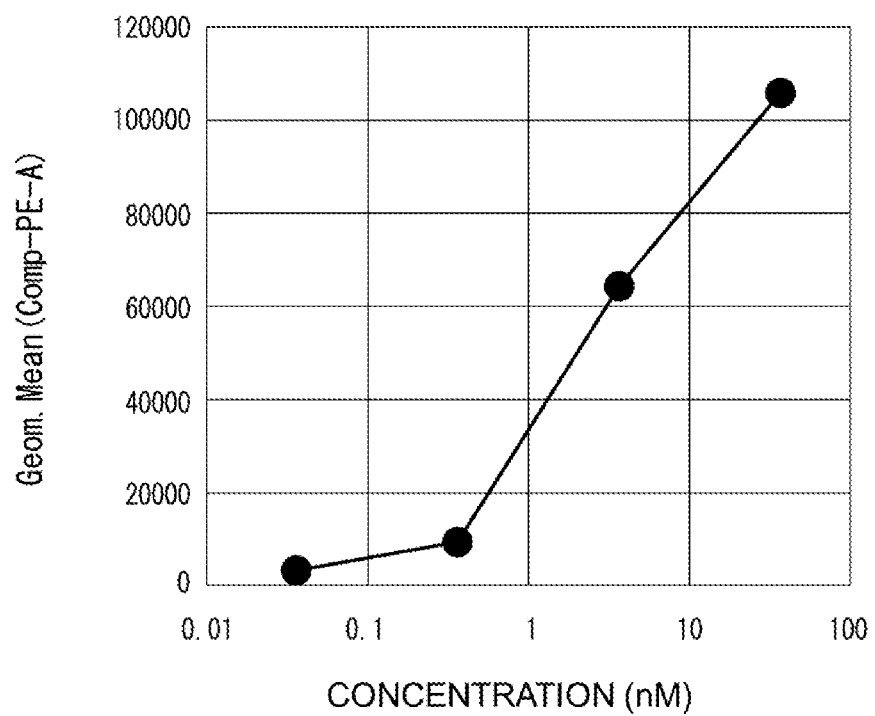
FIG. 26 shows the results of analysis using a flow cytometer of the affinity of an enzyme-fused antibody, MOG01 IgG4PE(R409K)-ASM to human MOG/L929 cells. The vertical axis shows the average fluorescence intensity, and the horizontal axis shows the antibody concentration.

The affinity of MOG01 IgG4PE(R409K)-ASM to MOG-expressing cells was examined by the same method as that of Example 23, and the results are shown in FIG. 26. Moreover, the affinity to MOG soluble antigen was examined by the same method as that of Example 8. As a result, the dissociation constant (KD value) of MOG01 IgG4PE(R409K)-ASM was $2.9 \times 10^{-9}$ (M), and excellent affinity was observed.

That an anti-ASM antibody (manufactured by LSBio) binds to produced MOG01 IgG4PE(R409K)-ASM and AVM IgG4PE(R409K)-ASM was confirmed by the ELISA method shown below.

In the ELISA, MOG01 IgG4PE(R409K)-ASM and AVM IgG4PE(R409K)-ASM were immobilized (100 ng/50 μL) on MAXISORP (manufactured by NUNC), and the sites to which MOG01 IgG4PE(R409K)-ASM and AVM IgG4PE(R409K)-ASM were not bound were blocked using SuperBlock Blocking Buffer (manufactured by Thermo Fisher Scientific Inc.). As a negative control, a plate on which anti-MOG01IgG antibody and anti-AVMIgG antibody were immobilized (50 ng/50 μL) was also prepared. The anti-ASM antibody which was diluted to a concentration of 0.2, 1 or 5 μg/mL with PBS-T was added to the wells and reacted at room temperature for an hour, and then the wells were washed with PBS-T.

Next, a solution obtained by diluting horseradish peroxidase-labeled anti-Mouse Immunoglobulins antibody (manufactured by Dako) with PBS-T was added to the wells and reacted at room temperature for an hour. A TMB chromogenic substrate solution (manufactured by DAKO) was added, and the plates were incubated at room temperature. The chromogenic reaction was stopped by adding 2 M hydrochloric acid to the wells, and the absorbances at the wavelength of 450 nm (reference wavelength of 570 nm) were measured. The results obtained are shown in FIG. 27.

Figure 27:
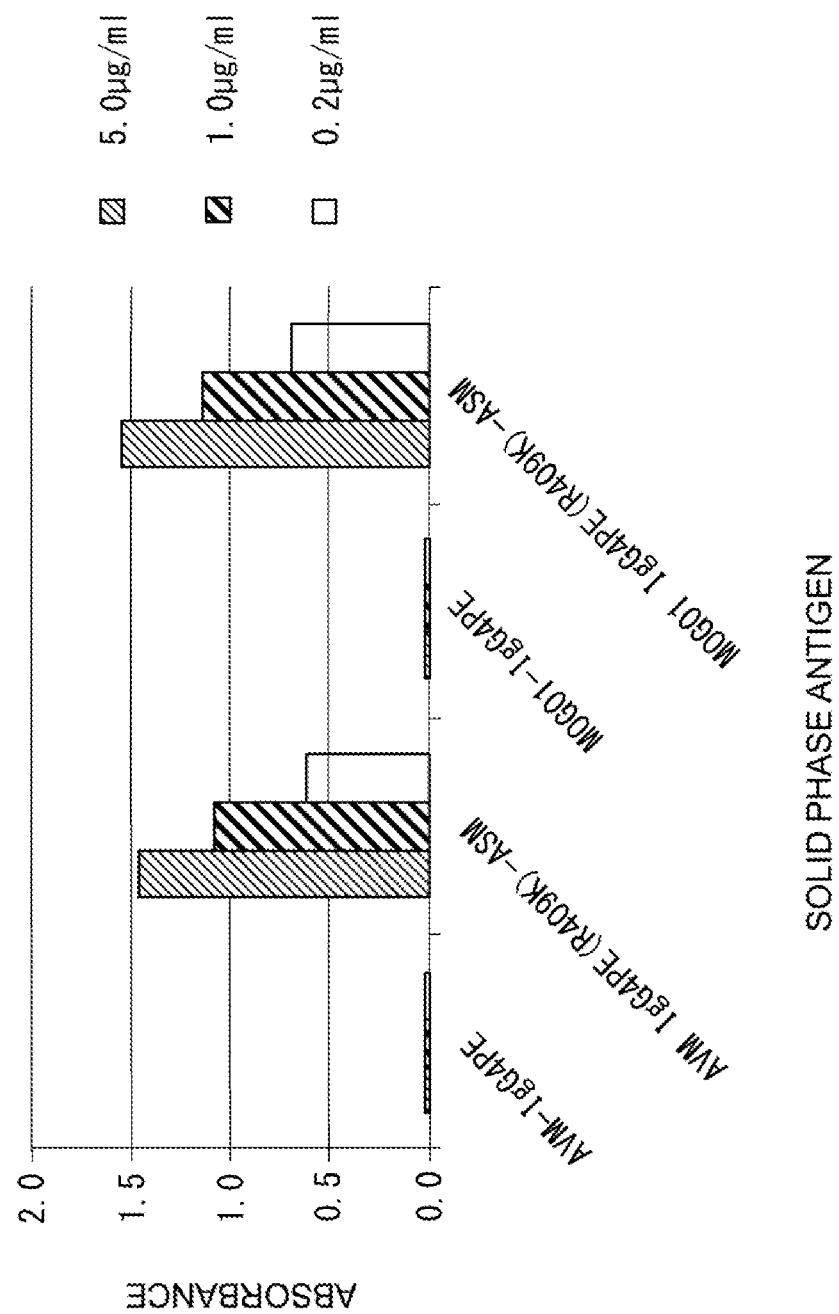
FIG. 27 shows the results of analysis by ELISA method of the affinities of anti-ASM antibodies (manufactured by LSBio) to MOG01 IgG4PE(R409K)-ASM and AVM IgG4PE(R409K)-ASM. The vertical axis shows the absorbance, and the horizontal axis shows the names of the immobilized antibodies. MOG01 IgG4PE and AVM IgG4PE were used as negative controls. The bars shaded with thin lines show the data of the anti-ASM antibodies at 5 µg/mL, and the bars shaded with thick lines show the data of the anti-ASM antibodies at 1 µg/mL. The white bars show the data of the anti-ASM antibodies at 0.2 µg/mL.

As shown in FIG. 27, it was shown that the anti-ASM antibody recognized and bound to the produced ASM-fused antibodies. Moreover, as a result of measurement of the sphingomyelinase activities of produced MOG01 IgG4PE(R409K)-ASM and AVM IgG4PE(R409K)-ASM using a sphingomyelinase activity measurement kit (manufactured by Echelon Biosciences), it was confirmed that the produced ASM-fused antibodies had enzymatic activities.

From the above results, it was confirmed that the enzyme-fused antibody obtained by fusing an enzyme to a MOG antibody maintains both the antigen binding activity and the enzymatic activity.

[Example 26] Evaluation of Mouse Brain Migration Properties of Enzyme-Fused Antibodies The mouse brain migration properties of the ASM-fused antibodies obtained in Example 24 were evaluated by the same method as that of Example 14. The antibody concentrations in the serum and the antibody amounts per unit brain weight in the brain tissues 10 days after administering the ASM-fused antibodies at 5 mg/kg are shown in FIGS. 28A and 28B.

As shown in FIGS. 28A and 28B, the antibody concentration of MOG01 IgG4PE(R409K)-ASM in the serum was not different from that of AVM IgG4PE(R409K)-ASM. On the other hand, it was shown that the antibody amount of MOG01 IgG4PE(R409K)-ASM in the brain increased to about 58 times the amount of AVM IgG4PE(R409K)-ASM.

The invention has been explained in detail using the specific aspects, but it is obvious for those skilled in the art that various changes and modifications can be made without departing from the spirit and scope of the invention. The present application is based on a Japanese patent application filed on Dec. 26, 2016 (patent application No. 2016-251106), which is incorporated by reference in its entirety.

SEQUENCE LISTING FREE TEXT

Definition of SEQ ID NO: 3—artificial sequence: amino acid sequence of VH of MOG01 excluding signal sequence
Definition of SEQ ID NO: 4—artificial sequence: amino acid sequence of HCDR1 of MOG01
Definition of SEQ ID NO: 5—artificial sequence: amino acid sequence of HCDR2 of MOG01
Definition of SEQ ID NO: 6—artificial sequence: amino acid sequence of HCDR3 of MOG01
Definition of SEQ ID NO: 9—artificial sequence: amino acid sequence of VL of MOG01 excluding signal sequence
Definition of SEQ ID NO: 10—artificial sequence: amino acid sequence of LCDR1 of MOG01
Definition of SEQ ID NO: 11—artificial sequence: amino acid sequence of LCDR2 of MOG01
Definition of SEQ ID NO: 12—artificial sequence: amino acid sequence of LCDR3 of MOG01
Definition of SEQ ID NO: 15—artificial sequence: amino acid sequence of VH of MOG09 excluding signal sequence
Definition of SEQ ID NO: 16—artificial sequence: amino acid sequence of HCDR1 of MOG09
Definition of SEQ ID NO: 17—artificial sequence: amino acid sequence of HCDR2 of MOG09
Definition of SEQ ID NO: 18—artificial sequence: amino acid sequence of HCDR3 of MOG09
Definition of SEQ ID NO: 21—artificial sequence: amino acid sequence of VL of MOG09 excluding signal sequence
Definition of SEQ ID NO: 22—artificial sequence: amino acid sequence of LCDR1 of MOG09
Definition of SEQ ID NO: 23—artificial sequence: amino acid sequence of LCDR2 of MOG09
Definition of SEQ ID NO: 24—artificial sequence: amino acid sequence of LCDR3 of MOG09
Definition of SEQ ID NO: 27—artificial sequence: amino acid sequence of VH of MOG14 excluding signal sequence
Definition of SEQ ID NO: 28—artificial sequence: amino acid sequence of HCDR1 of MOG14
Definition of SEQ ID NO: 29—artificial sequence: amino acid sequence of HCDR2 of MOG14
Definition of SEQ ID NO: 30—artificial sequence: amino acid sequence of HCDR3 of MOG14
Definition of SEQ ID NO: 33—artificial sequence: amino acid sequence of VL of MOG14 excluding signal sequence
Definition of SEQ ID NO: 34—artificial sequence: amino acid sequence of LCDR1 of MOG14
Definition of SEQ ID NO: 35—artificial sequence: amino acid sequence of LCDR2 of MOG14
Definition of SEQ ID NO: 36—artificial sequence: amino acid sequence of LCDR3 of MOG14
Definition of SEQ ID NO: 37—artificial sequence: nucleotide sequence of VHH of iMOG_3Rim1_S32 including signal sequence
Definition of SEQ ID NO: 38—artificial sequence: amino acid sequence of synthetic construct
Definition of SEQ ID NO: 39—artificial sequence: amino acid sequence of VHH of iMOG_3Rim1_S32 excluding signal sequence
Definition of SEQ ID NO: 40—artificial sequence: amino acid sequence of CDR1 of iMOG 3Rim1_S32
Definition of SEQ ID NO: 41—artificial sequence: amino acid sequence of CDR2 of iMOG 3Rim1_S32
Definition of SEQ ID NO: 42—artificial sequence: amino acid sequence of CDR3 of iMOG 3Rim1_S32
Definition of SEQ ID NO: 43—artificial sequence: nucleotide sequence of primer 1
Definition of SEQ ID NO: 44—artificial sequence: nucleotide sequence of primer 2
Definition of SEQ ID NO: 45—artificial sequence: nucleotide sequence of primer 3
Definition of SEQ ID NO: 46—artificial sequence: nucleotide sequence of primer 4
Definition of SEQ ID NO: 47—artificial sequence: nucleotide sequence of primer 5
Definition of SEQ ID NO: 48—artificial sequence: nucleotide sequence of primer 6
Definition of SEQ ID NO: 49—artificial sequence: nucleotide sequence of primer 7
Definition of SEQ ID NO: 50—artificial sequence: nucleotide sequence of primer 8
Definition of SEQ ID NO: 51—artificial sequence: nucleotide sequence of primer 9
Definition of SEQ ID NO: 52—artificial sequence: nucleotide sequence of primer 10
Definition of SEQ ID NO: 53—artificial sequence: nucleotide sequence of primer 11
Definition of SEQ ID NO: 54—artificial sequence: nucleotide sequence of primer 12
Definition of SEQ ID NO: 55—artificial sequence: nucleotide sequence of primer 13
Definition of SEQ ID NO: 56—artificial sequence: nucleotide sequence of primer 14
Definition of SEQ ID NO: 57—artificial sequence: nucleotide sequence of primer 15
Definition of SEQ ID NO: 58—artificial sequence: nucleotide sequence of primer 16
Definition of SEQ ID NO: 59—artificial sequence: nucleotide sequence of primer 17
Definition of SEQ ID NO: 60—artificial sequence: nucleotide sequence of primer 18
Definition of SEQ ID NO: 61—artificial sequence: nucleotide sequence of primer 19
Definition of SEQ ID NO: 62—artificial sequence: nucleotide sequence of primer 20

Definition of SEQ ID NO: 63—artificial sequence: nucleotide sequence of primer 21
Definition of SEQ ID NO: 64—artificial sequence: nucleotide sequence of primer 22
Definition of SEQ ID NO: 65—artificial sequence: nucleotide sequence of primer 23
Definition of SEQ ID NO: 66—artificial sequence: nucleotide sequence of primer 24
Definition of SEQ ID NO: 69—artificial sequence: nucleotide sequence of rMOG-FLAG-Fc
Definition of SEQ ID NO: 70—artificial sequence: amino acid sequence of synthetic construct
Definition of SEQ ID NO: 71—artificial sequence: nucleotide sequence of rMOG-GST
Definition of SEQ ID NO: 72—artificial sequence: amino acid sequence of synthetic construct
Definition of SEQ ID NO: 79—artificial sequence: nucleotide sequence of primer 25
Definition of SEQ ID NO: 80—artificial sequence: nucleotide sequence of primer 26
Definition of SEQ ID NO: 81—artificial sequence: nucleotide sequence of primer 27
Definition of SEQ ID NO: 82—artificial sequence: nucleotide sequence of primer 28
Definition of SEQ ID NO: 83—artificial sequence: nucleotide sequence of primer 29
Definition of SEQ ID NO: 84—artificial sequence: nucleotide sequence of primer 30
Definition of SEQ ID NO: 85—artificial sequence: nucleotide sequence of primer 31
Definition of SEQ ID NO: 86—artificial sequence: nucleotide sequence of primer 32
Definition of SEQ ID NO: 87—artificial sequence: nucleotide sequence of primer 33
Definition of SEQ ID NO: 88—artificial sequence: nucleotide sequence of primer 34
Definition of SEQ ID NO: 89—artificial sequence: nucleotide sequence of primer 35
Definition of SEQ ID NO: 90—artificial sequence: nucleotide sequence of primer 36
Definition of SEQ ID NO: 91—artificial sequence: nucleotide sequence of primer 37
Definition of SEQ ID NO: 92—artificial sequence: nucleotide sequence of primer 38
Definition of SEQ ID NO: 93—artificial sequence: nucleotide sequence of primer 39
Definition of SEQ ID NO: 94—artificial sequence: nucleotide sequence of primer 40
Definition of SEQ ID NO: 95—artificial sequence: nucleotide sequence of primer 41
Definition of SEQ ID NO: 96—artificial sequence: nucleotide sequence of primer 42
Definition of SEQ ID NO: 97—artificial sequence: nucleotide sequence of primer 43
Definition of SEQ ID NO: 98—artificial sequence: nucleotide sequence of hHER2-GST
Definition of SEQ ID NO: 99—artificial sequence: amino acid sequence of synthetic construct
Definition of SEQ ID NO: 100—artificial sequence: nucleotide sequence of hMOG-FLAG-Fc (including signal sequence)
Definition of SEQ ID NO: 101—artificial sequence: amino acid sequence of hMOG-FLAG-Fc (including signal sequence)
Definition of SEQ ID NO: 102—artificial sequence: nucleotide sequence of mMOG-FLAG-Fc (including signal sequence)
Definition of SEQ ID NO: 103—artificial sequence: amino acid sequence of mMOG-FLAG-Fc (including signal sequence)
Definition of SEQ ID NO: 104—artificial sequence: nucleotide sequence of hMOG-GST (including signal sequence)
Definition of SEQ ID NO: 105—artificial sequence: amino acid sequence of hMOG-GST (including signal sequence)
Definition of SEQ ID NO: 106—artificial sequence: nucleotide sequence of mMOG-GST (including signal sequence)
Definition of SEQ ID NO: 107—artificial sequence: amino acid sequence of mMOG-GST (including signal sequence)
Definition of SEQ ID NO: 108—artificial sequence: nucleotide sequence of antibody sequence of pCI-AVM-hLG4PE(R409K/S354C/T366W)-FLAG tag (excluding signal sequence)
Definition of SEQ ID NO: 109—artificial sequence: amino acid sequence of antibody sequence of pCI-AVM-hLG4PE(R409K/S354C/T366W)-FLAG tag (excluding signal sequence)
Definition of SEQ ID NO: 110—artificial sequence: nucleotide sequence of antibody sequence of pCI-MOG01-hLG4PE(R409K/Y349C/T366S/L368A/Y407V)-His tag (excluding signal sequence)
Definition of SEQ ID NO: 111—artificial sequence: amino acid sequence of antibody sequence of pCI-MOG01-hLG4PE(R409K/Y349C/T366S/L368A/Y407V)-His tag (excluding signal sequence)
Definition of SEQ ID NO: 112—artificial sequence: nucleotide sequence of antibody sequence of pCI-AVM-hLG4PE(R409K)-linker-MOG01VL-CL (excluding signal sequence)
Definition of SEQ ID NO: 113—artificial sequence: amino acid sequence of antibody sequence of pCI-AVM-hLG4PE(R409K)-linker-MOG01VL-CL (excluding signal sequence)
Definition of SEQ ID NO: 114—artificial sequence: nucleotide sequence of antibody sequence of pCI-MOG01VH-CH (excluding signal sequence)
Definition of SEQ ID NO: 115—artificial sequence: amino acid sequence of antibody sequence of pCI-MOG01VH-CH (excluding signal sequence)
Definition of SEQ ID NO: 116—artificial sequence: nucleotide sequence of antibody sequence of pCI-AVM-hLG4PE(R409K/S354C/T366W)-linker-MOG01scFv-FLAG tag (excluding signal sequence)
Definition of SEQ ID NO: 117—artificial sequence: amino acid sequence of antibody sequence of pCI-AVM-hLG4PE(R409K/S354C/T366W)-linker-MOG01scFv-FLAG tag (excluding signal sequence)
Definition of SEQ ID NO: 118—artificial sequence: nucleotide sequence of antibody sequence of pCI-AVM-hLG4PE(R409K/Y349C/T366S/L368A/Y407V)-His tag (excluding signal sequence)
Definition of SEQ ID NO: 119—artificial sequence: amino acid sequence of antibody sequence of pCI-AVM-hLG4PE(R409K/Y349C/T366S/L368A/Y407V)-His tag (excluding signal sequence)
Definition of SEQ ID NO: 120—artificial sequence: nucleotide sequence of antibody sequence of pCI-AVM-hLG4PE(R409K)_MOG01scFv2 (excluding signal sequence)

Definition of SEQ ID NO: 121—artificial sequence: amino acid sequence of antibody sequence of pCI-AVM-hLG4PE(R409K)_MOG01scFv2 (excluding signal sequence)

Definition of SEQ ID NO: 122—artificial sequence: nucleotide sequence of antibody sequence of pCI-AVM-hLG4PE(R409K)_MOG01scFv3 (excluding signal sequence)

Definition of SEQ ID NO: 123—artificial sequence: amino acid sequence of antibody sequence of pCI-AVM-hLG4PE(R409K)_MOG01scFv3 (excluding signal sequence)

Definition of SEQ ID NO: 124—artificial sequence: nucleotide sequence of antibody sequence of pCI-AVM-hLG4PE(R409K)_MOG01scFv4 (excluding signal sequence)

Definition of SEQ ID NO: 125—artificial sequence: amino acid sequence of antibody sequence of pCI-AVM-hLG4PE(R409K)_MOG01scFv4 (excluding signal sequence)

Definition of SEQ ID NO: 126—artificial sequence: nucleotide sequence of antibody sequence of pCI-AVM-hLG4PE(R409K)_MOG01scFv5 (excluding signal sequence)

Definition of SEQ ID NO: 127—artificial sequence: amino acid sequence of antibody sequence of pCI-AVM-hLG4PE(R409K)_MOG01scFv5 (excluding signal sequence)

Definition of SEQ ID NO: 128—artificial sequence: nucleotide sequence of antibody sequence of pCI-AVM-hLG4PE(R409K)_MOG01scFv6 (excluding signal sequence)

Definition of SEQ ID NO: 129—artificial sequence: amino acid sequence of antibody sequence of pCI-AVM-hLG4PE(R409K)_MOG01scFv6 (excluding signal sequence)

Definition of SEQ ID NO: 130—artificial sequence: nucleotide sequence of antibody sequence of pCI-AVM-hLG4PE(R409K)_MOG01scFv7 (excluding signal sequence)

Definition of SEQ ID NO: 131—artificial sequence: amino acid sequence of antibody sequence of pCI-AVM-hLG4PE(R409K)_MOG01scFv7 (excluding signal sequence)

Definition of SEQ ID NO: 132—artificial sequence: nucleotide sequence of antibody sequence of pCI-AVM-hLG4PE(R409K)_MOG01scFv8 (excluding signal sequence)

Definition of SEQ ID NO: 133—artificial sequence: amino acid sequence of antibody sequence of pCI-AVM-hLG4PE(R409K)_MOG01scFv8 (excluding signal sequence)

Definition of SEQ ID NO: 134—artificial sequence: nucleotide sequence of antibody sequence of pCI-AVM-hLG4PE(R409K)_MOG01scFv9 (excluding signal sequence)

Definition of SEQ ID NO: 135—artificial sequence: amino acid sequence of antibody sequence of pCI-AVM-hLG4PE(R409K)_MOG01scFv9 (excluding signal sequence)

Definition of SEQ ID NO: 136—artificial sequence: nucleotide sequence of antibody sequence of pCI-AVM-hLG4PE(R409K)_MOG01scFv10 (excluding signal sequence)

Definition of SEQ ID NO: 137—artificial sequence: amino acid sequence of antibody sequence of pCI-AVM-hLG4PE(R409K)_MOG01scFv10 (excluding signal sequence)

Definition of SEQ ID NO: 138—artificial sequence: nucleotide sequence of antibody sequence of pCI-AVM-hLG4PE(R409K)_MOG01scFv11 (excluding signal sequence)

Definition of SEQ ID NO: 139—artificial sequence: amino acid sequence of antibody sequence of pCI-AVM-hLG4PE(R409K)_MOG01scFv11 (excluding signal sequence)

Definition of SEQ ID NO: 140—artificial sequence: nucleotide sequence of antibody sequence of pCI-AVM-hLG4PE(R409K)-linker-AVMVL-CL (excluding signal sequence)

Definition of SEQ ID NO: 141—artificial sequence: amino acid sequence of antibody sequence of pCI-AVM-hLG4PE(R409K)-linker-AVMVL-CL (excluding signal sequence)

Definition of SEQ ID NO: 142—artificial sequence: nucleotide sequence of antibody sequence of pCI-AVMVH-CH (excluding signal sequence)

Definition of SEQ ID NO: 143—artificial sequence: amino acid sequence of antibody sequence of pCI-AVMVH-CH (excluding signal sequence)

Definition of SEQ ID NO: 144—artificial sequence: nucleotide sequence of antibody sequence of pCI-AVM-hLG4PE(R409K/S354C/T366W)-linker-AVMscFv-FLAG tag (excluding signal sequence)

Definition of SEQ ID NO: 145—artificial sequence: amino acid sequence of antibody sequence of pCI-AVM-hLG4PE(R409K/S354C/T366W)-linker-AVMscFv-FLAG tag (excluding signal sequence)

Definition of SEQ ID NO: 146—artificial sequence: nucleotide sequence of antibody sequence of pCI-AVM-hLG4PE(R409K)_AVMscFv3 (excluding signal sequence)

Definition of SEQ ID NO: 147—artificial sequence: amino acid sequence of antibody sequence of pCI-AVM-hLG4PE(R409K)_AVMscFv3 (excluding signal sequence)

Definition of SEQ ID NO: 148—artificial sequence: nucleotide sequence of antibody sequence of pCI-AVM-hLG4PE(R409K)_AVMscFv5 (excluding signal sequence)

Definition of SEQ ID NO: 149—artificial sequence: amino acid sequence of antibody sequence of pCI-AVM-hLG4PE(R409K)_AVMscFv5 (excluding signal sequence)

Definition of SEQ ID NO: 150—artificial sequence: nucleotide sequence of Acid Sphingomyelinase (ASM)

Definition of SEQ ID NO: 151—artificial sequence: nucleotide sequence encoding VH (excluding signal sequence) of MOG301

Definition of SEQ ID NO: 152—artificial sequence: amino acid sequence of VH (excluding signal sequence) of MOG301

Definition of SEQ ID NO: 153—artificial sequence: amino acid sequence of HCDR1 of MOG301

Definition of SEQ ID NO: 154—artificial sequence: amino acid sequence of HCDR2 of MOG301

Definition of SEQ ID NO: 155—artificial sequence: amino acid sequence of HCDR3 of MOG301

Definition of SEQ ID NO: 156—artificial sequence: nucleotide sequence encoding VL (excluding signal sequence) of MOG301

Definition of SEQ ID NO: 157—artificial sequence: amino acid sequence of VL (excluding signal sequence) of MOG301

Definition of SEQ ID NO: 158—artificial sequence: amino acid sequence of LCDR1 of MOG301

Definition of SEQ ID NO: 159—artificial sequence: amino acid sequence of LCDR2 of MOG301

Definition of SEQ ID NO: 160—artificial sequence: amino acid sequence of LCDR3 of MOG301

Definition of SEQ ID NO: 161—artificial sequence: nucleotide sequence encoding VH (excluding signal sequence) of MOG303

Definition of SEQ ID NO: 162—artificial sequence: amino acid sequence of VH (excluding signal sequence) of MOG303

Definition of SEQ ID NO: 163—artificial sequence: amino acid sequence of HCDR1 of MOG303

Definition of SEQ ID NO: 164—artificial sequence: amino acid sequence of HCDR2 of MOG303

Definition of SEQ ID NO: 165—artificial sequence: amino acid sequence of HCDR3 of MOG303

Definition of SEQ ID NO: 166—artificial sequence: nucleotide sequence encoding VL (excluding signal sequence) of MOG303

Definition of SEQ ID NO: 167—artificial sequence: amino acid sequence of VL (excluding signal sequence) of MOG303

Definition of SEQ ID NO: 168—artificial sequence: amino acid sequence of LCDR1 of MOG303

Definition of SEQ ID NO: 169—artificial sequence: amino acid sequence of LCDR2 of MOG303

Definition of SEQ ID NO: 170—artificial sequence: amino acid sequence of LCDR3 of MOG303

Definition of SEQ ID NO: 171—artificial sequence: nucleotide sequence encoding VH (excluding signal sequence) of MOG307

Definition of SEQ ID NO: 172—artificial sequence: amino acid sequence of VH (excluding signal sequence) of MOG307

Definition of SEQ ID NO: 173—artificial sequence: amino acid sequence of HCDR1 of MOG307

Definition of SEQ ID NO: 174—artificial sequence: amino acid sequence of HCDR2 of MOG307

Definition of SEQ ID NO: 175—artificial sequence: amino acid sequence of HCDR3 of MOG307

Definition of SEQ ID NO: 176—artificial sequence: nucleotide sequence encoding VL (excluding signal sequence) of MOG307

Definition of SEQ ID NO: 177—artificial sequence: amino acid sequence of VL (excluding signal sequence) of MOG307

Definition of SEQ ID NO: 178—artificial sequence: amino acid sequence of LCDR1 of MOG307

Definition of SEQ ID NO: 179—artificial sequence: amino acid sequence of LCDR2 of MOG307

Definition of SEQ ID NO: 180—artificial sequence: amino acid sequence of LCDR3 of MOG307

Definition of SEQ ID NO: 181—artificial sequence: nucleotide sequence encoding VH (excluding signal sequence) of MOG310

Definition of SEQ ID NO: 182—artificial sequence: amino acid sequence of VH (excluding signal sequence) of MOG310

Definition of SEQ ID NO: 183—artificial sequence: amino acid sequence of HCDR1 of MOG310

Definition of SEQ ID NO: 184—artificial sequence: amino acid sequence of HCDR2 of MOG310

Definition of SEQ ID NO: 185—artificial sequence: amino acid sequence of HCDR3 of MOG310

Definition of SEQ ID NO: 186—artificial sequence: nucleotide sequence encoding VL (excluding signal sequence) of MOG310

Definition of SEQ ID NO: 187—artificial sequence: amino acid sequence of VL (excluding signal sequence) of MOG310

Definition of SEQ ID NO: 188—artificial sequence: amino acid sequence of LCDR1 of MOG310

Definition of SEQ ID NO: 189—artificial sequence: amino acid sequence of LCDR2 of MOG310

Definition of SEQ ID NO: 190—artificial sequence: amino acid sequence of LCDR3 of MOG310

Definition of SEQ ID NO: 191—artificial sequence: nucleotide sequence encoding VH (excluding signal sequence) of MOG312

Definition of SEQ ID NO: 192—artificial sequence: amino acid sequence of VH (excluding signal sequence) of MOG312

Definition of SEQ ID NO: 193—artificial sequence: amino acid sequence of HCDR1 of MOG312

Definition of SEQ ID NO: 194—artificial sequence: amino acid sequence of HCDR2 of MOG312

Definition of SEQ ID NO: 195—artificial sequence: amino acid sequence of HCDR3 of MOG312

Definition of SEQ ID NO: 196—artificial sequence: nucleotide sequence encoding VL (excluding signal sequence) of MOG312

Definition of SEQ ID NO: 197—artificial sequence: amino acid sequence of VL (excluding signal sequence) of MOG312

Definition of SEQ ID NO: 198—artificial sequence: amino acid sequence of LCDR1 of MOG312

Definition of SEQ ID NO: 199—artificial sequence: amino acid sequence of LCDR2 of MOG312

Definition of SEQ ID NO: 200—artificial sequence: amino acid sequence of LCDR3 of MOG312

Definition of SEQ ID NO: 201—artificial sequence: nucleotide sequence encoding VH (excluding signal sequence) of MOG326

Definition of SEQ ID NO: 202—artificial sequence: amino acid sequence of VH (excluding signal sequence) of MOG326

Definition of SEQ ID NO: 203—artificial sequence: amino acid sequence of HCDR1 of MOG326

Definition of SEQ ID NO: 204—artificial sequence: amino acid sequence of HCDR2 of MOG326

Definition of SEQ ID NO: 205—artificial sequence: amino acid sequence of HCDR3 of MOG326

Definition of SEQ ID NO: 206—artificial sequence: nucleotide sequence encoding VL (excluding signal sequence) of MOG326

Definition of SEQ ID NO: 207—artificial sequence: amino acid sequence of VL (excluding signal sequence) of MOG326

Definition of SEQ ID NO: 208—artificial sequence: amino acid sequence of LCDR1 of MOG326

Definition of SEQ ID NO: 209—artificial sequence: amino acid sequence of LCDR2 of MOG326

Definition of SEQ ID NO: 210—artificial sequence: amino acid sequence of LCDR3 of MOG326

Definition of SEQ ID NO: 211—artificial sequence: nucleotide sequence encoding VH (excluding signal sequence) of MOG329

Definition of SEQ ID NO: 212—artificial sequence: amino acid sequence of VH (excluding signal sequence) of MOG329

Definition of SEQ ID NO: 213—artificial sequence: amino acid sequence of HCDR1 of MOG329

Definition of SEQ ID NO: 214—artificial sequence: amino acid sequence of HCDR2 of MOG329

Definition of SEQ ID NO: 215—artificial sequence: amino acid sequence of HCDR3 of MOG329

Definition of SEQ ID NO: 216—artificial sequence: nucleotide sequence encoding VL (excluding signal sequence) of MOG329

Definition of SEQ ID NO: 217—artificial sequence: amino acid sequence of VL (excluding signal sequence) of MOG329

Definition of SEQ ID NO: 218—artificial sequence: amino acid sequence of LCDR1 of MOG329

Definition of SEQ ID NO: 219—artificial sequence: amino acid sequence of LCDR2 of MOG329

Definition of SEQ ID NO: 220—artificial sequence: amino acid sequence of LCDR3 of MOG329

Definition of SEQ ID NO: 221—artificial sequence: nucleotide sequence encoding VH (excluding signal sequence) of MOG446

Definition of SEQ ID NO: 222—artificial sequence: amino acid sequence of VH (excluding signal sequence) of MOG446

Definition of SEQ ID NO: 223—artificial sequence: amino acid sequence of HCDR1 of MOG446

Definition of SEQ ID NO: 224—artificial sequence: amino acid sequence of HCDR2 of MOG446

Definition of SEQ ID NO: 225—artificial sequence: amino acid sequence of HCDR3 of MOG446

Definition of SEQ ID NO: 226—artificial sequence: nucleotide sequence encoding VL (excluding signal sequence) of MOG446

Definition of SEQ ID NO: 227—artificial sequence: amino acid sequence of VL (excluding signal sequence) of MOG446

Definition of SEQ ID NO: 228—artificial sequence: amino acid sequence of LCDR1 of MOG446

Definition of SEQ ID NO: 229—artificial sequence: amino acid sequence of LCDR2 of MOG446

Definition of SEQ ID NO: 230—artificial sequence: amino acid sequence of LCDR3 of MOG446

Definition of SEQ ID NO: 231—artificial sequence: nucleotide sequence encoding VH (excluding signal sequence) of MOG456

Definition of SEQ ID NO: 232—artificial sequence: amino acid sequence of VH (excluding signal sequence) of MOG456

Definition of SEQ ID NO: 233—artificial sequence: amino acid sequence of HCDR1 of MOG456

Definition of SEQ ID NO: 234—artificial sequence: amino acid sequence of HCDR2 of MOG456

Definition of SEQ ID NO: 235—artificial sequence: amino acid sequence of HCDR3 of MOG456

Definition of SEQ ID NO: 236—artificial sequence: nucleotide sequence encoding VL (excluding signal sequence) of MOG456

Definition of SEQ ID NO: 237—artificial sequence: amino acid sequence of VL (excluding signal sequence) of MOG456

Definition of SEQ ID NO: 238—artificial sequence: amino acid sequence of LCDR1 of MOG456

Definition of SEQ ID NO: 239—artificial sequence: amino acid sequence of LCDR2 of MOG456

Definition of SEQ ID NO: 240—artificial sequence: amino acid sequence of LCDR3 of MOG456

Definition of SEQ ID NO: 241—artificial sequence: nucleotide sequence encoding VH (excluding signal sequence) of MOG473

Definition of SEQ ID NO: 242—artificial sequence: amino acid sequence of VH (excluding signal sequence) of MOG473

Definition of SEQ ID NO: 243—artificial sequence: amino acid sequence of HCDR1 of MOG473

Definition of SEQ ID NO: 244—artificial sequence: amino acid sequence of HCDR2 of MOG473

Definition of SEQ ID NO: 245—artificial sequence: amino acid sequence of HCDR3 of MOG473

Definition of SEQ ID NO: 246—artificial sequence: nucleotide sequence encoding VL (excluding signal sequence) of MOG473

Definition of SEQ ID NO: 247—artificial sequence: amino acid sequence of VL (excluding signal sequence) of MOG473

Definition of SEQ ID NO: 248—artificial sequence: amino acid sequence of LCDR1 of MOG473

Definition of SEQ ID NO: 249—artificial sequence: amino acid sequence of LCDR2 of MOG473

Definition of SEQ ID NO: 250—artificial sequence: amino acid sequence of LCDR3 of MOG473

Definition of SEQ ID NO: 251—artificial sequence: nucleotide sequence encoding VH (excluding signal sequence) of MOG426

Definition of SEQ ID NO: 252—artificial sequence: amino acid sequence of VH (excluding signal sequence) of MOG426

Definition of SEQ ID NO: 253—artificial sequence: nucleotide sequence encoding VL (excluding signal sequence) of MOG426

Definition of SEQ ID NO: 254—artificial sequence: amino acid sequence of VL (excluding signal sequence) of MOG426

Definition of SEQ ID NO: 255—artificial sequence: nucleotide sequence encoding VH (excluding signal sequence) of MOG428

Definition of SEQ ID NO: 256—artificial sequence: amino acid sequence of VH (excluding signal sequence) of MOG428

Definition of SEQ ID NO: 257—artificial sequence: nucleotide sequence encoding VL (excluding signal sequence) of MOG428

Definition of SEQ ID NO: 258—artificial sequence: amino acid sequence of VL (excluding signal sequence) of MOG428

Definition of SEQ ID NO: 259—artificial sequence: nucleotide sequence encoding VH (excluding signal sequence) of MOG313

Definition of SEQ ID NO: 260—artificial sequence: amino acid sequence of VH (excluding signal sequence) of MOG313

Definition of SEQ ID NO: 261—artificial sequence: nucleotide sequence encoding VL (excluding signal sequence) of MOG313

Definition of SEQ ID NO: 262—artificial sequence: amino acid sequence of VL (excluding signal sequence) of MOG313

Definition of SEQ ID NO: 263—artificial sequence: nucleotide sequence encoding VH (excluding signal sequence) of MOG314

Definition of SEQ ID NO: 264—artificial sequence: amino acid sequence of VH (excluding signal sequence) of MOG314

Definition of SEQ ID NO: 265—artificial sequence: nucleotide sequence encoding VL (excluding signal sequence) of MOG314

Definition of SEQ ID NO: 266—artificial sequence: amino acid sequence of VL (excluding signal sequence) of MOG314

Definition of SEQ ID NO: 267—artificial sequence: nucleotide sequence encoding VH (excluding signal sequence) of MOG315

Definition of SEQ ID NO: 268—artificial sequence: amino acid sequence of VH (excluding signal sequence) of MOG315

Definition of SEQ ID NO: 269—artificial sequence: nucleotide sequence encoding VL (excluding signal sequence) of MOG315

Definition of SEQ ID NO: 270—artificial sequence: amino acid sequence of VL (excluding signal sequence) of MOG315

Definition of SEQ ID NO: 271—artificial sequence: nucleotide sequence encoding VH (excluding signal sequence) of MOG331

Definition of SEQ ID NO: 272—artificial sequence: amino acid sequence of VH (excluding signal sequence) of MOG331

Definition of SEQ ID NO: 273—artificial sequence: nucleotide sequence encoding VL (excluding signal sequence) of MOG331

Definition of SEQ ID NO: 274—artificial sequence: amino acid sequence of VL (excluding signal sequence) of MOG331

Definition of SEQ ID NO: 275—artificial sequence: nucleotide sequence encoding VH (excluding signal sequence) of MOG357

Definition of SEQ ID NO: 276—artificial sequence: amino acid sequence of VH (excluding signal sequence) of MOG357

Definition of SEQ ID NO: 277—artificial sequence: nucleotide sequence encoding VL (excluding signal sequence) of MOG357

Definition of SEQ ID NO: 278—artificial sequence: amino acid sequence of VL (excluding signal sequence) of MOG357

Definition of SEQ ID NO: 279—artificial sequence: nucleotide sequence encoding VH (excluding signal sequence) of MOG476

Definition of SEQ ID NO: 280—artificial sequence: amino acid sequence of VH (excluding signal sequence) of MOG476

Definition of SEQ ID NO: 281—artificial sequence: nucleotide sequence encoding VL (excluding signal sequence) of MOG476

Definition of SEQ ID NO: 282—artificial sequence: amino acid sequence of VL (excluding signal sequence) of MOG476

Definition of SEQ ID NO: 283—artificial sequence: nucleotide sequence encoding VH (excluding signal sequence) of MOG323

Definition of SEQ ID NO: 284—artificial sequence: amino acid sequence of VH (excluding signal sequence) of MOG323

Definition of SEQ ID NO: 285—artificial sequence: nucleotide sequence encoding VL (excluding signal sequence) of MOG323

Definition of SEQ ID NO: 286—artificial sequence: amino acid sequence of VL (excluding signal sequence) of MOG323

Definition of SEQ ID NO: 287—artificial sequence: nucleotide sequence encoding VH (excluding signal sequence) of MOG341

Definition of SEQ ID NO: 288—artificial sequence: amino acid sequence of VH (excluding signal sequence) of MOG341

Definition of SEQ ID NO: 289—artificial sequence: nucleotide sequence encoding VL (excluding signal sequence) of MOG341

Definition of SEQ ID NO: 290—artificial sequence: amino acid sequence of VL (excluding signal sequence) of MOG341

Definition of SEQ ID NO: 291—artificial sequence: nucleotide sequence encoding VH (excluding signal sequence) of MOG354

Definition of SEQ ID NO: 292—artificial sequence: amino acid sequence of VH (excluding signal sequence) of MOG354

Definition of SEQ ID NO: 293—artificial sequence: nucleotide sequence encoding VL (excluding signal sequence) of MOG354

Definition of SEQ ID NO: 294—artificial sequence: amino acid sequence of VL (excluding signal sequence) of MOG354

Definition of SEQ ID NO: 295—artificial sequence: nucleotide sequence encoding VH (excluding signal sequence) of MOG355

Definition of SEQ ID NO: 296—artificial sequence: amino acid sequence of VH (excluding signal sequence) of MOG355

Definition of SEQ ID NO: 297—artificial sequence: nucleotide sequence encoding VL (excluding signal sequence) of MOG355

Definition of SEQ ID NO: 298—artificial sequence: amino acid sequence of VL (excluding signal sequence) of MOG355

Definition of SEQ ID NO: 299—artificial sequence: nucleotide sequence encoding VH (excluding signal sequence) of MOG308

Definition of SEQ ID NO: 300—artificial sequence: amino acid sequence of VH (excluding signal sequence) of MOG308

Definition of SEQ ID NO: 301—artificial sequence: nucleotide sequence encoding VL (excluding signal sequence) of MOG308

Definition of SEQ ID NO: 302—artificial sequence: amino acid sequence of VL (excluding signal sequence) of MOG308

Definition of SEQ ID NO: 303—artificial sequence: nucleotide sequence encoding VH (excluding signal sequence) of MOG316

Definition of SEQ ID NO: 304—artificial sequence: amino acid sequence of VH (excluding signal sequence) of MOG316

Definition of SEQ ID NO: 305—artificial sequence: nucleotide sequence encoding VL (excluding signal sequence) of MOG316

Definition of SEQ ID NO: 306—artificial sequence: amino acid sequence of VL (excluding signal sequence) of MOG316

Definition of SEQ ID NO: 307—artificial sequence: nucleotide sequence encoding VH (excluding signal sequence) of MOG319

Definition of SEQ ID NO: 308—artificial sequence: amino acid sequence of VH (excluding signal sequence) of MOG319

Definition of SEQ ID NO: 309—artificial sequence: nucleotide sequence encoding VL (excluding signal sequence) of MOG319

Definition of SEQ ID NO: 310—artificial sequence: amino acid sequence of VL (excluding signal sequence) of MOG319

Definition of SEQ ID NO: 311—artificial sequence: nucleotide sequence encoding VH (excluding signal sequence) of MOG320

Definition of SEQ ID NO: 312—artificial sequence: amino acid sequence of VH (excluding signal sequence) of MOG320

Definition of SEQ ID NO: 313—artificial sequence: nucleotide sequence encoding VL (excluding signal sequence) of MOG320

Definition of SEQ ID NO: 314—artificial sequence: amino acid sequence of VL (excluding signal sequence) of MOG320

Definition of SEQ ID NO: 315—artificial sequence: nucleotide sequence encoding VH (excluding signal sequence) of MOG338

Definition of SEQ ID NO: 316—artificial sequence: amino acid sequence of VH (excluding signal sequence) of MOG338

Definition of SEQ ID NO: 317—artificial sequence: nucleotide sequence encoding VL (excluding signal sequence) of MOG338

Definition of SEQ ID NO: 318—artificial sequence: amino acid sequence of VL (excluding signal sequence) of MOG338

Definition of SEQ ID NO: 319—artificial sequence: nucleotide sequence encoding VH (excluding signal sequence) of MOG352

Definition of SEQ ID NO: 320—artificial sequence: amino acid sequence of VH (excluding signal sequence) of MOG352

Definition of SEQ ID NO: 321—artificial sequence: nucleotide sequence encoding VL (excluding signal sequence) of MOG352

Definition of SEQ ID NO: 322—artificial sequence: amino acid sequence of VL (excluding signal sequence) of MOG352

Definition of SEQ ID NO: 323—artificial sequence: nucleotide sequence encoding VH (excluding signal sequence) of MOG359

Definition of SEQ ID NO: 324—artificial sequence: amino acid sequence of VH (excluding signal sequence) of MOG359

Definition of SEQ ID NO: 325—artificial sequence: nucleotide sequence encoding VL (excluding signal sequence) of MOG359

Definition of SEQ ID NO: 326—artificial sequence: amino acid sequence of VL (excluding signal sequence) of MOG359

Definition of SEQ ID NO: 327—artificial sequence: nucleotide sequence encoding VH (excluding signal sequence) of MOG478

Definition of SEQ ID NO: 328—artificial sequence: amino acid sequence of VH (excluding signal sequence) of MOG478

Definition of SEQ ID NO: 329—artificial sequence: nucleotide sequence encoding VL (excluding signal sequence) of MOG478

Definition of SEQ ID NO: 330—artificial sequence: amino acid sequence of VL (excluding signal sequence) of MOG478

Definition of SEQ ID NO: 331—artificial sequence: nucleotide sequence encoding VH (excluding signal sequence) of MOG470

Definition of SEQ ID NO: 332—artificial sequence: amino acid sequence of VH (excluding signal sequence) of MOG470

Definition of SEQ ID NO: 333—artificial sequence: nucleotide sequence encoding VL (excluding signal sequence) of MOG470

Definition of SEQ ID NO: 334—artificial sequence: amino acid sequence of VL (excluding signal sequence) of MOG470

Definition of SEQ ID NO: 335—artificial sequence: nucleotide sequence encoding VH (excluding signal sequence) of MOG418

Definition of SEQ ID NO: 336—artificial sequence: amino acid sequence of VH (excluding signal sequence) of MOG418

Definition of SEQ ID NO: 337—artificial sequence: nucleotide sequence encoding VL (excluding signal sequence) of MOG418

Definition of SEQ ID NO: 338—artificial sequence: amino acid sequence of VL (excluding signal sequence) of MOG418

The invention claimed is:

1. An antibody which binds to myelin oligodendrocyte glycoprotein (MOG) or an antibody fragment thereof, wherein the antibody comprises an antibody in which the amino acid sequences of complementarity determining regions (CDRs) 1 to 3 of the heavy chain variable region (VH) of the antibody comprise the amino acid sequences of SEQ ID NOs: 4, 5 and 6, respectively, and in which the amino acid sequences of CDRs 1 to 3 of the light chain variable region (VL) of the antibody comprise the amino acid sequences of SEQ ID NOs: 10, 11 and 12, respectively.

2. The antibody or the antibody fragment according to claim 1, wherein the antibody comprises an antibody in which the amino acid sequence of VH comprises the amino acid sequence of SEQ ID NO: 3 and in which the amino acid sequence of VL comprises the amino acid sequence of SEQ ID NO: 9.

3. The antibody fragment according to claim 1 which is selected from the group consisting of Fab, Fab', F(ab')₂, a single chain antibody (scFv), a dimerized V region (diabody), a disulfide-stabilized V region (dsFv), VHH, and a peptide comprising CDR.

4. The antibody or the antibody fragment according to claim 1, wherein the antibody is a genetically recombinant antibody.

5. The antibody or the antibody fragment according to claim 1, wherein the antibody is selected from the group consisting of a chimeric antibody, a humanized antibody, and a human antibody.

6. A composition which comprises the antibody or the antibody fragment according to claim 1.

7. The composition according to claim 6, wherein the composition further comprises a carrier or a stabilizing agent.

8. The composition according to claim 6, wherein the composition further comprises one or more pharmacologically acceptable carriers.

* * * * *

UNITED STATES PATENT AND TRADEMARK OFFICE
CERTIFICATE OF CORRECTION

| | |
|---|---|
| PATENT NO. | : 11,117,963 B2 |
| APPLICATION NO. | : 16/473482 |
| DATED | : September 14, 2021 |
| INVENTOR(S) | : Takahashi et al. |

It is certified that error appears in the above-identified patent and that said Letters Patent is hereby corrected as shown below:

On the Title Page

Item (73) listing the Assignees, change "KYOWA HAKKO KIRIN CO., LTD." to --- KYOWA KIRIN CO., LTD. ---

Signed and Sealed this
Third Day of May, 2022

Katherine Kelly Vidal
Director of the United States Patent and Trademark Office

SEQUENCE LISTING

```
<160> NUMBER OF SEQ ID NOS: 338

<210> SEQ ID NO 1
<211> LENGTH: 438
<212> TYPE: DNA
<213> ORGANISM: Homo sapiens
<220> FEATURE:
<221> NAME/KEY: CDS
<222> LOCATION: (1)..(438)

<400> SEQUENCE: 1 atg aac ctc ggg ctc agt ttg att ttc ctt gcc ctc att tta aaa ggt      48
Met Asn Leu Gly Leu Ser Leu Ile Phe Leu Ala Leu Ile Leu Lys Gly
1               5                   10                  15 gtc cag tgt cag gta cag ctg cag cag tca ggc gca gga tta ttg aag      96
Val Gln Cys Gln Val Gln Leu Gln Gln Ser Gly Ala Gly Leu Leu Lys
            20                  25                  30 cct tcg gag acc ctt tcc ctc acc tgc gct gtg tct ggt ggg tcc ttc     144
```

```
               Pro Ser Glu Thr Leu Ser Leu Thr Cys Ala Val Ser Gly Gly Ser Phe
                       35                  40                  45 agt ggt tac tac tgg acc tgg atc cgc cag cgc cca ggg aag ggg ctg       192
Ser Gly Tyr Tyr Trp Thr Trp Ile Arg Gln Arg Pro Gly Lys Gly Leu
         50                  55                  60 gag tgg att gga gaa atc aat cat cgt gga agc acc gat tac aac ccg       240
Glu Trp Ile Gly Glu Ile Asn His Arg Gly Ser Thr Asp Tyr Asn Pro
 65                  70                  75                  80 tcc ctc aag agt cga gtc acc atg tca ata gac acg tcc aag agc cag       288
Ser Leu Lys Ser Arg Val Thr Met Ser Ile Asp Thr Ser Lys Ser Gln
                 85                  90                  95 ttc tcc ctg aat ttg aaa tct gtg acc gcc gcg gac acg gct gtg tat       336
Phe Ser Leu Asn Leu Lys Ser Val Thr Ala Ala Asp Thr Ala Val Tyr
            100                 105                 110 tac tgt gcg aga gcc gcc tgg ggg tct tgt tat gat ggg acc tgc tac       384
Tyr Cys Ala Arg Ala Ala Trp Gly Ser Cys Tyr Asp Gly Thr Cys Tyr
            115                 120                 125 ccc gct gaa tac ttc caa tac tgg ggc cag gga acc ctg gtc acc gtc       432
Pro Ala Glu Tyr Phe Gln Tyr Trp Gly Gln Gly Thr Leu Val Thr Val
        130                 135                 140 tcc tca                                                               438
Ser Ser
145

<210> SEQ ID NO 2
<211> LENGTH: 146
<212> TYPE: PRT
<213> ORGANISM: Homo sapiens

<400> SEQUENCE: 2

Met Asn Leu Gly Leu Ser Leu Ile Phe Leu Ala Leu Ile Leu Lys Gly
 1               5                  10                  15

Val Gln Cys Gln Val Gln Leu Gln Gln Ser Gly Ala Gly Leu Leu Lys
             20                  25                  30

Pro Ser Glu Thr Leu Ser Leu Thr Cys Ala Val Ser Gly Gly Ser Phe
         35                  40                  45

Ser Gly Tyr Tyr Trp Thr Trp Ile Arg Gln Arg Pro Gly Lys Gly Leu
     50                  55                  60

Glu Trp Ile Gly Glu Ile Asn His Arg Gly Ser Thr Asp Tyr Asn Pro
 65                  70                  75                  80

Ser Leu Lys Ser Arg Val Thr Met Ser Ile Asp Thr Ser Lys Ser Gln
                 85                  90                  95

Phe Ser Leu Asn Leu Lys Ser Val Thr Ala Ala Asp Thr Ala Val Tyr
            100                 105                 110

Tyr Cys Ala Arg Ala Ala Trp Gly Ser Cys Tyr Asp Gly Thr Cys Tyr
            115                 120                 125

Pro Ala Glu Tyr Phe Gln Tyr Trp Gly Gln Gly Thr Leu Val Thr Val
        130                 135                 140

Ser Ser
145

<210> SEQ ID NO 3
<211> LENGTH: 127
<212> TYPE: PRT
<213> ORGANISM: Artificial
<220> FEATURE:
<223> OTHER INFORMATION: Description of the artificial sequence: amino
      acid sequence of VH of MOG01 excluding signal sequence

<400> SEQUENCE: 3
```

Gln Val Gln Leu Gln Gln Ser Gly Ala Gly Leu Leu Lys Pro Ser Glu
1               5                   10                  15

Thr Leu Ser Leu Thr Cys Ala Val Ser Gly Gly Ser Phe Ser Gly Tyr
            20                  25                  30

Tyr Trp Thr Trp Ile Arg Gln Arg Pro Gly Lys Gly Leu Glu Trp Ile
            35                  40                  45

Gly Glu Ile Asn His Arg Gly Ser Thr Asp Tyr Asn Pro Ser Leu Lys
        50                  55                  60

Ser Arg Val Thr Met Ser Ile Asp Thr Ser Lys Ser Gln Phe Ser Leu
65                  70                  75                  80

Asn Leu Lys Ser Val Thr Ala Ala Asp Thr Ala Val Tyr Tyr Cys Ala
                85                  90                  95

Arg Ala Ala Trp Gly Ser Cys Tyr Asp Gly Thr Cys Tyr Pro Ala Glu
            100                 105                 110

Tyr Phe Gln Tyr Trp Gly Gln Gly Thr Leu Val Thr Val Ser Ser
            115                 120                 125

<210> SEQ ID NO 4
<211> LENGTH: 5
<212> TYPE: PRT
<213> ORGANISM: Artificial
<220> FEATURE:
<223> OTHER INFORMATION: Description of the artificial sequence: amino
      acid sequence of HCDR1 of MOG01

<400> SEQUENCE: 4

Gly Tyr Tyr Trp Thr
1               5

<210> SEQ ID NO 5
<211> LENGTH: 16
<212> TYPE: PRT
<213> ORGANISM: Artificial
<220> FEATURE:
<223> OTHER INFORMATION: Description of the artificial sequence: amino
      acid sequence of HCDR2 of MOG01

<400> SEQUENCE: 5

Glu Ile Asn His Arg Gly Ser Thr Asp Tyr Asn Pro Ser Leu Lys Ser
1               5                   10                  15

<210> SEQ ID NO 6
<211> LENGTH: 19
<212> TYPE: PRT
<213> ORGANISM: Artificial
<220> FEATURE:
<223> OTHER INFORMATION: Description of the artificial sequence: amino
      acid sequence of HCDR3 of MOG01

<400> SEQUENCE: 6

Ala Ala Trp Gly Ser Cys Tyr Asp Gly Thr Cys Tyr Pro Ala Glu Tyr
1               5                   10                  15

Phe Gln Tyr

<210> SEQ ID NO 7
<211> LENGTH: 390
<212> TYPE: DNA
<213> ORGANISM: Homo sapiens
<220> FEATURE:
<221> NAME/KEY: CDS
<222> LOCATION: (1)..(390)

<400> SEQUENCE: 7

```
atg aag ttg cct gtt agg ctg ttg gtg ctg atg ttc tgg att cct gct      48
Met Lys Leu Pro Val Arg Leu Leu Val Leu Met Phe Trp Ile Pro Ala
1               5                   10                  15 tcc agc agt cag tct gcc ctg act cag cct gcc tcc gtg tct ggg tct      96
Ser Ser Ser Gln Ser Ala Leu Thr Gln Pro Ala Ser Val Ser Gly Ser
            20                  25                  30 cct gga cag tcg atc acc atc tcc tgc act gga acc agc cgt gac gtt     144
Pro Gly Gln Ser Ile Thr Ile Ser Cys Thr Gly Thr Ser Arg Asp Val
        35                  40                  45 ggt ggt tat aac tat gtc tcc tgg tac caa caa cac cca ggc aaa gcc     192
Gly Gly Tyr Asn Tyr Val Ser Trp Tyr Gln Gln His Pro Gly Lys Ala
50                  55                  60 ccc aaa ctc atg att tat gat gtc aat aat cgg ccc tca ggg gtt tct     240
Pro Lys Leu Met Ile Tyr Asp Val Asn Asn Arg Pro Ser Gly Val Ser
65                  70                  75                  80 aat cgg ttc tct ggc tcc aag tct ggc aac acg gcc tcc ctg acc atc     288
Asn Arg Phe Ser Gly Ser Lys Ser Gly Asn Thr Ala Ser Leu Thr Ile
                85                  90                  95 tct ggg ctc cag gct gag gac gag gct gat tat ttc tgc agc tca tat     336
Ser Gly Leu Gln Ala Glu Asp Glu Ala Asp Tyr Phe Cys Ser Ser Tyr
            100                 105                 110 aca agc agt agc acc cct gtg gta ttc ggc ggt ggg acc aag ctg acc     384
Thr Ser Ser Ser Thr Pro Val Val Phe Gly Gly Gly Thr Lys Leu Thr
        115                 120                 125 gtc cta                                                              390
Val Leu
    130

<210> SEQ ID NO 8
<211> LENGTH: 130
<212> TYPE: PRT
<213> ORGANISM: Homo sapiens

<400> SEQUENCE: 8

Met Lys Leu Pro Val Arg Leu Leu Val Leu Met Phe Trp Ile Pro Ala
1               5                   10                  15

Ser Ser Ser Gln Ser Ala Leu Thr Gln Pro Ala Ser Val Ser Gly Ser
            20                  25                  30

Pro Gly Gln Ser Ile Thr Ile Ser Cys Thr Gly Thr Ser Arg Asp Val
        35                  40                  45

Gly Gly Tyr Asn Tyr Val Ser Trp Tyr Gln Gln His Pro Gly Lys Ala
50                  55                  60

Pro Lys Leu Met Ile Tyr Asp Val Asn Asn Arg Pro Ser Gly Val Ser
65                  70                  75                  80

Asn Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Phe Cys Ser Ser Tyr
            100                 105                 110

Thr Ser Ser Ser Thr Pro Val Val Phe Gly Gly Gly Thr Lys Leu Thr
        115                 120                 125

Val Leu
    130

<210> SEQ ID NO 9
<211> LENGTH: 111
<212> TYPE: PRT
<213> ORGANISM: Artificial
<220> FEATURE:
<223> OTHER INFORMATION: Description of the artificial sequence: amino
``` acid sequence of VL of MOG01 excluding signal sequence

<400> SEQUENCE: 9

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Arg Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Thr Ser Ser
                85                  90                  95

Ser Thr Pro Val Val Phe Gly Gly Gly Thr Lys Leu Thr Val Leu
            100                 105                 110
```

<210> SEQ ID NO 10
<211> LENGTH: 14
<212> TYPE: PRT
<213> ORGANISM: Artificial
<220> FEATURE:
<223> OTHER INFORMATION: Description of the artificial sequence: amino acid sequence of LCDR1 of MOG01

<400> SEQUENCE: 10

```
Thr Gly Thr Ser Arg Asp Val Gly Gly Tyr Asn Tyr Val Ser
1               5                   10
```

<210> SEQ ID NO 11
<211> LENGTH: 7
<212> TYPE: PRT
<213> ORGANISM: Artificial
<220> FEATURE:
<223> OTHER INFORMATION: Description of the artificial sequence: amino acid sequence of LCDR2 of MOG01

<400> SEQUENCE: 11

```
Asp Val Asn Asn Arg Pro Ser
1               5
```

<210> SEQ ID NO 12
<211> LENGTH: 11
<212> TYPE: PRT
<213> ORGANISM: Artificial
<220> FEATURE:
<223> OTHER INFORMATION: Description of the artificial sequence: amino acid sequence of LCDR3 of MOG01

<400> SEQUENCE: 12

```
Ser Ser Tyr Thr Ser Ser Ser Thr Pro Val Val
1               5                   10
```

<210> SEQ ID NO 13
<211> LENGTH: 423
<212> TYPE: DNA
<213> ORGANISM: Homo sapiens
<220> FEATURE:
<221> NAME/KEY: CDS
<222> LOCATION: (1)..(423)

<400> SEQUENCE: 13

```
atg aac ctc ggg ctc agt ttg att ttc ctt gcc ctc att tta aaa ggt      48
```

```
Met Asn Leu Gly Leu Ser Leu Ile Phe Leu Ala Leu Ile Leu Lys Gly
1               5                   10                  15 gtc cag tgt cag gtg cag ctg cag gag tcg ggc cca gga ctg gtg aag      96
Val Gln Cys Gln Val Gln Leu Gln Glu Ser Gly Pro Gly Leu Val Lys
                20                  25                  30 tct tcg gag acc ctg tcc ctc acc tgc gct gtc tct ggt cac tcc atc     144
Ser Ser Glu Thr Leu Ser Leu Thr Cys Ala Val Ser Gly His Ser Ile
            35                  40                  45 agc agt gct tac tac tgg ggc tgg atc cgg cag ccc cca ggg aag ggg     192
Ser Ser Ala Tyr Tyr Trp Gly Trp Ile Arg Gln Pro Pro Gly Lys Gly
        50                  55                  60 ctg gag tgg ctt ggg agt att tat cat agt ggg aac acc tac tac aac     240
Leu Glu Trp Leu Gly Ser Ile Tyr His Ser Gly Asn Thr Tyr Tyr Asn
65                  70                  75                  80 ccg tcc ctc aag agt cga gtc acc ata tca gta gac acg tcc aag aac     288
Pro Ser Leu Lys Ser Arg Val Thr Ile Ser Val Asp Thr Ser Lys Asn
                85                  90                  95 cag ttc tcc ctg agg ctg acc tct gtg acc gcc gca gac acg gcc gtg     336
Gln Phe Ser Leu Arg Leu Thr Ser Val Thr Ala Ala Asp Thr Ala Val
            100                 105                 110 tat tac tgt gcg aga ggg cgt gga tat agt ggc tac gat agc ggt atg     384
Tyr Tyr Cys Ala Arg Gly Arg Gly Tyr Ser Gly Tyr Asp Ser Gly Met
        115                 120                 125 gac gtc tgg ggc caa ggg acc acg gtc acc gtc tcc tca                 423
Asp Val Trp Gly Gln Gly Thr Thr Val Thr Val Ser Ser
130                 135                 140
```

<210> SEQ ID NO 14
<211> LENGTH: 141
<212> TYPE: PRT
<213> ORGANISM: Homo sapiens

<400> SEQUENCE: 14

```
Met Asn Leu Gly Leu Ser Leu Ile Phe Leu Ala Leu Ile Leu Lys Gly
1               5                   10                  15

Val Gln Cys Gln Val Gln Leu Gln Glu Ser Gly Pro Gly Leu Val Lys
                20                  25                  30

Ser Ser Glu Thr Leu Ser Leu Thr Cys Ala Val Ser Gly His Ser Ile
            35                  40                  45

Ser Ser Ala Tyr Tyr Trp Gly Trp Ile Arg Gln Pro Pro Gly Lys Gly
        50                  55                  60

Leu Glu Trp Leu Gly Ser Ile Tyr His Ser Gly Asn Thr Tyr Tyr Asn
65                  70                  75                  80

Pro Ser Leu Lys Ser Arg Val Thr Ile Ser Val Asp Thr Ser Lys Asn
                85                  90                  95

Gln Phe Ser Leu Arg Leu Thr Ser Val Thr Ala Ala Asp Thr Ala Val
            100                 105                 110

Tyr Tyr Cys Ala Arg Gly Arg Gly Tyr Ser Gly Tyr Asp Ser Gly Met
        115                 120                 125

Asp Val Trp Gly Gln Gly Thr Thr Val Thr Val Ser Ser
130                 135                 140
```

<210> SEQ ID NO 15
<211> LENGTH: 122
<212> TYPE: PRT
<213> ORGANISM: Artificial
<220> FEATURE:
<223> OTHER INFORMATION: Description of the artificial sequence: amino
      acid sequence of VH of MOG09 excluding signal sequence

```
<400> SEQUENCE: 15

Gln Val Gln Leu Gln Glu Ser Gly Pro Gly Leu Val Lys Ser Ser Glu
1               5                   10                  15

Thr Leu Ser Leu Thr Cys Ala Val Ser Gly His Ser Ile Ser Ser Ala
            20                  25                  30

Tyr Tyr Trp Gly Trp Ile Arg Gln Pro Pro Gly Lys Gly Leu Glu Trp
        35                  40                  45

Leu Gly Ser Ile Tyr His Ser Gly Asn Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Arg Leu Thr Ser Val Thr Ala Ala Asp Thr Ala Val Tyr Tyr Cys
                85                  90                  95

Ala Arg Gly Arg Gly Tyr Ser Gly Tyr Asp Ser Gly Met Asp Val Trp
            100                 105                 110

Gly Gln Gly Thr Thr Val Thr Val Ser Ser
        115                 120

<210> SEQ ID NO 16
<211> LENGTH: 6
<212> TYPE: PRT
<213> ORGANISM: Artificial
<220> FEATURE:
<223> OTHER INFORMATION: Description of the artificial sequence: amino
      acid sequence of HCDR1 of MOG09

<400> SEQUENCE: 16

Ser Ala Tyr Tyr Trp Gly
1               5

<210> SEQ ID NO 17
<211> LENGTH: 16
<212> TYPE: PRT
<213> ORGANISM: Artificial
<220> FEATURE:
<223> OTHER INFORMATION: Description of the artificial sequence: amino
      acid sequence of HCDR2 of MOG09

<400> SEQUENCE: 17

Ser Ile Tyr His Ser Gly Asn Thr Tyr Tyr Asn Pro Ser Leu Lys Ser
1               5                   10                  15

<210> SEQ ID NO 18
<211> LENGTH: 13
<212> TYPE: PRT
<213> ORGANISM: Artificial
<220> FEATURE:
<223> OTHER INFORMATION: Description of the artificial sequence: amino
      acid sequence of HCDR3 of MOG09

<400> SEQUENCE: 18

Gly Arg Gly Tyr Ser Gly Tyr Asp Ser Gly Met Asp Val
1               5                   10

<210> SEQ ID NO 19
<211> LENGTH: 387
<212> TYPE: DNA
<213> ORGANISM: Homo sapiens
<220> FEATURE:
<221> NAME/KEY: CDS
<222> LOCATION: (1)..(387)

<400> SEQUENCE: 19
```

```
atg aag ttg cct gtt agg ctg ttg gtg ctg atg ttc tgg att cct gct    48
Met Lys Leu Pro Val Arg Leu Leu Val Leu Met Phe Trp Ile Pro Ala
1               5                   10                  15 tcc agc agt tcc tat gtg ctg act cag cca ccc tca gcg tct ggg acc    96
Ser Ser Ser Ser Tyr Val Leu Thr Gln Pro Pro Ser Ala Ser Gly Thr
            20                  25                  30 ccc ggg cag agg gtc acc atc tct tgt tct gga acc agc tcc aac atc   144
Pro Gly Gln Arg Val Thr Ile Ser Cys Ser Gly Thr Ser Ser Asn Ile
        35                  40                  45 gga atc aat agt gta aac tgg tat caa cag ctc cca gga atg gcc ccc   192
Gly Ile Asn Ser Val Asn Trp Tyr Gln Gln Leu Pro Gly Met Ala Pro
    50                  55                  60 aaa ctc gtc atc tac agt agg gat cag cgg ccc tca ggg gtc cct gac   240
Lys Leu Val Ile Tyr Ser Arg Asp Gln Arg Pro Ser Gly Val Pro Asp
65                  70                  75                  80 cga ttc tct ggc tcc cag tct ggc acc tca gcc tcc ctg gcc atc aat   288
Arg Phe Ser Gly Ser Gln Ser Gly Thr Ser Ala Ser Leu Ala Ile Asn
                85                  90                  95 ggc ctc cag tct gag gat gag gct gat tat tgg tgt tca aca tgg gat   336
Gly Leu Gln Ser Glu Asp Glu Ala Asp Tyr Trp Cys Ser Thr Trp Asp
            100                 105                 110 gac agc ctg aat ggt tgg gtg ttc ggc gga ggg acc aag ctg acc gtc   384
Asp Ser Leu Asn Gly Trp Val Phe Gly Gly Gly Thr Lys Leu Thr Val
        115                 120                 125 cta                                                                387
Leu
```

<210> SEQ ID NO 20
<211> LENGTH: 129
<212> TYPE: PRT
<213> ORGANISM: Homo sapiens

<400> SEQUENCE: 20

```
Met Lys Leu Pro Val Arg Leu Leu Val Leu Met Phe Trp Ile Pro Ala
1               5                   10                  15

Ser Ser Ser Ser Tyr Val Leu Thr Gln Pro Pro Ser Ala Ser Gly Thr
            20                  25                  30

Pro Gly Gln Arg Val Thr Ile Ser Cys Ser Gly Thr Ser Ser Asn Ile
        35                  40                  45

Gly Ile Asn Ser Val Asn Trp Tyr Gln Gln Leu Pro Gly Met Ala Pro
    50                  55                  60

Lys Leu Val Ile Tyr Ser Arg Asp Gln Arg Pro Ser Gly Val Pro Asp
65                  70                  75                  80

Arg Phe Ser Gly Ser Gln Ser Gly Thr Ser Ala Ser Leu Ala Ile Asn
                85                  90                  95

Gly Leu Gln Ser Glu Asp Glu Ala Asp Tyr Trp Cys Ser Thr Trp Asp
            100                 105                 110

Asp Ser Leu Asn Gly Trp Val Phe Gly Gly Gly Thr Lys Leu Thr Val
        115                 120                 125

Leu
```

<210> SEQ ID NO 21
<211> LENGTH: 110
<212> TYPE: PRT
<213> ORGANISM: Artificial
<220> FEATURE:
<223> OTHER INFORMATION: Description of the artificial sequence: amino
      acid sequence of VL of MOG09 excluding signal sequence

<400> SEQUENCE: 21

```
Ser Tyr Val Leu Thr Gln Pro Pro Ser Ala Ser Gly Thr Pro Gly Gln
1               5                   10                  15

Arg Val Thr Ile Ser Cys Ser Gly Thr Ser Ser Asn Ile Gly Ile Asn
                20                  25                  30

Ser Val Asn Trp Tyr Gln Gln Leu Pro Gly Met Ala Pro Lys Leu Val
            35                  40                  45

Ile Tyr Ser Arg Asp Gln Arg Pro Ser Gly Val Pro Asp Arg Phe Ser
    50                  55                  60

Gly Ser Gln Ser Gly Thr Ser Ala Ser Leu Ala Ile Asn Gly Leu Gln
65                  70                  75                  80

Ser Glu Asp Glu Ala Asp Tyr Trp Cys Ser Thr Trp Asp Ser Leu
                85                  90                  95

Asn Gly Trp Val Phe Gly Gly Gly Thr Lys Leu Thr Val Leu
            100                 105                 110

<210> SEQ ID NO 22
<211> LENGTH: 13
<212> TYPE: PRT
<213> ORGANISM: Artificial
<220> FEATURE:
<223> OTHER INFORMATION: Description of the artificial sequence: amino
      acid sequence of LCDR1 of MOG09

<400> SEQUENCE: 22

Ser Gly Thr Ser Ser Asn Ile Gly Ile Asn Ser Val Asn
1               5                   10

<210> SEQ ID NO 23
<211> LENGTH: 7
<212> TYPE: PRT
<213> ORGANISM: Artificial
<220> FEATURE:
<223> OTHER INFORMATION: Description of the artificial sequence: amino
      acid sequence of LCDR2 of MOG09

<400> SEQUENCE: 23

Ser Arg Asp Gln Arg Pro Ser
1               5

<210> SEQ ID NO 24
<211> LENGTH: 11
<212> TYPE: PRT
<213> ORGANISM: Artificial
<220> FEATURE:
<223> OTHER INFORMATION: Description of the artificial sequence: amino
      acid sequence of LCDR3 of MOG09

<400> SEQUENCE: 24

Ser Thr Trp Asp Ser Leu Asn Gly Trp Val
1               5                   10

<210> SEQ ID NO 25
<211> LENGTH: 414
<212> TYPE: DNA
<213> ORGANISM: Homo sapiens
<220> FEATURE:
<221> NAME/KEY: CDS
<222> LOCATION: (1)..(414)

<400> SEQUENCE: 25 atg aac ctc ggg ctc agt ttg att ttc ctt gcc ctc att tta aaa ggt    48
Met Asn Leu Gly Leu Ser Leu Ile Phe Leu Ala Leu Ile Leu Lys Gly
1               5                   10                  15
```

```
gtc cag tgt cag gtg cag ctg gtg caa tct ggg gct gag gtg aag aag      96
Val Gln Cys Gln Val Gln Leu Val Gln Ser Gly Ala Glu Val Lys Lys
            20                  25                  30 cct ggg gcc tca gtg aag gtc tcc tgc cag gct tct gga tac acg ttc     144
Pro Gly Ala Ser Val Lys Val Ser Cys Gln Ala Ser Gly Tyr Thr Phe
        35                  40                  45 acc ggc gac tat att cac tgg gtg cga cag gcc cct gga caa ggg ctg     192
Thr Gly Asp Tyr Ile His Trp Val Arg Gln Ala Pro Gly Gln Gly Leu
    50                  55                  60 gaa tac ttg gga tgg atc aac cct gac agg ggt ttc aca tac tat aca     240
Glu Tyr Leu Gly Trp Ile Asn Pro Asp Arg Gly Phe Thr Tyr Tyr Thr
65                  70                  75                  80 cag aag ttt cag ggc agg gtc acc atg acc cgg gac acg tcc agc aac     288
Gln Lys Phe Gln Gly Arg Val Thr Met Thr Arg Asp Thr Ser Ser Asn
                85                  90                  95 aca gcc tac atg gag ctg agc agc ctg aga tct gac gac acg gcc atg     336
Thr Ala Tyr Met Glu Leu Ser Ser Leu Arg Ser Asp Asp Thr Ala Met
            100                 105                 110 tat tac tgt acg aga gag aac cct cgc gcg tac ttc ttt gac ctc tgg     384
Tyr Tyr Cys Thr Arg Glu Asn Pro Arg Ala Tyr Phe Phe Asp Leu Trp
        115                 120                 125 ggc cag gga acc ctg gtc acc gtc tcc tca                             414
Gly Gln Gly Thr Leu Val Thr Val Ser Ser
    130                 135
```

<210> SEQ ID NO 26
<211> LENGTH: 138
<212> TYPE: PRT
<213> ORGANISM: Homo sapiens

<400> SEQUENCE: 26

```
Met Asn Leu Gly Leu Ser Leu Ile Phe Leu Ala Leu Ile Leu Lys Gly
1               5                   10                  15

Val Gln Cys Gln Val Gln Leu Val Gln Ser Gly Ala Glu Val Lys Lys
            20                  25                  30

Pro Gly Ala Ser Val Lys Val Ser Cys Gln Ala Ser Gly Tyr Thr Phe
        35                  40                  45

Thr Gly Asp Tyr Ile His Trp Val Arg Gln Ala Pro Gly Gln Gly Leu
    50                  55                  60

Glu Tyr Leu Gly Trp Ile Asn Pro Asp Arg Gly Phe Thr Tyr Tyr Thr
65                  70                  75                  80

Gln Lys Phe Gln Gly Arg Val Thr Met Thr Arg Asp Thr Ser Ser Asn
                85                  90                  95

Thr Ala Tyr Met Glu Leu Ser Ser Leu Arg Ser Asp Asp Thr Ala Met
            100                 105                 110

Tyr Tyr Cys Thr Arg Glu Asn Pro Arg Ala Tyr Phe Phe Asp Leu Trp
        115                 120                 125

Gly Gln Gly Thr Leu Val Thr Val Ser Ser
    130                 135
```

<210> SEQ ID NO 27
<211> LENGTH: 119
<212> TYPE: PRT
<213> ORGANISM: Artificial
<220> FEATURE:
<223> OTHER INFORMATION: Description of the artificial sequence: amino
      acid sequence of VH of MOG14 excluding signal sequence

<400> SEQUENCE: 27

Gln Val Gln Leu Val Gln Ser Gly Ala Glu Val Lys Lys Pro Gly Ala

```
                1               5                   10                  15
            Ser Val Lys Val Ser Cys Gln Ala Ser Gly Tyr Thr Phe Thr Gly Asp
                            20                  25                  30

Tyr Ile His Trp Val Arg Gln Ala Pro Gly Gln Gly Leu Glu Tyr Leu
                        35                  40                  45

Gly Trp Ile Asn Pro Asp Arg Gly Phe Thr Tyr Tyr Thr Gln Lys Phe
                50                  55                  60

Gln Gly Arg Val Thr Met Thr Arg Asp Thr Ser Ser Asn Thr Ala Tyr
            65                  70                  75                  80

Met Glu Leu Ser Ser Leu Arg Ser Asp Asp Thr Ala Met Tyr Tyr Cys
                            85                  90                  95

Thr Arg Glu Asn Pro Arg Ala Tyr Phe Phe Asp Leu Trp Gly Gln Gly
                            100                 105                 110

Thr Leu Val Thr Val Ser Ser
                    115
```

<210> SEQ ID NO 28
<211> LENGTH: 5
<212> TYPE: PRT
<213> ORGANISM: Artificial
<220> FEATURE:
<223> OTHER INFORMATION: Description of the artificial sequence: amino
      acid sequence of HCDR1 of MOG14

<400> SEQUENCE: 28

```
Gly Asp Tyr Ile His
1               5
```

<210> SEQ ID NO 29
<211> LENGTH: 17
<212> TYPE: PRT
<213> ORGANISM: Artificial
<220> FEATURE:
<223> OTHER INFORMATION: Description of the artificial sequence: amino
      acid sequence of HCDR2 of MOG14

<400> SEQUENCE: 29

```
Trp Ile Asn Pro Asp Arg Gly Phe Thr Tyr Tyr Thr Gln Lys Phe Gln
1               5                   10                  15

Gly
```

<210> SEQ ID NO 30
<211> LENGTH: 10
<212> TYPE: PRT
<213> ORGANISM: Artificial
<220> FEATURE:
<223> OTHER INFORMATION: Description of the artificial sequence: amino
      acid sequence of HCDR3 of MOG14

<400> SEQUENCE: 30

```
Glu Asn Pro Arg Ala Tyr Phe Phe Asp Leu
1               5                   10
```

<210> SEQ ID NO 31
<211> LENGTH: 381
<212> TYPE: DNA
<213> ORGANISM: Homo sapiens
<220> FEATURE:
<221> NAME/KEY: CDS
<222> LOCATION: (1)..(381)

<400> SEQUENCE: 31

```
atg aag ttg cct gtt agg ctg ttg gtg ctg atg ttc tgg att cct gct      48
```

```
Met Lys Leu Pro Val Arg Leu Leu Val Leu Met Phe Trp Ile Pro Ala
1               5                   10                  15 tcc agc agt gaa ata gtg ttg acg cag tct cca ggc acc ctg tct ttg      96
Ser Ser Ser Glu Ile Val Leu Thr Gln Ser Pro Gly Thr Leu Ser Leu
                20                  25                  30 tct cca ggg gaa aga gcc act ctc tcc tgc agg gcc agt cag agt att     144
Ser Pro Gly Glu Arg Ala Thr Leu Ser Cys Arg Ala Ser Gln Ser Ile
            35                  40                  45 agc ggc agc tac gtg acc tgg tac cag cag aag cct ggc cag gct ccc     192
Ser Gly Ser Tyr Val Thr Trp Tyr Gln Gln Lys Pro Gly Gln Ala Pro
        50                  55                  60 agg ctc ctc atc tat gct aca tcc aat agg gcc att ggc atc cca gac     240
Arg Leu Leu Ile Tyr Ala Thr Ser Asn Arg Ala Ile Gly Ile Pro Asp
65                  70                  75                  80 aag ttc agt ggc ggt ggg tct ggg aga gac ttc act ctc acc atc aac     288
Lys Phe Ser Gly Gly Gly Ser Gly Arg Asp Phe Thr Leu Thr Ile Asn
                85                  90                  95 aga ctg gag cct gaa gat ttt gca gtg tat tac tgt cag cag agt gtt     336
Arg Leu Glu Pro Glu Asp Phe Ala Val Tyr Tyr Cys Gln Gln Ser Val
            100                 105                 110 agt tct ccg tac act ttt ggc cag ggg acc aag gtg gaa atc aaa         381
Ser Ser Pro Tyr Thr Phe Gly Gln Gly Thr Lys Val Glu Ile Lys
        115                 120                 125
```

<210> SEQ ID NO 32
<211> LENGTH: 127
<212> TYPE: PRT
<213> ORGANISM: Homo sapiens

<400> SEQUENCE: 32

```
Met Lys Leu Pro Val Arg Leu Leu Val Leu Met Phe Trp Ile Pro Ala
1               5                   10                  15

Ser Ser Ser Glu Ile Val Leu Thr Gln Ser Pro Gly Thr Leu Ser Leu
                20                  25                  30

Ser Pro Gly Glu Arg Ala Thr Leu Ser Cys Arg Ala Ser Gln Ser Ile
            35                  40                  45

Ser Gly Ser Tyr Val Thr Trp Tyr Gln Gln Lys Pro Gly Gln Ala Pro
        50                  55                  60

Arg Leu Leu Ile Tyr Ala Thr Ser Asn Arg Ala Ile Gly Ile Pro Asp
65                  70                  75                  80

Lys Phe Ser Gly Gly Gly Ser Gly Arg Asp Phe Thr Leu Thr Ile Asn
                85                  90                  95

Arg Leu Glu Pro Glu Asp Phe Ala Val Tyr Tyr Cys Gln Gln Ser Val
            100                 105                 110

Ser Ser Pro Tyr Thr Phe Gly Gln Gly Thr Lys Val Glu Ile Lys
        115                 120                 125
```

<210> SEQ ID NO 33
<211> LENGTH: 108
<212> TYPE: PRT
<213> ORGANISM: Artificial
<220> FEATURE:
<223> OTHER INFORMATION: Description of the artificial sequence: amino
      acid sequence of VL of MOG14 excluding signal sequence

<400> SEQUENCE: 33

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Gly Ser
                20                  25                  30
```

Tyr Val Thr Trp Tyr Gln Gln Lys Pro Gly Gln Ala Pro Arg Leu Leu
              35                  40                  45

Ile Tyr Ala Thr Ser Asn Arg Ala Ile Gly Ile Pro Asp Lys Phe Ser
      50                  55                  60

Gly Gly Gly Ser Gly Arg Asp Phe Thr Leu Thr Ile Asn Arg Leu Glu
65                  70                  75                  80

Pro Glu Asp Phe Ala Val Tyr Tyr Cys Gln Gln Ser Val Ser Ser Pro
                  85                  90                  95

Tyr Thr Phe Gly Gln Gly Thr Lys Val Glu Ile Lys
              100                 105

<210> SEQ ID NO 34
<211> LENGTH: 12
<212> TYPE: PRT
<213> ORGANISM: Artificial
<220> FEATURE:
<223> OTHER INFORMATION: Description of the artificial sequence: amino
      acid sequence of LCDR1 of MOG14

<400> SEQUENCE: 34

Arg Ala Ser Gln Ser Ile Ser Gly Ser Tyr Val Thr
1               5                   10

<210> SEQ ID NO 35
<211> LENGTH: 7
<212> TYPE: PRT
<213> ORGANISM: Artificial
<220> FEATURE:
<223> OTHER INFORMATION: Description of the artificial sequence: amino
      acid sequence of LCDR2 of MOG14

<400> SEQUENCE: 35

Ala Thr Ser Asn Arg Ala Ile
1               5

<210> SEQ ID NO 36
<211> LENGTH: 9
<212> TYPE: PRT
<213> ORGANISM: Artificial
<220> FEATURE:
<223> OTHER INFORMATION: Description of the artificial sequence: amino
      acid sequence of LCDR3 of MOG14

<400> SEQUENCE: 36

Gln Gln Ser Val Ser Ser Pro Tyr Thr
1               5

<210> SEQ ID NO 37
<211> LENGTH: 411
<212> TYPE: DNA
<213> ORGANISM: Artificial
<220> FEATURE:
<223> OTHER INFORMATION: Description of the artificial sequence:
      sequence of VHH of iMOG_3Rim1_S32 including signal sequence
<220> FEATURE:
<221> NAME/KEY: CDS
<222> LOCATION: (1)..(411)

<400> SEQUENCE: 37 atg tac agg atg caa ctc ctg tct tgc att gca cta agt ctt gca ctt    48
Met Tyr Arg Met Gln Leu Leu Ser Cys Ile Ala Leu Ser Leu Ala Leu
1               5                   10                  15 gtc acg aat tcg cag gtg cag ctc gtg gag tct ggg gga ggc ttg gtg    96
Val Thr Asn Ser Gln Val Gln Leu Val Glu Ser Gly Gly Gly Leu Val
              20                  25                  30

```
cag act ggg ggg tct ctg aga ctc tcc tgt gca gcc tct gga agc atg      144
Gln Thr Gly Gly Ser Leu Arg Leu Ser Cys Ala Ala Ser Gly Ser Met
            35                  40                  45 ttc agt acc atg ggc tgg ttc cgc cag gct cca ggg aac cag cgc gag      192
Phe Ser Thr Met Gly Trp Phe Arg Gln Ala Pro Gly Asn Gln Arg Glu
 50                  55                  60 ttg gtc gcc att atg tca tcc ggt ggt acc gca aac tat gca gac tct      240
Leu Val Ala Ile Met Ser Ser Gly Gly Thr Ala Asn Tyr Ala Asp Ser
65                  70                  75                  80 gtg aag ggc cga ttc acc atc tcc gga gac aac gtc aag aac acg gtg      288
Val Lys Gly Arg Phe Thr Ile Ser Gly Asp Asn Val Lys Asn Thr Val
                    85                  90                  95 act ctc caa atg aac agc ctg aat cca gag gac aca gcc gtc tat tat      336
Thr Leu Gln Met Asn Ser Leu Asn Pro Glu Asp Thr Ala Val Tyr Tyr
                100                 105                 110 tgt agg ttt acc ggt tgg gtc aag agt tcg ttc tct acg tac tgg ggc      384
Cys Arg Phe Thr Gly Trp Val Lys Ser Ser Phe Ser Thr Tyr Trp Gly
            115                 120                 125 cag ggg acc cag gtc acc gtc tcc tca                                  411
Gln Gly Thr Gln Val Thr Val Ser Ser
        130                 135

<210> SEQ ID NO 38
<211> LENGTH: 137
<212> TYPE: PRT
<213> ORGANISM: Artificial
<220> FEATURE:
<223> OTHER INFORMATION: Synthetic Construct

<400> SEQUENCE: 38

Met Tyr Arg Met Gln Leu Leu Ser Cys Ile Ala Leu Ser Leu Ala Leu
1               5                   10                  15

Val Thr Asn Ser Gln Val Gln Leu Val Glu Ser Gly Gly Gly Leu Val
                20                  25                  30

Gln Thr Gly Gly Ser Leu Arg Leu Ser Cys Ala Ala Ser Gly Ser Met
            35                  40                  45

Phe Ser Thr Met Gly Trp Phe Arg Gln Ala Pro Gly Asn Gln Arg Glu
 50                 55                  60

Leu Val Ala Ile Met Ser Ser Gly Gly Thr Ala Asn Tyr Ala Asp Ser
65                  70                  75                  80

Val Lys Gly Arg Phe Thr Ile Ser Gly Asp Asn Val Lys Asn Thr Val
                85                  90                  95

Thr Leu Gln Met Asn Ser Leu Asn Pro Glu Asp Thr Ala Val Tyr Tyr
                100                 105                 110

Cys Arg Phe Thr Gly Trp Val Lys Ser Ser Phe Ser Thr Tyr Trp Gly
            115                 120                 125

Gln Gly Thr Gln Val Thr Val Ser Ser
        130                 135

<210> SEQ ID NO 39
<211> LENGTH: 117
<212> TYPE: PRT
<213> ORGANISM: Artificial
<220> FEATURE:
<223> OTHER INFORMATION: Description of the artificial sequence: amino
      acid sequence of VHH of iMOG_3Rim1_S32 excluding signal sequence

<400> SEQUENCE: 39

Gln Val Gln Leu Val Glu Ser Gly Gly Gly Leu Val Gln Thr Gly Gly
1               5                   10                  15
```

```
Ser Leu Arg Leu Ser Cys Ala Ala Ser Gly Ser Met Phe Ser Thr Met
            20                  25                  30

Gly Trp Phe Arg Gln Ala Pro Gly Asn Gln Arg Glu Leu Val Ala Ile
        35                  40                  45

Met Ser Ser Gly Gly Thr Ala Asn Tyr Ala Asp Ser Val Lys Gly Arg
    50                  55                  60

Phe Thr Ile Ser Gly Asp Asn Val Lys Asn Thr Val Thr Leu Gln Met
65                  70                  75                  80

Asn Ser Leu Asn Pro Glu Asp Thr Ala Val Tyr Tyr Cys Arg Phe Thr
                85                  90                  95

Gly Trp Val Lys Ser Ser Phe Ser Thr Tyr Trp Gly Gln Gly Thr Gln
            100                 105                 110

Val Thr Val Ser Ser
            115

<210> SEQ ID NO 40
<211> LENGTH: 3
<212> TYPE: PRT
<213> ORGANISM: Artificial
<220> FEATURE:
<223> OTHER INFORMATION: Description of the artificial sequence: amino
      acid sequence of CDR1 of iMOG_3Rim1_S32

<400> SEQUENCE: 40

Thr Met Gly
1

<210> SEQ ID NO 41
<211> LENGTH: 16
<212> TYPE: PRT
<213> ORGANISM: Artificial
<220> FEATURE:
<223> OTHER INFORMATION: Description of the artificial sequence: amino
      acid sequence of CDR2 of iMOG_3Rim1_S32

<400> SEQUENCE: 41

Ile Met Ser Ser Gly Gly Thr Ala Asn Tyr Ala Asp Ser Val Lys Gly
1               5                   10                  15

<210> SEQ ID NO 42
<211> LENGTH: 11
<212> TYPE: PRT
<213> ORGANISM: Artificial
<220> FEATURE:
<223> OTHER INFORMATION: Description of the artificial sequence: amino
      acid sequence of CDR3 of iMOG_3Rim1_S32

<400> SEQUENCE: 42

Thr Gly Trp Val Lys Ser Ser Phe Ser Thr Tyr
1               5                   10

<210> SEQ ID NO 43
<211> LENGTH: 36
<212> TYPE: DNA
<213> ORGANISM: Artificial
<220> FEATURE:
<223> OTHER INFORMATION: Description of the artificial sequence: primer1

<400> SEQUENCE: 43
ggattcctgc ttccagcagt cagtctgccc tgactc                         36

<210> SEQ ID NO 44
<211> LENGTH: 36
```

```
<212> TYPE: DNA
<213> ORGANISM: Artificial
<220> FEATURE:
<223> OTHER INFORMATION: Description of the artificial sequence: primer2

<400> SEQUENCE: 44
ggcggccttg ggctgaccta ggacggtcag cttggt                              36

<210> SEQ ID NO 45
<211> LENGTH: 80
<212> TYPE: DNA
<213> ORGANISM: Artificial
<220> FEATURE:
<223> OTHER INFORMATION: Description of the artificial sequence: primer3

<400> SEQUENCE: 45
acgccatcac agatctgcct cttcaaaatg aagttgcctg ttaggctgtt ggtgctgatg   60
ttctggattc ctgcttccag                                               80

<210> SEQ ID NO 46
<211> LENGTH: 36
<212> TYPE: DNA
<213> ORGANISM: Artificial
<220> FEATURE:
<223> OTHER INFORMATION: Description of the artificial sequence: primer4

<400> SEQUENCE: 46
aaaaggtgtc cagtgtcagg tacagctgca gcagtc                             36

<210> SEQ ID NO 47
<211> LENGTH: 32
<212> TYPE: DNA
<213> ORGANISM: Artificial
<220> FEATURE:
<223> OTHER INFORMATION: primer5

<400> SEQUENCE: 47
gccccttggt gctagctgag gagacggtga cc                                 32

<210> SEQ ID NO 48
<211> LENGTH: 80
<212> TYPE: DNA
<213> ORGANISM: Artificial
<220> FEATURE:
<223> OTHER INFORMATION: Description of the artificial sequence: primer6

<400> SEQUENCE: 48
acacagaccc gtcgacccct caccatgaac ctcgggctca gtttgattt ccttgccctc   60 attttaaaag gtgtccagtg                                               80

<210> SEQ ID NO 49
<211> LENGTH: 36
<212> TYPE: DNA
<213> ORGANISM: Artificial
<220> FEATURE:
<223> OTHER INFORMATION: Description of the artificial sequence: primer7

<400> SEQUENCE: 49
ggattcctgc ttccagcagt tcctatgtgc tgactc                             36

<210> SEQ ID NO 50
<211> LENGTH: 36
<212> TYPE: DNA
<213> ORGANISM: Artificial
<220> FEATURE:
```

<223> OTHER INFORMATION: Description of the artificial sequence: primer8

<400> SEQUENCE: 50
ggcggccttg ggctgaccta ggacggtcag cttggt         36

<210> SEQ ID NO 51
<211> LENGTH: 36
<212> TYPE: DNA
<213> ORGANISM: Artificial
<220> FEATURE:
<223> OTHER INFORMATION: Description of the artificial sequence: primer9

<400> SEQUENCE: 51
aaaaggtgtc cagtgtcagg tgcagctgca ggagtc         36

<210> SEQ ID NO 52
<211> LENGTH: 32
<212> TYPE: DNA
<213> ORGANISM: Artificial
<220> FEATURE:
<223> OTHER INFORMATION: Description of the artificial sequence:
      primer10

<400> SEQUENCE: 52
gccccttggt gctagctgag gagacggtga cc         32

<210> SEQ ID NO 53
<211> LENGTH: 40
<212> TYPE: DNA
<213> ORGANISM: Artificial
<220> FEATURE:
<223> OTHER INFORMATION: Description of the artificial sequence:
      primer11

<400> SEQUENCE: 53
ggattcctgc ttccagcagt gaaatagtgt tgacgcagtc         40

<210> SEQ ID NO 54
<211> LENGTH: 36
<212> TYPE: DNA
<213> ORGANISM: Artificial
<220> FEATURE:
<223> OTHER INFORMATION: Description of the artificial sequence:
      primer12

<400> SEQUENCE: 54
gtgcagccac cgtacgtttg atttccacct tggtcc         36

<210> SEQ ID NO 55
<211> LENGTH: 36
<212> TYPE: DNA
<213> ORGANISM: Artificial
<220> FEATURE:
<223> OTHER INFORMATION: Description of the artificial sequence:
      primer13

<400> SEQUENCE: 55
aaaaggtgtc cagtgtcagg tgcagctggt gcaatc         36

<210> SEQ ID NO 56
<211> LENGTH: 32
<212> TYPE: DNA
<213> ORGANISM: Artificial
<220> FEATURE:
<223> OTHER INFORMATION: Description of the artificial sequence:
      primer14

<400> SEQUENCE: 56 gcccctggt gctagctgag gagacggtga cc        32

<210> SEQ ID NO 57
<211> LENGTH: 40
<212> TYPE: DNA
<213> ORGANISM: Artificial
<220> FEATURE:
<223> OTHER INFORMATION: Description of the artificial sequence:
      primer15

<400> SEQUENCE: 57
tgcacttgtc acgaattcgc aggtgcagct cgtggagtct        40

<210> SEQ ID NO 58
<211> LENGTH: 45
<212> TYPE: DNA
<213> ORGANISM: Artificial
<220> FEATURE:
<223> OTHER INFORMATION: Description of the artificial sequence:
      primer16

<400> SEQUENCE: 58
accatatttg gactcagatc tggccgctga ggagacggtg acctg        45

<210> SEQ ID NO 59
<211> LENGTH: 30
<212> TYPE: DNA
<213> ORGANISM: Artificial
<220> FEATURE:
<223> OTHER INFORMATION: Description of the artificial sequence:
      primer17

<400> SEQUENCE: 59
acagtctcct cagctagcac caaggggcca        30

<210> SEQ ID NO 60
<211> LENGTH: 36
<212> TYPE: DNA
<213> ORGANISM: Artificial
<220> FEATURE:
<223> OTHER INFORMATION: Description of the artificial sequence:
      primer18

<400> SEQUENCE: 60
ctgctgcagc tgtacctggg accctcctcc tccgga        36

<210> SEQ ID NO 61
<211> LENGTH: 33
<212> TYPE: DNA
<213> ORGANISM: Artificial
<220> FEATURE:
<223> OTHER INFORMATION: Description of the artificial sequence:
      primer19

<400> SEQUENCE: 61
ggaggaggag ggtcccaggt acagctgcag cag        33

<210> SEQ ID NO 62
<211> LENGTH: 33
<212> TYPE: DNA
<213> ORGANISM: Artificial
<220> FEATURE:
<223> OTHER INFORMATION: Description of the artificial sequence:
      primer20

<400> SEQUENCE: 62

```
aagcggccgc ctggatcctc ataggacggt cag                                33
```

<210> SEQ ID NO 63
<211> LENGTH: 39
<212> TYPE: DNA
<213> ORGANISM: Artificial
<220> FEATURE:
<223> OTHER INFORMATION: Description of the artificial sequence:
      primer21

<400> SEQUENCE: 63

```
tcagtcataa tgtctagagg agacatccag atgacccag                          39
```

<210> SEQ ID NO 64
<211> LENGTH: 37
<212> TYPE: DNA
<213> ORGANISM: Artificial
<220> FEATURE:
<223> OTHER INFORMATION: Description of the artificial sequence:
      primer22

<400> SEQUENCE: 64

```
gggcggcctt gggctgacct ttgatctcca ccttggt                            37
```

<210> SEQ ID NO 65
<211> LENGTH: 41
<212> TYPE: DNA
<213> ORGANISM: Artificial
<220> FEATURE:
<223> OTHER INFORMATION: Description of the artificial sequence:
      primer23

<400> SEQUENCE: 65

```
cagcctttcc tggtatactt agtgaggtgc agttggtgga g                       41
```

<210> SEQ ID NO 66
<211> LENGTH: 36
<212> TYPE: DNA
<213> ORGANISM: Artificial
<220> FEATURE:
<223> OTHER INFORMATION: Description of the artificial sequence:
      primer24

<400> SEQUENCE: 66

```
tggccccttg gtgctagccg aggagacggt gaccag                             36
```

<210> SEQ ID NO 67
<211> LENGTH: 738
<212> TYPE: DNA
<213> ORGANISM: Rattus norvegicus
<220> FEATURE:
<221> NAME/KEY: CDS
<222> LOCATION: (1)..(738)

<400> SEQUENCE: 67

```
atg gcc ggt gtg tgg agc ctt tct ctg ccc agc tgc ctc ctg tcc ctg     48
Met Ala Gly Val Trp Ser Leu Ser Leu Pro Ser Cys Leu Leu Ser Leu
1               5                   10                  15 ctc ctc ctc ctc cag ttg tca cgc agc tac gca gga cag ttc aga gtg     96
Leu Leu Leu Leu Gln Leu Ser Arg Ser Tyr Ala Gly Gln Phe Arg Val
            20                  25                  30 ata ggg cca ggg cat ccc atc cgg gct tta gtt ggg gat gaa gca gaa    144
Ile Gly Pro Gly His Pro Ile Arg Ala Leu Val Gly Asp Glu Ala Glu
        35                  40                  45 ctg ccg tgc cgt ata tct cct ggg aag aat gcc acg ggc atg gag gtg    192
```

```
Leu Pro Cys Arg Ile Ser Pro Gly Lys Asn Ala Thr Gly Met Glu Val
         50                  55                  60 ggg tgg tac cgt tct ccc ttt tca aga gtg gtt cat ctg tac cga aat     240
Gly Trp Tyr Arg Ser Pro Phe Ser Arg Val Val His Leu Tyr Arg Asn
 65                  70                  75                  80 ggc aag gac caa gac gca gag caa gcg cct gaa tac cgg gga cgc aca     288
Gly Lys Asp Gln Asp Ala Glu Gln Ala Pro Glu Tyr Arg Gly Arg Thr
                     85                  90                  95 gag ctt ctg aaa gag tct atc ggc gag gga aag gtt gcc ctc agg atc     336
Glu Leu Leu Lys Glu Ser Ile Gly Glu Gly Lys Val Ala Leu Arg Ile
                100                 105                 110 cag aac gtg agg ttc tcg gat gaa gga ggc tac aca tgc ttc ttc aga     384
Gln Asn Val Arg Phe Ser Asp Glu Gly Gly Tyr Thr Cys Phe Phe Arg
            115                 120                 125 gac cac tcc tac caa gaa gaa gcc gcc gtg gag ttg aaa gta gaa gat     432
Asp His Ser Tyr Gln Glu Glu Ala Ala Val Glu Leu Lys Val Glu Asp
        130                 135                 140 ccc ttc tac tgg atc aac cct ggc gtg ctg gct ctc att gcc ctt gtg     480
Pro Phe Tyr Trp Ile Asn Pro Gly Val Leu Ala Leu Ile Ala Leu Val
145                 150                 155                 160 cct atg ctg ctc ctg cag gtc tct gta ggc ctt gta ttc ctc ttc ctg     528
Pro Met Leu Leu Leu Gln Val Ser Val Gly Leu Val Phe Leu Phe Leu
                165                 170                 175 cag cac aga ctg aga gga aaa ctc cgt gca gaa gtc gag aat ctc cat     576
Gln His Arg Leu Arg Gly Lys Leu Arg Ala Glu Val Glu Asn Leu His
                180                 185                 190 cgg act ttt gat cct cac ttc ctg aga gtg ccc tgc tgg aag ata aca     624
Arg Thr Phe Asp Pro His Phe Leu Arg Val Pro Cys Trp Lys Ile Thr
            195                 200                 205 ctg ttt gtt att gtc cct gtt ctt gga ccc ctg gtt gct ttg atc atc     672
Leu Phe Val Ile Val Pro Val Leu Gly Pro Leu Val Ala Leu Ile Ile
        210                 215                 220 tgc tac aac tgg ctg cac cga aga ctg gca gga cag ttt ctt gaa gag     720
Cys Tyr Asn Trp Leu His Arg Arg Leu Ala Gly Gln Phe Leu Glu Glu
225                 230                 235                 240 cta aga aac ccc ttt tga                                             738
Leu Arg Asn Pro Phe
                245

<210> SEQ ID NO 68
<211> LENGTH: 245
<212> TYPE: PRT
<213> ORGANISM: Rattus norvegicus

<400> SEQUENCE: 68

Met Ala Gly Val Trp Ser Leu Ser Leu Pro Ser Cys Leu Leu Ser Leu
1                   5                   10                  15

Leu Leu Leu Leu Gln Leu Ser Arg Ser Tyr Ala Gly Gln Phe Arg Val
                20                  25                  30

Ile Gly Pro Gly His Pro Ile Arg Ala Leu Val Gly Asp Glu Ala Glu
            35                  40                  45

Leu Pro Cys Arg Ile Ser Pro Gly Lys Asn Ala Thr Gly Met Glu Val
        50                  55                  60

Gly Trp Tyr Arg Ser Pro Phe Ser Arg Val Val His Leu Tyr Arg Asn
65                  70                  75                  80

Gly Lys Asp Gln Asp Ala Glu Gln Ala Pro Glu Tyr Arg Gly Arg Thr
                85                  90                  95

Glu Leu Leu Lys Glu Ser Ile Gly Glu Gly Lys Val Ala Leu Arg Ile
            100                 105                 110
```

```
Gln Asn Val Arg Phe Ser Asp Glu Gly Gly Tyr Thr Cys Phe Phe Arg
            115                 120                 125

Asp His Ser Tyr Gln Glu Glu Ala Ala Val Glu Leu Lys Val Glu Asp
        130                 135                 140

Pro Phe Tyr Trp Ile Asn Pro Gly Val Leu Ala Leu Ile Ala Leu Val
145                 150                 155                 160

Pro Met Leu Leu Leu Gln Val Ser Val Gly Leu Val Phe Leu Phe Leu
                165                 170                 175

Gln His Arg Leu Arg Gly Lys Leu Arg Ala Glu Val Glu Asn Leu His
            180                 185                 190

Arg Thr Phe Asp Pro His Phe Leu Arg Val Pro Cys Trp Lys Ile Thr
        195                 200                 205

Leu Phe Val Ile Val Pro Val Leu Gly Pro Leu Val Ala Leu Ile Ile
210                 215                 220

Cys Tyr Asn Trp Leu His Arg Arg Leu Ala Gly Gln Phe Leu Glu Glu
225                 230                 235                 240

Leu Arg Asn Pro Phe
            245

<210> SEQ ID NO 69
<211> LENGTH: 1167
<212> TYPE: DNA
<213> ORGANISM: Artificial
<220> FEATURE:
<223> OTHER INFORMATION: Description of the artificial sequence:
      sequence of rMOG-FLAG-Fc
<220> FEATURE:
<221> NAME/KEY: CDS
<222> LOCATION: (1)..(1167)

<400> SEQUENCE: 69 atg gcc ggt gtg tgg agc ctt tct ctg ccc agc tgc ctc ctg tcc ctg      48
Met Ala Gly Val Trp Ser Leu Ser Leu Pro Ser Cys Leu Leu Ser Leu
1               5                  10                  15 ctc ctc ctc ctc cag ttg tca cgc agc tac gca gga cag ttc aga gtg      96
Leu Leu Leu Leu Gln Leu Ser Arg Ser Tyr Ala Gly Gln Phe Arg Val
                20                  25                  30 ata ggg cca ggg cat ccc atc cgg gct tta gtt ggg gat gaa gca gaa     144
Ile Gly Pro Gly His Pro Ile Arg Ala Leu Val Gly Asp Glu Ala Glu
            35                  40                  45 ctg ccg tgc cgt ata tct cct ggg aag aat gcc acg ggc atg gag gtg     192
Leu Pro Cys Arg Ile Ser Pro Gly Lys Asn Ala Thr Gly Met Glu Val
        50                  55                  60 ggg tgg tac cgt tct ccc ttt tca aga gtg gtt cat ctg tac cga aat     240
Gly Trp Tyr Arg Ser Pro Phe Ser Arg Val Val His Leu Tyr Arg Asn
65                  70                  75                  80 ggc aag gac caa gac gca gag caa gcg cct gaa tac cgg gga cgc aca     288
Gly Lys Asp Gln Asp Ala Glu Gln Ala Pro Glu Tyr Arg Gly Arg Thr
                85                  90                  95 gag ctt ctg aaa gag tct atc ggc gag gga aag gtt gcc ctc agg atc     336
Glu Leu Leu Lys Glu Ser Ile Gly Glu Gly Lys Val Ala Leu Arg Ile
                100                 105                 110 cag aac gtg agg ttc tcg gat gaa gga ggc tac aca tgc ttc ttc aga     384
Gln Asn Val Arg Phe Ser Asp Glu Gly Gly Tyr Thr Cys Phe Phe Arg
            115                 120                 125 gac cac tcc tac caa gaa gaa gcc gcc gtg gag ttg aaa gta gaa gat     432
Asp His Ser Tyr Gln Glu Glu Ala Ala Val Glu Leu Lys Val Glu Asp
        130                 135                 140 ccc ttc tac tgg tct aga gca gac tac aag gac gac gat gac aag act     480
Pro Phe Tyr Trp Ser Arg Ala Asp Tyr Lys Asp Asp Asp Asp Lys Thr
```

```
Pro Phe Tyr Trp Ser Arg Ala Asp Tyr Lys Asp Asp Asp Lys Thr
145                 150                 155                 160 agt gac aaa act cac aca tgc cca ccg tgc cca gca cct gaa ctc ctg      528
Ser Asp Lys Thr His Thr Cys Pro Pro Cys Pro Ala Pro Glu Leu Leu
                    165                 170                 175 ggg gga ccg tca gtc ttc ctc ttc ccc cca aaa ccc aag gac acc ctc      576
Gly Gly Pro Ser Val Phe Leu Phe Pro Pro Lys Pro Lys Asp Thr Leu
                180                 185                 190 atg atc tcc cgg acc cct gag gtc aca tgc gtg gtg gtg gac gtg agc      624
Met Ile Ser Arg Thr Pro Glu Val Thr Cys Val Val Val Asp Val Ser
            195                 200                 205 cac gaa gac cct gag gtc aag ttc aac tgg tac gtg gac ggc gtg gag      672
His Glu Asp Pro Glu Val Lys Phe Asn Trp Tyr Val Asp Gly Val Glu
        210                 215                 220 gtg cat aat gcc aag aca aag ccg cgg gag gag cag tac aac agc acg      720
Val His Asn Ala Lys Thr Lys Pro Arg Glu Glu Gln Tyr Asn Ser Thr
225                 230                 235                 240 tac cgt gtg gtc agc gtc ctc acc gtc ctg cac cag gac tgg ctg aat      768
Tyr Arg Val Val Ser Val Leu Thr Val Leu His Gln Asp Trp Leu Asn
                    245                 250                 255 ggc aag gag tac aag tgc aag gtc tcc aac aaa gcc ctc cca gcc ccc      816
Gly Lys Glu Tyr Lys Cys Lys Val Ser Asn Lys Ala Leu Pro Ala Pro
                260                 265                 270 atc gag aaa acc atc tcc aaa gcc aaa ggg cag ccc cga gaa cca cag      864
Ile Glu Lys Thr Ile Ser Lys Ala Lys Gly Gln Pro Arg Glu Pro Gln
            275                 280                 285 gtg tac acc ctg ccc cca tcc cgg gat gag ctg acc aag aac cag gtc      912
Val Tyr Thr Leu Pro Pro Ser Arg Asp Glu Leu Thr Lys Asn Gln Val
        290                 295                 300 agc ctg acc tgc ctg gtc aaa ggc ttc tat ccc agc gac atc gcc gtg      960
Ser Leu Thr Cys Leu Val Lys Gly Phe Tyr Pro Ser Asp Ile Ala Val
305                 310                 315                 320 gag tgg gag agc aat ggg cag ccg gag aac aac tac aag acc acg cct      1008
Glu Trp Glu Ser Asn Gly Gln Pro Glu Asn Asn Tyr Lys Thr Thr Pro
                    325                 330                 335 ccc gtg ctg gac tcc gac ggc tcc ttc ttc ctc tac agc aag ctc acc      1056
Pro Val Leu Asp Ser Asp Gly Ser Phe Phe Leu Tyr Ser Lys Leu Thr
                340                 345                 350 gtg gac aag agc agg tgg cag cag ggg aac gtc ttc tca tgc tcc gtg      1104
Val Asp Lys Ser Arg Trp Gln Gln Gly Asn Val Phe Ser Cys Ser Val
            355                 360                 365 atg cat gag gct ctg cac aac cac tac acg cag aag agc ctc tcc ctg      1152
Met His Glu Ala Leu His Asn His Tyr Thr Gln Lys Ser Leu Ser Leu
        370                 375                 380 tct ccg ggt aaa tga                                                   1167
Ser Pro Gly Lys
385
```

<210> SEQ ID NO 70
<211> LENGTH: 388
<212> TYPE: PRT
<213> ORGANISM: Artificial
<220> FEATURE:
<223> OTHER INFORMATION: Synthetic Construct

<400> SEQUENCE: 70

```
Met Ala Gly Val Trp Ser Leu Ser Leu Pro Ser Cys Leu Leu Ser Leu
1               5                   10                  15

Leu Leu Leu Leu Gln Leu Ser Arg Ser Tyr Ala Gly Gln Phe Arg Val
            20                  25                  30
```

```
Ile Gly Pro Gly His Pro Ile Arg Ala Leu Val Gly Asp Glu Ala Glu
         35                  40                  45

Leu Pro Cys Arg Ile Ser Pro Gly Lys Asn Ala Thr Gly Met Glu Val
 50                  55                  60

Gly Trp Tyr Arg Ser Pro Phe Ser Arg Val Val His Leu Tyr Arg Asn
 65                  70                  75                  80

Gly Lys Asp Gln Asp Ala Glu Gln Ala Pro Glu Tyr Arg Gly Arg Thr
                 85                  90                  95

Glu Leu Leu Lys Glu Ser Ile Gly Glu Gly Lys Val Ala Leu Arg Ile
            100                 105                 110

Gln Asn Val Arg Phe Ser Asp Glu Gly Gly Tyr Thr Cys Phe Phe Arg
            115                 120                 125

Asp His Ser Tyr Gln Glu Glu Ala Ala Val Glu Leu Lys Val Glu Asp
130                 135                 140

Pro Phe Tyr Trp Ser Arg Ala Asp Tyr Lys Asp Asp Asp Asp Lys Thr
145                 150                 155                 160

Ser Asp Lys Thr His Thr Cys Pro Pro Cys Pro Ala Pro Glu Leu Leu
                165                 170                 175

Gly Gly Pro Ser Val Phe Leu Phe Pro Pro Lys Pro Lys Asp Thr Leu
            180                 185                 190

Met Ile Ser Arg Thr Pro Glu Val Thr Cys Val Val Val Asp Val Ser
            195                 200                 205

His Glu Asp Pro Glu Val Lys Phe Asn Trp Tyr Val Asp Gly Val Glu
        210                 215                 220

Val His Asn Ala Lys Thr Lys Pro Arg Glu Glu Gln Tyr Asn Ser Thr
225                 230                 235                 240

Tyr Arg Val Val Ser Val Leu Thr Val Leu His Gln Asp Trp Leu Asn
                245                 250                 255

Gly Lys Glu Tyr Lys Cys Lys Val Ser Asn Lys Ala Leu Pro Ala Pro
            260                 265                 270

Ile Glu Lys Thr Ile Ser Lys Ala Lys Gly Gln Pro Arg Glu Pro Gln
            275                 280                 285

Val Tyr Thr Leu Pro Pro Ser Arg Asp Glu Leu Thr Lys Asn Gln Val
        290                 295                 300

Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
                325                 330                 335

Pro Val Leu Asp Ser Asp Gly Ser Phe Phe Leu Tyr Ser Lys Leu Thr
            340                 345                 350

Val Asp Lys Ser Arg Trp Gln Gln Gly Asn Val Phe Ser Cys Ser Val
            355                 360                 365

Met His Glu Ala Leu His Asn His Tyr Thr Gln Lys Ser Leu Ser Leu
370                 375                 380

Ser Pro Gly Lys
385

<210> SEQ ID NO 71
<211> LENGTH: 1137
<212> TYPE: DNA
<213> ORGANISM: Artificial
<220> FEATURE:
<223> OTHER INFORMATION: Description of the artificial sequence:
      sequence of rMOG-GST
<220> FEATURE:
<221> NAME/KEY: CDS
```

-continued

<222> LOCATION: (1)..(1137)

<400> SEQUENCE: 71

```
atg gcc ggt gtg tgg agc ctt tct ctg ccc agc tgc ctc ctg tcc ctg        48
Met Ala Gly Val Trp Ser Leu Ser Leu Pro Ser Cys Leu Leu Ser Leu
 1               5                  10                  15 ctc ctc ctc ctc cag ttg tca cgc agc tac gca gga cag ttc aga gtg        96
Leu Leu Leu Leu Gln Leu Ser Arg Ser Tyr Ala Gly Gln Phe Arg Val
             20                  25                  30 ata ggg cca ggg cat ccc atc cgg gct tta gtt ggg gat gaa gca gaa       144
Ile Gly Pro Gly His Pro Ile Arg Ala Leu Val Gly Asp Glu Ala Glu
         35                  40                  45 ctg ccg tgc cgt ata tct cct ggg aag aat gcc acg ggc atg gag gtg       192
Leu Pro Cys Arg Ile Ser Pro Gly Lys Asn Ala Thr Gly Met Glu Val
     50                  55                  60 ggg tgg tac cgt tct ccc ttt tca aga gtg gtt cat ctg tac cga aat       240
Gly Trp Tyr Arg Ser Pro Phe Ser Arg Val Val His Leu Tyr Arg Asn
 65                  70                  75                  80 ggc aag gac caa gac gca gag caa gcg cct gaa tac cgg gga cgc aca       288
Gly Lys Asp Gln Asp Ala Glu Gln Ala Pro Glu Tyr Arg Gly Arg Thr
                 85                  90                  95 gag ctt ctg aaa gag tct atc ggc gag gga aag gtt gcc ctc agg atc       336
Glu Leu Leu Lys Glu Ser Ile Gly Glu Gly Lys Val Ala Leu Arg Ile
            100                 105                 110 cag aac gtg agg ttc tcg gat gaa gga ggc tac aca tgc ttc ttc aga       384
Gln Asn Val Arg Phe Ser Asp Glu Gly Gly Tyr Thr Cys Phe Phe Arg
        115                 120                 125 gac cac tcc tac caa gaa gaa gcc gcc gtg gag ttg aaa gta gaa gat       432
Asp His Ser Tyr Gln Glu Glu Ala Ala Val Glu Leu Lys Val Glu Asp
    130                 135                 140 ccc ttc tac tgg ggt acc ctg gaa gtt ctg ttc cag ggg ccc atg tcc       480
Pro Phe Tyr Trp Gly Thr Leu Glu Val Leu Phe Gln Gly Pro Met Ser
145                 150                 155                 160 cct ata cta ggt tat tgg aaa att aag ggc ctt gtg caa ccc act cga       528
Pro Ile Leu Gly Tyr Trp Lys Ile Lys Gly Leu Val Gln Pro Thr Arg
                165                 170                 175 ctt ctt ttg gaa tat ctt gaa gaa aaa tat gaa gag cat ttg tat gag       576
Leu Leu Leu Glu Tyr Leu Glu Glu Lys Tyr Glu Glu His Leu Tyr Glu
            180                 185                 190 cgc gat gaa ggt gat aaa tgg cga aac aaa aag ttt gaa ttg ggt ttg       624
Arg Asp Glu Gly Asp Lys Trp Arg Asn Lys Lys Phe Glu Leu Gly Leu
        195                 200                 205 gag ttt ccc aat ctt cct tat tat att gat ggt gat gtt aaa tta aca       672
Glu Phe Pro Asn Leu Pro Tyr Tyr Ile Asp Gly Asp Val Lys Leu Thr
    210                 215                 220 cag tct atg gcc atc ata cgt tat ata gct gac aag cac aac atg ttg       720
Gln Ser Met Ala Ile Ile Arg Tyr Ile Ala Asp Lys His Asn Met Leu
225                 230                 235                 240 ggt ggt tgt cca aaa gag cgt gca gag att tca atg ctt gaa gga gcg       768
Gly Gly Cys Pro Lys Glu Arg Ala Glu Ile Ser Met Leu Glu Gly Ala
                245                 250                 255 gtt ttg gat att aga tac ggt gtt tcg aga att gca tat agt aaa gac       816
Val Leu Asp Ile Arg Tyr Gly Val Ser Arg Ile Ala Tyr Ser Lys Asp
            260                 265                 270 ttt gaa act ctc aaa gtt gat ttt ctt agc aag cta cct gaa atg ctg       864
Phe Glu Thr Leu Lys Val Asp Phe Leu Ser Lys Leu Pro Glu Met Leu
        275                 280                 285 aaa atg ttc gaa gat cgt tta tgt cat aaa aca tat tta aat ggt gat       912
Lys Met Phe Glu Asp Arg Leu Cys His Lys Thr Tyr Leu Asn Gly Asp
    290                 295                 300
```

```
cat gta acc cat cct gac ttc atg ttg tat gac gct ctt gat gtt gtt        960
His Val Thr His Pro Asp Phe Met Leu Tyr Asp Ala Leu Asp Val Val
305                 310                 315                 320 tta tac atg gac cca atg tgc ctg gat gcg ttc cca aaa tta gtt tgt       1008
Leu Tyr Met Asp Pro Met Cys Leu Asp Ala Phe Pro Lys Leu Val Cys
                325                 330                 335 ttt aaa aaa cgt att gaa gct atc cca caa att gat aag tac ttg aaa       1056
Phe Lys Lys Arg Ile Glu Ala Ile Pro Gln Ile Asp Lys Tyr Leu Lys
            340                 345                 350 tcc agc aag tat ata gca tgg cct ttg cag ggc tgg caa gcc acg ttt       1104
Ser Ser Lys Tyr Ile Ala Trp Pro Leu Gln Gly Trp Gln Ala Thr Phe
        355                 360                 365 ggt ggt ggc gac cat cct cca aaa tcg gat tga                           1137
Gly Gly Gly Asp His Pro Pro Lys Ser Asp
    370                 375
```

<210> SEQ ID NO 72
<211> LENGTH: 378
<212> TYPE: PRT
<213> ORGANISM: Artificial
<220> FEATURE:
<223> OTHER INFORMATION: Synthetic Construct

<400> SEQUENCE: 72

```
Met Ala Gly Val Trp Ser Leu Ser Leu Pro Ser Cys Leu Leu Ser Leu
1               5                   10                  15

Leu Leu Leu Leu Gln Leu Ser Arg Ser Tyr Ala Gly Gln Phe Arg Val
            20                  25                  30

Ile Gly Pro Gly His Pro Ile Arg Ala Leu Val Gly Asp Glu Ala Glu
        35                  40                  45

Leu Pro Cys Arg Ile Ser Pro Gly Lys Asn Ala Thr Gly Met Glu Val
    50                  55                  60

Gly Trp Tyr Arg Ser Pro Phe Ser Arg Val Val His Leu Tyr Arg Asn
65                  70                  75                  80

Gly Lys Asp Gln Asp Ala Glu Gln Ala Pro Glu Tyr Arg Gly Arg Thr
                85                  90                  95

Glu Leu Leu Lys Glu Ser Ile Gly Glu Gly Lys Val Ala Leu Arg Ile
            100                 105                 110

Gln Asn Val Arg Phe Ser Asp Glu Gly Gly Tyr Thr Cys Phe Phe Arg
        115                 120                 125

Asp His Ser Tyr Gln Glu Glu Ala Ala Val Glu Leu Lys Val Glu Asp
    130                 135                 140

Pro Phe Tyr Trp Gly Thr Leu Glu Val Leu Phe Gln Gly Pro Met Ser
145                 150                 155                 160

Pro Ile Leu Gly Tyr Trp Lys Ile Lys Gly Leu Val Gln Pro Thr Arg
                165                 170                 175

Leu Leu Leu Glu Tyr Leu Glu Glu Lys Tyr Glu Glu His Leu Tyr Glu
            180                 185                 190

Arg Asp Glu Gly Asp Lys Trp Arg Asn Lys Lys Phe Glu Leu Gly Leu
        195                 200                 205

Glu Phe Pro Asn Leu Pro Tyr Tyr Ile Asp Gly Asp Val Lys Leu Thr
    210                 215                 220

Gln Ser Met Ala Ile Ile Arg Tyr Ile Ala Asp Lys His Asn Met Leu
225                 230                 235                 240

Gly Gly Cys Pro Lys Glu Arg Ala Glu Ile Ser Met Leu Glu Gly Ala
                245                 250                 255
```

```
Val Leu Asp Ile Arg Tyr Gly Val Ser Arg Ile Ala Tyr Ser Lys Asp
            260                 265                 270

Phe Glu Thr Leu Lys Val Asp Phe Leu Ser Lys Leu Pro Glu Met Leu
        275                 280                 285

Lys Met Phe Glu Asp Arg Leu Cys His Lys Thr Tyr Leu Asn Gly Asp
    290                 295                 300

His Val Thr His Pro Asp Phe Met Leu Tyr Asp Ala Leu Asp Val Val
305                 310                 315                 320

Leu Tyr Met Asp Pro Met Cys Leu Asp Ala Phe Pro Lys Leu Val Cys
                325                 330                 335

Phe Lys Lys Arg Ile Glu Ala Ile Pro Gln Ile Asp Lys Tyr Leu Lys
            340                 345                 350

Ser Ser Lys Tyr Ile Ala Trp Pro Leu Gln Gly Trp Gln Ala Thr Phe
        355                 360                 365

Gly Gly Gly Asp His Pro Pro Lys Ser Asp
    370                 375
```

```
<210> SEQ ID NO 73
<211> LENGTH: 744
<212> TYPE: DNA
<213> ORGANISM: Mus musculus
<220> FEATURE:
<221> NAME/KEY: CDS
<222> LOCATION: (1)..(744)

<400> SEQUENCE: 73
```

```
atg gcc tgt ttg tgg agc ttc tct tgg ccc agc tgc ttc ctc tcc ctt      48
Met Ala Cys Leu Trp Ser Phe Ser Trp Pro Ser Cys Phe Leu Ser Leu
1               5                   10                  15 ctc ctc ctc ctt ctc ctc cag ttg tca tgc agc tat gca gga caa ttc      96
Leu Leu Leu Leu Leu Leu Gln Leu Ser Cys Ser Tyr Ala Gly Gln Phe
                20                  25                  30 aga gtg ata gga cca ggg tat ccc atc cgg gct tta gtt ggg gat gaa     144
Arg Val Ile Gly Pro Gly Tyr Pro Ile Arg Ala Leu Val Gly Asp Glu
            35                  40                  45 gca gag ctg ccg tgc cgc atc tct cct ggg aaa aat gcc acg ggc atg     192
Ala Glu Leu Pro Cys Arg Ile Ser Pro Gly Lys Asn Ala Thr Gly Met
        50                  55                  60 gag gtg ggt tgg tac cgt tct ccc ttc tca aga gtg gtt cac ctc tac     240
Glu Val Gly Trp Tyr Arg Ser Pro Phe Ser Arg Val Val His Leu Tyr
65                  70                  75                  80 cga aat ggc aag gac caa gat gca gag caa gca cct gaa tac cgg gga     288
Arg Asn Gly Lys Asp Gln Asp Ala Glu Gln Ala Pro Glu Tyr Arg Gly
                85                  90                  95 cgc aca gag ctt ctg aaa gag act atc agt gag gga aag gtt acc ctt     336
Arg Thr Glu Leu Leu Lys Glu Thr Ile Ser Glu Gly Lys Val Thr Leu
            100                 105                 110 agg att cag aac gtg aga ttc tca gat gaa gga ggc tac acc tgc ttc     384
Arg Ile Gln Asn Val Arg Phe Ser Asp Glu Gly Gly Tyr Thr Cys Phe
        115                 120                 125 ttc aga gac cac tct tac caa gaa gag gca gca atg gag ttg aaa gtg     432
Phe Arg Asp His Ser Tyr Gln Glu Glu Ala Ala Met Glu Leu Lys Val
    130                 135                 140 gaa gat ccc ttc tat tgg gtc aac ccc ggt gtg ctg act ctc atc gca     480
Glu Asp Pro Phe Tyr Trp Val Asn Pro Gly Val Leu Thr Leu Ile Ala
145                 150                 155                 160 ctt gtg cct acg atc ctc ctg cag gtc tct gta ggc ctt gta ttc ctc     528
Leu Val Pro Thr Ile Leu Leu Gln Val Ser Val Gly Leu Val Phe Leu
                165                 170                 175
```

-continued

| | | |
|---|---|---|
| ttc ctg cag cac aga ctg aga gga aaa ctt cgt gca gaa gta gag aat<br>Phe Leu Gln His Arg Leu Arg Gly Lys Leu Arg Ala Glu Val Glu Asn<br>180                         185                     190 | 576 |
| ctc cat cgg act ttt gat cct cac ttc ctg agg gtg ccc tgc tgg aag<br>Leu His Arg Thr Phe Asp Pro His Phe Leu Arg Val Pro Cys Trp Lys<br>195                         200                     205 | 624 |
| ata aca ctg ttt gtt att gtg cct gtt ctt gga ccc ctg gtt gcc ttg<br>Ile Thr Leu Phe Val Ile Val Pro Val Leu Gly Pro Leu Val Ala Leu<br>210                         215                     220 | 672 |
| atc atc tgc tac aac tgg ctg cac cga aga ctg gca gga cag ttt ctt<br>Ile Ile Cys Tyr Asn Trp Leu His Arg Arg Leu Ala Gly Gln Phe Leu<br>225                         230                     235                     240 | 720 |
| gaa gag cta aga aac ccc ttt tga<br>Glu Glu Leu Arg Asn Pro Phe<br>245 | 744 |

<210> SEQ ID NO 74
<211> LENGTH: 247
<212> TYPE: PRT
<213> ORGANISM: Mus musculus

<400> SEQUENCE: 74

Met Ala Cys Leu Trp Ser Phe Ser Trp Pro Ser Cys Phe Leu Ser Leu
1                  5                    10                 15

Leu Leu Leu Leu Leu Leu Gln Leu Ser Cys Ser Tyr Ala Gly Gln Phe
                20                    25                    30

Arg Val Ile Gly Pro Gly Tyr Pro Ile Arg Ala Leu Val Gly Asp Glu
                35                    40                    45

Ala Glu Leu Pro Cys Arg Ile Ser Pro Gly Lys Asn Ala Thr Gly Met
50                        55                    60

Glu Val Gly Trp Tyr Arg Ser Pro Phe Ser Arg Val Val His Leu Tyr
65                  70                    75                    80

Arg Asn Gly Lys Asp Gln Asp Ala Glu Gln Ala Pro Glu Tyr Arg Gly
                85                    90                    95

Arg Thr Glu Leu Leu Lys Glu Thr Ile Ser Glu Gly Lys Val Thr Leu
                100                 105                 110

Arg Ile Gln Asn Val Arg Phe Ser Asp Glu Gly Gly Tyr Thr Cys Phe
                115                 120                 125

Phe Arg Asp His Ser Tyr Gln Glu Glu Ala Ala Met Glu Leu Lys Val
130                        135                    140

Glu Asp Pro Phe Tyr Trp Val Asn Pro Gly Val Leu Thr Leu Ile Ala
145                 150                 155                 160

Leu Val Pro Thr Ile Leu Leu Gln Val Ser Val Gly Leu Val Phe Leu
                165                 170                 175

Phe Leu Gln His Arg Leu Arg Gly Lys Leu Arg Ala Glu Val Glu Asn
                180                 185                 190

Leu His Arg Thr Phe Asp Pro His Phe Leu Arg Val Pro Cys Trp Lys
                195                 200                 205

Ile Thr Leu Phe Val Ile Val Pro Val Leu Gly Pro Leu Val Ala Leu
210                        215                    220

Ile Ile Cys Tyr Asn Trp Leu His Arg Arg Leu Ala Gly Gln Phe Leu
225                 230                 235                 240

Glu Glu Leu Arg Asn Pro Phe
245

<210> SEQ ID NO 75
<211> LENGTH: 744

<212> TYPE: DNA
<213> ORGANISM: Macaca fascicularis
<220> FEATURE:
<221> NAME/KEY: CDS
<222> LOCATION: (1)..(744)

<400> SEQUENCE: 75

```
atg gca agc tta tca aga ccc tct ctg ccc agc tgc ctc tgc tcc ttc      48
Met Ala Ser Leu Ser Arg Pro Ser Leu Pro Ser Cys Leu Cys Ser Phe
1               5                   10                  15 ctc ctc ctc ctg ctc ctc caa gtg tct tcc agc tac gca gga cag ttc      96
Leu Leu Leu Leu Leu Leu Gln Val Ser Ser Ser Tyr Ala Gly Gln Phe
            20                  25                  30 aga gtg ata gga cca aga caa cct atc cgg gct ctg gtc ggt gat gaa     144
Arg Val Ile Gly Pro Arg Gln Pro Ile Arg Ala Leu Val Gly Asp Glu
        35                  40                  45 gtg gaa ttg cca tgt cgc ata tct cct ggg aag aac gct aca ggc atg     192
Val Glu Leu Pro Cys Arg Ile Ser Pro Gly Lys Asn Ala Thr Gly Met
50                  55                  60 gaa gtg gga tgg tac cgg ccc ccc ttc tct agg gtg gtt cat ctc tac     240
Glu Val Gly Trp Tyr Arg Pro Pro Phe Ser Arg Val Val His Leu Tyr
65                  70                  75                  80 aga aat ggc agg gac caa gat gga gag caa gca cct gaa tat cgg ggc     288
Arg Asn Gly Arg Asp Gln Asp Gly Glu Gln Ala Pro Glu Tyr Arg Gly
                85                  90                  95 cgg aca gag ctg ctg aaa gac gct att ggt gag gga aag gtg act ctc     336
Arg Thr Glu Leu Leu Lys Asp Ala Ile Gly Glu Gly Lys Val Thr Leu
            100                 105                 110 agg atc cgg aat gta agg ttc tca gat gaa gga ggt ttc acc tgc ttc     384
Arg Ile Arg Asn Val Arg Phe Ser Asp Glu Gly Gly Phe Thr Cys Phe
        115                 120                 125 ttc cga gat cat tct tac caa gag gag gca gca ata gaa ttg aaa gtg     432
Phe Arg Asp His Ser Tyr Gln Glu Glu Ala Ala Ile Glu Leu Lys Val
    130                 135                 140 gaa gat ccc ttc tac tgg gtc agc cct gca gtg ctg gtt ctc ctc gcg     480
Glu Asp Pro Phe Tyr Trp Val Ser Pro Ala Val Leu Val Leu Leu Ala
145                 150                 155                 160 gtg ctg cct gtg ctc ctt ctg cag atc act gtc ggc ctc gtc ttc ctc     528
Val Leu Pro Val Leu Leu Leu Gln Ile Thr Val Gly Leu Val Phe Leu
                165                 170                 175 tgc ctg cag tat aga ctg aga gga aaa ctt cga gca gag ata gag aat     576
Cys Leu Gln Tyr Arg Leu Arg Gly Lys Leu Arg Ala Glu Ile Glu Asn
            180                 185                 190 ctc cac cgg act ttt gat ccc cac ttt ctg agg gtg ccc tgc tgg aag     624
Leu His Arg Thr Phe Asp Pro His Phe Leu Arg Val Pro Cys Trp Lys
        195                 200                 205 ata acc ctg ttt gta att gtg ccg gtt ctt gga ccc ctg gtt gcc ttg     672
Ile Thr Leu Phe Val Ile Val Pro Val Leu Gly Pro Leu Val Ala Leu
    210                 215                 220 atc atc tgc tac aac tgg cta cat cga aga cta gca ggg caa ttc ctt     720
Ile Ile Cys Tyr Asn Trp Leu His Arg Arg Leu Ala Gly Gln Phe Leu
225                 230                 235                 240 gaa gag cta aga aac cct ttc tga                                      744
Glu Glu Leu Arg Asn Pro Phe
                245
```

<210> SEQ ID NO 76
<211> LENGTH: 247
<212> TYPE: PRT
<213> ORGANISM: Macaca fascicularis

<400> SEQUENCE: 76

```
Met Ala Ser Leu Ser Arg Pro Ser Leu Pro Ser Cys Leu Cys Ser Phe
1               5                   10                  15

Leu Leu Leu Leu Leu Leu Gln Val Ser Ser Tyr Ala Gly Gln Phe
            20                  25                  30

Arg Val Ile Gly Pro Arg Gln Pro Ile Arg Ala Leu Val Gly Asp Glu
            35                  40                  45

Val Glu Leu Pro Cys Arg Ile Ser Pro Gly Lys Asn Ala Thr Gly Met
50                  55                  60

Glu Val Gly Trp Tyr Arg Pro Pro Phe Ser Arg Val Val His Leu Tyr
65                  70                  75                  80

Arg Asn Gly Arg Asp Gln Asp Gly Glu Gln Ala Pro Glu Tyr Arg Gly
                85                  90                  95

Arg Thr Glu Leu Leu Lys Asp Ala Ile Gly Glu Gly Lys Val Thr Leu
            100                 105                 110

Arg Ile Arg Asn Val Arg Phe Ser Asp Glu Gly Gly Phe Thr Cys Phe
            115                 120                 125

Phe Arg Asp His Ser Tyr Gln Glu Glu Ala Ala Ile Glu Leu Lys Val
130                 135                 140

Glu Asp Pro Phe Tyr Trp Val Ser Pro Ala Val Leu Val Leu Leu Ala
145                 150                 155                 160

Val Leu Pro Val Leu Leu Leu Gln Ile Thr Val Gly Leu Val Phe Leu
            165                 170                 175

Cys Leu Gln Tyr Arg Leu Arg Gly Lys Leu Arg Ala Glu Ile Glu Asn
            180                 185                 190

Leu His Arg Thr Phe Asp Pro His Phe Leu Arg Val Pro Cys Trp Lys
            195                 200                 205

Ile Thr Leu Phe Val Ile Val Pro Val Leu Gly Pro Leu Val Ala Leu
            210                 215                 220

Ile Ile Cys Tyr Asn Trp Leu His Arg Arg Leu Ala Gly Gln Phe Leu
225                 230                 235                 240

Glu Glu Leu Arg Asn Pro Phe
                245

<210> SEQ ID NO 77
<211> LENGTH: 744
<212> TYPE: DNA
<213> ORGANISM: Homo sapiens
<220> FEATURE:
<221> NAME/KEY: CDS
<222> LOCATION: (1)..(744)

<400> SEQUENCE: 77 atg gca agc tta tca aga ccc tct ctg ccc agc tgc ctc tgc tcc ttc    48
Met Ala Ser Leu Ser Arg Pro Ser Leu Pro Ser Cys Leu Cys Ser Phe
1               5                   10                  15 ctc ctc ctc ctc ctc ctc caa gtg tct tcc agc tat gca ggg cag ttc    96
Leu Leu Leu Leu Leu Leu Gln Val Ser Ser Ser Tyr Ala Gly Gln Phe
            20                  25                  30 aga gtg ata gga cca aga cac cct atc cgg gct ctg gtc ggg gat gaa   144
Arg Val Ile Gly Pro Arg His Pro Ile Arg Ala Leu Val Gly Asp Glu
            35                  40                  45 gtg gaa ttg cca tgt cgc ata tct cct ggg aag aac gct aca ggc atg   192
Val Glu Leu Pro Cys Arg Ile Ser Pro Gly Lys Asn Ala Thr Gly Met
50                  55                  60 gag gtg ggg tgg tac cgc ccc ccc ttc tct agg gtg gtt cat ctc tac   240
Glu Val Gly Trp Tyr Arg Pro Pro Phe Ser Arg Val Val His Leu Tyr
65                  70                  75                  80
```

```
aga aat ggc aag gac caa gat gga gac cag gca cct gaa tat cgg ggc    288
Arg Asn Gly Lys Asp Gln Asp Gly Asp Gln Ala Pro Glu Tyr Arg Gly
            85                  90                  95 cgg aca gag ctg ctg aaa gat gct att ggt gag gga aag gtg act ctc    336
Arg Thr Glu Leu Leu Lys Asp Ala Ile Gly Glu Gly Lys Val Thr Leu
        100                 105                 110 agg atc cgg aat gta agg ttc tca gat gaa gga ggt ttc acc tgc ttc    384
Arg Ile Arg Asn Val Arg Phe Ser Asp Glu Gly Gly Phe Thr Cys Phe
        115                 120                 125 ttc cga gat cat tct tac caa gag gag gca gca atg gaa ttg aaa gta    432
Phe Arg Asp His Ser Tyr Gln Glu Glu Ala Ala Met Glu Leu Lys Val
    130                 135                 140 gaa gat cct ttc tac tgg gtg agc cct gga gtg ctg gtt ctc ctc gcg    480
Glu Asp Pro Phe Tyr Trp Val Ser Pro Gly Val Leu Val Leu Leu Ala
145                 150                 155                 160 gtg ctg cct gtg ctc ctc ctg cag atc act gtt ggc ctc gtc ttc ctc    528
Val Leu Pro Val Leu Leu Leu Gln Ile Thr Val Gly Leu Val Phe Leu
                165                 170                 175 tgc ctg cag tac aga ctg aga gga aaa ctt cga gca gag ata gag aat    576
Cys Leu Gln Tyr Arg Leu Arg Gly Lys Leu Arg Ala Glu Ile Glu Asn
            180                 185                 190 ctc cac cgg act ttt gat ccc cac ttt ctg agg gtg ccc tgc tgg aag    624
Leu His Arg Thr Phe Asp Pro His Phe Leu Arg Val Pro Cys Trp Lys
        195                 200                 205 ata acc ctg ttt gta att gtg ccg gtt ctt gga ccc ttg gtt gcc ttg    672
Ile Thr Leu Phe Val Ile Val Pro Val Leu Gly Pro Leu Val Ala Leu
        210                 215                 220 atc atc tgc tac aac tgg cta cat cga aga cta gca ggg caa ttc ctt    720
Ile Ile Cys Tyr Asn Trp Leu His Arg Arg Leu Ala Gly Gln Phe Leu
225                 230                 235                 240 gaa gag cta cga aat ccc ttc tga                                    744
Glu Glu Leu Arg Asn Pro Phe
                245

<210> SEQ ID NO 78
<211> LENGTH: 247
<212> TYPE: PRT
<213> ORGANISM: Homo sapiens

<400> SEQUENCE: 78

Met Ala Ser Leu Ser Arg Pro Ser Leu Pro Ser Cys Leu Cys Ser Phe
1               5                   10                  15

Leu Leu Leu Leu Leu Leu Gln Val Ser Ser Ser Tyr Ala Gly Gln Phe
            20                  25                  30

Arg Val Ile Gly Pro Arg His Pro Ile Arg Ala Leu Val Gly Asp Glu
        35                  40                  45

Val Glu Leu Pro Cys Arg Ile Ser Pro Gly Lys Asn Ala Thr Gly Met
    50                  55                  60

Glu Val Gly Trp Tyr Arg Pro Pro Phe Ser Arg Val Val His Leu Tyr
65                  70                  75                  80

Arg Asn Gly Lys Asp Gln Asp Gly Asp Gln Ala Pro Glu Tyr Arg Gly
            85                  90                  95

Arg Thr Glu Leu Leu Lys Asp Ala Ile Gly Glu Gly Lys Val Thr Leu
        100                 105                 110

Arg Ile Arg Asn Val Arg Phe Ser Asp Glu Gly Gly Phe Thr Cys Phe
        115                 120                 125

Phe Arg Asp His Ser Tyr Gln Glu Glu Ala Ala Met Glu Leu Lys Val
    130                 135                 140
```

Glu Asp Pro Phe Tyr Trp Val Ser Pro Gly Val Leu Val Leu Leu Ala
145                 150                 155                 160

Val Leu Pro Val Leu Leu Gln Ile Thr Val Gly Leu Val Phe Leu
            165                 170                 175

Cys Leu Gln Tyr Arg Leu Arg Gly Lys Leu Arg Ala Glu Ile Glu Asn
        180                 185                 190

Leu His Arg Thr Phe Asp Pro His Phe Leu Arg Val Pro Cys Trp Lys
        195                 200                 205

Ile Thr Leu Phe Val Ile Val Pro Val Leu Gly Pro Leu Val Ala Leu
225                 215                 220

Ile Ile Cys Tyr Asn Trp Leu His Arg Arg Leu Ala Gly Gln Phe Leu
225                 230                 235                 240

Glu Glu Leu Arg Asn Pro Phe
                245

<210> SEQ ID NO 79
<211> LENGTH: 33
<212> TYPE: DNA
<213> ORGANISM: Artificial
<220> FEATURE:
<223> OTHER INFORMATION: Description of the artificial sequence:
      primer25

<400> SEQUENCE: 79
gagacgccat cacagatcat cccaccatgt aca                              33

<210> SEQ ID NO 80
<211> LENGTH: 33
<212> TYPE: DNA
<213> ORGANISM: Artificial
<220> FEATURE:
<223> OTHER INFORMATION: Description of the artificial sequence:
      primer26

<400> SEQUENCE: 80
gtaaccgtta acggatcctc atttacccag aga                              33

<210> SEQ ID NO 81
<211> LENGTH: 36
<212> TYPE: DNA
<213> ORGANISM: Artificial
<220> FEATURE:
<223> OTHER INFORMATION: Description of the artificial sequence:
      primer27

<400> SEQUENCE: 81
accaaggtgg agatcaaacg tacggtggct gcacca                           36

<210> SEQ ID NO 82
<211> LENGTH: 36
<212> TYPE: DNA
<213> ORGANISM: Artificial
<220> FEATURE:
<223> OTHER INFORMATION: Description of the artificial sequence:
      primer28

<400> SEQUENCE: 82
cggccacacg ttgaattctc aacactctcc cctgtt                           36

<210> SEQ ID NO 83
<211> LENGTH: 36
<212> TYPE: DNA
<213> ORGANISM: Artificial

```
<220> FEATURE:
<223> OTHER INFORMATION: Description of the artificial sequence:
      primer29

<400> SEQUENCE: 83
gattcctgct tccagcagtc agtttgtgct ttctca                              36

<210> SEQ ID NO 84
<211> LENGTH: 36
<212> TYPE: DNA
<213> ORGANISM: Artificial
<220> FEATURE:
<223> OTHER INFORMATION: Description of the artificial sequence:
      primer30

<400> SEQUENCE: 84
ggcggccttg ggctgaccta ggacagtgag cttggt                              36

<210> SEQ ID NO 85
<211> LENGTH: 36
<212> TYPE: DNA
<213> ORGANISM: Artificial
<220> FEATURE:
<223> OTHER INFORMATION: Description of the artificial sequence:
      primer31

<400> SEQUENCE: 85
ttaaaaggtg tccagtgtga ggtgcagctg gtggaa                              36

<210> SEQ ID NO 86
<211> LENGTH: 36
<212> TYPE: DNA
<213> ORGANISM: Artificial
<220> FEATURE:
<223> OTHER INFORMATION: Description of the artificial sequence:
      primer32

<400> SEQUENCE: 86
tggccccttg gtgctagctg aggagactgt gaccat                              36

<210> SEQ ID NO 87
<211> LENGTH: 38
<212> TYPE: DNA
<213> ORGANISM: Artificial
<220> FEATURE:
<223> OTHER INFORMATION: Description of the artificial sequence:
      primer33

<400> SEQUENCE: 87
tcagtcataa tgtctagagg acagtttgtg ctttctca                            38

<210> SEQ ID NO 88
<211> LENGTH: 36
<212> TYPE: DNA
<213> ORGANISM: Artificial
<220> FEATURE:
<223> OTHER INFORMATION: Description of the artificial sequence:
      primer34

<400> SEQUENCE: 88
cggccacacg ttgaattctc atgaacattc tgtagg                              36

<210> SEQ ID NO 89
<211> LENGTH: 41
<212> TYPE: DNA
<213> ORGANISM: Artificial
<220> FEATURE:
```

```
<223> OTHER INFORMATION: Description of the artificial sequence:
      primer35

<400> SEQUENCE: 89
cagcctttcc tggtatactt agtgaggtgc agctggtgga a                   41

<210> SEQ ID NO 90
<211> LENGTH: 30
<212> TYPE: DNA
<213> ORGANISM: Artificial
<220> FEATURE:
<223> OTHER INFORMATION: Description of the artificial sequence:
      primer36

<400> SEQUENCE: 90
acagtctcct cagctagcac caaggggcca                                30

<210> SEQ ID NO 91
<211> LENGTH: 35
<212> TYPE: DNA
<213> ORGANISM: Artificial
<220> FEATURE:
<223> OTHER INFORMATION: Description of the artificial sequence:
      primer37

<400> SEQUENCE: 91
tccaccagct gcacctcgga ccctcctcct ccgga                          35

<210> SEQ ID NO 92
<211> LENGTH: 33
<212> TYPE: DNA
<213> ORGANISM: Artificial
<220> FEATURE:
<223> OTHER INFORMATION: Description of the artificial sequence:
      primer38

<400> SEQUENCE: 92
ggaggaggag ggtccgaggt gcagctggtg gaa                            33

<210> SEQ ID NO 93
<211> LENGTH: 36
<212> TYPE: DNA
<213> ORGANISM: Artificial
<220> FEATURE:
<223> OTHER INFORMATION: Description of the artificial sequence:
      primer39

<400> SEQUENCE: 93
aagcggccgc ctggatcctc ataggacagt gagctt                         36

<210> SEQ ID NO 94
<211> LENGTH: 33
<212> TYPE: DNA
<213> ORGANISM: Artificial
<220> FEATURE:
<223> OTHER INFORMATION: Description of the artificial sequence:
      primer40

<400> SEQUENCE: 94
agacgccatc acagatctgc ctcttcaaaa tga                            33

<210> SEQ ID NO 95
<211> LENGTH: 36
<212> TYPE: DNA
<213> ORGANISM: Artificial
<220> FEATURE:
<223> OTHER INFORMATION: Description of the artificial sequence:
``` primer41

<400> SEQUENCE: 95
tggtgcagcc accgtacgtt tgatttccag cttggt                                    36

<210> SEQ ID NO 96
<211> LENGTH: 33
<212> TYPE: DNA
<213> ORGANISM: Artificial
<220> FEATURE:
<223> OTHER INFORMATION: Description of the artificial sequence:
      primer42

<400> SEQUENCE: 96
gaacacagac ccgtcgaccc ctcaccatga acc                                       33

<210> SEQ ID NO 97
<211> LENGTH: 36
<212> TYPE: DNA
<213> ORGANISM: Artificial
<220> FEATURE:
<223> OTHER INFORMATION: Description of the artificial sequence:
      primer43

<400> SEQUENCE: 97
tggccccttg gtgctagcgg aggagactgt gagagt                                    36

<210> SEQ ID NO 98
<211> LENGTH: 2640
<212> TYPE: DNA
<213> ORGANISM: Artificial
<220> FEATURE:
<223> OTHER INFORMATION: Description of the artificial sequence:
      sequence of hHER2-GST
<220> FEATURE:
<221> NAME/KEY: CDS
<222> LOCATION: (1)..(2640)

<400> SEQUENCE: 98

| | | | | | | | | | | | | | | | | |
|---|---|---|---|---|---|---|---|---|---|---|---|---|---|---|---|---|---|
| atg | gag | ctg | gcg | gcc | ttg | tgc | cgc | tgg | ggg | ctc | ctc | ctc | gcc | ctc | ttg | | 48 |
| Met | Glu | Leu | Ala | Ala | Leu | Cys | Arg | Trp | Gly | Leu | Leu | Leu | Ala | Leu | Leu | | |
| 1 | | | | 5 | | | | | 10 | | | | | 15 | | | |
| ccc | ccc | gga | gcc | gcg | agc | acc | caa | gtg | tgc | acc | ggc | aca | gac | atg | aag | | 96 |
| Pro | Pro | Gly | Ala | Ala | Ser | Thr | Gln | Val | Cys | Thr | Gly | Thr | Asp | Met | Lys | | |
| | | | 20 | | | | | 25 | | | | | 30 | | | | |
| ctg | cgg | ctc | cct | gcc | agt | ccc | gag | acc | cac | ctg | gac | atg | ctc | cgc | cac | | 144 |
| Leu | Arg | Leu | Pro | Ala | Ser | Pro | Glu | Thr | His | Leu | Asp | Met | Leu | Arg | His | | |
| | 35 | | | | | 40 | | | | | 45 | | | | | | |
| ctc | tac | cag | ggc | tgc | cag | gtg | gtg | cag | gga | aac | ctg | gaa | ctc | acc | tac | | 192 |
| Leu | Tyr | Gln | Gly | Cys | Gln | Val | Val | Gln | Gly | Asn | Leu | Glu | Leu | Thr | Tyr | | |
| 50 | | | | | 55 | | | | | 60 | | | | | | | |
| ctg | ccc | acc | aat | gcc | agc | ctg | tcc | ttc | ctg | cag | gat | atc | cag | gag | gtg | | 240 |
| Leu | Pro | Thr | Asn | Ala | Ser | Leu | Ser | Phe | Leu | Gln | Asp | Ile | Gln | Glu | Val | | |
| 65 | | | | 70 | | | | | 75 | | | | | 80 | | | |
| cag | ggc | tac | gtg | ctc | atc | gct | cac | aac | caa | gtg | agg | cag | gtc | cca | ctg | | 288 |
| Gln | Gly | Tyr | Val | Leu | Ile | Ala | His | Asn | Gln | Val | Arg | Gln | Val | Pro | Leu | | |
| | | | | 85 | | | | | 90 | | | | | 95 | | | |
| cag | agg | ctg | cgg | att | gtg | cga | ggc | acc | cag | ctc | ttt | gag | gac | aac | tat | | 336 |
| Gln | Arg | Leu | Arg | Ile | Val | Arg | Gly | Thr | Gln | Leu | Phe | Glu | Asp | Asn | Tyr | | |
| | | | 100 | | | | | 105 | | | | | 110 | | | | |
| gcc | ctg | gcc | gtg | cta | gac | aat | gga | gac | ccg | ctg | aac | aat | acc | acc | cct | | 384 |
| Ala | Leu | Ala | Val | Leu | Asp | Asn | Gly | Asp | Pro | Leu | Asn | Asn | Thr | Thr | Pro | | |
| | | 115 | | | | | 120 | | | | | 125 | | | | | |
| gtc | aca | ggg | gcc | tcc | cca | gga | ggc | ctg | cgg | gag | ctg | cag | ctt | cga | agc | | 432 |

```
                Val Thr Gly Ala Ser Pro Gly Gly Leu Arg Glu Leu Gln Leu Arg Ser
                    130             135                 140 ctc aca gag atc ttg aaa gga ggg gtc ttg atc cag cgg aac ccc cag        480
Leu Thr Glu Ile Leu Lys Gly Gly Val Leu Ile Gln Arg Asn Pro Gln
145                 150                 155                 160 ctc tgc tac cag gac acg att ttg tgg aag gac atc ttc cac aag aac        528
Leu Cys Tyr Gln Asp Thr Ile Leu Trp Lys Asp Ile Phe His Lys Asn
                165                 170                 175 aac cag ctg gct ctc aca ctg ata gac acc aac cgc tct cgg gcc tgc        576
Asn Gln Leu Ala Leu Thr Leu Ile Asp Thr Asn Arg Ser Arg Ala Cys
            180                 185                 190 cac ccc tgt tct ccg atg tgt aag ggc tcc cgc tgc tgg gga gag agt        624
His Pro Cys Ser Pro Met Cys Lys Gly Ser Arg Cys Trp Gly Glu Ser
        195                 200                 205 tct gag gat tgt cag agc ctg acg cgc act gtc tgt gcc ggt ggc tgt        672
Ser Glu Asp Cys Gln Ser Leu Thr Arg Thr Val Cys Ala Gly Gly Cys
    210                 215                 220 gcc cgc tgc aag ggg cca ctg ccc act gac tgc tgc cat gag cag tgt        720
Ala Arg Cys Lys Gly Pro Leu Pro Thr Asp Cys Cys His Glu Gln Cys
225                 230                 235                 240 gct gcc ggc tgc acg ggc ccc aag cac tct gac tgc ctg gcc tgc ctc        768
Ala Ala Gly Cys Thr Gly Pro Lys His Ser Asp Cys Leu Ala Cys Leu
                245                 250                 255 cac ttc aac cac agt ggc atc tgt gag ctg cac tgc cca gcc ctg gtc        816
His Phe Asn His Ser Gly Ile Cys Glu Leu His Cys Pro Ala Leu Val
                260                 265                 270 acc tac aac aca gac acg ttt gag tcc atg ccc aat ccc gag ggc cgg        864
Thr Tyr Asn Thr Asp Thr Phe Glu Ser Met Pro Asn Pro Glu Gly Arg
            275                 280                 285 tat aca ttc ggc gcc agc tgt gtg act gcc tgt ccc tac aac tac ctt        912
Tyr Thr Phe Gly Ala Ser Cys Val Thr Ala Cys Pro Tyr Asn Tyr Leu
        290                 295                 300 tct acg gac gtg gga tcc tgc acc ctc gtc tgc ccc ctg cac aac caa        960
Ser Thr Asp Val Gly Ser Cys Thr Leu Val Cys Pro Leu His Asn Gln
305                 310                 315                 320 gag gtg aca gca gag gat gga aca cag cgg tgt gag aag tgc agc aag       1008
Glu Val Thr Ala Glu Asp Gly Thr Gln Arg Cys Glu Lys Cys Ser Lys
                325                 330                 335 ccc tgt gcc cga gtg tgc tat ggt ctg ggc atg gag cac ttg cga gag       1056
Pro Cys Ala Arg Val Cys Tyr Gly Leu Gly Met Glu His Leu Arg Glu
                340                 345                 350 gtg agg gca gtt acc agt gcc aat atc cag gag ttt gct ggc tgc aag       1104
Val Arg Ala Val Thr Ser Ala Asn Ile Gln Glu Phe Ala Gly Cys Lys
            355                 360                 365 aag atc ttt ggg agc ctg gca ttt ctg ccg gag agc ttt gat ggg gac       1152
Lys Ile Phe Gly Ser Leu Ala Phe Leu Pro Glu Ser Phe Asp Gly Asp
        370                 375                 380 cca gcc tcc aac act gcc ccg ctc cag cca gag cag ctc caa gtg ttt       1200
Pro Ala Ser Asn Thr Ala Pro Leu Gln Pro Glu Gln Leu Gln Val Phe
385                 390                 395                 400 gag act ctg gaa gag atc aca ggt tac cta tac atc tca gca tgg ccg       1248
Glu Thr Leu Glu Glu Ile Thr Gly Tyr Leu Tyr Ile Ser Ala Trp Pro
                405                 410                 415 gac agc ctg cct gac ctc agc gtc ttc cag aac ctg caa gta atc cgg       1296
Asp Ser Leu Pro Asp Leu Ser Val Phe Gln Asn Leu Gln Val Ile Arg
                420                 425                 430 gga cga att ctg cac aat ggc gcc tac tcg ctg acc ctg caa ggg ctg       1344
Gly Arg Ile Leu His Asn Gly Ala Tyr Ser Leu Thr Leu Gln Gly Leu
            435                 440                 445
```

```
                                                       -continued ggc atc agc tgg ctg ggg ctg cgc tca ctg agg gaa ctg ggc agt gga    1392
Gly Ile Ser Trp Leu Gly Leu Arg Ser Leu Arg Glu Leu Gly Ser Gly
    450             455                 460 ctg gcc ctc atc cac cat aac acc cac ctc tgc ttc gtg cac acg gtg    1440
Leu Ala Leu Ile His His Asn Thr His Leu Cys Phe Val His Thr Val
465                 470                 475                 480 ccc tgg gac cag ctc ttt cgg aac ccg cac caa gct ctg ctc cac act    1488
Pro Trp Asp Gln Leu Phe Arg Asn Pro His Gln Ala Leu Leu His Thr
                485                 490                 495 gcc aac cgg cca gag gac gag tgt gtg ggc gag ggc ctg gcc tgc cac    1536
Ala Asn Arg Pro Glu Asp Glu Cys Val Gly Glu Gly Leu Ala Cys His
            500                 505                 510 cag ctg tgc gcc cga ggg cac tgc tgg ggt cca ggg ccc acc cag tgt    1584
Gln Leu Cys Ala Arg Gly His Cys Trp Gly Pro Gly Pro Thr Gln Cys
        515                 520                 525 gtc aac tgc agc cag ttc ctt cgg ggc cag gag tgc gtg gag gaa tgc    1632
Val Asn Cys Ser Gln Phe Leu Arg Gly Gln Glu Cys Val Glu Glu Cys
    530                 535                 540 cga gta ctg cag ggg ctc ccc agg gag tat gtg aat gcc agg cac tgt    1680
Arg Val Leu Gln Gly Leu Pro Arg Glu Tyr Val Asn Ala Arg His Cys
545                 550                 555                 560 ttg ccg tgc cac cct gag tgt cag ccc cag aat ggc tca gtg acc tgt    1728
Leu Pro Cys His Pro Glu Cys Gln Pro Gln Asn Gly Ser Val Thr Cys
                565                 570                 575 ttt gga ccg gag gct gac cag tgt gtg gcc tgt gcc cac tat aag gac    1776
Phe Gly Pro Glu Ala Asp Gln Cys Val Ala Cys Ala His Tyr Lys Asp
            580                 585                 590 cct ccc ttc tgc gtg gcc cgc tgc ccc agc ggt gtg aaa cct gac ctc    1824
Pro Pro Phe Cys Val Ala Arg Cys Pro Ser Gly Val Lys Pro Asp Leu
        595                 600                 605 tcc tac atg ccc atc tgg aag ttt cca gat gag gag ggc gca tgc cag    1872
Ser Tyr Met Pro Ile Trp Lys Phe Pro Asp Glu Glu Gly Ala Cys Gln
    610                 615                 620 cct tgc ccc atc aac tgc acc cac tcc tgt gtg gac ctg gat gac aag    1920
Pro Cys Pro Ile Asn Cys Thr His Ser Cys Val Asp Leu Asp Asp Lys
625                 630                 635                 640 ggc tgc ccc gcc gag cag aga gcc agc ggt acc ctg gaa gtt ctg ttc    1968
Gly Cys Pro Ala Glu Gln Arg Ala Ser Gly Thr Leu Glu Val Leu Phe
                645                 650                 655 cag ggg ccc atg tcc cct ata cta ggt tat tgg aaa att aag ggc ctt    2016
Gln Gly Pro Met Ser Pro Ile Leu Gly Tyr Trp Lys Ile Lys Gly Leu
            660                 665                 670 gtg caa ccc act cga ctt ctt ttg gaa tat ctt gaa gaa aaa tat gaa    2064
Val Gln Pro Thr Arg Leu Leu Leu Glu Tyr Leu Glu Glu Lys Tyr Glu
        675                 680                 685 gag cat ttg tat gag cgc gat gaa ggt gat aaa tgg cga aac aaa aag    2112
Glu His Leu Tyr Glu Arg Asp Glu Gly Asp Lys Trp Arg Asn Lys Lys
    690                 695                 700 ttt gaa ttg ggt ttg gag ttt ccc aat ctt cct tat tat att gat ggt    2160
Phe Glu Leu Gly Leu Glu Phe Pro Asn Leu Pro Tyr Tyr Ile Asp Gly
705                 710                 715                 720 gat gtt aaa tta aca cag tct atg gcc atc ata cgt tat ata gct gac    2208
Asp Val Lys Leu Thr Gln Ser Met Ala Ile Ile Arg Tyr Ile Ala Asp
                725                 730                 735 aag cac aac atg ttg ggt ggt tgt cca aaa gag cgt gca gag att tca    2256
Lys His Asn Met Leu Gly Gly Cys Pro Lys Glu Arg Ala Glu Ile Ser
            740                 745                 750 atg ctt gaa gga gcg gtt ttg gat att aga tac ggt gtt tcg aga att    2304
Met Leu Glu Gly Ala Val Leu Asp Ile Arg Tyr Gly Val Ser Arg Ile
        755                 760                 765
```

| | | | | | | | | | | | | | | | |
|---|---|---|---|---|---|---|---|---|---|---|---|---|---|---|---|
| gca | tat | agt | aaa | gac | ttt | gaa | act | ctc | aaa | gtt | gat | ttt | ctt | agc | aag | 2352 |
| Ala | Tyr | Ser | Lys | Asp | Phe | Glu | Thr | Leu | Lys | Val | Asp | Phe | Leu | Ser | Lys |
| | 770 | | | | 775 | | | | | 780 | | | | | |
| cta | cct | gaa | atg | ctg | aaa | atg | ttc | gaa | gat | cgt | tta | tgt | cat | aaa | aca | 2400 |
| Leu | Pro | Glu | Met | Leu | Lys | Met | Phe | Glu | Asp | Arg | Leu | Cys | His | Lys | Thr |
| 785 | | | | | 790 | | | | | 795 | | | | | 800 |
| tat | tta | aat | ggt | gat | cat | gta | acc | cat | cct | gac | ttc | atg | ttg | tat | gac | 2448 |
| Tyr | Leu | Asn | Gly | Asp | His | Val | Thr | His | Pro | Asp | Phe | Met | Leu | Tyr | Asp |
| | | | | 805 | | | | | 810 | | | | | 815 | |
| gct | ctt | gat | gtt | gtt | tta | tac | atg | gac | cca | atg | tgc | ctg | gat | gcg | ttc | 2496 |
| Ala | Leu | Asp | Val | Val | Leu | Tyr | Met | Asp | Pro | Met | Cys | Leu | Asp | Ala | Phe |
| | | | | 820 | | | | | 825 | | | | | 830 | |
| cca | aaa | tta | gtt | tgt | ttt | aaa | aaa | cgt | att | gaa | gct | atc | cca | caa | att | 2544 |
| Pro | Lys | Leu | Val | Cys | Phe | Lys | Lys | Arg | Ile | Glu | Ala | Ile | Pro | Gln | Ile |
| | | | | 835 | | | | | 840 | | | | | 845 | |
| gat | aag | tac | ttg | aaa | tcc | agc | aag | tat | ata | gca | tgg | cct | ttg | cag | ggc | 2592 |
| Asp | Lys | Tyr | Leu | Lys | Ser | Ser | Lys | Tyr | Ile | Ala | Trp | Pro | Leu | Gln | Gly |
| | 850 | | | | | 855 | | | | | 860 | | | | |
| tgg | caa | gcc | acg | ttt | ggt | ggt | ggc | gac | cat | cct | cca | aaa | tcg | gat | tga | 2640 |
| Trp | Gln | Ala | Thr | Phe | Gly | Gly | Gly | Asp | His | Pro | Pro | Lys | Ser | Asp |
| 865 | | | | | 870 | | | | | 875 | | | | | |

<210> SEQ ID NO 99
<211> LENGTH: 879
<212> TYPE: PRT
<213> ORGANISM: Artificial
<220> FEATURE:
<223> OTHER INFORMATION: Synthetic Construct

<400> SEQUENCE: 99

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys

```
            210                 215                 220
Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
                260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
        290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
                340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
        370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
        450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
        530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
        610                 615                 620

Pro Cys Pro Ile Asn Cys Thr His Ser Cys Val Asp Leu Asp Asp Lys
625                 630                 635                 640
```

```
Gly Cys Pro Ala Glu Gln Arg Ala Ser Gly Thr Leu Glu Val Leu Phe
                645                 650                 655
Gln Gly Pro Met Ser Pro Ile Leu Gly Tyr Trp Lys Ile Lys Gly Leu
            660                 665                 670
Val Gln Pro Thr Arg Leu Leu Leu Glu Tyr Leu Glu Glu Lys Tyr Glu
        675                 680                 685
Glu His Leu Tyr Glu Arg Asp Glu Gly Asp Lys Trp Arg Asn Lys Lys
    690                 695                 700
Phe Glu Leu Gly Leu Glu Phe Pro Asn Leu Pro Tyr Tyr Ile Asp Gly
705                 710                 715                 720
Asp Val Lys Leu Thr Gln Ser Met Ala Ile Ile Arg Tyr Ile Ala Asp
                725                 730                 735
Lys His Asn Met Leu Gly Gly Cys Pro Lys Glu Arg Ala Glu Ile Ser
            740                 745                 750
Met Leu Glu Gly Ala Val Leu Asp Ile Arg Tyr Gly Val Ser Arg Ile
        755                 760                 765
Ala Tyr Ser Lys Asp Phe Glu Thr Leu Lys Val Asp Phe Leu Ser Lys
    770                 775                 780
Leu Pro Glu Met Leu Lys Met Phe Glu Asp Arg Leu Cys His Lys Thr
785                 790                 795                 800
Tyr Leu Asn Gly Asp His Val Thr His Pro Asp Phe Met Leu Tyr Asp
                805                 810                 815
Ala Leu Asp Val Val Leu Tyr Met Asp Pro Met Cys Leu Asp Ala Phe
            820                 825                 830
Pro Lys Leu Val Cys Phe Lys Lys Arg Ile Glu Ala Ile Pro Gln Ile
        835                 840                 845
Asp Lys Tyr Leu Lys Ser Ser Lys Tyr Ile Ala Trp Pro Leu Gln Gly
    850                 855                 860
Trp Gln Ala Thr Phe Gly Gly Asp His Pro Pro Lys Ser Asp
865                 870                 875
```

<210> SEQ ID NO 100
<211> LENGTH: 1182
<212> TYPE: DNA
<213> ORGANISM: Artificial Sequence
<220> FEATURE:
<223> OTHER INFORMATION: Description of the artificial sequence: base sequence of hMOG-FLAG-Fc including signal sequence

<400> SEQUENCE: 100

```
atggcaagct tatcaagacc ctctctgccc agctgcctct gctccttcct cctcctcctc      60
ctcctccaag tgtcttccag ctatgcaggg cagttcagag tgataggacc aagacaccct     120
atccgggctc tggtcgggga tgaagtggaa ttgccatgtc gcatatctcc tgggaagaac     180
gctacaggca tggaggtggg gtggtaccgc ccccccttct ctagggtggt tcatctctac     240
agaaatggca aggaccaaga tgagaccagg cacctgaat atcggggccg acagagctg      300
ctgaaagatg ctattggtga gggaaaggtg actctcagga tccggaatgt aaggttctca     360
gatgaaggag gtttcacctg cttcttccga gatcattctt accaagagga ggcagcaatg     420
gaattgaaag tagaagatcc tttctactgg gtgagccctg atctagagc agactacaag     480
gacgacgatg acaagactag tgacaaaact cacacatgcc cacgtgccc agcacctgaa     540
ctcctggggg gaccgtcagt cttcctcttc cccccaaaac ccaaggacac cctcatgatc     600
tcccggaccc ctgaggtcac atgcgtggtg gtggacgtga gccacgaaga ccctgaggtc     660
```

```
aagttcaact ggtacgtgga cggcgtggag gtgcataatg ccaagacaaa gccgcgggag    720
gagcagtaca acagcacgta ccgtgtggtc agcgtcctca ccgtcctgca ccaggactgg    780
ctgaatggca aggagtacaa gtgcaaggtc tccaacaaag ccctcccagc ccccatcgag    840
aaaaccatct ccaaagccaa agggcagccc cgagaaccac aggtgtacac cctgccccca    900
tcccgggatg agctgaccaa gaaccaggtc agcctgacct gcctggtcaa aggcttctat    960
cccagcgaca tcgccgtgga gtgggagagc aatgggcagc cggagaacaa ctacaagacc   1020
acgcctcccg tgctggactc cgacggctcc ttcttcctct acagcaagct caccgtggac   1080
aagagcaggt ggcagcaggg gaacgtcttc tcatgctccg tgatgcatga ggctctgcac   1140
aaccactaca cgcagaagag cctctccctg tctccgggta aa                      1182
```

<210> SEQ ID NO 101
<211> LENGTH: 394
<212> TYPE: PRT
<213> ORGANISM: Artificial Sequence
<220> FEATURE:
<223> OTHER INFORMATION: Description of the artificial sequence: amino
      acid sequence of hMOG-FLAG-Fc including signal sequence

<400> SEQUENCE: 101

```
Met Ala Ser Leu Ser Arg Pro Ser Leu Pro Ser Cys Leu Cys Ser Phe
1               5                   10                  15

Leu Leu Leu Leu Leu Gln Val Ser Ser Ser Tyr Ala Gly Gln Phe
            20                  25                  30

Arg Val Ile Gly Pro Arg His Pro Ile Arg Ala Leu Val Gly Asp Glu
        35                  40                  45

Val Glu Leu Pro Cys Arg Ile Ser Pro Gly Lys Asn Ala Thr Gly Met
    50                  55                  60

Glu Val Gly Trp Tyr Arg Pro Pro Phe Ser Arg Val Val His Leu Tyr
65                  70                  75                  80

Arg Asn Gly Lys Asp Gln Asp Gly Asp Gln Ala Pro Glu Tyr Arg Gly
                85                  90                  95

Arg Thr Glu Leu Leu Lys Asp Ala Ile Gly Glu Gly Lys Val Thr Leu
            100                 105                 110

Arg Ile Arg Asn Val Arg Phe Ser Asp Glu Gly Gly Phe Thr Cys Phe
        115                 120                 125

Phe Arg Asp His Ser Tyr Gln Glu Glu Ala Ala Met Glu Leu Lys Val
    130                 135                 140

Glu Asp Pro Phe Tyr Trp Val Ser Pro Gly Ser Arg Ala Asp Tyr Lys
145                 150                 155                 160

Asp Asp Asp Asp Lys Thr Ser Asp Lys Thr His Thr Cys Pro Pro Cys
                165                 170                 175

Pro Ala Pro Glu Leu Leu Gly Gly Pro Ser Val Phe Leu Phe Pro Pro
            180                 185                 190

Lys Pro Lys Asp Thr Leu Met Ile Ser Arg Thr Pro Glu Val Thr Cys
        195                 200                 205

Val Val Val Asp Val Ser His Glu Asp Pro Glu Val Lys Phe Asn Trp
    210                 215                 220

Tyr Val Asp Gly Val Glu Val His Asn Ala Lys Thr Lys Pro Arg Glu
225                 230                 235                 240

Glu Gln Tyr Asn Ser Thr Tyr Arg Val Val Ser Val Leu Thr Val Leu
                245                 250                 255

His Gln Asp Trp Leu Asn Gly Lys Glu Tyr Lys Cys Lys Val Ser Asn
            260                 265                 270
```

Lys Ala Leu Pro Ala Pro Ile Glu Lys Thr Ile Ser Lys Ala Lys Gly
            275                 280                 285

Gln Pro Arg Glu Pro Gln Val Tyr Thr Leu Pro Pro Ser Arg Asp Glu
        290                 295                 300

Leu Thr Lys Asn Gln Val Ser Leu Thr Cys Leu Val Lys Gly Phe Tyr
305                 310                 315                 320

Pro Ser Asp Ile Ala Val Glu Trp Glu Ser Asn Gly Gln Pro Glu Asn
                325                 330                 335

Asn Tyr Lys Thr Thr Pro Pro Val Leu Asp Ser Asp Gly Ser Phe Phe
            340                 345                 350

Leu Tyr Ser Lys Leu Thr Val Asp Lys Ser Arg Trp Gln Gln Gly Asn
        355                 360                 365

Val Phe Ser Cys Ser Val Met His Glu Ala Leu His Asn His Tyr Thr
370                 375                 380

Gln Lys Ser Leu Ser Leu Ser Pro Gly Lys
385                 390

<210> SEQ ID NO 102
<211> LENGTH: 1182
<212> TYPE: DNA
<213> ORGANISM: Artificial Sequence
<220> FEATURE:
<223> OTHER INFORMATION: The Description of the artificial sequence:
      base sequence of mMOG-FLAG-Fc including signal sequence

<400> SEQUENCE: 102
atggcctgtt tgtggagctt ctcttggccc agctgcttcc tctcccttct cctcctcctt      60
ctcctccagt tgtcatgcag ctatgcagga caattcagag tgataggacc agggtatccc     120
atccgggctt tagttgggga tgaagcagag ctgccgtgcc gcatctctcc tgggaaaaat     180
gccacgggca tggaggtggg ttggtaccgt tctcccttct caagagtggt tcacctctac     240
cgaaatggca aggaccaaga tgcagagcaa gcacctgaat accggggacg cacagagctt     300
ctgaaagaga ctatcagtga gggaaaggtt acccttagga ttcagaacgt gagattctca     360
gatgaaggag ctacacctg cttcttcaga gaccactctt accaagaaga ggcagcaatg     420
gagttgaaag tggaagatcc cttctattgg gtcaaccccg ttctagagc agactacaag     480 gacgacgatg acaagactag tgacaaaact cacacatgcc caccgtgccc agcacctgaa     540
ctcctggggg gaccgtcagt cttcctcttc cccccaaaac ccaaggacac cctcatgatc     600
tcccggaccc ctgaggtcac atgcgtggtg gtggacgtga gccacgaaga ccctgaggtc     660
aagttcaact ggtacgtgga cggcgtggag gtgcataatg ccaagacaaa gccgcgggag     720
gagcagtaca acagcacgta ccgtgtggtc agcgtcctca ccgtcctgca ccaggactgg     780
ctgaatggca aggagtacaa gtgcaaggtc tccaacaaag ccctcccagc ccccatcgag     840
aaaaccatct ccaaagccaa agggcagccc cgagaaccac aggtgtacac cctgccccca     900
tcccgggatg agctgaccaa gaaccaggtc agcctgacct gcctggtcaa aggcttctat     960
cccagcgaca tcgccgtgga gtgggagagc aatgggcagc cggagaacaa ctacaagacc    1020
acgcctcccg tgctggactc cgacggctcc ttcttcctct acagcaagct caccgtggac    1080
aagagcaggt ggcagcaggg gaacgtcttc tcatgctccg tgatgcatga ggctctgcac    1140
aaccactaca cgcagaagag cctctccctg tctccgggta aa                      1182

<210> SEQ ID NO 103
<211> LENGTH: 394

<212> TYPE: PRT
<213> ORGANISM: Artificial Sequence
<220> FEATURE:
<223> OTHER INFORMATION: Description of the artificial sequence: amino
      acid sequence of mMOG-FLAG-Fc including signal sequence

<400> SEQUENCE: 103

```
Met Ala Cys Leu Trp Ser Phe Ser Trp Pro Ser Cys Phe Leu Ser Leu
1               5                   10                  15

Leu Leu Leu Leu Leu Leu Gln Leu Ser Cys Ser Tyr Ala Gly Gln Phe
            20                  25                  30

Arg Val Ile Gly Pro Gly Tyr Pro Ile Arg Ala Leu Val Gly Asp Glu
        35                  40                  45

Ala Glu Leu Pro Cys Arg Ile Ser Pro Gly Lys Asn Ala Thr Gly Met
    50                  55                  60

Glu Val Gly Trp Tyr Arg Ser Pro Phe Ser Arg Val Val His Leu Tyr
65                  70                  75                  80

Arg Asn Gly Lys Asp Gln Asp Ala Glu Gln Ala Pro Glu Tyr Arg Gly
                85                  90                  95

Arg Thr Glu Leu Leu Lys Glu Thr Ile Ser Glu Gly Lys Val Thr Leu
            100                 105                 110

Arg Ile Gln Asn Val Arg Phe Ser Asp Glu Gly Gly Tyr Thr Cys Phe
        115                 120                 125

Phe Arg Asp His Ser Tyr Gln Glu Glu Ala Ala Met Glu Leu Lys Val
130                 135                 140

Glu Asp Pro Phe Tyr Trp Val Asn Pro Gly Ser Arg Ala Asp Tyr Lys
145                 150                 155                 160

Asp Asp Asp Asp Lys Thr Ser Asp Lys Thr His Thr Cys Pro Pro Cys
                165                 170                 175

Pro Ala Pro Glu Leu Leu Gly Gly Pro Ser Val Phe Leu Phe Pro Pro
            180                 185                 190

Lys Pro Lys Asp Thr Leu Met Ile Ser Arg Thr Pro Glu Val Thr Cys
        195                 200                 205

Val Val Val Asp Val Ser His Glu Asp Pro Glu Val Lys Phe Asn Trp
210                 215                 220

Tyr Val Asp Gly Val Glu Val His Asn Ala Lys Thr Lys Pro Arg Glu
225                 230                 235                 240

Glu Gln Tyr Asn Ser Thr Tyr Arg Val Val Ser Val Leu Thr Val Leu
                245                 250                 255

His Gln Asp Trp Leu Asn Gly Lys Glu Tyr Lys Cys Lys Val Ser Asn
            260                 265                 270

Lys Ala Leu Pro Ala Pro Ile Glu Lys Thr Ile Ser Lys Ala Lys Gly
        275                 280                 285

Gln Pro Arg Glu Pro Gln Val Tyr Thr Leu Pro Pro Ser Arg Asp Glu
290                 295                 300

Leu Thr Lys Asn Gln Val Ser Leu Thr Cys Leu Val Lys Gly Phe Tyr
305                 310                 315                 320

Pro Ser Asp Ile Ala Val Glu Trp Glu Ser Asn Gly Gln Pro Glu Asn
                325                 330                 335

Asn Tyr Lys Thr Thr Pro Pro Val Leu Asp Ser Asp Gly Ser Phe Phe
            340                 345                 350

Leu Tyr Ser Lys Leu Thr Val Asp Lys Ser Arg Trp Gln Gln Gly Asn
        355                 360                 365

Val Phe Ser Cys Ser Val Met His Glu Ala Leu His Asn His Tyr Thr
370                 375                 380
```

Gln Lys Ser Leu Ser Leu Ser Pro Gly Lys
385             390

<210> SEQ ID NO 104
<211> LENGTH: 1152
<212> TYPE: DNA
<213> ORGANISM: Artificial Sequence
<220> FEATURE:
<223> OTHER INFORMATION: Description of the artificial sequence: base
      sequence of hMOG-GST including signal sequence

<400> SEQUENCE: 104

```
atggcaagct tatcaagacc ctctctgccc agctgcctct gctccttcct cctcctcctc      60
ctcctccaag tgtcttccag ctatgcaggg cagttcagag tgataggacc aagacaccct     120
atccgggctc tggtcgggga tgaagtggaa ttgccatgtc gcatatctcc tgggaagaac     180
gctacaggca tggaggtggg gtggtaccgc ccccccttct ctagggtggt tcatctctac     240
agaaatggca aggaccaaga tggagaccag gcacctgaat atcggggccg gacagagctg     300
ctgaaagatg ctattggtga gggaaaggtg actctcagga tccggaatgt aaggttctca     360
gatgaaggag gtttcacctg cttcttccga gatcattctt accaagagga ggcagcaatg     420
gaattgaaag tagaagatcc tttctactgg gtgagccctg aggtaccct ggaagttctg      480
ttccaggggc ccatgtcccc tatactaggt tattggaaaa ttaagggcct tgtgcaaccc     540
actcgacttc ttttggaata tcttgaagaa aaatatgaag agcatttgta tgagcgcgat     600
gaaggtgata aatggcgaaa caaaaagttt gaattgggtt tggagttccc caatcttcct     660
tattatattg atggtgatgt taaattaaca cagtctatgg ccatcatacg ttatatagct     720
gacaagcaca catgttgggg tggttgtcca aaagagcgtg cagagatttc aatgcttgaa     780
ggagcggttt tggatattag atacggtgtt tcgagaattg catatagtaa agactttgaa     840
actctcaaag ttgattttct tagcaagcta cctgaaatgc tgaaaatgtt cgaagatcgt     900
ttatgtcata aaacatattt aaatggtgat catgtaaccc atcctgactt catgttgtat     960
gacgctcttg atgttgtttt atacatggac ccaatgtgcc tggatgcgtt cccaaaatta    1020
gtttgtttta aaaacgtat tgaagctatc ccacaaattg ataagtactt gaaatccagc     1080
aagtatatag catggcctt gcagggctgg caagccacgt ttggtggtgg cgaccatcct    1140
ccaaaatcgg at                                                       1152
```

<210> SEQ ID NO 105
<211> LENGTH: 384
<212> TYPE: PRT
<213> ORGANISM: Artificial Sequence
<220> FEATURE:
<223> OTHER INFORMATION: Description of the artificial sequence: amino
      acid sequence of hMOG-GST including signal sequence

<400> SEQUENCE: 105

Met Ala Ser Leu Ser Arg Pro Ser Leu Pro Ser Cys Leu Cys Ser Phe
1               5                   10                  15

Leu Leu Leu Leu Leu Leu Gln Val Ser Ser Ser Tyr Ala Gly Gln Phe
            20                  25                  30

Arg Val Ile Gly Pro Arg His Pro Ile Arg Ala Leu Val Gly Asp Glu
        35                  40                  45

Val Glu Leu Pro Cys Arg Ile Ser Pro Gly Lys Asn Ala Thr Gly Met
    50                  55                  60

Glu Val Gly Trp Tyr Arg Pro Pro Phe Ser Arg Val Val His Leu Tyr

```
            65                  70                  75                  80
        Arg Asn Gly Lys Asp Gln Asp Gly Asp Gln Ala Pro Glu Tyr Arg Gly
                        85                  90                  95
        Arg Thr Glu Leu Leu Lys Asp Ala Ile Gly Glu Gly Lys Val Thr Leu
                        100                 105                 110
        Arg Ile Arg Asn Val Arg Phe Ser Asp Glu Gly Gly Phe Thr Cys Phe
                        115                 120                 125
        Phe Arg Asp His Ser Tyr Gln Glu Ala Ala Met Glu Leu Lys Val
                        130                 135                 140
        Glu Asp Pro Phe Tyr Trp Val Ser Pro Gly Gly Thr Leu Glu Val Leu
        145                 150                 155                 160
        Phe Gln Gly Pro Met Ser Pro Ile Leu Gly Tyr Trp Lys Ile Lys Gly
                        165                 170                 175
        Leu Val Gln Pro Thr Arg Leu Leu Leu Glu Tyr Leu Glu Glu Lys Tyr
                        180                 185                 190
        Glu Glu His Leu Tyr Glu Arg Asp Glu Gly Asp Lys Trp Arg Asn Lys
                        195                 200                 205
        Lys Phe Glu Leu Gly Leu Glu Phe Pro Asn Leu Pro Tyr Tyr Ile Asp
                        210                 215                 220
        Gly Asp Val Lys Leu Thr Gln Ser Met Ala Ile Ile Arg Tyr Ile Ala
        225                 230                 235                 240
        Asp Lys His Asn Met Leu Gly Gly Cys Pro Lys Glu Arg Ala Glu Ile
                        245                 250                 255
        Ser Met Leu Glu Gly Ala Val Leu Asp Ile Arg Tyr Gly Val Ser Arg
                        260                 265                 270
        Ile Ala Tyr Ser Lys Asp Phe Glu Thr Leu Lys Val Asp Phe Leu Ser
                        275                 280                 285
        Lys Leu Pro Glu Met Leu Lys Met Phe Glu Asp Arg Leu Cys His Lys
                        290                 295                 300
        Thr Tyr Leu Asn Gly Asp His Val Thr His Pro Asp Phe Met Leu Tyr
        305                 310                 315                 320
        Asp Ala Leu Asp Val Val Leu Tyr Met Asp Pro Met Cys Leu Asp Ala
                        325                 330                 335
        Phe Pro Lys Leu Val Cys Phe Lys Lys Arg Ile Glu Ala Ile Pro Gln
                        340                 345                 350
        Ile Asp Lys Tyr Leu Lys Ser Ser Lys Tyr Ile Ala Trp Pro Leu Gln
                        355                 360                 365
        Gly Trp Gln Ala Thr Phe Gly Gly Asp His Pro Pro Lys Ser Asp
        370                 375                 380
```

<210> SEQ ID NO 106
<211> LENGTH: 1152
<212> TYPE: DNA
<213> ORGANISM: Artificial Sequence
<220> FEATURE:
<223> OTHER INFORMATION: Description of the artificial sequence: base
      sequence of mMOG-GST including signal sequence

<400> SEQUENCE: 106
atggcctgtt tgtggagctt ctcttggccc agctgcttcc tctcccttct cctcctcctt      60
ctcctccagt tgtcatgcag ctatgcagga caattcagag tgataggacc agggtatccc     120
atccgggctt tagttgggga tgaagcagag ctgccgtgcc gcatctctcc tggaaaaat      180 gccacgggca tggaggtggg ttggtaccgt tctcccttct caagagtggt tcacctctac     240
cgaaatggca aggaccaaga tgcagagcaa gcacctgaat accggggacg cacagagctt     300

```
ctgaaagaga ctatcagtga gggaaaggtt acccttagga ttcagaacgt gagattctca    360
gatgaaggag gctacacctg cttcttcaga gaccactctt accaagaaga ggcagcaatg    420
gagttgaaag tggaagatcc cttctattgg gtcaaccccg gtggtaccct ggaagttctg    480
ttccaggggc ccatgtcccc tatactaggt tattggaaaa ttaagggcct tgtgcaaccc    540
actcgacttc ttttggaata tcttgaagaa aaatatgaag agcatttgta tgagcgcgat    600
gaaggtgata aatggcgaaa caaaaagttt gaattgggtt tggagtttcc caatcttcct    660
tattatattg atggtgatgt taaattaaca cagtctatgg ccatcatacg ttatatagct    720
gacaagcaca acatgttggg tggttgtcca aaagagcgtg cagagatttc aatgcttgaa    780
ggagcggttt tggatattag atacggtgtt tcgagaattg catatagtaa agactttgaa    840
actctcaaag ttgattttct tagcaagcta cctgaaatgc tgaaaatgtt cgaagatcgt    900
ttatgtcata aacatatttt aaatggtgat catgtaaccc atcctgactt catgttgtat    960
gacgctcttg atgttgtttt atacatggac ccaatgtgcc tggatgcgtt cccaaaatta   1020
gtttgtttta aaaacgtat tgaagctatc ccacaaattg ataagtactt gaaatccagc   1080
aagtatatag catggccttt gcagggctgg caagccacgt ttggtggtgg cgaccatcct   1140
ccaaaatcgg at                                                      1152

<210> SEQ ID NO 107
<211> LENGTH: 384
<212> TYPE: PRT
<213> ORGANISM: Artificial Sequence
<220> FEATURE:
<223> OTHER INFORMATION: Description of the artificial sequence: amino
      acid sequence of mMOG-GST including signal sequence

<400> SEQUENCE: 107

Met Ala Cys Leu Trp Ser Phe Ser Trp Pro Ser Cys Phe Leu Ser Leu
1               5                   10                  15

Leu Leu Leu Leu Leu Gln Leu Ser Cys Ser Tyr Ala Gly Gln Phe
            20                  25                  30

Arg Val Ile Gly Pro Gly Tyr Pro Ile Arg Ala Leu Val Gly Asp Glu
        35                  40                  45

Ala Glu Leu Pro Cys Arg Ile Ser Pro Gly Lys Asn Ala Thr Gly Met
    50                  55                  60

Glu Val Gly Trp Tyr Arg Ser Pro Phe Ser Arg Val Val His Leu Tyr
65                  70                  75                  80

Arg Asn Gly Lys Asp Gln Asp Ala Glu Gln Ala Pro Glu Tyr Arg Gly
                85                  90                  95

Arg Thr Glu Leu Leu Lys Glu Thr Ile Ser Glu Gly Lys Val Thr Leu
            100                 105                 110

Arg Ile Gln Asn Val Arg Phe Ser Asp Glu Gly Gly Tyr Thr Cys Phe
        115                 120                 125

Phe Arg Asp His Ser Tyr Gln Glu Glu Ala Ala Met Glu Leu Lys Val
    130                 135                 140

Glu Asp Pro Phe Tyr Trp Val Asn Pro Gly Gly Thr Leu Glu Val Leu
145                 150                 155                 160

Phe Gln Gly Pro Met Ser Pro Ile Leu Gly Tyr Trp Lys Ile Lys Gly
                165                 170                 175

Leu Val Gln Pro Thr Arg Leu Leu Leu Glu Tyr Leu Glu Glu Lys Tyr
            180                 185                 190

Glu Glu His Leu Tyr Glu Arg Asp Glu Gly Asp Lys Trp Arg Asn Lys
```

```
                195                 200                 205
Lys Phe Glu Leu Gly Leu Glu Phe Pro Asn Leu Pro Tyr Tyr Ile Asp
    210                 215                 220

Gly Asp Val Lys Leu Thr Gln Ser Met Ala Ile Ile Arg Tyr Ile Ala
225                 230                 235                 240

Asp Lys His Asn Met Leu Gly Gly Cys Pro Lys Glu Arg Ala Glu Ile
                245                 250                 255

Ser Met Leu Glu Gly Ala Val Leu Asp Ile Arg Tyr Gly Val Ser Arg
            260                 265                 270

Ile Ala Tyr Ser Lys Asp Phe Glu Thr Leu Lys Val Asp Phe Leu Ser
        275                 280                 285

Lys Leu Pro Glu Met Leu Lys Met Phe Glu Asp Arg Leu Cys His Lys
    290                 295                 300

Thr Tyr Leu Asn Gly Asp His Val Thr His Pro Asp Phe Met Leu Tyr
305                 310                 315                 320

Asp Ala Leu Asp Val Val Leu Tyr Met Asp Pro Met Cys Leu Asp Ala
                325                 330                 335

Phe Pro Lys Leu Val Cys Phe Lys Lys Arg Ile Glu Ala Ile Pro Gln
            340                 345                 350

Ile Asp Lys Tyr Leu Lys Ser Ser Lys Tyr Ile Ala Trp Pro Leu Gln
        355                 360                 365

Gly Trp Gln Ala Thr Phe Gly Gly Asp His Pro Pro Lys Ser Asp
    370                 375                 380

<210> SEQ ID NO 108
<211> LENGTH: 1371
<212> TYPE: DNA
<213> ORGANISM: Artificial Sequence
<220> FEATURE:
<223> OTHER INFORMATION: Description of the artificial sequence: base
      sequence of the antibody sequence of pCI-AVM-hLG4PE (R409K / S354C
      / T366W) -FLAG tag excluding signal sequence

<400> SEQUENCE: 108
gaggtgcagc tggtggaatc tgggggaggc ttagtgcagc ctggaagatc cctgaaactc      60
tcctgtgcag cctcaggatt cactttcagt aactatgcca tggcttgggt ccgccgggct     120
ccaacgaagg gtctggagtg ggtcgcatcc attagtaatg gtggtggtaa cacttactat     180
cgcgactccg tgaagggccg attcactatc tccagagatg caaaaaaa cacccctata      240 ctgcaaatgg acagtctgag gtctgaggac acggccactt attactgtgc aagacacggg     300
aattatatat attatgggtc cttctttgat tactggggcc aaggagtcat ggtcacagtc     360
tcctcagcta gcaccaaggg gccatccgtc ttccccctgg cgccctgctc caggagcacc     420
tccgagagca cagccgccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600
aagacctaca cctgcaacgt agatcacaag cccagcaaca ccaaggtgga caagagagtt     660
gagtccaaat atggtccccc atgcccacca tgcccagcac ctgagttcga ggggggacca     720
tcagtcttcc tgttcccccc aaaacccaag gacactctca tgatctcccg gacccctgag     780
gtcacgtgcg tggtggtgga cgtgagccag gaagacccg aggtccagtt caactggtac      840
gtggatggcg tggaggtgca taatgccaag acaaagccgc gggaggagca gttcaacagc     900
acgtaccgtg tggtcagcgt cctcaccgtc ctgcaccagg actggctgaa cggcaaggag     960
```

```
tacaagtgca aggtctccaa caaaggcctc ccgtcctcca tcgagaaaac catctccaaa    1020
gccaaagggc agccccgaga gccacaggtg tacaccctgc ccccatgcca ggaggagatg    1080
accaagaacc aggtcagcct gtggtgcctg gtcaaaggct tctaccccag cgacatcgcc    1140
gtggagtggg agagcaatgg gcagccggag aacaactaca agaccacgcc tcccgtgctg    1200
gactccgacg gctccttctt cctctacagc aagctaaccg tggacaagag caggtggcag    1260
gaggggaatg tcttctcatg ctccgtgatg catgaggctc tgcacaacca ctacacacag    1320
aagagcctct ccctgtctct gggtaaagac tacaaggacg acgatgacaa g             1371
```

<210> SEQ ID NO 109
<211> LENGTH: 457
<212> TYPE: PRT
<213> ORGANISM: Artificial Sequence
<220> FEATURE:
<223> OTHER INFORMATION: Description of the artificial sequence: amino acid sequence of the antibody sequence of pCI-AVM-hLG4PE (R409K / S354C / T366W) -FLAG tag excluding signal sequence

<400> SEQUENCE: 109

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Ala Met Ala Trp Val Arg Arg Ala Pro Thr Lys Gly Leu Glu Trp Val
        35                  40                  45

Ala Ser Ile Ser Asn Gly Gly Gly Asn Thr Tyr Tyr Arg Asp Ser Val
    50                  55                  60

Lys Gly Arg Phe Thr Ile Ser Arg Asp Asp Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Asn Tyr Ile Tyr Tyr Gly Ser Phe Phe Asp Tyr Trp
            100                 105                 110

Gly Gln Gly Val Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285
```

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Cys Gln Glu Glu Met Thr Lys Asn Gln Val Ser Leu Trp
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
            435                 440                 445

Lys Asp Tyr Lys Asp Asp Asp Lys
    450                 455

<210> SEQ ID NO 110
<211> LENGTH: 1380
<212> TYPE: DNA
<213> ORGANISM: Artificial Sequence
<220> FEATURE:
<223> OTHER INFORMATION: Description of the artificial sequence: base
      sequence of the antibody sequence of pCI-MOG01-hLG4PE (R409K /
      Y349C / T366S / L368A / Y407V) -His tag excluding signal sequence

<400> SEQUENCE: 110
caggtacagc tgcagcagtc aggcgcagga ttattgaagc cttcggagac cctttccctc      60
acctgcgctg tgtctggtgg gtccttcagt ggttactact ggacctggat ccgccagcgc     120
ccagggaagg gctggagtg gattggagaa atcaatcatc gtggaagcac cgattacaac     180
ccgtccctca gagtcgagt caccatgtca atagacacgt ccaagagcca gttctccctg     240
aatttgaaat ctgtgaccgc cgcggacacg gctgtgtatt actgtgcgag agccgcctgg     300
gggtcttgtt atgatgggac tgctaccccc gctgaatact ccaatactg gggccaggga     360
accctggtca ccgtctcctc agctagcacc aagggcccat ccgtcttccc cctggcgccc     420
tgctccagga gcacctccga gagcacagcc gccctgggct gcctggtcaa ggactacttc     480
cccgaaccgg tgacggtgtc gtggaactca ggcgccctga ccagcggcgt gcacaccttc     540
ccggctgtcc tacagtcctc aggactctac tccctcagca gcgtggtgac cgtgccctcc     600
agcagcttgg gcacgaagac ctacacctgc aacgtagatc acaagcccag caacaccaag     660
gtggacaaga gagttgagtc caaatatggt cccccatgcc caccatgccc agcacctgag     720
ttcgaggggg gaccatcagt cttcctgttc ccccaaaac ccaaggacac tctcatgatc     780
tcccggaccc ctgaggtcac gtgcgtggtg gtggacgtga gccaggaaga ccccgaggtc     840
cagttcaact ggtacgtgga tggcgtggag gtgcataatg ccaagacaaa gccgcgggag     900
gagcagttca acagcacgta ccgtgtggtc agcgtcctca ccgtcctgca ccaggactgg     960
ctgaacggca aggagtacaa gtgcaaggtc tccaacaaag gcctcccgtc ctccatcgag    1020

```
aaaaccatct ccaaagccaa agggcagccc cgagagccac aggtgtgcac cctgccccca   1080
tcccaggagg agatgaccaa gaaccaggtc agcctgtcct gcgcggtcaa aggcttctac   1140
cccagcgaca tcgccgtgga gtgggagagc aatgggcagc cggagaacaa ctacaagacc   1200
acgcctcccg tgctggactc cgacggctcc ttcttcctcg tcagcaagct aaccgtggac   1260
aagagcaggt ggcaggaggg gaatgtcttc tcatgctccg tgatgcatga ggctctgcac   1320
aaccactaca cacagaagag cctctcccctg tctctgggta acaccaccaa ccaccaccac   1380
```

<210> SEQ ID NO 111
<211> LENGTH: 460
<212> TYPE: PRT
<213> ORGANISM: Artificial Sequence
<220> FEATURE:
<223> OTHER INFORMATION: Description of the artificial sequence: amino
acid sequence of the antibody sequence of pCI-MOG01-hLG4PE (R409K
/ Y349C / T366S / L368A / Y407V) -His tag excluding signal
sequence

<400> SEQUENCE: 111

```
Gln Val Gln Leu Gln Gln Ser Gly Ala Gly Leu Leu Lys Pro Ser Glu
1               5                   10                  15

Thr Leu Ser Leu Thr Cys Ala Val Ser Gly Gly Ser Phe Ser Gly Tyr
            20                  25                  30

Tyr Trp Thr Trp Ile Arg Gln Arg Pro Gly Lys Gly Leu Glu Trp Ile
        35                  40                  45

Gly Glu Ile Asn His Arg Gly Ser Thr Asp Tyr Asn Pro Ser Leu Lys
    50                  55                  60

Ser Arg Val Thr Met Ser Ile Asp Thr Ser Lys Ser Gln Phe Ser Leu
65                  70                  75                  80

Asn Leu Lys Ser Val Thr Ala Ala Asp Thr Ala Val Tyr Tyr Cys Ala
                85                  90                  95

Arg Ala Ala Trp Gly Ser Cys Tyr Asp Gly Thr Cys Tyr Pro Ala Glu
            100                 105                 110

Tyr Phe Gln Tyr Trp Gly Gln Gly Thr Leu Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Glu
225                 230                 235                 240

Phe Glu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285
```

Val Glu Val His Asn Ala Lys Thr Lys Pro Arg Glu Glu Gln Phe Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
            340                 345                 350

Pro Gln Val Cys Thr Leu Pro Pro Ser Gln Glu Glu Met Thr Lys Asn
        355                 360                 365

Gln Val Ser Leu Ser Cys Ala Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Val Ser Lys
                405                 410                 415

Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Leu Gly Lys His His His His His His
    450                 455                 460

<210> SEQ ID NO 112
<211> LENGTH: 2043
<212> TYPE: DNA
<213> ORGANISM: Artificial Sequence
<220> FEATURE:
<223> OTHER INFORMATION: Description of the artificial sequence: base
      sequence of the antibody sequence of pCI-AVM-hLG4PE (R409K)
      -linker-MOG01 VL-CL excluding signal sequence

<400> SEQUENCE: 112
gaggtgcagc tggtggaatc tgggggaggc ttagtgcagc ctggaagatc cctgaaactc      60
tcctgtgcag cctcaggatt cactttcagt aactatgcca tggcttgggt ccgccgggct     120
ccaacgaagg gtctggagtg ggtcgcatcc attagtaatg gtggtggtaa cacttactat     180
cgcgactccg tgaagggccg attcactatc tccagagatg atgcaaaaaa cacccctatac    240 ctgcaaatgg acagtctgag gtctgaggac acggccactt attactgtgc aagacacggg     300
aattatatat attatgggtc cttctttgat tactggggcc aaggagtcat ggtcacagtc     360
tcctcagcta gcaccaaggg gccatccgtc ttccccctgg cgccctgctc caggagcacc     420
tccgagagca gccgccct gggctgcctg gtcaaggact acttccccga accggtgacg       480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600
aagacctaca cctgcaacgt agatcacaag cccagcaaca ccaaggtgga caagagagtt     660
gagtccaaat atggtccccc atgcccacca tgcccagcac ctgagttcga gggggaccca    720
tcagtcttcc tgttcccccc aaaacccaag gacactctca tgatctcccg gaccctgag    780 gtcacgtgcg tggtggtgga cgtgagccag gaagacccg aggtccagtt caactggtac    840
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa  1020

```
gccaaagggc agccccgaga gccacaggtg tacaccctgc ccccatccca ggaggagatg   1080
accaagaacc aggtcagcct gacctgcctg gtcaaaggct tctacccag cgacatcgcc    1140 gtggagtggg agagcaatgg gcagccggag aacaactaca agaccacgcc tcccgtgctg   1200
gactccgacg gctccttctt cctctacagc aagctaaccg tggacaagag caggtggcag   1260
gaggggaatg tcttctcatg ctccgtgatg catgaggctc tgcacaacca ctacacacag   1320
aagagcctct ccctgtctct gggtaaagga ggagagggt ccggaggagg agggtccgga    1380
ggaggagggt cccagtctgc cctgactcag cctgcctccg tgtctgggtc tcctggacag   1440
tcgatcacca tctcctgcac tggaaccagc cgtgacgttg gtggttataa ctatgtctcc   1500
tggtaccaac aacacccagg caaagccccc aaactcatga tttatgatgt caataatcgg   1560
ccctcagggg tttctaatcg gttctctggc tccaagtctg gcaacacggc ctccctgacc   1620
atctctgggc tccaggctga ggacgaggct gattatttct gcagctcata taagcagt    1680 agcaccctg tggtattcgg cggtgggacc aagctgaccg tcctaggtca gcccaaggcc    1740
gccccctcgg tcactctgtt cccgccctcc tctgaggagc ttcaagccaa caaggccaca   1800
ctggtgtgtc tcataagtga cttctacccg ggagccgtga cagtggcctg gaaggcagat   1860
agcagccccg tcaaggcggg agtggagacc accacaccct ccaaacaaag caacaacaag   1920
tacgcggcca gcagctacct gagcctgacg cctgagcagt ggaagtccca cagaagctac   1980
agctgccagg tcacgcatga agggagcacc gtggagaaga cagtggcccc tacagaatgt   2040
tca                                                                 2043
```

<210> SEQ ID NO 113
<211> LENGTH: 681
<212> TYPE: PRT
<213> ORGANISM: Artificial Sequence
<220> FEATURE:
<223> OTHER INFORMATION: Description of the artificial sequence: amino
      acid sequence of the antibody sequence of pCI-AVM-hLG4PE (R409K)
      -linker-MOG01 VL-CL excluding signal sequence

<400> SEQUENCE: 113

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Ala Met Ala Trp Val Arg Arg Ala Pro Thr Lys Gly Leu Glu Trp Val
        35                  40                  45

Ala Ser Ile Ser Asn Gly Gly Gly Asn Thr Tyr Tyr Arg Asp Ser Val
    50                  55                  60

Lys Gly Arg Phe Thr Ile Ser Arg Asp Asp Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Asn Tyr Ile Tyr Tyr Gly Ser Phe Phe Asp Tyr Trp
            100                 105                 110

Gly Gln Gly Val Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

-continued

```
Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
        210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys Gly Gly Gly Gly Ser Gly Gly Gly Ser Gly Gly Gly Gly Ser
450                 455                 460

Gln Ser Ala Leu Thr Gln Pro Ala Ser Val Ser Gly Ser Pro Gly Gln
465                 470                 475                 480

Ser Ile Thr Ile Ser Cys Thr Gly Thr Ser Arg Asp Val Gly Gly Tyr
                485                 490                 495

Asn Tyr Val Ser Trp Tyr Gln Gln His Pro Gly Lys Ala Pro Lys Leu
            500                 505                 510

Met Ile Tyr Asp Val Asn Asn Arg Pro Ser Gly Val Ser Asn Arg Phe
        515                 520                 525

Ser Gly Ser Lys Ser Gly Asn Thr Ala Ser Leu Thr Ile Ser Gly Leu
530                 535                 540

Gln Ala Glu Asp Glu Ala Asp Tyr Phe Cys Ser Ser Tyr Thr Ser Ser
545                 550                 555                 560

Ser Thr Pro Val Val Phe Gly Gly Gly Thr Lys Leu Thr Val Leu Gly
                565                 570                 575

Gln Pro Lys Ala Ala Pro Ser Val Thr Leu Phe Pro Pro Ser Ser Glu
```

```
                580             585             590
Glu Leu Gln Ala Asn Lys Ala Thr Leu Val Cys Leu Ile Ser Asp Phe
            595             600             605

Tyr Pro Gly Ala Val Thr Val Ala Trp Lys Ala Asp Ser Ser Pro Val
        610             615             620

Lys Ala Gly Val Glu Thr Thr Thr Pro Ser Lys Gln Ser Asn Asn Lys
625             630             635             640

Tyr Ala Ser Ser Tyr Leu Ser Leu Thr Pro Glu Gln Trp Lys Ser
            645             650             655

His Arg Ser Tyr Ser Cys Gln Val Thr His Glu Gly Ser Thr Val Glu
            660             665             670

Lys Thr Val Ala Pro Thr Glu Cys Ser
        675             680

<210> SEQ ID NO 114
<211> LENGTH: 675
<212> TYPE: DNA
<213> ORGANISM: Artificial Sequence
<220> FEATURE:
<223> OTHER INFORMATION: Description of the artificial sequence: base
      sequence of antibody sequence of pCI-MOG01 VH-CH excluding signal
      sequence

<400> SEQUENCE: 114
caggtacagc tgcagcagtc aggcgcagga ttattgaagc cttcggagac cctttccctc    60
acctgcgctg tgtctggtgg gtccttcagt ggttactact ggacctggat ccgccagcgc   120
ccagggaagg ggctggagtg gattggagaa atcaatcatc gtggaagcac cgattacaac   180
ccgtccctca agagtcgagt caccatgtca atagacacgt ccaagagcca gttctccctg   240
aatttgaaat ctgtgaccgc cgcggacacg gctgtgtatt actgtgcgag agccgcctgg   300
gggtcttgtt atgatgggac tgctacccc gctgaatact tccaatactg gggccaggga   360
accctggtca ccgtctcctc agctagcacc aagggcccat ccgtcttccc cctggcgccc   420
tgctccagga gcacctccga gagcacagcc gccctgggct gcctggtcaa ggactacttc   480
cccgaaccgg tgacggtgtc gtggaactca ggcgccctga ccagcggcgt gcacaccttc   540
ccggctgtcc tacagtcctc aggactctac tccctcagca gcgtggtgac cgtgccctcc   600
agcagcttgg gcacgaagac ctacacctgc aacgtagatc acaagcccag caacaccaag   660
gtggacaaga gagtt                                                   675

<210> SEQ ID NO 115
<211> LENGTH: 225
<212> TYPE: PRT
<213> ORGANISM: Artificial Sequence
<220> FEATURE:
<223> OTHER INFORMATION: Description of the artificial sequence: amino
      acid sequence of antibody sequence of pCI-MOG01 VH-CH excluding
      signal sequence

<400> SEQUENCE: 115

Gln Val Gln Leu Gln Gln Ser Gly Ala Gly Leu Leu Lys Pro Ser Glu
1               5                   10                  15

Thr Leu Ser Leu Thr Cys Ala Val Ser Gly Gly Ser Phe Ser Gly Tyr
            20                  25                  30

Tyr Trp Thr Trp Ile Arg Gln Arg Pro Gly Lys Gly Leu Glu Trp Ile
        35                  40                  45

Gly Glu Ile Asn His Arg Gly Ser Thr Asp Tyr Asn Pro Ser Leu Lys
    50                  55                  60
```

```
Ser Arg Val Thr Met Ser Ile Asp Thr Ser Lys Ser Gln Phe Ser Leu
 65                  70                  75                  80

Asn Leu Lys Ser Val Thr Ala Ala Asp Thr Ala Val Tyr Tyr Cys Ala
                 85                  90                  95

Arg Ala Ala Trp Gly Ser Cys Tyr Asp Gly Thr Cys Tyr Pro Ala Glu
            100                 105                 110

Tyr Phe Gln Tyr Trp Gly Gln Gly Thr Leu Val Thr Val Ser Ser Ala
        115                 120                 125

Ser Thr Lys Gly Pro Ser Val Phe Pro Leu Ala Pro Cys Ser Arg Ser
130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
    210                 215                 220

Val
225

<210> SEQ ID NO 116
<211> LENGTH: 2181
<212> TYPE: DNA
<213> ORGANISM: Artificial Sequence
<220> FEATURE:
<223> OTHER INFORMATION: Description of the artificial sequence: base
      sequence of antibody sequence of pCI-AVM-hLG4PE (R409K / S354C /
      T366W) -linker-MOG01 scFv-FLAG tag excluding signal sequence

<400> SEQUENCE: 116
gaggtgcagc tggtggaatc tgggggaggc ttagtgcagc ctggaagatc cctgaaactc      60
tcctgtgcag cctcaggatt cactttcagt aactatgcca tggcttgggt ccgccgggct     120
ccaacgaagg gtctggagtg ggtcgcatcc attagtaatg gtggtggtaa cacttactat     180
cgcgactccg tgaagggccg attcactatc tccagagatg atgcaaaaaa caccctatac     240
ctgcaaatgg acagtctgag gtctgaggac acggccactt attactgtgc aagacacggg     300
aattatatat attatgggtc cttctttgat tactgggggcc aaggagtcat ggtcacagtc     360
tcctcagcta gcaccaaggg gccatccgtc ttccccctgg cgccctgctc caggagcacc     420
tccgagagca gccgccct gggctgcctg gtcaaggact acttcccga accggtgacg     480 gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600
aagacctaca cctgcaacgt agatcacaag cccagcaaca ccaaggtgga caagagagtt     660
gagtccaaat atggtccccc atgcccacca tgcccagcac ctgagttcga gggggacca     720 tcagtcttcc tgttcccccc aaaacccaag gacactctca tgatctcccg gacccctgag     780
gtcacgtgcg tggtggtgga cgtgagccag gaagacccg aggtccagtt caactggtac     840
gtggatggcg tggaggtgca taatgccaag acaaagccgc gggaggagca gttcaacagc     900
acgtaccgtg tggtcagcgt cctcaccgtc ctgcaccagg actggctgaa cggcaaggag     960
tacaagtgca aggtctccaa caaaggcctc ccgtcctcca tcgagaaaac catctccaaa    1020
```

```
gccaaagggc agccccgaga gccacaggtg tacaccctgc ccccatgcca ggaggagatg    1080
accaagaacc aggtcagcct gtggtgcctg gtcaaaggct tctacccag cgacatcgcc    1140 gtggagtggg agagcaatgg gcagccggag aacaactaca agaccacgcc tcccgtgctg    1200
gactccgacg gctccttctt cctctacagc aagctaaccg tggacaagag caggtggcag    1260
gaggggaatg tcttctcatg ctccgtgatg catgaggctc tgcacaacca ctacacacag    1320
aagagcctct ccctgtctct gggtggagga gcggaggag gagggtccgg aggaggaggg    1380
tccggaggag gagggtccca ggtacagctg cagcagtcag gcgcaggatt attgaagcct    1440
tcggagaccc tttcccctca ctgcgctgtg tctggtgggt ccttcagtgg ttactactgg    1500
acctggatcc gccagcgccc agggaagggg ctggagtgga ttggagaaat caatcatcgt    1560
ggaagcaccg attacaaccc gtccctcaag agtcgagtca ccatgtcaat agacacgtcc    1620
aagagccagt tctccctgaa tttgaaatct gtgaccgccg cggacacggc tgtgtattac    1680
tgtgcgagag ccgcctgggg gtcttgttat gatgggacct gctaccccgc tgaatacttc    1740
caatactggg gccagggaac cctggtcacc gtctcctcag gaggcggtgg cagcggtggg    1800
cgcgcctcgg gcggaggtgg ttcacagtct gccctgactc agcctgcctc cgtgtctggg    1860
tctcctggac agtcgatcac catctcctgc actggaacca gccgtgacgt tggtggttat    1920
aactatgtct cctggtacca acaacaccca ggcaaagccc ccaaactcat gatttatgat    1980
gtcaataatc ggccctcagg ggtttctaat cggttctctg gctccaagtc tggcaacacg    2040
gcctccctga ccatctctgg gctccaggct gaggacgagg ctgattattt ctgcagctca    2100
tatacaagca gtagcacccc tgtggtattc ggcggtggga ccaagctgac cgtcctagac    2160
tacaaggacg acgatgacaa g                                              2181
```

<210> SEQ ID NO 117
<211> LENGTH: 727
<212> TYPE: PRT
<213> ORGANISM: Artificial Sequence
<220> FEATURE:
<223> OTHER INFORMATION: Description of the artificial sequence: amino
      acid sequence of the antibody sequence of pCI-AVM-hLG4PE (R409K /
      S354C / T366W) -linker-MOG01 scFv-FLAG tag excluding signal
      sequence

<400> SEQUENCE: 117

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Ala Met Ala Trp Val Arg Arg Ala Pro Thr Lys Gly Leu Glu Trp Val
        35                  40                  45

Ala Ser Ile Ser Asn Gly Gly Gly Asn Thr Tyr Tyr Arg Asp Ser Val
    50                  55                  60

Lys Gly Arg Phe Thr Ile Ser Arg Asp Asp Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Asn Tyr Ile Tyr Tyr Gly Ser Phe Phe Asp Tyr Trp
            100                 105                 110

Gly Gln Gly Val Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr

-continued

```
            130                 135                 140
Ala Ala Leu Gly Cys Leu Val Lys Asp Tyr Phe Pro Glu Pro Val Thr
145                 150                 155                 160

Val Ser Trp Asn Ser Gly Ala Leu Thr Ser Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
                195                 200                 205

His Lys Pro Ser Asn Thr Lys Val Asp Lys Arg Val Glu Ser Lys Tyr
            210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
                275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Cys Gln Glu Glu Met Thr Lys Asn Gln Val Ser Leu Trp
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
                435                 440                 445

Gly Gly Ser Gly Gly Gly Ser Gly Gly Gly Ser Gly Gly Gly
            450                 455                 460

Gly Ser Gln Val Gln Leu Gln Gln Ser Gly Ala Gly Leu Leu Lys Pro
465                 470                 475                 480

Ser Glu Thr Leu Ser Leu Thr Cys Ala Val Ser Gly Gly Ser Phe Ser
                485                 490                 495

Gly Tyr Tyr Trp Thr Trp Ile Arg Gln Arg Pro Gly Lys Gly Leu Glu
                500                 505                 510

Trp Ile Gly Glu Ile Asn His Arg Gly Ser Thr Asp Tyr Asn Pro Ser
                515                 520                 525

Leu Lys Ser Arg Val Thr Met Ser Ile Asp Thr Ser Lys Ser Gln Phe
            530                 535                 540

Ser Leu Asn Leu Lys Ser Val Thr Ala Ala Asp Thr Ala Val Tyr Tyr
545                 550                 555                 560
```

```
Cys Ala Arg Ala Ala Trp Gly Ser Cys Tyr Asp Gly Thr Cys Tyr Pro
                565                 570                 575
Ala Glu Tyr Phe Gln Tyr Trp Gly Gln Gly Thr Leu Val Thr Val Ser
            580                 585                 590
Ser Gly Gly Gly Ser Gly Gly Arg Ala Ser Gly Gly Gly Ser
        595                 600                 605
Gln Ser Ala Leu Thr Gln Pro Ala Ser Val Ser Gly Ser Pro Gly Gln
    610                 615                 620
Ser Ile Thr Ile Ser Cys Thr Gly Thr Ser Arg Asp Val Gly Gly Tyr
625                 630                 635                 640
Asn Tyr Val Ser Trp Tyr Gln Gln His Pro Gly Lys Ala Pro Lys Leu
                645                 650                 655
Met Ile Tyr Asp Val Asn Asn Arg Pro Ser Gly Val Ser Asn Arg Phe
            660                 665                 670
Ser Gly Ser Lys Ser Gly Asn Thr Ala Ser Leu Thr Ile Ser Gly Leu
        675                 680                 685
Gln Ala Glu Asp Glu Ala Asp Tyr Phe Cys Ser Ser Tyr Thr Ser Ser
    690                 695                 700
Ser Thr Pro Val Val Phe Gly Gly Gly Thr Lys Leu Thr Val Leu Asp
705                 710                 715                 720
Tyr Lys Asp Asp Asp Asp Lys
                725
```

<210> SEQ ID NO 118
<211> LENGTH: 1365
<212> TYPE: DNA
<213> ORGANISM: Artificial Sequence
<220> FEATURE:
<223> OTHER INFORMATION: Description of the artificial sequence: base
      sequence of the antibody sequence of pCI-AVM-hLG4PE (R409K / Y349C
      / T366S / L368A / Y407V) -His tag excluding signal sequence

<400> SEQUENCE: 118

```
gaggtgcagc tggtggaatc tgggggaggc ttagtgcagc ctggaagatc cctgaaactc      60
tcctgtgcag cctcaggatt cactttcagt aactatgcca tggcttgggt ccgccgggct     120
ccaacgaagg gtctggagtg gtcgcatcc attagtaatg gtggtggtaa cacttactat     180
cgcgactccg tgaagggccg attcactatc tccagagatg atgcaaaaaa cacccctatac     240 ctgcaaatgg acagtctgag gtctgaggac acggccactt attactgtgc aagacacggg     300
aattatatat attatgggtc cttctttgat tactggggcc aaggagtcat ggtcacagtc     360
tcctcagcta gcaccaaggg gccatccgtc ttccccctgg cgccctgctc caggagcacc     420
tccgagagca gccgcccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600
aagacctaca cctgcaacgt agatcacaag cccagcaaca ccaaggtgga caagagagtt     660
gagtccaaat atggtccccc atgcccacca tgcccagcac ctgagttcga gggggaccca     720
tcagtcttcc tgttcccccc aaaacccaag gacactctca tgatctcccg gacccctgag     780
gtcacgtgcg tggtggtgga cgtgagccag gaagaccccg aggtccagtt caactggtac     840
gtggatggcg tggaggtgca taatgccaag acaaagccgc gggaggagca gttcaacagc     900
acgtaccgtg tggtcagcgt cctcaccgtc ctgcaccagg actggctgaa cggcaaggag     960
tacaagtgca aggtctccaa caaaggcctc ccgtcctcca tcgagaaaac catctccaaa    1020
```

```
gccaaagggc agccccgaga gccacaggtg tgcaccctgc ccccatccca ggaggagatg    1080
accaagaacc aggtcagcct gtcctgcgcg gtcaaaggct tctacccccag cgacatcgcc   1140 gtggagtggg agagcaatgg gcagccggag aacaactaca agaccacgcc tcccgtgctg    1200
gactccgacg gctccttctt cctcgtcagc aagctaaccg tggacaagag caggtggcag    1260 gagggggaatg tcttctcatg ctccgtgatg catgaggctc tgcacaacca ctacacacag   1320
aagagcctct ccctgtctct gggtaaacac caccaccacc accac                     1365
```

<210> SEQ ID NO 119
<211> LENGTH: 455
<212> TYPE: PRT
<213> ORGANISM: Artificial Sequence
<220> FEATURE:
<223> OTHER INFORMATION: Description of the artificial sequence: amino
acid sequence of the antibody sequence of pCI-AVM-hLG4PE (R409K /
Y349C / T366S / L368A / Y407V) -His tag excluding signal sequence

<400> SEQUENCE: 119

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Ala Met Ala Trp Val Arg Arg Ala Pro Thr Lys Gly Leu Glu Trp Val
        35                  40                  45

Ala Ser Ile Ser Asn Gly Gly Gly Asn Thr Tyr Tyr Arg Asp Ser Val
    50                  55                  60

Lys Gly Arg Phe Thr Ile Ser Arg Asp Asp Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Asn Tyr Ile Tyr Tyr Gly Ser Phe Phe Asp Tyr Trp
            100                 105                 110

Gly Gln Gly Val Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285
```

```
Ala Lys Thr Lys Pro Arg Glu Glu Gln Phe Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Cys Thr
                340                 345                 350
Leu Pro Pro Ser Gln Glu Glu Met Thr Lys Asn Gln Val Ser Leu Ser
            355                 360                 365
Cys Ala Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Val Ser Lys Leu Thr Val Asp Lys
                405                 410                 415
Ser Arg Trp Gln Glu Gly Asn Val Phe Ser Cys Ser Val Met His Glu
                420                 425                 430
Ala Leu His Asn His Tyr Thr Gln Lys Ser Leu Ser Leu Ser Leu Gly
            435                 440                 445
Lys His His His His His His
    450                 455

<210> SEQ ID NO 120
<211> LENGTH: 2151
<212> TYPE: DNA
<213> ORGANISM: Artificial Sequence
<220> FEATURE:
<223> OTHER INFORMATION: Description of the artificial sequence: base
      sequence of the antibody sequence of pCI-AVM-hLG4PE (R409K) _MOG01
      scFv2 excluding signal sequence

<400> SEQUENCE: 120
gaggtgcagc tggtggaatc tggggggaggc ttagtgcagc ctggaagatc cctgaaactc      60
tcctgtgcag cctcaggatt cactttcagt aactatgcca tggcttgggt ccgccgggct     120
ccaacgaagg gtctggagtg gtcgcatcc attagtaatg gtggtggtaa cacttactat     180
cgcgactccg tgaagggccg attcactatc tccagagatg atgcaaaaaa caccctatac     240
ctgcaaatgg acagtctgag gtctgaggac acggccactt attactgtgc aagacacggg     300
aattatatat attatgggtc cttctttgat tactggggcc aaggagtcat ggtcacagtc     360
tcctcagcta gcaccaaggg gccatccgtc ttccccctgg cgccctgctc caggagcacc     420
tccgagagca cagccgccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600
aagacctaca cctgcaacgt agatcacaag cccagcaaca ccaaggtgga caagagagtt     660
gagtccaaat atggtccccc atgcccacca tgcccagcac ctgagttcga gggggaccca     720
tcagtcttcc tgttcccccc aaaacccaag gacactctca tgatctcccg gacccctgag     780
gtcacgtgcg tggtggtgga cgtgagccag gaagaccccg aggtccagtt caactggtac     840
gtggatggcg tggaggtgca taatgccaag acaaagccgc gggaggagca gttcaacagc     900
acgtaccgtg tggtcagcgt cctcaccgtc ctgcaccagg actggctgaa cggcaaggag     960
tacaagtgca aggtctccaa caaaggcctc ccgtcctcca tcgagaaaac catctccaaa    1020
```

```
gccaaagggc agccccgaga gccacaggtg tacaccctgc ccccatccca ggaggagatg    1080
accaagaacc aggtcagcct gacctgcctg gtcaaaggct tctacccag cgacatcgcc    1140 gtggagtggg agagcaatgg gcagccggag aacaactaca agaccacgcc tcccgtgctg    1200
gactccgacg gctccttctt cctctacagc aagctaaccg tggacaagag caggtggcag    1260 gagggaatg tcttctcatg ctccgtgatg catgaggctc tgcacaacca ctacacacag    1320
aagagcctct ccctgtctct gggtaaagga ggaggaggt ccggaggagg agggtccgga    1380 ggaggaggt cccaggtaca gctgcagcag tcaggcgcag gattattgaa gccttcggag    1440
accctttccc tcacctgcgc tgtgtctggt gggtccttca gtggttacta ctggacctgg    1500
atccgccagc gcccagggaa ggggctggag tggattggag aaatcaatca tcgtggaagc    1560
accgattaca acccgtccct caagagtcga gtcaccatgt caatagacac gtccaagagc    1620
cagttctccc tgaatttgaa atctgtgacc gccgcggaca cggctgtgta ttactgtgcg    1680
agagccgcct gggggtcttg ttatgatggg acctgctacc ccgctgaata cttccaatac    1740
tggggccagg gaaccctggt caccgtctcc tcaggaggcg gtggcagcgg tgggcgcgcc    1800
tcgggcggag gtggttcaca gtctgccctg actcagcctg cctccgtgtc tgggtctcct    1860
ggacagtcga tcaccatctc ctgcactgga accagccgtg acgttggtgg ttataactat    1920
gtctcctggt accaacaaca cccaggcaaa gcccccaaac tcatgattta tgatgtcaat    1980
aatcggccct caggggtttc taatcggttc tctggctcca agtctggcaa cacggcctcc    2040
ctgaccatct ctgggctcca ggctgaggac gaggctgatt atttctgcag ctcatataca    2100
agcagtagca cccctgtggt attcggcggt gggaccaagc tgaccgtcct a            2151
```

<210> SEQ ID NO 121
<211> LENGTH: 717
<212> TYPE: PRT
<213> ORGANISM: Artificial Sequence
<220> FEATURE:
<223> OTHER INFORMATION: Description of the artificial sequence: amino
acid sequence of antibody sequence of pCI-AVM-hLG4PE (R409K)_MOG
01 scFv 2 excluding signal sequence

<400> SEQUENCE: 121

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Ala Met Ala Trp Val Arg Arg Ala Pro Thr Lys Gly Leu Glu Trp Val
        35                  40                  45

Ala Ser Ile Ser Asn Gly Gly Gly Asn Thr Tyr Tyr Arg Asp Ser Val
    50                  55                  60

Lys Gly Arg Phe Thr Ile Ser Arg Asp Asp Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Asn Tyr Ile Tyr Tyr Gly Ser Phe Phe Asp Tyr Trp
            100                 105                 110

Gly Gln Gly Val Met Val Thr Val Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160
```

-continued

```
Val Ser Trp Asn Ser Gly Ala Leu Thr Ser Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys Gly Gly Gly Gly Ser Gly Gly Gly Gly Ser Gly Gly Gly Gly Ser
    450                 455                 460

Gln Val Gln Leu Gln Gln Ser Gly Ala Gly Leu Leu Lys Pro Ser Glu
465                 470                 475                 480

Thr Leu Ser Leu Thr Cys Ala Val Ser Gly Gly Ser Phe Ser Gly Tyr
                485                 490                 495

Tyr Trp Thr Trp Ile Arg Gln Arg Pro Gly Lys Gly Leu Glu Trp Ile
            500                 505                 510

Gly Glu Ile Asn His Arg Gly Ser Thr Asp Tyr Asn Pro Ser Leu Lys
        515                 520                 525

Ser Arg Val Thr Met Ser Ile Asp Thr Ser Lys Ser Gln Phe Ser Leu
    530                 535                 540

Asn Leu Lys Ser Val Thr Ala Ala Asp Thr Ala Val Tyr Tyr Cys Ala
545                 550                 555                 560

Arg Ala Ala Trp Gly Ser Cys Tyr Asp Gly Thr Cys Tyr Pro Ala Glu
                565                 570                 575
```

Tyr Phe Gln Tyr Trp Gly Gln Gly Thr Leu Val Thr Val Ser Ser Gly
                580                 585                 590

Gly Gly Gly Ser Gly Gly Arg Ala Ser Gly Gly Gly Ser Gln Ser
            595                 600                 605

Ala Leu Thr Gln Pro Ala Ser Val Ser Gly Ser Pro Gly Gln Ser Ile
        610                 615                 620

Thr Ile Ser Cys Thr Gly Thr Ser Arg Asp Val Gly Gly Tyr Asn Tyr
625                 630                 635                 640

Val Ser Trp Tyr Gln Gln His Pro Gly Lys Ala Pro Lys Leu Met Ile
                645                 650                 655

Tyr Asp Val Asn Asn Arg Pro Ser Gly Val Ser Asn Arg Phe Ser Gly
            660                 665                 670

Ser Lys Ser Gly Asn Thr Ala Ser Leu Thr Ile Ser Gly Leu Gln Ala
        675                 680                 685

Glu Asp Glu Ala Asp Tyr Phe Cys Ser Ser Tyr Thr Ser Ser Ser Thr
    690                 695                 700

Pro Val Val Phe Gly Gly Gly Thr Lys Leu Thr Val Leu
705                 710                 715

<210> SEQ ID NO 122
<211> LENGTH: 2157
<212> TYPE: DNA
<213> ORGANISM: Artificial Sequence
<220> FEATURE:
<223> OTHER INFORMATION: Description of the artificial sequence: base
      sequence of antibody sequence of pCI-AVM-hLG4PE (R409K) _MOG01
      scFv3 excluding signal sequence

<400> SEQUENCE: 122
gaggtgcagc tggtggaatc tgggggaggc ttagtgcagc ctggaagatc cctgaaactc      60
tcctgtgcag cctcaggatt cactttcagt aactatgcca tggcttgggt ccgccgggct     120
ccaacgaagg gtctggagtg ggtcgcatcc attagtaatg gtggtggtaa cacttactat     180
cgcgactccg tgaagggccg attcactatc tccagagatg atgcaaaaaa caccctatac     240
ctgcaaatgg acagtctgag gtctgaggac acggccactt attactgtgc aagacacggg     300
aattatatat attatgggtc cttctttgat tactggggcc aaggagtcat ggtcacagtc     360
tcctcagcta gcaccaaggg gccatccgtc ttccccctgg cgccctgctc caggagcacc     420
tccgagagca cagccgccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600
aagacctaca cctgcaacgt agatcacaag cccagcaaca ccaaggtgga caagagagtt     660
gagtccaaat atggtccccc atgcccacca tgcccagcac ctgagttcga gggggaccca     720
tcagtcttcc tgttcccccc aaaacccaag gacactctca tgatctcccg gacccctgag     780
gtcacgtgcg tggtggtgga cgtgagccag gaagaccccg aggtccagtt caactggtac     840
gtggatggcg tggaggtgca taatgccaag acaaagccgc gggaggagca gttcaacagc     900
acgtaccgtg tggtcagcgt cctcaccgtc ctgcaccagg actggctgaa cggcaaggag     960
tacaagtgca aggtctccaa caaaggcctc ccgtcctcca tcgagaaaac catctccaaa    1020
gccaaagggc agccccgaga gccacaggtg tacaccctgc cccatcccag gaggagatg     1080 accaagaacc aggtcagcct gacctgcctg gtcaaaggct tctacccag cgacatcgcc     1140 gtggagtggg agagcaatgg gcagccggag aacaactaca agaccacgcc tcccgtgctg    1200

```
gactccgacg gctccttctt cctctacagc aagctaaccg tggacaagag caggtggcag    1260
gaggggaatg tcttctcatg ctccgtgatg catgaggctc tgcacaacca ctacacacag    1320
aagagcctct ccctgtctct gggtggagga agcggaggag gagggtccgg aggaggaggg    1380
tccggaggag gagggtccca gtctgccctg actcagcctg cctccgtgtc tgggtctcct    1440
ggacagtcga tcaccatctc ctgcactgga accagccgtg acgttggtgg ttataactat    1500
gtctcctggt accaacaaca cccaggcaaa gcccccaaac tcatgattta tgatgtcaat    1560
aatcggccct caggggtttc taatcggttc tctggctcca agtctggcaa cacggcctcc    1620
ctgaccatct ctgggctcca ggctgaggac gaggctgatt atttctgcag ctcatataca    1680
agcagtagca cccctgtggt attcggcggt gggaccaagc tgaccgtcct aggaggcggt    1740
ggcagcggtg ggcgcgcctc gggcggaggt ggttcacagg tacagctgca gcagtcaggc    1800
gcaggattat tgaagccttc ggagacccct tccctcacct cgctgtgtc tggtgggtcc    1860 ttcagtggtt actactggac ctggatccgc cagcgcccag ggaagggggct ggagtggatt    1920 ggagaaatca atcatcgtgg aagcaccgat acaacccgt ccctcaagag tcgagtcacc    1980
atgtcaatag acacgtccaa gagccagttc tccctgaatt tgaaatctgt gaccgccgcg    2040
gacacggctg tgtattactg tgcgagagcc gcctgggggg cttgttatga tgggacctgc    2100
taccccgctg aatacttcca atactggggc cagggaaccc tggtcaccgt ctcctca      2157
```

<210> SEQ ID NO 123
<211> LENGTH: 719
<212> TYPE: PRT
<213> ORGANISM: Artificial Sequence
<220> FEATURE:
<223> OTHER INFORMATION: Description of the artificial sequence: amino acid sequence of the antibody sequence of pCI-AVM-hLG4PE (R409K) _MOG 01 scFv 3 excluding signal sequence

<400> SEQUENCE: 123

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Ala Met Ala Trp Val Arg Arg Ala Pro Thr Lys Gly Leu Glu Trp Val
        35                  40                  45

Ala Ser Ile Ser Asn Gly Gly Asn Thr Tyr Tyr Arg Asp Ser Val
    50                  55                  60

Lys Gly Arg Phe Thr Ile Ser Arg Asp Asp Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Asn Tyr Ile Tyr Tyr Gly Ser Phe Phe Asp Tyr Trp
            100                 105                 110

Gly Gln Gly Val Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190
```

```
Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
                275                 280                 285

Ala Lys Thr Lys Pro Arg Glu Glu Gln Phe Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
            435                 440                 445

Gly Gly Ser Gly Gly Gly Ser Gly Gly Gly Ser Gly Gly Gly
            450                 455                 460

Gly Ser Gln Ser Ala Leu Thr Gln Pro Ala Ser Val Ser Gly Ser Pro
465                 470                 475                 480

Gly Gln Ser Ile Thr Ile Ser Cys Thr Gly Thr Ser Arg Asp Val Gly
                485                 490                 495

Gly Tyr Asn Tyr Val Ser Trp Tyr Gln Gln His Pro Gly Lys Ala Pro
                500                 505                 510

Lys Leu Met Ile Tyr Asp Val Asn Asn Arg Pro Ser Gly Val Ser Asn
            515                 520                 525

Arg Phe Ser Gly Ser Lys Ser Gly Asn Thr Ala Ser Leu Thr Ile Ser
            530                 535                 540

Gly Leu Gln Ala Glu Asp Glu Ala Asp Tyr Phe Cys Ser Ser Tyr Thr
545                 550                 555                 560

Ser Ser Ser Thr Pro Val Val Phe Gly Gly Gly Thr Lys Leu Thr Val
                565                 570                 575

Leu Gly Gly Gly Gly Ser Gly Gly Arg Ala Ser Gly Gly Gly Gly Ser
            580                 585                 590

Gln Val Gln Leu Gln Gln Ser Gly Ala Gly Leu Leu Lys Pro Ser Glu
            595                 600                 605
```

```
Thr Leu Ser Leu Thr Cys Ala Val Ser Gly Gly Ser Phe Ser Gly Tyr
    610                 615                 620

Tyr Trp Thr Trp Ile Arg Gln Arg Pro Gly Lys Gly Leu Glu Trp Ile
625                 630                 635                 640

Gly Glu Ile Asn His Arg Gly Ser Thr Asp Tyr Asn Pro Ser Leu Lys
                645                 650                 655

Ser Arg Val Thr Met Ser Ile Asp Thr Ser Lys Ser Gln Phe Ser Leu
            660                 665                 670

Asn Leu Lys Ser Val Thr Ala Ala Asp Thr Ala Val Tyr Tyr Cys Ala
        675                 680                 685

Arg Ala Ala Trp Gly Ser Cys Tyr Asp Gly Thr Cys Tyr Pro Ala Glu
    690                 695                 700

Tyr Phe Gln Tyr Trp Gly Gln Gly Thr Leu Val Thr Val Ser Ser
705                 710                 715
```

<210> SEQ ID NO 124
<211> LENGTH: 2175
<212> TYPE: DNA
<213> ORGANISM: Artificial Sequence
<220> FEATURE:
<223> OTHER INFORMATION: Description of the artificial sequence: base
      sequence of the antibody sequence of pCI-AVM-hLG4PE (R409K) _MOG
      01 scFv 4 excluding signal sequence

<400> SEQUENCE: 124

```
gaggtgcagc tggtggaatc tgggggaggc ttagtgcagc ctggaagatc cctgaaactc      60
tcctgtgcag cctcaggatt cactttcagt aactatgcca tggcttgggt ccgccgggct     120
ccaacgaagg gtctggagtg gtcgcatcc attagtaatg gtggtggtaa cacttactat     180
cgcgactccg tgaagggccg attcactatc tccagagatg atgcaaaaaa caccctatac     240
ctgcaaatgg acagtctgag gtctgaggac acggccactt attactgtgc aagacacggg     300
aattatatat attatgggtc cttctttgat tactggggcc aaggagtcat ggtcacagtc     360
tcctcagcta gcaccaaggg gccatccgtc ttccccctgg cgccctgctc caggagcacc     420
tccgagagca cagccgccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600
aagacctaca cctgcaacgt agatcacaag cccagcaaca ccaaggtgga caagagagtt     660
gagtccaaat atggtccccc atgcccacca tgcccagcac ctgagttcga ggggggacca     720
tcagtcttcc tgttccccccc aaaacccaag gacactctca tgatctcccg gacccctgag     780
gtcacgtgcg tggtggtgga cgtgagccag gaagacccccg aggtccagtt caactggtac     840
gtggatggcg tggaggtgca taatgccaag acaaagccgc gggaggagca gttcaacagc     900
acgtaccgtg tggtcagcgt cctcaccgtc ctgcaccagg actggctgaa cggcaaggag     960
tacaagtgca aggtctccaa caaaggcctc ccgtcctcca tcgagaaaac catctccaaa    1020
gccaaagggc agccccgaga gccacaggtg tacaccctgc ccccatccca ggaggagatg    1080
accaagaacc aggtcagcct gacctgcctg gtcaaaggct tctacccag cgacatcgcc    1140 gtggagtggg agagcaatgg gcagccggag aacaactaca agaccacgcc tcccgtgctg    1200
gactccgacg gctccttctt cctctacagc aagctaaccg tggacaagag caggtggcag    1260
gaggggaatg tcttctcatg ctccgtgatg catgaggctc tgcacaacca ctacacacag    1320
aagagcctct ccctgtctct gggtggagga ggagggtccg gaggaggagg gtccggtgga    1380
```

```
ggtgggtccc aggtacagct gcagcagtca ggcgcaggat tattgaagcc ttcggagacc    1440 ctttcccctca cctgcgctgt gtctggtggg tccttcagtg gttactactg gacctggatc    1500
cgccagcgcc cagggaaggg gctggagtgg attggagaaa tcaatcatcg tggaagcacc    1560
gattacaacc cgtccctcaa gagtcgagtc accatgtcaa tagacacgtc caagagccag    1620
ttctccctga atttgaaatc tgtgaccgcc gcggacacgg ctgtgtatta ctgtgcgaga    1680
gccgcctggg ggtcttgtta tgatgggacc tgctacccg ctgaatactt ccaatactgg    1740
ggccagggaa ccctggtcac cgtctcctca gctagcaccg gaggcggtgg cagcggagga    1800
ggagggtccg gtggggcgg ctcgggcgga ggtggttcac agtctgccct gactcagcct    1860
gcctccgtgt ctgggtctcc tggacagtcg atcaccatct cctgcactgg aaccagccgt    1920
gacgttggtg gttataacta tgtctcctgg taccaacaac acccaggcaa agcccccaaa    1980
ctcatgattt atgatgtcaa taatcggccc tcaggggttt ctaatcggtt ctctggctcc    2040
aagtctggca acacggcctc cctgaccatc tctgggctcc aggctgagga cgaggctgat    2100
tatttctgca gctcatatac aagcagtagc accctgtgg tattcggcgg tgggaccaag    2160
ctgaccgtcc taggt                                                       2175
```

<210> SEQ ID NO 125
<211> LENGTH: 725
<212> TYPE: PRT
<213> ORGANISM: Artificial Sequence
<220> FEATURE:
<223> OTHER INFORMATION: Description of the artificial sequence: amino
      acid sequence of the antibody sequence of pCI-AVM-hLG4PE (R409K)
      _MOG 01 scFv 4 excluding signal sequence

<400> SEQUENCE: 125

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Ala Met Ala Trp Val Arg Arg Ala Pro Thr Lys Gly Leu Glu Trp Val
        35                  40                  45

Ala Ser Ile Ser Asn Gly Gly Asn Thr Tyr Tyr Arg Asp Ser Val
    50                  55                  60

Lys Gly Arg Phe Thr Ile Ser Arg Asp Asp Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Asn Tyr Ile Tyr Tyr Gly Ser Phe Phe Asp Tyr Trp
            100                 105                 110

Gly Gln Gly Val Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205
```

```
His Lys Pro Ser Asn Thr Lys Val Asp Lys Arg Val Glu Ser Lys Tyr
    210                 215                 220
Gly Pro Pro Cys Pro Pro Cys Pro Ala Pro Glu Phe Glu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Gln Glu Asp
            260                 265                 270
Pro Glu Val Gln Phe Asn Trp Tyr Val Asp Gly Val Glu Val His Asn
        275                 280                 285
Ala Lys Thr Lys Pro Arg Glu Glu Gln Phe Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Gln Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Glu Gly Asn Val Phe Ser Cys Ser Val Met His Glu
            420                 425                 430
Ala Leu His Asn His Tyr Thr Gln Lys Ser Leu Ser Leu Ser Leu Gly
        435                 440                 445
Gly Gly Gly Gly Ser Gly Gly Gly Ser Gly Gly Gly Gly Ser Gly Gln
    450                 455                 460
Val Gln Leu Gln Gln Ser Gly Ala Gly Leu Leu Lys Pro Ser Glu Thr
465                 470                 475                 480
Leu Ser Leu Thr Cys Ala Val Ser Gly Gly Ser Phe Ser Gly Tyr Tyr
                485                 490                 495
Trp Thr Trp Ile Arg Gln Arg Pro Gly Lys Gly Leu Glu Trp Ile Gly
            500                 505                 510
Glu Ile Asn His Arg Gly Ser Thr Asp Tyr Asn Pro Ser Leu Lys Ser
        515                 520                 525
Arg Val Thr Met Ser Ile Asp Thr Ser Lys Ser Gln Phe Ser Leu Asn
    530                 535                 540
Leu Lys Ser Val Thr Ala Ala Asp Thr Ala Val Tyr Tyr Cys Ala Arg
545                 550                 555                 560
Ala Ala Trp Gly Ser Cys Tyr Asp Gly Thr Cys Tyr Pro Ala Glu Tyr
                565                 570                 575
Phe Gln Tyr Trp Gly Gln Gly Thr Leu Val Thr Val Ser Ser Ala Ser
            580                 585                 590
Thr Gly Gly Gly Gly Ser Gly Gly Gly Ser Gly Gly Gly Gly Ser
        595                 600                 605
Gly Gly Gly Gly Ser Gln Ser Ala Leu Thr Gln Pro Ala Ser Val Ser
    610                 615                 620
Gly Ser Pro Gly Gln Ser Ile Thr Ile Ser Cys Thr Gly Thr Ser Arg
```

Asp Val Gly Gly Tyr Asn Tyr Val Ser Trp Tyr Gln Gln His Pro Gly
625             630                 635                 640
                645                     650                 655

Lys Ala Pro Lys Leu Met Ile Tyr Asp Val Asn Asn Arg Pro Ser Gly
                660                 665                 670

Val Ser Asn Arg Phe Ser Gly Ser Lys Ser Gly Asn Thr Ala Ser Leu
                675                 680                 685

Thr Ile Ser Gly Leu Gln Ala Glu Asp Glu Ala Asp Tyr Phe Cys Ser
        690                 695                 700

Ser Tyr Thr Ser Ser Ser Thr Pro Val Val Phe Gly Gly Gly Thr Lys
705                 710                 715                 720

Leu Thr Val Leu Gly
                725

<210> SEQ ID NO 126
<211> LENGTH: 2175
<212> TYPE: DNA
<213> ORGANISM: Artificial Sequence
<220> FEATURE:
<223> OTHER INFORMATION: Description of the artificial sequence: base
      sequence of antibody sequence of pCI-AVM-hLG4PE (R409K) _MOG 01
      scFv 5 excluding signal sequence

<400> SEQUENCE: 126
gaggtgcagc tggtggaatc tgggggaggc ttagtgcagc ctggaagatc cctgaaactc        60
tcctgtgcag cctcaggatt cactttcagt aactatgcca tggcttgggt ccgccgggct       120
ccaacgaagg gtctggagtg ggtcgcatcc attagtaatg gtggtggtaa cacttactat       180
cgcgactccg tgaagggccg attcactatc tccagagatg atgcaaaaaa caccctatac       240
ctgcaaatgg acagtctgag gtctgaggac acggccactt attactgtgc aagacacggg       300
aattatatat attatgggtc cttctttgat tactggggcc aaggagtcat ggtcacagtc       360
tcctcagcta gcaccaaggg gccatccgtc ttccccctgg cgccctgctc caggagcacc       420
tccgagagca cagccgccct gggctgcctg gtcaaggact acttccccga accggtgacg       480
gtgtcgtgga actcaggcgc cctgaccagc ggcgtgcaca ccttcccggc tgtcctacag       540
tcctcaggac tctactccct cagcagcgtg gtgaccgtgc cctccagcag cttgggcacg       600
aagacctaca cctgcaacgt agatcacaag cccagcaaca ccaaggtgga caagagagtt       660
gagtccaaat atggtccccc atgcccacca tgcccagcac ctgagttcga gggggggacca       720 tcagtcttcc tgttcccccc aaaacccaag gacactctca tgatctcccg gacccctgag       780
gtcacgtgcg tggtggtgga cgtgagccag gaagaccccg aggtccagtt caactggtac       840
gtggatggcg tggaggtgca taatgccaag acaaagccgc gggaggagca gttcaacagc       900
acgtaccgtg tggtcagcgt cctcaccgtc ctgcaccagg actggctgaa cggcaaggag       960
tacaagtgca aggtctccaa caaaggcctc ccgtcctcca tcgagaaaac catctccaaa      1020
gccaaagggc agccccgaga gccacaggtg tacaccctgc ccccatccca ggaggagatg      1080
accaagaacc aggtcagcct gacctgcctg gtcaaaggct tctacccag cgacatcgcc       1140 gtggagtggg agagcaatgg gcagccggag aacaactaca agaccacgcc tcccgtgctg      1200
gactccgacg gctccttctt cctctacagc aagctaaccg tggacaagag caggtggcag      1260 gagggggaatg tcttctcatg ctccgtgatg catgaggctc tgcacaacca ctacacacag      1320
aagagcctct ccctgtctct gggtggagga ggagggtccg aggaggagg gtccggtgga      1380 ggtgggtccc agtctgccct gactcagcct gcctccgtgt ctgggtctcc tggacagtcg      1440

```
atcaccatct cctgcactgg aaccagccgt gacgttggtg gttataacta tgtctcctgg    1500
taccaacaac acccaggcaa agcccccaaa ctcatgattt atgatgtcaa taatcggccc    1560 tcagggggttt ctaatcggtt ctctggctcc aagtctggca acacggcctc cctgaccatc    1620
tctgggctcc aggctgagga cgaggctgat tatttctgca gctcatatac aagcagtagc    1680 accctgtgg tattcggcgg tgggaccaag ctgaccgtcc taggtggagg cggtggcagc    1740
ggaggaggag ggtccggtgg gggcggctcg gcggaggtg gttcacaggt acagctgcag    1800
cagtcaggcg caggattatt gaagccttcg gagaccctt ccctcacctg cgctgtgtct    1860
ggtgggtcct tcagtggtta ctactggacc tggatccgcc agcgcccagg aaggggctg    1920 gagtggattg gagaaatcaa tcatcgtgga agcaccgatt acaacccgtc cctcaagagt    1980
cgagtcacca tgtcaataga cacgtccaag agccagttct ccctgaattt gaaatctgtg    2040
accgccgcgg acacggctgt gtattactgt gcgagagccg cctggggggtc ttgttatgat    2100 gggacctgct accccgctga atacttccaa tactggggcc agggaaccct ggtcaccgtc    2160
tcctcagcta gcacc                                                     2175
```

<210> SEQ ID NO 127
<211> LENGTH: 725
<212> TYPE: PRT
<213> ORGANISM: Artificial Sequence
<220> FEATURE:
<223> OTHER INFORMATION: Description of the artificial sequence: amino
      acid sequence of the antibody sequence of pCI-AVM-hLG4PE (R409K)
      _MOG01 scFv5 excluding signal sequence

<400> SEQUENCE: 127

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Ala Met Ala Trp Val Arg Arg Ala Pro Thr Lys Gly Leu Glu Trp Val
        35                  40                  45

Ala Ser Ile Ser Asn Gly Gly Gly Asn Thr Tyr Tyr Arg Asp Ser Val
    50                  55                  60

Lys Gly Arg Phe Thr Ile Ser Arg Asp Asp Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Asn Tyr Ile Tyr Tyr Gly Ser Phe Phe Asp Tyr Trp
            100                 105                 110

Gly Gln Gly Val Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
```

```
            210                 215                 220
Gly Pro Pro Cys Pro Pro Cys Pro Ala Pro Glu Phe Glu Gly Pro
225                 230                 235                 240

Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Gly Gly Gly Gly Ser Gly Gly Gly Gly Ser Gly Gly Gly Gly Ser Gln
                450                 455                 460

Ser Ala Leu Thr Gln Pro Ala Ser Val Ser Gly Ser Pro Gly Gln Ser
465                 470                 475                 480

Ile Thr Ile Ser Cys Thr Gly Thr Ser Arg Asp Val Gly Gly Tyr Asn
                485                 490                 495

Tyr Val Ser Trp Tyr Gln Gln His Pro Gly Lys Ala Pro Lys Leu Met
            500                 505                 510

Ile Tyr Asp Val Asn Asn Arg Pro Ser Gly Val Ser Asn Arg Phe Ser
        515                 520                 525

Gly Ser Lys Ser Gly Asn Thr Ala Ser Leu Thr Ile Ser Gly Leu Gln
        530                 535                 540

Ala Glu Asp Glu Ala Asp Tyr Phe Cys Ser Ser Tyr Thr Ser Ser Ser
545                 550                 555                 560

Thr Pro Val Val Phe Gly Gly Gly Thr Lys Leu Thr Val Leu Gly Gly
                565                 570                 575

Gly Gly Ser Gly Gly Gly Gly Ser Gly Gly Gly Ser Gly Gly
            580                 585                 590

Gly Gly Ser Gln Val Gln Leu Gln Gln Ser Gly Ala Gly Leu Leu Lys
        595                 600                 605

Pro Ser Glu Thr Leu Ser Leu Thr Cys Ala Val Ser Gly Gly Ser Phe
        610                 615                 620

Ser Gly Tyr Tyr Trp Thr Trp Ile Arg Gln Arg Pro Gly Lys Gly Leu
625                 630                 635                 640
```

```
Glu Trp Ile Gly Glu Ile Asn His Arg Gly Ser Thr Asp Tyr Asn Pro
                645                 650                 655
Ser Leu Lys Ser Arg Val Thr Met Ser Ile Asp Thr Ser Lys Ser Gln
            660                 665                 670
Phe Ser Leu Asn Leu Lys Ser Val Thr Ala Ala Asp Thr Ala Val Tyr
            675                 680                 685
Tyr Cys Ala Arg Ala Ala Trp Gly Ser Cys Tyr Asp Gly Thr Cys Tyr
        690                 695                 700
Pro Ala Glu Tyr Phe Gln Tyr Trp Gly Gln Gly Thr Leu Val Thr Val
705                 710                 715                 720
Ser Ser Ala Ser Thr
            725

<210> SEQ ID NO 128
<211> LENGTH: 2148
<212> TYPE: DNA
<213> ORGANISM: Artificial Sequence
<220> FEATURE:
<223> OTHER INFORMATION: Description of the artificial sequence: base
      sequence of the antibody sequence of pCI-AVM-hLG4PE (R409K)
      _MOG01 scFv6 excluding signal sequence

<400> SEQUENCE: 128
gaggtgcagc tggtggaatc tgggggaggc ttagtgcagc ctggaagatc cctgaaactc      60
tcctgtgcag cctcaggatt cactttcagt aactatgcca tggcttgggt ccgccgggct     120
ccaacgaagg gtctggagtg ggtcgcatcc attagtaatg gtggtggtaa cacttactat     180
cgcgactccg tgaagggccg attcactatc tccagagatg atgcaaaaaa caccctatac     240
ctgcaaatgg acagtctgag gtctgaggac acggccactt attactgtgc aagacacggg     300
aattatatat attatgggtc cttctttgat tactggggcc aaggagtcat ggtcacagtc     360
tcctcagcta gcaccaaggg gccatccgtc ttccccctgg cgccctgctc caggagcacc     420
tccgagagca gccgccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600
aagacctaca cctgcaacgt agatcacaag cccagcaaca ccaaggtgga caagagagtt     660
gagtccaaat atggtccccc atgcccacca tgcccagcac ctgagttcga ggggggacca     720
tcagtcttcc tgttcccccc aaaacccaag gacactctca tgatctcccg gacccctgag     780
gtcacgtgcg tggtggtgga cgtgagccag gaagaccccg aggtccagtt caactggtac     840
gtggatggcg tggaggtgca taatgccaag acaaagccgc gggaggagca gttcaacagc     900
acgtaccgtg tggtcagcgt cctcaccgtc ctgcaccagg actggctgaa cggcaaggag     960
tacaagtgca aggtctccaa caaaggcctc ccgtcctcca tcgagaaaac catctccaaa    1020
gccaaagggc agccccgaga gccacaggtg tacaccctgc ccccatccca ggaggagatg    1080
accaagaacc aggtcagcct gacctgcctg gtcaaaggct tctaccccag cgacatcgcc    1140
gtggagtggg agagcaatgg gcagccggag aacaactaca agaccacgcc tcccgtgctg    1200
gactccgacg gctccttctt cctctacagc aagctaaccg tggacaagag caggtggcag    1260
gaggggaatg tcttctcatg ctccgtgatg catgaggctc tgcacaacca ctacacacag    1320
aagagcctct ccctgtctct gggtggagga ggagggtccg gaggaggagg tccggtggaa    1380
ggtgggtccc agtctgccct gactcagcct gcctccgtgt ctgggtctcc tggacagtcg    1440
```

```
atcaccatct cctgcactgg aaccagccgt gacgttggtg gttataacta tgtctcctgg   1500
taccaacaac acccaggcaa agcccccaaa ctcatgattt atgatgtcaa taatcggccc   1560
tcagggtttt ctaatcggtt ctctggctcc aagtctggca acacggcctc cctgaccatc   1620
tctgggctcc aggctgagga cgaggctgat tatttctgca gctcatatac aagcagtagc   1680
acccctgtgg tattcggcgg tgggaccaag ctgaccgtcc taggaggcgg tggcagcggt   1740
gggcgcgcct cgggcggagg tggttcacag gtacagctgc agcagtcagg cgcaggatta   1800
ttgaagcctt cggagaccct tccctcacc tgcgctgtgt ctggtgggtc cttcagtggt    1860
tactactgga cctggatccg ccagcgccca gggaagggc tggagtggat tggagaaatc    1920
aatcatcgtg gaagcaccga ttacaacccg tccctcaaga gtcgagtcac catgtcaata   1980
gacacgtcca agagccagtt ctccctgaat ttgaaatctg tgaccgccgc ggacacggct   2040
gtgtattact gtgcgagagc cgcctggggg tcttgttatg atgggacctg ctaccccgct   2100
gaatacttcc aatactgggg ccagggaacc ctggtcaccg tctcctca                2148
```

```
<210> SEQ ID NO 129
<211> LENGTH: 716
<212> TYPE: PRT
<213> ORGANISM: Artificial Sequence
<220> FEATURE:
<223> OTHER INFORMATION: Description of the artificial sequence: amino
      acid sequence of the antibody sequence of pCI-AVM-hLG4PE (R409K)
      _MOG 01 scFv 6 excluding signal sequence

<400> SEQUENCE: 129
```

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Ala Met Ala Trp Val Arg Ala Pro Thr Lys Gly Leu Glu Trp Val
        35                  40                  45

Ala Ser Ile Ser Asn Gly Gly Gly Asn Thr Tyr Tyr Arg Asp Ser Val
    50                  55                  60

Lys Gly Arg Phe Thr Ile Ser Arg Asp Asp Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Asn Tyr Ile Tyr Tyr Gly Ser Phe Phe Asp Tyr Trp
            100                 105                 110

Gly Gln Gly Val Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Glu Gly Gly Pro
```

```
                225                 230                 235                 240
Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser Gln Glu Asp
                    260                 265                 270

Pro Glu Val Gln Phe Asn Trp Tyr Val Asp Gly Val Glu Val His Asn
                    275                 280                 285

Ala Lys Thr Lys Pro Arg Glu Glu Gln Phe Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                    340                 345                 350

Leu Pro Pro Ser Gln Glu Glu Met Thr Lys Asn Gln Val Ser Leu Thr
                    355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Met His Glu
                    420                 425                 430

Ala Leu His Asn His Tyr Thr Gln Lys Ser Leu Ser Leu Ser Leu Gly
        435                 440                 445

Gly Gly Gly Gly Ser Gly Gly Gly Ser Gly Gly Gly Gly Ser Gln
450                 455                 460

Ser Ala Leu Thr Gln Pro Ala Ser Val Ser Gly Ser Pro Gly Gln Ser
465                 470                 475                 480

Ile Thr Ile Ser Cys Thr Gly Thr Ser Arg Asp Val Gly Gly Tyr Asn
                485                 490                 495

Tyr Val Ser Trp Tyr Gln Gln His Pro Gly Lys Ala Pro Lys Leu Met
                    500                 505                 510

Ile Tyr Asp Val Asn Asn Arg Pro Ser Gly Val Ser Asn Arg Phe Ser
                515                 520                 525

Gly Ser Lys Ser Gly Asn Thr Ala Ser Leu Thr Ile Ser Gly Leu Gln
        530                 535                 540

Ala Glu Asp Glu Ala Asp Tyr Phe Cys Ser Ser Tyr Thr Ser Ser Ser
545                 550                 555                 560

Thr Pro Val Val Phe Gly Gly Gly Thr Lys Leu Thr Val Leu Gly Gly
                    565                 570                 575

Gly Gly Ser Gly Gly Arg Ala Ser Gly Gly Gly Gly Ser Gln Val Gln
                580                 585                 590

Leu Gln Gln Ser Gly Ala Gly Leu Leu Lys Pro Ser Glu Thr Leu Ser
        595                 600                 605

Leu Thr Cys Ala Val Ser Gly Gly Ser Phe Ser Gly Tyr Tyr Trp Thr
            610                 615                 620

Trp Ile Arg Gln Arg Pro Gly Lys Gly Leu Glu Trp Ile Gly Glu Ile
625                 630                 635                 640

Asn His Arg Gly Ser Thr Asp Tyr Asn Pro Ser Leu Lys Ser Arg Val
                645                 650                 655
```

Thr Met Ser Ile Asp Thr Ser Lys Ser Gln Phe Ser Leu Asn Leu Lys
            660                 665                 670

Ser Val Thr Ala Ala Asp Thr Ala Val Tyr Tyr Cys Ala Arg Ala Ala
            675                 680                 685

Trp Gly Ser Cys Tyr Asp Gly Thr Cys Tyr Pro Ala Glu Tyr Phe Gln
            690                 695                 700

Tyr Trp Gly Gln Gly Thr Leu Val Thr Val Ser Ser
705                 710                 715

<210> SEQ ID NO 130
<211> LENGTH: 2172
<212> TYPE: DNA
<213> ORGANISM: Artificial Sequence
<220> FEATURE:
<223> OTHER INFORMATION: Description of the artificial sequence: base
      sequence of the antibody sequence of pCI-AVM-hLG4PE (R409K)
      _MOG01 scFv7 excluding signal sequence

<400> SEQUENCE: 130
gaggtgcagc tggtggaatc tgggggaggc ttagtgcagc ctggaagatc cctgaaactc      60
tcctgtgcag cctcaggatt cactttcagt aactatgcca tggcttgggt ccgccgggct     120
ccaacgaagg gtctggagtg ggtcgcatcc attagtaatg gtggtggtaa cacttactat     180
cgcgactccg tgaagggccg attcactatc tccagagatg atgcaaaaaa caccctatac     240
ctgcaaatgg acagtctgag gtctgaggac acggccactt attactgtgc aagacacggg     300
aattatatat attatgggtc cttctttgat tactggggcc aaggagtcat ggtcacagtc     360
tcctcagcta gcaccaaggg gccatccgtc ttccccctgg cgcctgctc caggagcacc     420 tccgagagca gccgccct gggctgcctg gtcaaggact acttcccga accggtgacg     480 gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600
aagacctaca cctgcaacgt agatcacaag cccagcaaca ccaaggtgga caagagagtt     660
gagtccaaat atggtccccc atgcccacca tgcccagcac ctgagttcga ggggggacca     720
tcagtcttcc tgttcccccc aaaacccaag gacactctca tgatctcccg gacccctgag     780
gtcacgtgcg tggtggtgga cgtgagccag gaagacccg aggtccagtt caactggtac     840
gtggatggcg tggaggtgca taatgccaag acaaagccgc gggaggagca gttcaacagc     900
acgtaccgtg tggtcagcgt cctcaccgtc ctgcaccagg actggctgaa cggcaaggag     960
tacaagtgca aggtctccaa caaaggcctc ccgtcctcca tcgagaaaac catctccaaa    1020
gccaaagggc agccccgaga gccacaggtg tacaccctgc ccccatccca ggaggagatg    1080
accaagaacc aggtcagcct gacctgcctg gtcaaaggct tctacccag cgacatcgcc    1140 gtggagtggg agagcaatgg gcagccggag aacaactaca agaccacgcc tcccgtgctg    1200
gactccgacg gctccttctt cctctacagc aagctaaccg tggacaagag caggtggcag    1260
gaggggaatg tcttctcatg ctccgtgatg catgaggctc tgcacaacca ctacacacag    1320
aagagcctct ccctgtctct gggtggagga agcggaggag gagggtccgg aggaggaggg    1380
tccggaggag gagggtccca gtctgccctg actcagcctg cctccgtgtc tgggtctcct    1440
ggacagtcga tcaccatctc ctgcactgga accagccgtg acgttggtgg ttataactat    1500
gtctcctggt accaacaaca cccaggcaaa gcccccaaac tcatgattta tgatgtcaat    1560
aatcggccct caggggtttc taatcggttc tctggctcca agtctggcaa cacggcctcc    1620

-continued

```
ctgaccatct ctgggctcca ggctgaggac gaggctgatt atttctgcag ctcatataca    1680
agcagtagca cccctgtggt attcggcggt gggaccaagc tgaccgtcct aggaggcggt    1740
ggcagcggag gaggagggtc cggtggggc ggctcgggcg gaggtggttc acaggtacag     1800
ctgcagcagt caggcgcagg attattgaag ccttcggaga ccctttccct cacctgcgct    1860
gtgtctggtg gtccttcag tggttactac tggacctgga tccgccagcg cccagggaag     1920
gggctggagt ggattggaga aatcaatcat cgtggaagca ccgattacaa cccgtccctc    1980
aagagtcgag tcaccatgtc aatagacacg tccaagagcc agttctccct gaatttgaaa    2040
tctgtgaccg ccgcggacac ggctgtgtat tactgtgcga gagccgcctg ggggtcttgt    2100
tatgatggga cctgctaccc cgctgaatac ttccaatact ggggccaggg aaccctggtc    2160
accgtctcct ca                                                        2172
```

<210> SEQ ID NO 131
<211> LENGTH: 724
<212> TYPE: PRT
<213> ORGANISM: Artificial Sequence
<220> FEATURE:
<223> OTHER INFORMATION: Description of the artificial sequence: amino acid sequence of the antibody sequence of pCI-AVM-hLG4PE (R409K) _MOG01 scFv7 excluding signal sequence

<400> SEQUENCE: 131

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Ala Met Ala Trp Val Arg Ala Pro Thr Lys Gly Leu Glu Trp Val
        35                  40                  45

Ala Ser Ile Ser Asn Gly Gly Asn Thr Tyr Tyr Arg Asp Ser Val
    50                  55                  60

Lys Gly Arg Phe Thr Ile Ser Arg Asp Asp Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Asn Tyr Ile Tyr Tyr Gly Ser Phe Phe Asp Tyr Trp
            100                 105                 110

Gly Gln Gly Val Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Gly Gly Ser Gly Gly Gly Ser Gly Gly Gly Ser Gly Gly Gly
            450                 455                 460

Gly Ser Gln Ser Ala Leu Thr Gln Pro Ala Ser Val Ser Gly Ser Pro
465                 470                 475                 480

Gly Gln Ser Ile Thr Ile Ser Cys Thr Gly Thr Ser Arg Asp Val Gly
                485                 490                 495

Gly Tyr Asn Tyr Val Ser Trp Tyr Gln Gln His Pro Gly Lys Ala Pro
            500                 505                 510

Lys Leu Met Ile Tyr Asp Val Asn Asn Arg Pro Ser Gly Val Ser Asn
            515                 520                 525

Arg Phe Ser Gly Ser Lys Ser Gly Asn Thr Ala Ser Leu Thr Ile Ser
530                 535                 540

Gly Leu Gln Ala Glu Asp Glu Ala Asp Tyr Phe Cys Ser Ser Tyr Thr
545                 550                 555                 560

Ser Ser Ser Thr Pro Val Val Phe Gly Gly Gly Thr Lys Leu Thr Val
                565                 570                 575

Leu Gly Gly Gly Gly Ser Gly Gly Gly Gly Ser Gly Gly Gly Gly Ser
            580                 585                 590

Gly Gly Gly Gly Ser Gln Val Gln Leu Gln Gln Ser Gly Ala Gly Leu
            595                 600                 605

Leu Lys Pro Ser Glu Thr Leu Ser Leu Thr Cys Ala Val Ser Gly Gly
            610                 615                 620

Ser Phe Ser Gly Tyr Tyr Trp Thr Trp Ile Arg Gln Arg Pro Gly Lys
625                 630                 635                 640

Gly Leu Glu Trp Ile Gly Glu Ile Asn His Arg Gly Ser Thr Asp Tyr
                645                 650                 655

Asn Pro Ser Leu Lys Ser Arg Val Thr Met Ser Ile Asp Thr Ser Lys
            660                 665                 670
```

```
Ser Gln Phe Ser Leu Asn Leu Lys Ser Val Thr Ala Ala Asp Thr Ala
            675                 680                 685

Val Tyr Tyr Cys Ala Arg Ala Ala Trp Gly Ser Cys Tyr Asp Gly Thr
        690                 695                 700

Cys Tyr Pro Ala Glu Tyr Phe Gln Tyr Trp Gly Gln Gly Thr Leu Val
705                 710                 715                 720

Thr Val Ser Ser

<210> SEQ ID NO 132
<211> LENGTH: 2169
<212> TYPE: DNA
<213> ORGANISM: Artificial Sequence
<220> FEATURE:
<223> OTHER INFORMATION: Description of the artificial sequence: base
      sequence of the antibody sequence of pCI-AVM-hLG4PE (R409K)_MOG
      01 scFv 8 excluding signal sequence

<400> SEQUENCE: 132
```

| | | | | | |
|---|---|---|---|---|---|
| gaggtgcagc | tggtggaatc | tgggggaggc | ttagtgcagc | ctggaagatc | cctgaaactc | 60 |
| tcctgtgcag | cctcaggatt | cactttcagt | aactatgcca | tggcttgggt | ccgccgggct | 120 |
| ccaacgaagg | gtctggagtg | ggtcgcatcc | attagtaatg | gtggtggtaa | cacttactat | 180 |
| cgcgactccg | tgaagggccg | attcactatc | tccagagatg | atgcaaaaaa | caccctatac | 240 |
| ctgcaaatgg | acagtctgag | gtctgaggac | acggccactt | attactgtgc | aagacacggg | 300 |
| aattatatat | attatgggtc | cttctttgat | tactggggcc | aaggagtcat | ggtcacagtc | 360 |
| tcctcagcta | gcaccaaggg | gccatccgtc | ttccccctgg | cgccctgctc | caggagcacc | 420 |
| tccgagagca | cagccgccct | gggctgcctg | gtcaaggact | acttccccga | accggtgacg | 480 |
| gtgtcgtgga | actcaggcgc | cctgaccagc | ggcgtgcaca | ccttcccggc | tgtcctacag | 540 |
| tcctcaggac | tctactccct | cagcagcgtg | gtgaccgtgc | cctccagcag | cttgggcacg | 600 |
| aagacctaca | cctgcaacgt | agatcacaag | cccagcaaca | ccaaggtgga | caagagagtt | 660 |
| gagtccaaat | atggtccccc | atgcccacca | tgcccagcac | ctgagttcga | gggggaccca | 720 |
| tcagtcttcc | tgttcccccc | aaaacccaag | gacactctca | tgatctcccg | gacccctgag | 780 |
| gtcacgtgcg | tggtggtgga | cgtgagccag | gaagaccccg | aggtccagtt | caactggtac | 840 |
| gtggatggcg | tggaggtgca | taatgccaag | acaaagccgc | gggaggagca | gttcaacagc | 900 |
| acgtaccgtg | tggtcagcgt | cctcaccgtc | ctgcaccagg | actggctgaa | cggcaaggag | 960 |
| tacaagtgca | aggtctccaa | caaaggcctc | ccgtcctcca | tcgagaaaac | catctccaaa | 1020 |
| gccaaagggc | agccccgaga | gccacaggtg | tacaccctgc | ccccatccca | ggaggagatg | 1080 |
| accaagaacc | aggtcagcct | gacctgcctg | gtcaaaggct | tctacccag | cgacatcgcc | 1140 |
| gtggagtggg | agagcaatgg | gcagccggag | aacaactaca | agaccacgcc | tcccgtgctg | 1200 |
| gactccgacg | gctccttctt | cctctacagc | aagctaaccg | tggacaagag | caggtggcag | 1260 |
| gaggggaatg | tcttctcatg | ctccgtgatg | catgaggctc | tgcacaacca | ctacacacag | 1320 |
| aagagcctct | ccctgtctct | gggtggagga | agcggaggag | gagggtccgg | aggaggaggg | 1380 |
| tccggaggag | gagggtccca | gtctgccctg | actcagcctg | cctccgtgtc | tgggtctcct | 1440 |
| ggacagtcga | tcaccatctc | ctgcactgga | accagccgtg | acgttggtgg | ttataactat | 1500 |
| gtctcctggt | accaacaaca | cccaggcaaa | gcccccaaac | tcatgattta | tgatgtcaat | 1560 |
| aatcggccct | caggggtttc | taatcggttc | tctggctcca | agtctggcaa | cacggcctcc | 1620 |
| ctgaccatct | ctgggctcca | ggctgaggac | gaggctgatt | atttctgcag | ctcatataca | 1680 |

```
agcagtagca ccccctgtggt attcggcggt gggaccaagc tgaccgtcct aggtggaggc    1740
ggtggcagcg gtgggcgcgc ctcgggcgga ggtggttcac aggtacagct gcagcagtca    1800
ggcgcaggat tattgaagcc ttcggagacc ctttcccctca cctgcgctgt gtctggtggg   1860
tccttcagtg gttactactg gacctggatc cgccagcgcc cagggaaggg gctggagtgg    1920
attggagaaa tcaatcatcg tggaagcacc gattacaacc cgtccctcaa gagtcgagtc    1980
accatgtcaa tagacacgtc caagagccag ttctccctga atttgaaatc tgtgaccgcc    2040
gcggacacgg ctgtgtatta ctgtgcgaga gccgcctggg ggtcttgtta tgatgggacc    2100
tgctaccccg ctgaatactt ccaatactgg ggccagggaa ccctggtcac cgtctcctca    2160
gctagcacc                                                            2169
```

<210> SEQ ID NO 133
<211> LENGTH: 723
<212> TYPE: PRT
<213> ORGANISM: Artificial Sequence
<220> FEATURE:
<223> OTHER INFORMATION: Description of the artificial sequence: amino
    acid sequence of the antibody sequence of pCI-AVM-hLG4PE (R409K)
    _MOG 01 scFv 8 excluding signal sequence

<400> SEQUENCE: 133

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Ala Met Ala Trp Val Arg Arg Ala Pro Thr Lys Gly Leu Glu Trp Val
        35                  40                  45

Ala Ser Ile Ser Asn Gly Gly Gly Asn Thr Tyr Tyr Arg Asp Ser Val
    50                  55                  60

Lys Gly Arg Phe Thr Ile Ser Arg Asp Asp Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Asn Tyr Ile Tyr Tyr Gly Ser Phe Phe Asp Tyr Trp
            100                 105                 110

Gly Gln Gly Val Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
```

```
            260                 265                 270
Pro Glu Val Gln Phe Asn Trp Tyr Val Asp Gly Val Glu Val His Asn
    275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
            435                 440                 445

Gly Gly Ser Gly Gly Gly Ser Gly Gly Gly Ser Gly Gly Gly
        450                 455                 460

Gly Ser Gln Ser Ala Leu Thr Gln Pro Ala Ser Val Ser Gly Ser Pro
465                 470                 475                 480

Gly Gln Ser Ile Thr Ile Ser Cys Thr Gly Thr Ser Arg Asp Val Gly
                485                 490                 495

Gly Tyr Asn Tyr Val Ser Trp Tyr Gln Gln His Pro Gly Lys Ala Pro
            500                 505                 510

Lys Leu Met Ile Tyr Asp Val Asn Asn Arg Pro Ser Gly Val Ser Asn
        515                 520                 525

Arg Phe Ser Gly Ser Lys Ser Gly Asn Thr Ala Ser Leu Thr Ile Ser
    530                 535                 540

Gly Leu Gln Ala Glu Asp Glu Ala Asp Tyr Phe Cys Ser Ser Tyr Thr
545                 550                 555                 560

Ser Ser Ser Thr Pro Val Val Phe Gly Gly Gly Thr Lys Leu Thr Val
                565                 570                 575

Leu Gly Gly Gly Gly Ser Gly Gly Arg Ala Ser Gly Gly Gly Gly
            580                 585                 590

Ser Gln Val Gln Leu Gln Ser Gly Ala Gly Leu Leu Lys Pro Ser
        595                 600                 605

Glu Thr Leu Ser Leu Thr Cys Ala Val Ser Gly Ser Phe Ser Gly
    610                 615                 620

Tyr Tyr Trp Thr Trp Ile Arg Gln Arg Pro Gly Lys Gly Leu Glu Trp
625                 630                 635                 640

Ile Gly Glu Ile Asn His Arg Gly Ser Thr Asp Tyr Asn Pro Ser Leu
                645                 650                 655

Lys Ser Arg Val Thr Met Ser Ile Asp Thr Ser Lys Ser Gln Phe Ser
                660                 665                 670

Leu Asn Leu Lys Ser Val Thr Ala Ala Asp Thr Ala Val Tyr Tyr Cys
            675                 680                 685
```

```
Ala Arg Ala Ala Trp Gly Ser Cys Tyr Asp Gly Thr Cys Tyr Pro Ala
        690                 695                 700

Glu Tyr Phe Gln Tyr Trp Gly Gln Gly Thr Leu Val Thr Val Ser Ser
705                 710                 715                 720

Ala Ser Thr

<210> SEQ ID NO 134
<211> LENGTH: 2163
<212> TYPE: DNA
<213> ORGANISM: Artificial Sequence
<220> FEATURE:
<223> OTHER INFORMATION: Description of the artificial sequence: base
      sequence of antibody sequence of pCI-AVM-hLG4PE (R409K) _MOG01
      scFv9 excluding signal sequence

<400> SEQUENCE: 134
gaggtgcagc tggtggaatc tgggggaggc ttagtgcagc ctggaagatc cctgaaactc      60
tcctgtgcag cctcaggatt cactttcagt aactatgcca tggcttgggt ccgccgggct     120
ccaacgaagg gtctggagtg ggtcgcatcc attagtaatg gtggtggtaa cacttactat     180
cgcgactccg tgaagggccg attcactatc tccagagatg atgcaaaaaa cacccctatac    240 ctgcaaatgg acagtctgag gtctgaggac acggccactt attactgtgc aagacacggg    300
aattatatat attatgggtc cttctttgat tactggggcc aaggagtcat ggtcacagtc    360
tcctcagcta gcaccaaggg gccatccgtc ttccccctgg cgccctgctc caggagcacc    420
tccgagagca cagccgccct gggctgcctg gtcaaggact acttcccga accggtgacg    480 gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacg    600
aagacctaca cctgcaacgt agatcacaag cccagcaaca ccaaggtgga caagagagtt    660
gagtccaaat atggtccccc atgcccacca tgcccagcac ctgagttcga gggggaccca    720
tcagtcttcc tgttcccccc aaaacccaag gacactctca tgatctcccg gacccctgag    780
gtcacgtgcg tggtggtgga cgtgagccag gaagaccccg aggtccagtt caactggtac    840
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa   1020
gccaaagggc agccccgaga gccacaggtg tacaccctgc ccccatccca ggaggagatg   1080
accaagaacc aggtcagcct gacctgcctg gtcaaaggct tctacccag cgacatcgcc   1140 gtggagtggg agagcaatgg gcagccggag aacaactaca agaccacgcc tcccgtgctg   1200
gactccgacg gctccttctt cctctacagc aagctaaccg tggacaagag caggtggcag   1260
gaggggaatg tcttctcatg ctccgtgatg catgaggctc tgcacaacca ctacacacag   1320
aagagcctct ccctgtctct gggtggagga ggagggtccg gaggaggagg tccggtgga   1380 ggtgggtccc agtctgccct gactcagcct gcctccgtgt ctgggtctcc tggacagtcg   1440
atcaccatct cctgcactgg aaccagccgt gacgttggtg gttataacta tgtctcctgg   1500
taccaacaac acccaggcaa agcccccaaa ctcatgattt atgatgtcaa taatcggccc   1560
tcaggggttt ctaatcggtt ctctggctcc aagtctggca acacggcctc cctgaccatc   1620
tctgggctcc aggctgagga cgaggctgat tatttctgca gctcatatac aagcagtagc   1680
acccctgtgg tattcggcgg tgggaccaag ctgaccgtcc taggaggcgg tggcagcgga   1740
```

```
ggaggagggt ccggtggggg cggctcgggc ggaggtggtt cacaggtaca gctgcagcag    1800
tcaggcgcag gattattgaa gccttcggag acccttcccc tcacctgcgc tgtgtctggt    1860
gggtccttca gtggttacta ctggacctgg atccgccagc cccagggaa ggggctggag     1920 tggattggag aaatcaatca tcgtggaagc accgattaca acccgtccct caagagtcga    1980
gtcaccatgt caatagacac gtccaagagc cagttctccc tgaatttgaa atctgtgacc    2040
gccgcggaca cggctgtgta ttactgtgcg agagccgcct gggggtcttg ttatgatggg    2100
acctgctacc ccgctgaata cttccaatac tggggccagg gaaccctggt caccgtctcc    2160
tca                                                                  2163
```

<210> SEQ ID NO 135
<211> LENGTH: 721
<212> TYPE: PRT
<213> ORGANISM: Artificial Sequence
<220> FEATURE:
<223> OTHER INFORMATION: Description of the artificial sequence: amino
      acid sequence of the antibody sequence of pCI-AVM-hLG4PE (R409K)
      _MOG01 scFv9 excluding signal sequence

<400> SEQUENCE: 135

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Ala Met Ala Trp Val Arg Arg Ala Pro Thr Lys Gly Leu Glu Trp Val
        35                  40                  45

Ala Ser Ile Ser Asn Gly Gly Asn Thr Tyr Tyr Arg Asp Ser Val
    50                  55                  60

Lys Gly Arg Phe Thr Ile Ser Arg Asp Asp Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Asn Tyr Ile Tyr Tyr Gly Ser Phe Phe Asp Tyr Trp
            100                 105                 110

Gly Gln Gly Val Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270
```

```
Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Gly Gly Gly Gly Ser Gly Gly Gly Gly Ser Gly Gly Gly Gly Ser Gln
450                 455                 460

Ser Ala Leu Thr Gln Pro Ala Ser Val Ser Gly Ser Pro Gly Gln Ser
465                 470                 475                 480

Ile Thr Ile Ser Cys Thr Gly Thr Ser Arg Asp Val Gly Gly Tyr Asn
                485                 490                 495

Tyr Val Ser Trp Tyr Gln Gln His Pro Gly Lys Ala Pro Lys Leu Met
            500                 505                 510

Ile Tyr Asp Val Asn Asn Arg Pro Ser Gly Val Ser Asn Arg Phe Ser
        515                 520                 525

Gly Ser Lys Ser Gly Asn Thr Ala Ser Leu Thr Ile Ser Gly Leu Gln
530                 535                 540

Ala Glu Asp Glu Ala Asp Tyr Phe Cys Ser Ser Tyr Thr Ser Ser Ser
545                 550                 555                 560

Thr Pro Val Val Phe Gly Gly Gly Thr Lys Leu Thr Val Leu Gly Gly
                565                 570                 575

Gly Gly Ser Gly Gly Gly Ser Gly Gly Gly Gly Ser Gly Gly Gly Gly
            580                 585                 590

Gly Ser Gln Val Gln Leu Gln Gln Ser Gly Ala Gly Leu Leu Lys Pro
        595                 600                 605

Ser Glu Thr Leu Ser Leu Thr Cys Ala Val Ser Gly Gly Ser Phe Ser
610                 615                 620

Gly Tyr Tyr Trp Thr Trp Ile Arg Gln Arg Pro Gly Lys Gly Leu Glu
625                 630                 635                 640

Trp Ile Gly Glu Ile Asn His Arg Gly Ser Thr Asp Tyr Asn Pro Ser
                645                 650                 655

Leu Lys Ser Arg Val Thr Met Ser Ile Asp Thr Ser Lys Ser Gln Phe
            660                 665                 670

Ser Leu Asn Leu Lys Ser Val Thr Ala Ala Asp Thr Ala Val Tyr Tyr
        675                 680                 685

Cys Ala Arg Ala Ala Trp Gly Ser Cys Tyr Asp Gly Thr Cys Tyr Pro
```

```
                690               695               700
Ala Glu Tyr Phe Gln Tyr Trp Gly Gln Gly Thr Leu Val Thr Val Ser
705                 710               715               720

Ser
```

<210> SEQ ID NO 136
<211> LENGTH: 2160
<212> TYPE: DNA
<213> ORGANISM: Artificial Sequence
<220> FEATURE:
<223> OTHER INFORMATION: Description of the artificial sequence: base
      sequence of antibody sequence of pCI-AVM-hLG4PE (R409K) _MOG 01
      scFv 10 excluding signal sequence

<400> SEQUENCE: 136

```
gaggtgcagc tggtggaatc tgggggaggc ttagtgcagc ctggaagatc cctgaaactc    60
tcctgtgcag cctcaggatt cactttcagt aactatgcca tggcttgggt ccgccgggct   120
ccaacgaagg gtctggagtg ggtcgcatcc attagtaatg gtggtggtaa cacttactat   180
cgcgactccg tgaagggccg attcactatc tccagagatg atgcaaaaaa caccctatac   240
ctgcaaatgg acagtctgag gtctgaggac acggccactt attactgtgc aagacacggg   300
aattatatat attatgggtc cttctttgat tactggggcc aaggagtcat ggtcacagtc   360
tcctcagcta gcaccaaggg gccatccgtc ttccccctgg cgccctgctc caggagcacc   420
tccgagagca gccgccctg ggctgcctg gtcaaggact acttccccga accggtgacg   480
gtgtcgtgga actcaggcgc cctgaccagc ggcgtgcaca ccttcccggc tgtcctacag   540
tcctcaggac tctactccct cagcagcgtg gtgaccgtgc cctccagcag cttgggcacg   600
aagacctaca cctgcaacgt agatcacaag cccagcaaca ccaaggtgga caagagagtt   660
gagtccaaat atggtccccc atgcccacca tgcccagcac ctgagttcga gggggacca   720
tcagtcttcc tgttccccc aaaacccaag gacactctca tgatctcccg gacccctgag   780
gtcacgtgcg tggtggtgga cgtgagccag gaagaccccg aggtccagtt caactggtac   840
gtggatggcg tggaggtgca taatgccaag acaaagccgc gggaggagca gttcaacagc   900
acgtaccgtg tggtcagcgt cctcaccgtc ctgcaccagg actggctgaa cggcaaggag   960
tacaagtgca aggtctccaa caaaggcctc ccgtcctcca tcgagaaaac catctccaaa  1020
gccaaagggc agccccgaga gccacaggtg tacaccctgc ccccatccca ggaggagatg  1080
accaagaacc aggtcagcct gacctgcctg gtcaaaggct tctacccag cgacatcgcc  1140
gtggagtggg agagcaatgg gcagccggag aacaactaca agaccacgcc tcccgtgctg  1200
gactccgacg gctccttctt cctctacagc aagctaaccg tggacaagag caggtggcag  1260
gaggggaatg tcttctcatg ctccgtgatg catgaggctc tgcacaacca ctacacacag  1320
aagagcctct ccctgtctct gggtggagga ggagggtccg gaggaggagg gtccggtgga  1380
ggtgggtccc agtctgccct gactcagcct gcctccgtgt ctgggtctcc tggacagtcg  1440
atcaccatct cctgcactgg aaccagccgt gacgttggtg gttataacta tgtctcctgg  1500
taccaacaac acccaggcaa agccccccaaa ctcatgattt atgatgtcaa taatcggccc  1560
tcagggttt ctaatcggtt ctctggctcc aagtctggca cacggcctc cctgaccatc  1620
tctgggctcc aggctgagga cgaggctgat tatttctgca gctcatatac aagcagtagc  1680
accccctgtgg tattcggcgg tgggaccaag ctgaccgtcc taggtggagg cggtggcagc  1740
ggtgggcgcg cctcgggcgg aggtggttca caggtacagc tgcagcagtc aggcgcagga  1800
```

-continued

```
ttattgaagc cttcggagac cctttccctc acctgcgctg tgtctggtgg gtccttcagt    1860
ggttactact ggacctggat ccgccagcgc ccagggaagg ggctggagtg gattggagaa    1920
atcaatcatc gtggaagcac cgattacaac ccgtccctca agagtcgagt caccatgtca    1980
atagacacgt ccaagagcca gttctccctg aatttgaaat ctgtgaccgc cgcggacacg    2040
gctgtgtatt actgtgcgag agccgcctgg gggtcttgtt atgatgggac ctgctacccc    2100
gctgaatact ccaatactg gggccaggga accctggtca ccgtctcctc agctagcacc     2160
```

<210> SEQ ID NO 137
<211> LENGTH: 720
<212> TYPE: PRT
<213> ORGANISM: Artificial Sequence
<220> FEATURE:
<223> OTHER INFORMATION: Description of the artificial sequence: amino
      acid sequence of the antibody sequence of pCI-AVM-hLG4PE (R409K)
      _MOG 01 scFv 10 excluding signal sequence

<400> SEQUENCE: 137

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Ala Met Ala Trp Val Arg Arg Ala Pro Thr Lys Gly Leu Glu Trp Val
        35                  40                  45

Ala Ser Ile Ser Asn Gly Gly Gly Asn Thr Tyr Tyr Arg Asp Ser Val
    50                  55                  60

Lys Gly Arg Phe Thr Ile Ser Arg Asp Asp Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Asn Tyr Ile Tyr Tyr Gly Ser Phe Phe Asp Tyr Trp
            100                 105                 110

Gly Gln Gly Val Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
```

```
            290                 295                 300
Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Gly Gly Gly Gly Ser Gly Gly Gly Gly Ser Gly Gly Gly Gly Ser Gln
        450                 455                 460

Ser Ala Leu Thr Gln Pro Ala Ser Val Ser Gly Ser Pro Gly Gln Ser
465                 470                 475                 480

Ile Thr Ile Ser Cys Thr Gly Thr Ser Arg Asp Val Gly Gly Tyr Asn
                485                 490                 495

Tyr Val Ser Trp Tyr Gln Gln His Pro Gly Lys Ala Pro Lys Leu Met
            500                 505                 510

Ile Tyr Asp Val Asn Asn Arg Pro Ser Gly Val Ser Asn Arg Phe Ser
        515                 520                 525

Gly Ser Lys Ser Gly Asn Thr Ala Ser Leu Thr Ile Ser Gly Leu Gln
530                 535                 540

Ala Glu Asp Glu Ala Asp Tyr Phe Cys Ser Ser Tyr Thr Ser Ser Ser
545                 550                 555                 560

Thr Pro Val Val Phe Gly Gly Gly Thr Lys Leu Thr Val Leu Gly Gly
                565                 570                 575

Gly Gly Gly Ser Gly Gly Arg Ala Ser Gly Gly Gly Ser Gln Val
            580                 585                 590

Gln Leu Gln Gln Ser Gly Ala Gly Leu Leu Lys Pro Ser Glu Thr Leu
        595                 600                 605

Ser Leu Thr Cys Ala Val Ser Gly Gly Ser Phe Ser Gly Tyr Tyr Trp
        610                 615                 620

Thr Trp Ile Arg Gln Arg Pro Gly Lys Gly Leu Glu Trp Ile Gly Glu
625                 630                 635                 640

Ile Asn His Arg Gly Ser Thr Asp Tyr Asn Pro Ser Leu Lys Ser Arg
                645                 650                 655

Val Thr Met Ser Ile Asp Thr Ser Lys Ser Gln Phe Ser Leu Asn Leu
            660                 665                 670

Lys Ser Val Thr Ala Ala Asp Thr Ala Val Tyr Tyr Cys Ala Arg Ala
        675                 680                 685

Ala Trp Gly Ser Cys Tyr Asp Gly Thr Cys Tyr Pro Ala Glu Tyr Phe
        690                 695                 700

Gln Tyr Trp Gly Gln Gly Thr Leu Val Thr Val Ser Ser Ala Ser Thr
705                 710                 715                 720
```

<210> SEQ ID NO 138
<211> LENGTH: 2184
<212> TYPE: DNA
<213> ORGANISM: Artificial Sequence
<220> FEATURE:
<223> OTHER INFORMATION: Description of the artificial sequence: base sequence of the antibody sequence of pCI-AVM-hLG4PE (R409K) _MOG01 scFv11 excluding signal sequence

<400> SEQUENCE: 138

```
gaggtgcagc tggtggaatc tgggggaggc ttagtgcagc ctggaagatc cctgaaactc      60
tcctgtgcag cctcaggatt cactttcagt aactatgcca tggcttgggt ccgccgggct     120
ccaacgaagg gtctggagtg ggtcgcatcc attagtaatg gtggtggtaa cacttactat     180
cgcgactccg tgaagggccg attcactatc tccagagatg atgcaaaaaa caccctatac     240
ctgcaaatgg acagtctgag gtctgaggac acggccactt attactgtgc aagacacggg     300
aattatatat attatgggtc cttctttgat tactggggcc aaggagtcat ggtcacagtc     360
tcctcagcta gcaccaaggg gccatccgtc ttccccctgg cgccctgctc caggagcacc     420
tccgagagca cagccgccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600
aagacctaca cctgcaacgt agatcacaag cccagcaaca ccaaggtgga caagagagtt     660
gagtccaaat atggtccccc atgcccacca tgcccagcac ctgagttcga gggggaccca     720
tcagtcttcc tgttcccccc aaaacccaag gacactctca tgatctcccg gacccctgag     780
gtcacgtgcg tggtggtgga cgtgagccag gaagacccccg aggtccagtt caactggtac     840
gtggatggcg tggaggtgca taatgccaag acaaagccgc gggaggagca gttcaacagc     900
acgtaccgtg tggtcagcgt cctcaccgtc ctgcaccagg actggctgaa cggcaaggag     960
tacaagtgca aggtctccaa caaaggcctc ccgtcctcca tcgagaaaac catctccaaa    1020
gccaaagggc agccccgaga gccacaggtg tacaccctgc ccccatccca ggaggagatg    1080
accaagaacc aggtcagcct gacctgcctg gtcaaaggct tctacccag cgacatcgcc     1140
gtggagtggg agagcaatgg gcagccggag aacaactaca agaccacgcc tcccgtgctg    1200
gactccgacg gctccttctt cctctacagc aagctaaccg tggacaagag caggtggcag    1260
gaggggaatg tcttctcatg ctccgtgatg catgaggctc tgcacaacca ctacacacag    1320
aagagcctct ccctgtctct gggtggagga gcggaggag gagggtccgg aggaggaggg    1380
tccggaggag gagggtccca gtctgccctg actcagcctg cctccgtgtc tgggtctcct    1440
ggacagtcga tcaccatctc ctgcactgga accagccgtg acgttggtgg ttataactat    1500
gtctcctggt accaacaaca cccaggcaaa gcccccaaac tcatgattta tgatgtcaat    1560
aatcggccct caggggtttc taatcggttc tctggctcca agtctggcaa cacggcctcc    1620
ctgaccatct ctgggctcca ggctgaggac gaggctgatt atttctgcag ctcatataca    1680
agcagtagca cccctgtggt attcggcggt gggaccaagc tgaccgtcct aggtggaggc    1740
ggtggcagcg gaggaggagg gtccggtggg ggcggctcgg gcggaggtgg ttcacaggta    1800
cagctgcagc agtcaggcgc aggattattg aagccttcgg agacccttc cctcacctgc    1860
gctgtgtctg gtgggtcctt cagtggttac tactggacct ggatccgcca gcgcccaggg    1920
aaggggctgg agtggattgg agaaatcaat catcgtggaa gcaccgatta caacccgtcc    1980
```

-continued

```
ctcaagagtc gagtcaccat gtcaatagac acgtccaaga gccagttctc cctgaatttg    2040
aaatctgtga ccgccgcgga cacggctgtg tattactgtg cgagagccgc ctggggtct     2100 tgttatgatg ggacctgcta ccccgctgaa tacttccaat actggggcca gggaaccctg   2160
gtcaccgtct cctcagctag cacc                                            2184
```

<210> SEQ ID NO 139
<211> LENGTH: 728
<212> TYPE: PRT
<213> ORGANISM: Artificial Sequence
<220> FEATURE:
<223> OTHER INFORMATION: Description of the artificial sequence: amino acid sequence of the antibody sequence of pCI-AVM-hLG4PE (R409K) _MOG 01 scFv 11 excluding signal sequence

<400> SEQUENCE: 139

```
Glu Val Gln Leu Val Glu Ser Gly Gly Gly Leu Val Gln Pro Gly Arg
 1               5                  10                  15

Ser Leu Lys Leu Ser Cys Ala Ala Ser Gly Phe Thr Phe Ser Asn Tyr
            20                  25                  30

Ala Met Ala Trp Val Arg Arg Ala Pro Thr Lys Gly Leu Glu Trp Val
        35                  40                  45

Ala Ser Ile Ser Asn Gly Gly Gly Asn Thr Tyr Tyr Arg Asp Ser Val
    50                  55                  60

Lys Gly Arg Phe Thr Ile Ser Arg Asp Asp Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Asn Tyr Ile Tyr Tyr Gly Ser Phe Phe Asp Tyr Trp
            100                 105                 110

Gly Gln Gly Val Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
                435                 440                 445

Gly Gly Ser Gly Gly Gly Ser Gly Gly Gly Ser Gly Gly Gly
            450                 455                 460

Gly Ser Gln Ser Ala Leu Thr Gln Pro Ala Ser Val Ser Gly Ser Pro
465                 470                 475                 480

Gly Gln Ser Ile Thr Ile Ser Cys Thr Gly Thr Ser Arg Asp Val Gly
                485                 490                 495

Gly Tyr Asn Tyr Val Ser Trp Tyr Gln Gln His Pro Gly Lys Ala Pro
                500                 505                 510

Lys Leu Met Ile Tyr Asp Val Asn Asn Arg Pro Ser Gly Val Ser Asn
                515                 520                 525

Arg Phe Ser Gly Ser Lys Ser Gly Asn Thr Ala Ser Leu Thr Ile Ser
530                 535                 540

Gly Leu Gln Ala Glu Asp Glu Ala Asp Tyr Phe Cys Ser Ser Tyr Thr
545                 550                 555                 560

Ser Ser Ser Thr Pro Val Val Phe Gly Gly Gly Thr Lys Leu Thr Val
                565                 570                 575

Leu Gly Gly Gly Gly Ser Gly Gly Gly Gly Ser Gly Gly Gly Gly
            580                 585                 590

Ser Gly Gly Gly Gly Ser Gln Val Gln Leu Gln Gln Ser Gly Ala Gly
            595                 600                 605

Leu Leu Lys Pro Ser Glu Thr Leu Ser Leu Thr Cys Ala Val Ser Gly
            610                 615                 620

Gly Ser Phe Ser Gly Tyr Tyr Trp Thr Trp Ile Arg Gln Arg Pro Gly
625                 630                 635                 640

Lys Gly Leu Glu Trp Ile Gly Glu Ile Asn His Arg Gly Ser Thr Asp
                645                 650                 655

Tyr Asn Pro Ser Leu Lys Ser Arg Val Thr Met Ser Ile Asp Thr Ser
                660                 665                 670

Lys Ser Gln Phe Ser Leu Asn Leu Lys Ser Val Thr Ala Ala Asp Thr
                675                 680                 685

Ala Val Tyr Tyr Cys Ala Arg Ala Ala Trp Gly Ser Cys Tyr Asp Gly
                690                 695                 700

Thr Cys Tyr Pro Ala Glu Tyr Phe Gln Tyr Trp Gly Gln Gly Thr Leu
705                 710                 715                 720

Val Thr Val Ser Ser Ala Ser Thr
                725
```

<210> SEQ ID NO 140
<211> LENGTH: 2040
<212> TYPE: DNA
<213> ORGANISM: Artificial Sequence
<220> FEATURE:
<223> OTHER INFORMATION: Description of the artificial sequence: base
      sequence of the antibody sequence of pCI-AVM-hLG4PE (R409K)
      -linker-AVMVL-CL excluding signal sequence

<400> SEQUENCE: 140

```
gaggtgcagc tggtggaatc tgggggaggc ttagtgcagc ctggaagatc cctgaaactc      60
tcctgtgcag cctcaggatt cactttcagt aactatgcca tggcttgggt ccgccgggct     120
ccaacgaagg gtctggagtg gtcgcatcc attagtaatg gtggtggtaa cacttactat     180
cgcgactccg tgaagggccg attcactatc tccagagatg atgcaaaaaa caccctatac     240
ctgcaaatgg acagtctgag gtctgaggac acggccactt attactgtgc aagacacggg     300
aattatatat attatgggtc cttctttgat tactggggcc aaggagtcat ggtcacagtc     360
tcctcagcta gcaccaaggg gccatccgtc ttccccctgg cgccctgctc caggagcacc     420
tccgagagca cagccgccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600
aagacctaca cctgcaacgt agatcacaag cccagcaaca ccaaggtgga caagagagtt     660
gagtccaaat atggtccccc atgcccacca tgcccagcac ctgagttcga gggggggacca     720
tcagtcttcc tgttcccccc aaaacccaag gacactctca tgatctcccg gacccctgag     780
gtcacgtgcg tggtggtgga cgtgagccag gaagacccccg aggtccagtt caactggtac     840
gtggatggcg tggaggtgca taatgccaag acaaagccgc gggaggagca gttcaacagc     900
acgtaccgtg tggtcagcgt cctcaccgtc ctgcaccagg actggctgaa cggcaaggag     960
tacaagtgca aggtctccaa caaaggcctc ccgtcctcca tcgagaaaac catctccaaa    1020
gccaaagggc agccccgaga gccacaggtg tacaccctgc cccatccca ggaggagatg    1080
accaagaacc aggtcagcct gacctgcctg gtcaaaggct tctacccag cgacatcgcc    1140
gtggagtggg agagcaatgg gcagccggag aacaactaca agaccacgcc tcccgtgctg    1200
gactccgacg gctccttctt cctctacagc aagctaaccg tggacaagag caggtggcag    1260
gaggggaatg tcttctcatg ctccgtgatg catgaggctc tgcacaacca ctacacacag    1320
aagagcctct ccctgtctct gggtaaagga ggagagggt ccggaggagg agggtccgga    1380
ggaggagggt cccagtttgt gctttctcag ccaaactctg tgtctacgaa tctcggaagc    1440
acagtcaaac tgtcttgcaa gcgcagcact ggtaacattg gaagcaatta tgtgagctgg    1500
taccagcagc atgagggaag atctcccacc actatgattt ataggatga taagagacca    1560
gatggagttc ctgacaggtt ctctggctcc attgacagat cttccgactc agccctcctg    1620
acaatcaata atgtgcagac tgaagatgaa gctgactact ctgtcagtc ttacagtagt    1680
ggtattaata ttttcggcgg tggaaccaag ctcactgtcc taggtcagcc caaggccgcc    1740
ccctcggtca ctctgttccc gccctcctct gaggagcttc aagccaacaa ggccacactg    1800
gtgtgtctca taagtgactt ctacccggga gccgtgacag tggcctggaa ggcagatagc    1860
agccccgtca aggcgggagt ggagaccacc acaccctcca acaaagcaa caacaagtac    1920
gcggccagca gctacctgag cctgacgcct gagcagtgga gtcccacag aagctacagc    1980
tgccaggtca cgcatgaagg gagcaccgtg gagaagacag tggcccctac agaatgttca    2040
```

-continued

```
<210> SEQ ID NO 141
<211> LENGTH: 680
<212> TYPE: PRT
<213> ORGANISM: Artificial Sequence
<220> FEATURE:
<223> OTHER INFORMATION: Description of the artificial sequence: amino
      acid sequence of the antibody sequence of pCI-AVM-hLG4PE (R409K)
      -linker-AVMVL-CL excluding signal sequence

<400> SEQUENCE: 141
```

| | | | | | | | | | | | | | | |
|---|---|---|---|---|---|---|---|---|---|---|---|---|---|---|
Glu Val Gln Leu Val Glu Ser Gly Gly Gly Leu Val Gln Pro Gly Arg
 1               5                  10                  15

Ser Leu Lys Leu Ser Cys Ala Ala Ser Gly Phe Thr Phe Ser Asn Tyr
             20                  25                  30

Ala Met Ala Trp Val Arg Arg Ala Pro Thr Lys Gly Leu Glu Trp Val
         35                  40                  45

Ala Ser Ile Ser Asn Gly Gly Asn Thr Tyr Tyr Arg Asp Ser Val
     50                  55                  60

Lys Gly Arg Phe Thr Ile Ser Arg Asp Asp Ala Lys Asn Thr Leu Tyr
 65                  70                  75                  80

Leu Gln Met Asp Ser Leu Arg Ser Glu Asp Thr Ala Thr Tyr Tyr Cys
                 85                  90                  95

Ala Arg His Gly Asn Tyr Ile Tyr Tyr Gly Ser Phe Phe Asp Tyr Trp
            100                 105                 110

Gly Gln Gly Val Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Leu Gly
            435                 440                 445

Lys Gly Gly Gly Gly Ser Gly Gly Gly Gly Ser Gly Gly Gly Gly Ser
450                 455                 460

Gln Phe Val Leu Ser Gln Pro Asn Ser Val Ser Thr Asn Leu Gly Ser
465                 470                 475                 480

Thr Val Lys Leu Ser Cys Lys Arg Ser Thr Gly Asn Ile Gly Ser Asn
                485                 490                 495

Tyr Val Ser Trp Tyr Gln Gln His Glu Gly Arg Ser Pro Thr Thr Met
                500                 505                 510

Ile Tyr Arg Asp Asp Lys Arg Pro Asp Gly Val Pro Asp Arg Phe Ser
            515                 520                 525

Gly Ser Ile Asp Arg Ser Ser Asp Ser Ala Leu Leu Thr Ile Asn Asn
            530                 535                 540

Val Gln Thr Glu Asp Glu Ala Asp Tyr Phe Cys Gln Ser Tyr Ser Ser
545                 550                 555                 560

Gly Ile Asn Ile Phe Gly Gly Gly Thr Lys Leu Thr Val Leu Gly Gln
                565                 570                 575

Pro Lys Ala Ala Pro Ser Val Thr Leu Phe Pro Pro Ser Ser Glu Glu
            580                 585                 590

Leu Gln Ala Asn Lys Ala Thr Leu Val Cys Leu Ile Ser Asp Phe Tyr
            595                 600                 605

Pro Gly Ala Val Thr Val Ala Trp Lys Ala Asp Ser Ser Pro Val Lys
610                 615                 620

Ala Gly Val Glu Thr Thr Thr Pro Ser Lys Gln Ser Asn Asn Lys Tyr
625                 630                 635                 640

Ala Ala Ser Ser Tyr Leu Ser Leu Thr Pro Glu Gln Trp Lys Ser His
                645                 650                 655

Arg Ser Tyr Ser Cys Gln Val Thr His Glu Gly Ser Thr Val Glu Lys
                660                 665                 670

Thr Val Ala Pro Thr Glu Cys Ser
            675                 680

<210> SEQ ID NO 142
<211> LENGTH: 660
<212> TYPE: DNA
<213> ORGANISM: Artificial Sequence
<220> FEATURE:
<223> OTHER INFORMATION: Description of the artificial sequence: base
      sequence of antibody sequence of pCI-AVMVH-CH excluding signal
      sequence

<400> SEQUENCE: 142
gaggtgcagc tggtggaatc tggggggaggc ttagtgcagc ctggaagatc cctgaaactc      60
tcctgtgcag cctcaggatt cactttcagt aactatgcca tggcttgggt ccgccgggct     120

| ccaacgaagg gtctggagtg ggtcgcatcc attagtaatg gtggtggtaa cacttactat | 180 |
| cgcgactccg tgaagggccg attcactatc tccagagatg atgcaaaaaa caccctatac | 240 |
| ctgcaaatgg acagtctgag gtctgaggac acggccactt attactgtgc aagacacggg | 300 |
| aattatatat attatgggtc cttctttgat tactggggcc aaggagtcat ggtcacagtc | 360 |
| tcctcagcta gcaccaaggg gccatccgtc ttccccctgg cgccctgctc caggagcacc | 420 |
| tccgagagca cagccgccct gggctgcctg gtcaaggact acttccccga accggtgacg | 480 |
| gtgtcgtgga actcaggcgc cctgaccagc ggcgtgcaca ccttcccggc tgtcctacag | 540 |
| tcctcaggac tctactccct cagcagcgtg gtgaccgtgc cctccagcag cttgggcacg | 600 |
| aagacctaca cctgcaacgt agatcacaag cccagcaaca ccaaggtgga caagagagtt | 660 |

<210> SEQ ID NO 143
<211> LENGTH: 220
<212> TYPE: PRT
<213> ORGANISM: Artificial Sequence
<220> FEATURE:
<223> OTHER INFORMATION: Description of the artificial sequence: amino
      acid sequence of antibody sequence of pCI-AVMVH-CH excluding
      signal sequence

<400> SEQUENCE: 143

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Ala Met Ala Trp Val Arg Arg Ala Pro Thr Lys Gly Leu Glu Trp Val
        35                  40                  45

Ala Ser Ile Ser Asn Gly Gly Gly Asn Thr Tyr Tyr Arg Asp Ser Val
    50                  55                  60

Lys Gly Arg Phe Thr Ile Ser Arg Asp Asp Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Asn Tyr Ile Tyr Tyr Gly Ser Phe Phe Asp Tyr Trp
            100                 105                 110

Gly Gln Gly Val Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val
    210                 215                 220

<210> SEQ ID NO 144
<211> LENGTH: 2163
<212> TYPE: DNA
<213> ORGANISM: Artificial Sequence
<220> FEATURE:
<223> OTHER INFORMATION: Description of the artificial sequence: base sequence of the antibody sequence of pCI-AVM-hLG4PE (R409K / S354C / T366W)-linker-AVMscFv-FLAG tag excluding signal sequence

<400> SEQUENCE: 144

```
gaggtgcagc tggtggaatc tgggggaggc ttagtgcagc ctggaagatc cctgaaactc      60
tcctgtgcag cctcaggatt cactttcagt aactatgcca tggcttgggt ccgccgggct     120
ccaacgaagg gtctggagtg ggtcgcatcc attagtaatg gtggtggtaa cacttactat     180
cgcgactccg tgaagggccg attcactatc tccagagatg atgcaaaaaa caccctatac     240
ctgcaaatgg acagtctgag gtctgaggac acggccactt attactgtgc aagacacggg     300
aattatatat attatgggtc cttctttgat tactggggcc aaggagtcat ggtcacagtc     360
tcctcagcta gcaccaaggg gccatccgtc ttccccctgg cgcctgctc caggagcacc     420
tccgagagca gcgccccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600
aagacctaca cctgcaacgt agatcacaag cccagcaaca ccaaggtgga caagagagtt     660
gagtccaaat atggtccccc atgcccacca tgcccagcac ctgagttcga ggggggacca     720
tcagtcttcc tgttcccccc aaaacccaag gacactctca tgatctcccg gacccctgag     780
gtcacgtgcg tggtggtgga cgtgagccag gaagaccccg aggtccagtt caactggtac     840
gtggatggcg tggaggtgca taatgccaag acaaagccgc gggaggagca gttcaacagc     900
acgtaccgtg tggtcagcgt cctcaccgtc ctgcaccagg actggctgaa cggcaaggag     960
tacaagtgca aggtctccaa caaaggcctc ccgtcctcca tcgagaaaac catctccaaa    1020
gccaaagggc agccccgaga gccacaggtg tacaccctgc ccccatgcca ggaggagatg    1080
accaagaacc aggtcagcct gtggtgcctg gtcaaaggct tctaccccag cgacatcgcc    1140
gtggagtggg agagcaatgg gcagccggag aacaactaca agaccacgcc tcccgtgctg    1200
gactccgacg gctccttctt cctctacagc aagctaaccg tggacaagag caggtggcag    1260
gaggggaatg tcttctcatg ctccgtgatg catgaggctc tgcacaacca ctacacacag    1320
aagagcctct ccctgtctct gggtggagga agcggaggag gagggtccgg aggaggaggg    1380
tccggaggag gagggtccga ggtgcagctg gtggaatctg ggggaggctt agtgcagcct    1440
ggaagatccc tgaaactctc ctgtgcagcc tcaggattca ctttcagtaa ctatgccatg    1500
gcttgggtcc gccgggctcc aacgaagggt ctggagtggg tcgcatccat tagtaatggt    1560
ggtggtaaca cttactatcg cgactccgtg aagggccgat tcactatctc cagagatgat    1620
gcaaaaaaca ccctatacct gcaaatggac agtctgaggt ctgaggacac ggccacttat    1680
tactgtgcaa gacacgggaa ttatatatat tatgggtcct tctttgatta ctggggccaa    1740
ggagtcatgg tcacagtctc ctcaggaggc ggtggcagcg gtgggcgcgc ctcgggcgga    1800
ggtggttcac agtttgtgct ttctcagcca actctgtgt ctacgaatct cggaagcaca    1860
gtcaaactgt cttgcaagcg cagcactggt aacattggaa gcaattatgt gagctggtac    1920
cagcagcatg aggaagatc tcccaccact atgatttata gggatgataa agaccagat    1980
ggagttcctg acaggttctc tggctccatt gacagatctt ccgactcagc cctcctgaca    2040
atcaataatg tgcagactga agatgaagct gactacttct gtcagtctta cagtagtggt    2100
attaatattt tcggcggtgg aaccaagctc actgtcctag actacaagga cgacgatgac    2160
aag                                                                  2163
```

```
<210> SEQ ID NO 145
<211> LENGTH: 721
<212> TYPE: PRT
<213> ORGANISM: Artificial Sequence
<220> FEATURE:
<223> OTHER INFORMATION: Description of the artificial sequence: amino
      acid sequence of the antibody sequence of pCI-AVM-hLG4PE (R409K /
      S354C / T366W) -linker-AVMscFv-FLAG tag excluding signal sequence

<400> SEQUENCE: 145
```

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Arg |
| 1 | | | | 5 | | | | | 10 | | | | | 15 | |
| Ser | Leu | Lys | Leu | Ser | Cys | Ala | Ala | Ser | Gly | Phe | Thr | Phe | Ser | Asn | Tyr |
| | | | 20 | | | | | 25 | | | | | 30 | | |
| Ala | Met | Ala | Trp | Val | Arg | Arg | Ala | Pro | Thr | Lys | Gly | Leu | Glu | Trp | Val |
| | | 35 | | | | | 40 | | | | | 45 | | | |
| Ala | Ser | Ile | Ser | Asn | Gly | Gly | Gly | Asn | Thr | Tyr | Tyr | Arg | Asp | Ser | Val |
| | 50 | | | | | 55 | | | | | 60 | | | | |
| Lys | Gly | Arg | Phe | Thr | Ile | Ser | Arg | Asp | Asp | Ala | Lys | Asn | Thr | Leu | Tyr |
| 65 | | | | | 70 | | | | | 75 | | | | | 80 |
| Leu | Gln | Met | Asp | Ser | Leu | Arg | Ser | Glu | Asp | Thr | Ala | Thr | Tyr | Tyr | Cys |
| | | | | 85 | | | | | 90 | | | | | 95 | |
| Ala | Arg | His | Gly | Asn | Tyr | Ile | Tyr | Tyr | Gly | Ser | Phe | Phe | Asp | Tyr | Trp |
| | | | 100 | | | | | 105 | | | | | 110 | | |
| Gly | Gln | Gly | Val | Met | Val | Thr | Val | Ser | Ser | Ala | Ser | Thr | Lys | Gly | Pro |
| | | 115 | | | | | 120 | | | | | 125 | | | |
| Ser | Val | Phe | Pro | Leu | Ala | Pro | Cys | Ser | Arg | Ser | Thr | Ser | Glu | Ser | Thr |
| | 130 | | | | | 135 | | | | | 140 | | | | |
| Ala | Ala | Leu | Gly | Cys | Leu | Val | Lys | Asp | Tyr | Phe | Pro | Glu | Pro | Val | Thr |
| 145 | | | | | 150 | | | | | 155 | | | | | 160 |
| Val | Ser | Trp | Asn | Ser | Gly | Ala | Leu | Thr | Ser | Gly | Val | His | Thr | Phe | Pro |
| | | | | 165 | | | | | 170 | | | | | 175 | |
| Ala | Val | Leu | Gln | Ser | Ser | Gly | Leu | Tyr | Ser | Leu | Ser | Ser | Val | Val | Thr |
| | | | 180 | | | | | 185 | | | | | 190 | | |
| Val | Pro | Ser | Ser | Ser | Leu | Gly | Thr | Lys | Thr | Tyr | Thr | Cys | Asn | Val | Asp |
| | | 195 | | | | | 200 | | | | | 205 | | | |
| His | Lys | Pro | Ser | Asn | Thr | Lys | Val | Asp | Lys | Arg | Val | Glu | Ser | Lys | Tyr |
| | 210 | | | | | 215 | | | | | 220 | | | | |
| Gly | Pro | Pro | Cys | Pro | Pro | Cys | Pro | Ala | Pro | Glu | Phe | Glu | Gly | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | Gln | Glu | Asp |
| | | | 260 | | | | | 265 | | | | | 270 | | |
| Pro | Glu | Val | Gln | Phe | Asn | Trp | Tyr | Val | Asp | Gly | Val | Glu | Val | His | Asn |
| | | 275 | | | | | 280 | | | | | 285 | | | |
| Ala | Lys | Thr | Lys | Pro | Arg | Glu | Glu | Gln | Phe | Asn | Ser | Thr | Tyr | Arg | Val |
| | 290 | | | | | 295 | | | | | 300 | | | | |
| Val | Ser | Val | Leu | Thr | Val | Leu | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Gly | Leu | Pro | Ser | Ser | Ile | Glu | Lys |
| | | | | 325 | | | | | 330 | | | | | 335 | |
| Thr | Ile | Ser | Lys | Ala | Lys | Gly | Gln | Pro | Arg | Glu | Pro | Gln | Val | Tyr | Thr |
| | | | 340 | | | | | 345 | | | | | 350 | | |
| Leu | Pro | Pro | Cys | Gln | Glu | Glu | Met | Thr | Lys | Asn | Gln | Val | Ser | Leu | Trp |

355                 360                 365
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Gly Gly Ser Gly Gly Gly Ser Gly Gly Gly Ser Gly Gly Gly
    450                 455                 460

Gly Ser Glu Val Gln Leu Val Glu Ser Gly Gly Gly Leu Val Gln Pro
465                 470                 475                 480

Gly Arg Ser Leu Lys Leu Ser Cys Ala Ala Ser Gly Phe Thr Phe Ser
                485                 490                 495

Asn Tyr Ala Met Ala Trp Val Arg Arg Ala Pro Thr Lys Gly Leu Glu
            500                 505                 510

Trp Val Ala Ser Ile Ser Asn Gly Gly Asn Thr Tyr Tyr Arg Asp
        515                 520                 525

Ser Val Lys Gly Arg Phe Thr Ile Ser Arg Asp Asp Ala Lys Asn Thr
    530                 535                 540

Leu Tyr Leu Gln Met Asp Ser Leu Arg Ser Glu Asp Thr Ala Thr Tyr
545                 550                 555                 560

Tyr Cys Ala Arg His Gly Asn Tyr Ile Tyr Tyr Gly Ser Phe Phe Asp
                565                 570                 575

Tyr Trp Gly Gln Gly Val Met Val Thr Val Ser Ser Gly Gly Gly Gly
            580                 585                 590

Ser Gly Gly Arg Ala Ser Gly Gly Gly Ser Gln Phe Val Leu Ser
        595                 600                 605

Gln Pro Asn Ser Val Ser Thr Asn Leu Gly Ser Thr Val Lys Leu Ser
    610                 615                 620

Cys Lys Arg Ser Thr Gly Asn Ile Gly Ser Asn Tyr Val Ser Trp Tyr
625                 630                 635                 640

Gln Gln His Glu Gly Arg Ser Pro Thr Thr Met Ile Tyr Arg Asp Asp
                645                 650                 655

Lys Arg Pro Asp Gly Val Pro Asp Arg Phe Ser Gly Ser Ile Asp Arg
            660                 665                 670

Ser Ser Asp Ser Ala Leu Leu Thr Ile Asn Asn Val Gln Thr Glu Asp
        675                 680                 685

Glu Ala Asp Tyr Phe Cys Gln Ser Tyr Ser Ser Gly Ile Asn Ile Phe
    690                 695                 700

Gly Gly Gly Thr Lys Leu Thr Val Leu Asp Tyr Lys Asp Asp Asp Asp
705                 710                 715                 720

Lys

<210> SEQ ID NO 146
<211> LENGTH: 2139
<212> TYPE: DNA
<213> ORGANISM: Artificial Sequence
<220> FEATURE:
<223> OTHER INFORMATION: Description of the artificial sequence: base
      sequence of the antibody sequence of pCI-AVM-hLG4PE (R409K)
      _AVMscFv3 excluding signal sequence

<400> SEQUENCE: 146

```
gaggtgcagc tggtggaatc tggggaggc ttagtgcagc ctggaagatc cctgaaactc      60
tcctgtgcag cctcaggatt cactttcagt aactatgcca tggcttgggt ccgccgggct    120
ccaacgaagg gtctggagtg gtcgcatcc attagtaatg gtggtggtaa cacttactat    180
cgcgactccg tgaagggccg attcactatc tccagagatg atgcaaaaaa caccctatac    240
ctgcaaatgg acagtctgag gtctgaggac acggccactt attactgtgc aagacacggg    300
aattatatat attatgggtc cttctttgat tactggggcc aaggagtcat ggtcacagtc    360
tcctcagcta gcaccaaggg gccatccgtc ttccccctgg cgccctgctc caggagcacc    420
tccgagagca cagccgccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacg    600
aagacctaca cctgcaacgt agatcacaag cccagcaaca ccaaggtgga caagagagtt    660
gagtccaaat atggtccccc atgcccacca tgcccagcac ctgagttcga ggggggacca    720
tcagtcttcc tgttcccccc aaaacccaag gacactctca tgatctcccg gacccctgag    780
gtcacgtgcg tggtggtgga cgtgagccag gaagacccg aggtccagtt caactggtac    840
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa   1020
gccaaagggc agccccgaga gccacaggtg tacaccctgc cccatccca ggaggagatg    1080
accaagaacc aggtcagcct gacctgcctg gtcaaaggct tctacccag cgacatcgcc    1140
gtggagtggg agagcaatgg gcagccggag aacaactaca agaccacgcc tcccgtgctg   1200
gactccgacg gctccttctt cctctacagc aagctaaccg tggacaagag caggtggcag   1260
gaggggaatg tcttctcatg ctccgtgatg catgaggctc tgcacaacca ctacacacag   1320
aagagcctct ccctgtctct gggtggagga agcggaggag gagggtccgg aggaggaggg   1380
tccggaggag gagggtccca gtttgtgctt tctcagccaa actctgtgtc tacgaatctc   1440
ggaagcacag tcaaactgtc ttgcaagcgc agcactggta acattggaag caattatgtg   1500
agctggtacc agcagcatga gggaagatct cccaccacta tgatttatag ggatgataag   1560
agaccagatg gagttcctga caggttctct ggctccattg acagatcttc gactcagcc    1620
ctcctgacaa tcaataatgt gcagactgaa gatgaagctg actactttg tcagtcttac   1680
agtagtggta ttaatatttt cggcggtgga accaagctca ctgtcctagg aggcggtggc   1740
agcggtgggc gcgcctcggg cggaggtggt tcagaggtgc agctggtgga atctggggga   1800
ggcttagtgc agcctggaag atccctgaaa ctctcctgtg cagcctcagg attcactttc   1860
agtaactatg ccatggcttg gtccgccgg gctccaacga agggtctgga gtgggtcgca   1920
tccattagta atggtggtgg taacacttac tatcgcgact ccgtgaaggg ccgattcact   1980
atctccagag atgatgcaaa aaacacccta tacctgcaaa tggacagtct gaggtctgag   2040
gacacggcca cttattactg tgcaagacac gggaattata tattatgg gtccttcttt   2100
gattactggg gccaaggagt catggtcaca gtctcctca                          2139
```

<210> SEQ ID NO 147
<211> LENGTH: 713
<212> TYPE: PRT

<213> ORGANISM: Artificial Sequence
<220> FEATURE:
<223> OTHER INFORMATION: Description of the artificial sequence: amino
      acid sequence of the antibody sequence of pCI-AVM-hLG4PE (R409K)
      _AVMscFv3 excluding signal sequence

<400> SEQUENCE: 147

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Ala Met Ala Trp Val Arg Ala Pro Thr Lys Gly Leu Glu Trp Val
        35                  40                  45

Ala Ser Ile Ser Asn Gly Gly Asn Thr Tyr Tyr Arg Asp Ser Val
    50                  55                  60

Lys Gly Arg Phe Thr Ile Ser Arg Asp Asp Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Asn Tyr Ile Tyr Tyr Gly Ser Phe Phe Asp Tyr Trp
            100                 105                 110

Gly Gln Gly Val Met Val Thr Val Ser Ser Ala Ser Thr Lys Gly Pro
            115                 120                 125

Ser Val Phe Pro Leu Ala Pro Cys Ser Arg Ser Thr Ser Glu Ser Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380
```

```
Ser Asn Gly Gln Pro Glu Asn Tyr Lys Thr Thr Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Gly Gly Ser Gly Gly Gly Ser Gly Gly Gly Ser Gly Gly Gly
        450                 455                 460

Gly Ser Gln Phe Val Leu Ser Gln Pro Asn Ser Val Ser Thr Asn Leu
465                 470                 475                 480

Gly Ser Thr Val Lys Leu Ser Cys Lys Arg Ser Thr Gly Asn Ile Gly
                485                 490                 495

Ser Asn Tyr Val Ser Trp Tyr Gln Gln His Glu Gly Arg Ser Pro Thr
            500                 505                 510

Thr Met Ile Tyr Arg Asp Asp Lys Arg Pro Asp Gly Val Pro Asp Arg
            515                 520                 525

Phe Ser Gly Ser Ile Asp Arg Ser Ser Asp Ser Ala Leu Leu Thr Ile
530                 535                 540

Asn Asn Val Gln Thr Glu Asp Glu Ala Asp Tyr Phe Cys Gln Ser Tyr
545                 550                 555                 560

Ser Ser Gly Ile Asn Ile Phe Gly Gly Gly Thr Lys Leu Thr Val Leu
                565                 570                 575

Gly Gly Gly Gly Ser Gly Gly Arg Ala Ser Gly Gly Gly Ser Glu
                580                 585                 590

Val Gln Leu Val Glu Ser Gly Gly Gly Leu Val Gln Pro Gly Arg Ser
            595                 600                 605

Leu Lys Leu Ser Cys Ala Ala Ser Gly Phe Thr Phe Ser Asn Tyr Ala
            610                 615                 620

Met Ala Trp Val Arg Arg Ala Pro Thr Lys Gly Leu Glu Trp Val Ala
625                 630                 635                 640

Ser Ile Ser Asn Gly Gly Gly Asn Thr Tyr Tyr Arg Asp Ser Val Lys
                645                 650                 655

Gly Arg Phe Thr Ile Ser Arg Asp Asp Ala Lys Asn Thr Leu Tyr Leu
            660                 665                 670

Gln Met Asp Ser Leu Arg Ser Glu Asp Thr Ala Thr Tyr Tyr Cys Ala
            675                 680                 685

Arg His Gly Asn Tyr Ile Tyr Tyr Gly Ser Phe Phe Asp Tyr Trp Gly
            690                 695                 700

Gln Gly Val Met Val Thr Val Ser Ser
705                 710

<210> SEQ ID NO 148
<211> LENGTH: 2157
<212> TYPE: DNA
<213> ORGANISM: Artificial Sequence
<220> FEATURE:
<223> OTHER INFORMATION: Description of the artificial sequence: base
      sequence of the antibody sequence of pCI-AVM-hLG4PE (R409K)
      _AVMscFv5 excluding signal sequence

<400> SEQUENCE: 148
gaggtgcagc tggtggaatc tgggggaggc ttagtgcagc ctggaagatc cctgaaactc      60
tcctgtgcag cctcaggatt cactttcagt aactatgcca tggcttgggt ccgccgggct     120
```

```
ccaacgaagg gtctggagtg ggtcgcatcc attagtaatg gtggtggtaa cacttactat    180
cgcgactccg tgaagggccg attcactatc tccagagatg atgcaaaaaa cacccctatac   240
ctgcaaatgg acagtctgag gtctgaggac acggccactt attactgtgc aagacacggg    300
aattatatat attatgggtc cttctttgat tactggggcc aaggagtcat ggtcacagtc    360
tcctcagcta gcaccaaggg gccatccgtc ttccccctgg cgcctgctc caggagcacc     420
tccgagagca cagccgccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacg    600
aagacctaca cctgcaacgt agatcacaag cccagcaaca ccaaggtgga caagagagtt    660
gagtccaaat atggtccccc atgcccacca tgcccagcac ctgagttcga ggggggacca    720
tcagtcttcc tgttccccc aaaacccaag gacactctca tgatctcccg gacccctgag     780
gtcacgtgcg tggtggtgga cgtgagccag gaagaccccg aggtccagtt caactggtac    840
gtggatggcg tggaggtgca taatgccaag acaaagccgc gggaggagca gttcaacagc    900
acgtaccgtg tggtcagcgt cctcaccgtc ctgcaccagg actggctgaa cggcaaggag    960
tacaagtgca aggtctccaa caaaggcctc ccgtcctcca tcgagaaaac catctccaaa    1020
gccaaagggc agccccgaga gccacaggtg tacaccctgc ccccatccca ggaggagatg    1080
accaagaacc aggtcagcct gacctgcctg gtcaaaggct tctaccccag cgacatcgcc    1140
gtggagtggg agagcaatgg gcagccggag aacaactaca agaccacgcc tcccgtgctg    1200
gactccgacg gctccttctt cctctacagc aagctaaccg tggacaagag caggtggcag    1260
gaggggaatg tcttctcatg ctccgtgatg catgaggctc tgcacaacca ctacacacag    1320
aagagcctct ccctgtctct gggtggagga ggagggtccg gaggaggagg gtccggtgga    1380
ggtgggtccc agtttgtgct ttctcagcca aactctgtgt ctacgaatct cggaagcaca    1440
gtcaaactgt cttgcaagcg cagcactggt aacattggaa gcaattatgt gagctggtac    1500
cagcagcatg agggaagatc tcccaccact atgatttata gggatgataa gagaccagat    1560
ggagttcctg acaggttctc tggctccatt gacagatctt ccgactcagc cctcctgaca    1620
atcaataatg tgcagactga agatgaagct gactacttct gtcagtctta cagtagtggt    1680
attaatattt tcggcggtgg aaccaagctc actgtcctag gtggaggcgg tggcagcgga    1740
ggaggagggt ccggtggggg cggctcgggc ggaggtggtt cagaggtgca gctggtggaa    1800
tctgggggag gcttagtgca gcctggaaga tccctgaaac tctcctgtgc agcctcagga    1860
ttcactttca gtaactatgc catggcttgg gtccgccggg ctccaacgaa gggtctggag    1920
tgggtcgcat ccattagtaa tggtggtggt aacacttact atcgcgactc cgtgaagggc    1980
cgattcacta tctccagaga tgatgcaaaa aacaccctat acctgcaaat ggacagtctg    2040
aggtctgagg acacggccac ttattactgt gcaagacacg gaattatat atattatggg    2100
tccttctttg attactgggg ccaaggagtc atggtcacag tctcctcagc tagcacc       2157
```

<210> SEQ ID NO 149
<211> LENGTH: 719
<212> TYPE: PRT
<213> ORGANISM: Artificial Sequence
<220> FEATURE:
<223> OTHER INFORMATION: Description of the artificial sequence: amino
      acid sequence of the antibody sequence of pCI-AVM-hLG4PE (R409K)
      _AVMscFv5

<400> SEQUENCE: 149

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Ala Met Ala Trp Val Arg Arg Ala Pro Thr Lys Gly Leu Glu Trp Val
        35                  40                  45

Ala Ser Ile Ser Asn Gly Gly Asn Thr Tyr Tyr Arg Asp Ser Val
    50                  55                  60

Lys Gly Arg Phe Thr Ile Ser Arg Asp Asp Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg His Gly Asn Tyr Ile Tyr Tyr Gly Ser Phe Phe Asp Tyr Trp
            100                 105                 110

Gly Gln Gly Val Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

| Ser | Arg | Trp | Gln | Glu | Gly | Asn | Val | Phe | Ser | Cys | Ser | Val | Met | His | Glu |
|---|---|---|---|---|---|---|---|---|---|---|---|---|---|---|---|
| | | | 420 | | | | 425 | | | | 430 | | | | |

| Ala | Leu | His | Asn | His | Tyr | Thr | Gln | Lys | Ser | Leu | Ser | Leu | Ser | Leu | Gly |
|---|---|---|---|---|---|---|---|---|---|---|---|---|---|---|---|
| | | | 435 | | | | 440 | | | | 445 | | | | |

| Gly | Gly | Gly | Gly | Ser | Gly | Gly | Gly | Ser | Gly | Gly | Gly | Ser | Gln |
|---|---|---|---|---|---|---|---|---|---|---|---|---|---|
| 450 | | | | | 455 | | | | 460 | | | | |

| Phe | Val | Leu | Ser | Gln | Pro | Asn | Ser | Val | Ser | Thr | Asn | Leu | Gly | Ser | Thr |
|---|---|---|---|---|---|---|---|---|---|---|---|---|---|---|---|
| 465 | | | | | 470 | | | | 475 | | | | | | 480 |

| Val | Lys | Leu | Ser | Cys | Lys | Arg | Ser | Thr | Gly | Asn | Ile | Gly | Ser | Asn | Tyr |
|---|---|---|---|---|---|---|---|---|---|---|---|---|---|---|---|
| | | | | 485 | | | | 490 | | | | | 495 | | |

| Val | Ser | Trp | Tyr | Gln | Gln | His | Glu | Gly | Arg | Ser | Pro | Thr | Thr | Met | Ile |
|---|---|---|---|---|---|---|---|---|---|---|---|---|---|---|---|
| | | | 500 | | | | 505 | | | | 510 | | | | |

| Tyr | Arg | Asp | Asp | Lys | Arg | Pro | Asp | Gly | Val | Pro | Asp | Arg | Phe | Ser | Gly |
|---|---|---|---|---|---|---|---|---|---|---|---|---|---|---|---|
| | | | 515 | | | | 520 | | | | 525 | | | | |

| Ser | Ile | Asp | Arg | Ser | Ser | Asp | Ser | Ala | Leu | Leu | Thr | Ile | Asn | Asn | Val |
|---|---|---|---|---|---|---|---|---|---|---|---|---|---|---|---|
| 530 | | | | | 535 | | | | 540 | | | | | | |

| Gln | Thr | Glu | Asp | Glu | Ala | Asp | Tyr | Phe | Cys | Gln | Ser | Tyr | Ser | Ser | Gly |
|---|---|---|---|---|---|---|---|---|---|---|---|---|---|---|---|
| 545 | | | | | 550 | | | | | 555 | | | | | 560 |

| Ile | Asn | Ile | Phe | Gly | Gly | Thr | Lys | Leu | Thr | Val | Leu | Gly | Gly | Gly |
|---|---|---|---|---|---|---|---|---|---|---|---|---|---|---|
| | | | | 565 | | | | 570 | | | | | 575 | |

| Gly | Gly | Ser | Gly | Gly | Gly | Gly | Ser | Gly | Gly | Gly | Ser | Gly | Gly | Gly |
|---|---|---|---|---|---|---|---|---|---|---|---|---|---|---|
| | | 580 | | | | | 585 | | | | | 590 | | |

| Gly | Ser | Glu | Val | Gln | Leu | Val | Glu | Ser | Gly | Gly | Leu | Val | Gln | Pro |
|---|---|---|---|---|---|---|---|---|---|---|---|---|---|---|
| | | 595 | | | | 600 | | | | | 605 | | | |

| Gly | Arg | Ser | Leu | Lys | Leu | Ser | Cys | Ala | Ala | Ser | Gly | Phe | Thr | Phe | Ser |
|---|---|---|---|---|---|---|---|---|---|---|---|---|---|---|---|
| | 610 | | | | | 615 | | | | | 620 | | | | |

| Asn | Tyr | Ala | Met | Ala | Trp | Val | Arg | Arg | Ala | Pro | Thr | Lys | Gly | Leu | Glu |
|---|---|---|---|---|---|---|---|---|---|---|---|---|---|---|---|
| 625 | | | | 630 | | | | | 635 | | | | | 640 | |

| Trp | Val | Ala | Ser | Ile | Ser | Asn | Gly | Gly | Asn | Thr | Tyr | Tyr | Arg | Asp |
|---|---|---|---|---|---|---|---|---|---|---|---|---|---|---|
| | | | | 645 | | | | 650 | | | | | 655 | |

| Ser | Val | Lys | Gly | Arg | Phe | Thr | Ile | Ser | Arg | Asp | Asp | Ala | Lys | Asn | Thr |
|---|---|---|---|---|---|---|---|---|---|---|---|---|---|---|---|
| | | | 660 | | | | | 665 | | | | 670 | | | |

| Leu | Tyr | Leu | Gln | Met | Asp | Ser | Leu | Arg | Ser | Glu | Asp | Thr | Ala | Thr | Tyr |
|---|---|---|---|---|---|---|---|---|---|---|---|---|---|---|---|
| | | 675 | | | | 680 | | | | | 685 | | | | |

| Tyr | Cys | Ala | Arg | His | Gly | Asn | Tyr | Ile | Tyr | Tyr | Gly | Ser | Phe | Phe | Asp |
|---|---|---|---|---|---|---|---|---|---|---|---|---|---|---|---|
| | 690 | | | | | 695 | | | | | 700 | | | | |

| Tyr | Trp | Gly | Gln | Gly | Val | Met | Val | Thr | Val | Ser | Ser | Ala | Ser | Thr |
|---|---|---|---|---|---|---|---|---|---|---|---|---|---|---|
| 705 | | | | 710 | | | | | 715 | | | | | |

<210> SEQ ID NO 150
<211> LENGTH: 1887
<212> TYPE: DNA
<213> ORGANISM: Artificial Sequence
<220> FEATURE:
<223> OTHER INFORMATION: Description of the artificial sequence: base
      sequence of Acid Sphingomyelinase (ASM)

<400> SEQUENCE: 150

```
atgccccgct acggagcgtc actccgccag agctgcccca ggtccggccg ggagcaggga      60
caagacggga ccgccggagc ccccggactc ctttggatgg gctggtgct ggcgctggcg      120 ctggcgctgg cgctggctct gtctgactct cgggttctct gggctccggc agaggctcac      180
cctctttctc cccaaggcca tcctgccagg ttacatcgca tagtgccccg gctccgagat      240
gtctttgggt gggggaacct cacctgccca atctgcaaag gtctattcac cgccatcaac      300
```

```
ctcgggctga agaaggaacc caatgtggct cgcgtgggct ccgtggccat caagctgtgc    360
aatctgctga agatagcacc acctgccgtg tgccaatcca ttgtccacct ctttgaggat    420
gacatggtgg aggtgtggag acgctcagtg ctgagcccat ctgaggcctg tggcctgctc    480
ctgggctcca cctgtgggca ctgggacatt ttctcatctt ggaacatctc tttgcctact    540
gtgccgaagc cgcccccaa accccctagc ccccagccc caggtgcccc tgtcagccgc      600
atcctcttcc tcactgacct gcactgggat catgactacc tggagggcac ggaccctgac    660
tgtgcagacc cactgtgctg ccgccggggt tctggcctgc cgcccgcatc ccggccaggt    720
gccggatact ggggcgaata cagcaagtgt gacctgcccc tgaggaccct ggagagcctg    780
ttgagtgggc tgggcccagc cggcccttt gatatggtgt actggacagg agacatcccc     840
gcacatgatg tctggcacca gactcgtcag gaccaactgc gggccctgac caccgtcaca    900
gcacttgtga ggaagttcct ggggccagtg ccagtgtacc ctgctgtggg taaccatgaa    960
agcataccctg tcaatagctt ccctcccccc ttcattgagg caaccactc ctcccgctgg   1020
ctctatgaag cgatggccaa ggcttgggag ccctggctgc ctgccgaagc cctgcgcacc   1080
ctcagaattg gggggttcta tgctctttcc ccataccccg gtctccgcct catctctctc   1140
aatatgaatt tttgttcccg tgagaacttc tggctcttga tcaactccac ggatcccgca   1200
ggacagctcc agtggctggt gggggagctt caggctgctg aggatcgagg agacaaagtg   1260
catataattg gccacattcc cccagggcac tgtctgaaga ctggagctg gaattattac    1320
cgaattgtag ccaggtatga aacaccctg gctgctcagt tctttggcca cactcatgtg    1380
gatgaatttg aggtcttcta tgatgaagag actctgagcc ggccgctggc tgtagccttc   1440
ctggcaccca gtgcaactac ctacatcggc cttaatcctg gttaccgtgt gtaccaaata   1500
gatggaaact actccaggag ctctcacgtg gtcctggacc atgagaccta catcctgaat   1560
ctgacccagg caaacatacc gggagccata ccgcactggc agcttctcta cagggctcga   1620
gaaacctatg gctgcccaa cacactgcct accgcctggc acaacctggt atatcgcatg   1680
cgggggcgaca tgcaacttttt ccagaccttc tggtttctct accataaggg ccacccaccc   1740
tcggagccct gtggcacgcc ctgccgtctg gctactcttt gtgccagct ctctgcccgt     1800
gctgacagcc ctgctctgtg ccgccacctg atgccagatg ggagcctccc agaggcccag   1860
agcctgtggc caaggccact gttttgc                                        1887
```

<210> SEQ ID NO 151
<211> LENGTH: 369
<212> TYPE: DNA
<213> ORGANISM: Artificial Sequence
<220> FEATURE:
<223> OTHER INFORMATION: Description of the artificial sequence: base
      sequence  encoding VH excluding signal sequence of MOG 301

<400> SEQUENCE: 151

```
caggtgcagc tggtgcagtc tggagctgag gtgaagaagc ctggggcctc agtgaaggtc     60
tcctgcaagg cttctggtta cagctttacc agctatggta tcaactgggt gcgacaggcc   120
ccaggacaag gcttgagtg gatgggatgg atcagcgctt acaatggtta cacaaactat   180
gcacagaagc tccagggcag agtcaccatg accagagaca tccacgcg cacagcctac    240
atggagctga ggagcctgag atctgacgac acggccgtgt attactgtgc gagagagtac   300
gatatttga ctggttattc cgatgctttt gatatctggg gccaagggac cctggtcact    360
gtctcctca                                                            369
```

<210> SEQ ID NO 152
<211> LENGTH: 123
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG 301

<400> SEQUENCE: 152

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Gly Ile Asn Trp Val Arg Gln Ala Pro Gly Gln Gly Leu Glu Trp Met
        35                  40                  45

Gly Trp Ile Ser Ala Tyr Asn Gly Tyr Thr Asn Tyr Ala Gln Lys Leu
    50                  55                  60

Gln Gly Arg Val Thr Met Thr Arg Asp Thr Ser Thr Arg Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Tyr Asp Ile Leu Thr Gly Tyr Ser Asp Ala Phe Asp Ile
            100                 105                 110

Trp Gly Gln Gly Thr Leu Val Thr Val Ser Ser
        115                 120

<210> SEQ ID NO 153
<211> LENGTH: 5
<212> TYPE: PRT
<213> ORGANISM: Artificial Sequence
<220> FEATURE:
<223> OTHER INFORMATION: The Description of the artificial sequence:
      amino acid sequence of HCDR1 of MOG 301

<400> SEQUENCE: 153

Ser Tyr Gly Ile Asn
1               5

<210> SEQ ID NO 154
<211> LENGTH: 17
<212> TYPE: PRT
<213> ORGANISM: Artificial Sequence
<220> FEATURE:
<223> OTHER INFORMATION: The Description of the artificial sequence:
      amino acid sequence of HCDR2 of MOG 301

<400> SEQUENCE: 154

Trp Ile Ser Ala Tyr Asn Gly Tyr Thr Asn Tyr Ala Gln Lys Leu Gln
1               5                   10                  15

Gly

<210> SEQ ID NO 155
<211> LENGTH: 14
<212> TYPE: PRT
<213> ORGANISM: Artificial Sequence
<220> FEATURE:
<223> OTHER INFORMATION: The Description of the artificial sequence:
      amino acid sequence of HCDR3 of MOG 301

<400> SEQUENCE: 155

Glu Tyr Asp Ile Leu Thr Gly Tyr Ser Asp Ala Phe Asp Ile
1               5                   10

<210> SEQ ID NO 156
<211> LENGTH: 324
<212> TYPE: DNA
<213> ORGANISM: Artificial Sequence
<220> FEATURE:
<223> OTHER INFORMATION: Description of the artificial sequence: base
      sequence encoding VL excluding signal sequence of MOG 301

<400> SEQUENCE: 156

```
gaaatagtga tgacacagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccgct cactttcggc     300
ggagggacca aggtggaaat caaa                                            324
```

<210> SEQ ID NO 157
<211> LENGTH: 108
<212> TYPE: PRT
<213> ORGANISM: Artificial Sequence
<220> FEATURE:
<223> OTHER INFORMATION: Description of the artificial sequence: amino
      acid sequence of VL excluding signal sequence of MOG 301

<400> SEQUENCE: 157

Glu Ile Val Met Thr Gln Ser Pro Gly Thr Leu Ser Leu Ser Pro Gly
1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 158
<211> LENGTH: 12
<212> TYPE: PRT
<213> ORGANISM: Artificial Sequence
<220> FEATURE:
<223> OTHER INFORMATION: The Description of the artificial sequence:
      amino acid sequence of LCDR 1 of MOG 301

<400> SEQUENCE: 158

Arg Ala Ser Gln Ser Val Ser Ser Ser Tyr Leu Ala
1               5                  10

<210> SEQ ID NO 159
<211> LENGTH: 7
<212> TYPE: PRT
<213> ORGANISM: Artificial Sequence
<220> FEATURE:
<223> OTHER INFORMATION: The Description of the artificial sequence:
      amino acid sequence of LCDR 2 of MOG 301

<400> SEQUENCE: 159

```
<210> SEQ ID NO 160
<211> LENGTH: 9
<212> TYPE: PRT
<213> ORGANISM: Artificial Sequence
<220> FEATURE:
<223> OTHER INFORMATION: The Description of the artificial sequence:
      amino acid sequence of LCDR 3 of MOG 301

<400> SEQUENCE: 160

Gly Ala Ser Ser Arg Ala Thr
1               5
```

```
<210> SEQ ID NO 160
<211> LENGTH: 9
<212> TYPE: PRT
<213> ORGANISM: Artificial Sequence
<220> FEATURE:
<223> OTHER INFORMATION: The Description of the artificial sequence:
      amino acid sequence of LCDR 3 of MOG 301

<400> SEQUENCE: 160

Gln Gln Tyr Gly Ser Ser Pro Leu Thr
1               5
```

```
<210> SEQ ID NO 161
<211> LENGTH: 366
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG 303

<400> SEQUENCE: 161
gaggtgcagc tggtggagtc tgggggaggc ttggtacagc ctgggggtc cctgagactc      60 tcctgtgcag cctctggatt cacctttagc agctatgcca tgggctgggt ccgccaggct    120
ccagggaagg ggctggaatg ggtctcagct gttagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaaaggagga    300
tacgatattt tgactggtta cttctttgac tactggggcc agggaaccac ggtcactgtc    360
tcctca                                                              366
```

```
<210> SEQ ID NO 162
<211> LENGTH: 122
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG303

<400> SEQUENCE: 162

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Leu Glu Trp Val
        35                  40                  45

Ser Ala Val Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Tyr Asp Ile Leu Thr Gly Tyr Phe Phe Asp Tyr Trp
            100                 105                 110

Gly Gln Gly Thr Thr Val Thr Val Ser Ser
        115                 120
```

<210> SEQ ID NO 163
<211> LENGTH: 5
<212> TYPE: PRT
<213> ORGANISM: Artificial Sequence
<220> FEATURE:
<223> OTHER INFORMATION: The Description of the artificial sequence:
      amino acid sequence of HCDR1 of MOG303

<400> SEQUENCE: 163

Ser Tyr Ala Met Gly
1               5

<210> SEQ ID NO 164
<211> LENGTH: 17
<212> TYPE: PRT
<213> ORGANISM: Artificial Sequence
<220> FEATURE:
<223> OTHER INFORMATION: The Description of the artificial sequence:
      amino acid sequence of HCDR2 of MOG303

<400> SEQUENCE: 164

Ala Val Ser Gly Ser Gly Gly Ser Thr Tyr Tyr Ala Asp Ser Val Lys
1               5                   10                  15

Gly

<210> SEQ ID NO 165
<211> LENGTH: 13
<212> TYPE: PRT
<213> ORGANISM: Artificial Sequence
<220> FEATURE:
<223> OTHER INFORMATION: The Description of the artificial sequence:
      amino acid sequence of HCDR3 of MOG303

<400> SEQUENCE: 165

Gly Gly Tyr Asp Ile Leu Thr Gly Tyr Phe Phe Asp Tyr
1               5                   10

<210> SEQ ID NO 166
<211> LENGTH: 321
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG 303

<400> SEQUENCE: 166
gccatccaga tgacccagtc tccatcctcc ctgtctgcat ctgtaggaga cagagtcacc      60
atcacttgcc gggcaagtca gggcattagc agtgctttag cctggtatca gcagaaacca     120
gggaaagctc ctaagctcct gatctatgat gcctccagtt tggaaagtgg ggtcccatca     180
aggttcagcg gcagtggatc tgggacagat tcactctcac catcagcag cctgcagcct      240 gaagattttg caacttatta ctgtcaacag tttaatagtt acccattcac tttcggccct     300
gggacacgac tggagattaa a                                               321

<210> SEQ ID NO 167
<211> LENGTH: 107
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG 303

<400> SEQUENCE: 167

Ala Ile Gln Met Thr Gln Ser Pro Ser Ser Leu Ser Ala Ser Val Gly
1               5                   10                  15

```
Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Phe
                85                  90                  95

Thr Phe Gly Pro Gly Thr Arg Leu Glu Ile Lys
            100                 105

<210> SEQ ID NO 168
<211> LENGTH: 11
<212> TYPE: PRT
<213> ORGANISM: Artificial Sequence
<220> FEATURE:
<223> OTHER INFORMATION: The Description of the artificial sequence:
      amino acid sequence of LCDR 1 of MOG 303

<400> SEQUENCE: 168

Arg Ala Ser Gln Gly Ile Ser Ser Ala Leu Ala
1               5                   10

<210> SEQ ID NO 169
<211> LENGTH: 7
<212> TYPE: PRT
<213> ORGANISM: Artificial Sequence
<220> FEATURE:
<223> OTHER INFORMATION: The Description of the artificial sequence:
      amino acid sequence of LCDR 2 of MOG 303

<400> SEQUENCE: 169

Asp Ala Ser Ser Leu Glu Ser
1               5

<210> SEQ ID NO 170
<211> LENGTH: 9
<212> TYPE: PRT
<213> ORGANISM: Artificial Sequence
<220> FEATURE:
<223> OTHER INFORMATION: The Description of the artificial sequence:
      amino acid sequence of LCDR 3 of MOG 303

<400> SEQUENCE: 170

Gln Gln Phe Asn Ser Tyr Pro Phe Thr
1               5

<210> SEQ ID NO 171
<211> LENGTH: 381
<212> TYPE: DNA
<213> ORGANISM: Artificial Sequence
<220> FEATURE:
<223> OTHER INFORMATION: The Description of the artificial sequence:
      base sequence encoding VH (excluding signal sequence) of MOG 307

<400> SEQUENCE: 171
cgggtcacct tgagggagtc tggtcctacg ctggtgaaac ccacacagac cctcacgctg     60
acctgcacct tctctgggtt ctcactcagc actagtggag tgggtgtggg ctggatccgt    120
cagcccccag gaaaggccct ggagtggctt gcactcattt tttgggatga tgatagtcac    180
tacagcccat ctctgaagag caggctcacc atcaccaagg acacctccaa aaaccaggtg    240
```

```
gtccttacaa tgaccaacat ggaccctgtg gacacagcca catattactg tgcacggtat    300
tactttggtt cggggagtta tttccctagc tactggtact tcgatctctg gggccgtggc    360
accctggtca ctgtctcctc a                                              381
```

<210> SEQ ID NO 172
<211> LENGTH: 127
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG 307

<400> SEQUENCE: 172

```
Arg Val Thr Leu Arg Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Phe Trp Asp Asp Asp Ser His Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Tyr Tyr Phe Gly Ser Gly Ser Tyr Phe Pro Ser Tyr Trp
            100                 105                 110

Tyr Phe Asp Leu Trp Gly Arg Gly Thr Leu Val Thr Val Ser Ser
        115                 120                 125
```

<210> SEQ ID NO 173
<211> LENGTH: 7
<212> TYPE: PRT
<213> ORGANISM: Artificial Sequence
<220> FEATURE:
<223> OTHER INFORMATION: The Description of the artificial sequence:
      amino acid sequence of HCDR1 of MOG 307

<400> SEQUENCE: 173

```
Thr Ser Gly Val Gly Val Gly
1               5
```

<210> SEQ ID NO 174
<211> LENGTH: 16
<212> TYPE: PRT
<213> ORGANISM: Artificial Sequence
<220> FEATURE:
<223> OTHER INFORMATION: The Description of the artificial sequence:
      amino acid sequence of HCDR2 of MOG 307

<400> SEQUENCE: 174

```
Leu Ile Phe Trp Asp Asp Asp Ser His Tyr Ser Pro Ser Leu Lys Ser
1               5                   10                  15
```

<210> SEQ ID NO 175
<211> LENGTH: 17
<212> TYPE: PRT
<213> ORGANISM: Artificial Sequence
<220> FEATURE:
<223> OTHER INFORMATION: The Description of the artificial sequence:
      amino acid sequence of HCDR3 of MOG 307

<400> SEQUENCE: 175

Tyr Tyr Phe Gly Ser Gly Ser Tyr Phe Pro Ser Tyr Trp Tyr Phe Asp
1               5                   10                  15
Leu

<210> SEQ ID NO 176
<211> LENGTH: 321
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG 307

<400> SEQUENCE: 176
gaaatagtga tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctccgac gttcggccaa   300
gggaccaagg tggagatcaa a                                             321

<210> SEQ ID NO 177
<211> LENGTH: 107
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG 307

<400> SEQUENCE: 177

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 178
<211> LENGTH: 11
<212> TYPE: PRT
<213> ORGANISM: Artificial Sequence
<220> FEATURE:
<223> OTHER INFORMATION: The Description of the artificial sequence:
      amino acid sequence of LCDR 1 of MOG 307

<400> SEQUENCE: 178

Arg Ala Ser Gln Ser Val Ser Ser Tyr Leu Ala
1               5                   10

<210> SEQ ID NO 179
<211> LENGTH: 7

<212> TYPE: PRT
<213> ORGANISM: Artificial Sequence
<220> FEATURE:
<223> OTHER INFORMATION: The Description of the artificial sequence:
      amino acid sequence of LCDR 2 of MOG 307

<400> SEQUENCE: 179

Asp Ala Ser Asn Arg Ala Thr
1               5

<210> SEQ ID NO 180
<211> LENGTH: 9
<212> TYPE: PRT
<213> ORGANISM: Artificial Sequence
<220> FEATURE:
<223> OTHER INFORMATION: The Description of the artificial sequence:
      amino acid sequence of LCDR 3 of MOG 307

<400> SEQUENCE: 180

Gln Gln Arg Ser Asn Trp Pro Pro Thr
1               5

<210> SEQ ID NO 181
<211> LENGTH: 360
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG 310

<400> SEQUENCE: 181
caggtgcagc tggtgcaatc tggggctgag gtgaagaagc ctgggtcctc ggtgaaggtc      60
tcctgcaagg cttctggagg caccttcagc agatatgcta tcagctgggt gcgacaggcc     120
cctggacaag gcttgagtg gatgggaggg atcatcccta tgtttagtac agcaaactac     180
gcacagaagt tccagggcag agtcacgatt accgcggacg aatccacgag cacagcctac     240
atggagctga gcagcctgag atctgaggac acggccgtgt attactgtgc gagagattgg     300
gcagtggctg gtatgggctt taactactgg ggccagggaa ccctggtcac tgtctcctca     360

<210> SEQ ID NO 182
<211> LENGTH: 120
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG 310

<400> SEQUENCE: 182

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30

Ala Ile Ser Trp Val Arg Gln Ala Pro Gly Gln Gly Leu Glu Trp Met
        35                  40                  45

Gly Gly Ile Ile Pro Met Phe Ser Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Trp Ala Val Ala Gly Met Gly Phe Asn Tyr Trp Gly Gln
            100                 105                 110

Gly Thr Leu Val Thr Val Ser Ser
        115              120

<210> SEQ ID NO 183
<211> LENGTH: 5
<212> TYPE: PRT
<213> ORGANISM: Artificial Sequence
<220> FEATURE:
<223> OTHER INFORMATION: The Description of the artificial sequence:
      amino acid sequence of HCDR1 of MOG 310

<400> SEQUENCE: 183

Arg Tyr Ala Ile Ser
1               5

<210> SEQ ID NO 184
<211> LENGTH: 17
<212> TYPE: PRT
<213> ORGANISM: Artificial Sequence
<220> FEATURE:
<223> OTHER INFORMATION: The Description of the artificial sequence:
      amino acid sequence of HCDR2 of MOG 310

<400> SEQUENCE: 184

Gly Ile Ile Pro Met Phe Ser Thr Ala Asn Tyr Ala Gln Lys Phe Gln
1               5                   10                  15

Gly

<210> SEQ ID NO 185
<211> LENGTH: 11
<212> TYPE: PRT
<213> ORGANISM: Artificial Sequence
<220> FEATURE:
<223> OTHER INFORMATION: The Description of the artificial sequence:
      amino acid sequence of HCDR3 of MOG 310

<400> SEQUENCE: 185

Asp Trp Ala Val Ala Gly Met Gly Phe Asn Tyr
1               5                   10

<210> SEQ ID NO 186
<211> LENGTH: 324
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG 310

<400> SEQUENCE: 186
gaaattgtgt tgacacagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccgta cacttttggc     300
caggggacca aagtggatat caaa                                             324

<210> SEQ ID NO 187
<211> LENGTH: 108
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG 310

<400> SEQUENCE: 187

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Val Asp Ile Lys
            100                 105

<210> SEQ ID NO 188
<211> LENGTH: 12
<212> TYPE: PRT
<213> ORGANISM: Artificial Sequence
<220> FEATURE:
<223> OTHER INFORMATION: The Description of the artificial sequence:
      amino acid sequence of LCDR1 of MOG 310

<400> SEQUENCE: 188

Arg Ala Ser Gln Ser Val Ser Ser Ser Tyr Leu Ala
1               5                   10

<210> SEQ ID NO 189
<211> LENGTH: 7
<212> TYPE: PRT
<213> ORGANISM: Artificial Sequence
<220> FEATURE:
<223> OTHER INFORMATION: The Description of the artificial sequence:
      amino acid sequence of LCDR 2 of MOG 310

<400> SEQUENCE: 189

Gly Ala Ser Ser Arg Ala Thr
1               5

<210> SEQ ID NO 190
<211> LENGTH: 9
<212> TYPE: PRT
<213> ORGANISM: Artificial Sequence
<220> FEATURE:
<223> OTHER INFORMATION: The Description of the artificial sequence:
      amino acid sequence of LCDR3 of MOG 310

<400> SEQUENCE: 190

Gln Gln Tyr Gly Ser Ser Pro Tyr Thr
1               5

<210> SEQ ID NO 191
<211> LENGTH: 354
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG 312

<400> SEQUENCE: 191
caggtgcagc tacagcagtg gggcgcagga ctgttgaagc cttcggagac cctgtccctc     60

-continued

```
acctgcgctg tctatggtgg gtccttaagt ggttactact ggagctggat ccgccagccc    120
ccagggaagg ggctggagtg gattggggat atcactcata gtggaagcac caactacaac    180
ccgtccctca agagtcgagt caccatgtca gttgacacgt ccaaaaacca gttctccctg    240
aacctgaact ctgtgaccgc cgcggacacg gctgtgtatt actgtgcgag aaggggggata    300 ggagctgctg tctttgacct ctggggccag ggaaccctgg tcactgtctc ctca          354
```

<210> SEQ ID NO 192
<211> LENGTH: 118
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG 312

<400> SEQUENCE: 192

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Leu Ser Gly Tyr
            20                  25                  30

Tyr Trp Ser Trp Ile Arg Gln Pro Pro Gly Lys Gly Leu Glu Trp Ile
        35                  40                  45

Gly Asp Ile Thr His Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Asn Leu Asn Ser Val Thr Ala Ala Asp Thr Ala Val Tyr Tyr Cys Ala
                85                  90                  95

Arg Arg Gly Ile Gly Ala Ala Val Phe Asp Leu Trp Gly Gln Gly Thr
            100                 105                 110

Leu Val Thr Val Ser Ser
        115
```

<210> SEQ ID NO 193
<211> LENGTH: 5
<212> TYPE: PRT
<213> ORGANISM: Artificial Sequence
<220> FEATURE:
<223> OTHER INFORMATION: The Description of the artificial sequence:
      amino acid sequence of HCDR1 of MOG 312

<400> SEQUENCE: 193

```
Gly Tyr Tyr Trp Ser
1               5
```

<210> SEQ ID NO 194
<211> LENGTH: 16
<212> TYPE: PRT
<213> ORGANISM: Artificial Sequence
<220> FEATURE:
<223> OTHER INFORMATION: The Description of the artificial sequence:
      amino acid sequence of HCDR2 of MOG 312

<400> SEQUENCE: 194

```
Asp Ile Thr His Ser Gly Ser Thr Asn Tyr Asn Pro Ser Leu Lys Ser
1               5                   10                  15
```

<210> SEQ ID NO 195
<211> LENGTH: 10
<212> TYPE: PRT
<213> ORGANISM: Artificial Sequence
<220> FEATURE:

<223> OTHER INFORMATION: The Description of the artificial sequence:
      amino acid sequence of HCDR3 of MOG 312

<400> SEQUENCE: 195

Arg Gly Ile Gly Ala Ala Val Phe Asp Leu
1               5                   10

<210> SEQ ID NO 196
<211> LENGTH: 324
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG 312

<400> SEQUENCE: 196
gaaatagtgt tgacgcagtc tccagccacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagcgtagca actggcctct cactttcggc     300
ggagggacca aggtggagat caaa                                            324

<210> SEQ ID NO 197
<211> LENGTH: 108
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG 312

<400> SEQUENCE: 197

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Arg Ser Asn Trp Pro
                85                  90                  95

Leu Thr Phe Gly Gly Gly Thr Lys Val Glu Ile Lys
            100                 105

<210> SEQ ID NO 198
<211> LENGTH: 12
<212> TYPE: PRT
<213> ORGANISM: Artificial Sequence
<220> FEATURE:
<223> OTHER INFORMATION: The Description of the artificial sequence:
      amino acid sequence of LCDR 1 of MOG 312

<400> SEQUENCE: 198

Arg Ala Ser Gln Ser Val Ser Ser Ser Tyr Leu Ala
1               5                   10

<210> SEQ ID NO 199

```
<211> LENGTH: 7
<212> TYPE: PRT
<213> ORGANISM: Artificial Sequence
<220> FEATURE:
<223> OTHER INFORMATION: The Description of the artificial sequence:
      amino acid sequence of LCDR 2 of MOG 312

<400> SEQUENCE: 199

Gly Ala Ser Ser Arg Ala Thr
1               5

<210> SEQ ID NO 200
<211> LENGTH: 9
<212> TYPE: PRT
<213> ORGANISM: Artificial Sequence
<220> FEATURE:
<223> OTHER INFORMATION: The Description of the artificial sequence:
      amino acid sequence of LCDR 3 of MOG 312

<400> SEQUENCE: 200

Gln Gln Arg Ser Asn Trp Pro Leu Thr
1               5

<210> SEQ ID NO 201
<211> LENGTH: 366
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG 326

<400> SEQUENCE: 201
gaggtccagc tggtacagtc tggggctgag gtgaagaagc ctggggcctc agtgaaggtt    60
tcctgcaagg catctggata caccttcacc agctactata tgcactgggt gcgacaggcc   120
cctggacaag gcttgagtg gatgggaata atcaaccta gtggtggtag cacaagctac    180
gcacagaagt tccagggcag agtcaccatg accaggaca cgtccacgag cacagtctac    240
atggagctga gcagcctgag atctgaggac acggccgtgt attactgtgc gagagggtat   300
tacgatattt tgactggttc cttctttgac tactggggcc agggaaccct ggtcactgtc   360
tcctca                                                              366

<210> SEQ ID NO 202
<211> LENGTH: 122
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG 326

<400> SEQUENCE: 202

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

Ala Arg Gly Tyr Tyr Asp Ile Leu Thr Gly Ser Phe Phe Asp Tyr Trp
            100                 105                 110

Gly Gln Gly Thr Leu Val Thr Val Ser Ser
        115                 120

<210> SEQ ID NO 203
<211> LENGTH: 5
<212> TYPE: PRT
<213> ORGANISM: Artificial Sequence
<220> FEATURE:
<223> OTHER INFORMATION: The Description of the artificial sequence:
      amino acid sequence of HCDR1 of MOG 326

<400> SEQUENCE: 203

Ser Tyr Tyr Met His
1               5

<210> SEQ ID NO 204
<211> LENGTH: 17
<212> TYPE: PRT
<213> ORGANISM: Artificial Sequence
<220> FEATURE:
<223> OTHER INFORMATION: The Description of the artificial sequence:
      amino acid sequence of HCDR2 of MOG 326

<400> SEQUENCE: 204

Ile Ile Asn Pro Ser Gly Gly Ser Thr Ser Tyr Ala Gln Lys Phe Gln
1               5                   10                  15

Gly

<210> SEQ ID NO 205
<211> LENGTH: 13
<212> TYPE: PRT
<213> ORGANISM: Artificial Sequence
<220> FEATURE:
<223> OTHER INFORMATION: The Description of the artificial sequence:
      amino acid sequence of HCDR3 of MOG 326

<400> SEQUENCE: 205

Gly Tyr Tyr Asp Ile Leu Thr Gly Ser Phe Phe Asp Tyr
1               5                   10

<210> SEQ ID NO 206
<211> LENGTH: 321
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG 326

<400> SEQUENCE: 206
gacatcgtga tgacccagtc tccatcctcc ctgtctgcat ctgtaggaga cagagtcacc      60
atcacttgcc gggcaagtca gggcattagc agtgctttag tctggtatca gcagaaacca    120
gggaaagctc ctaagctcct gatctatgat gcctccagtt tggaaagtgg ggtcccatca    180
aggttcagcg gcagtggatc tgggacagat ttcactctca ccatcagcag cctgcagcct    240
gaagattttg caacttatta ctgtcaacag tttaatagtt accctctcac tttcggcgga    300
gggaccaaag tggatatcaa a                                              321

<210> SEQ ID NO 207
<211> LENGTH: 107
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG 326

<400> SEQUENCE: 207

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Val Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Asp Ile Lys
            100                 105

<210> SEQ ID NO 208
<211> LENGTH: 11
<212> TYPE: PRT
<213> ORGANISM: Artificial Sequence
<220> FEATURE:
<223> OTHER INFORMATION: The Description of the artificial sequence:
      amino acid sequence of LCDR 1 of MOG 326

<400> SEQUENCE: 208

Arg Ala Ser Gln Gly Ile Ser Ser Ala Leu Val
1               5                   10

<210> SEQ ID NO 209
<211> LENGTH: 7
<212> TYPE: PRT
<213> ORGANISM: Artificial Sequence
<220> FEATURE:
<223> OTHER INFORMATION: The Description of the artificial sequence:
      amino acid sequence of LCDR 2 of MOG 326

<400> SEQUENCE: 209

Asp Ala Ser Ser Leu Glu Ser
1               5

<210> SEQ ID NO 210
<211> LENGTH: 9
<212> TYPE: PRT
<213> ORGANISM: Artificial Sequence
<220> FEATURE:
<223> OTHER INFORMATION: The Description of the artificial sequence:
      amino acid sequence of LCDR 3 of MOG 326

<400> SEQUENCE: 210

Gln Gln Phe Asn Ser Tyr Pro Leu Thr
1               5

<210> SEQ ID NO 211
<211> LENGTH: 357
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG 329

<400> SEQUENCE: 211

```
caggtgcagc tggtggagtc tgggggaggc ttggtacagc ctggggggtc cctgagactc      60
tcctgtgcag cctctggatt cgcctttcgc aactatgcca tgaactgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgttt attactgtgc gagagactac     300
ggtggtatct cccccttgac tactggggc cagggaaccc tggtcactgt ctcctca        357
```

<210> SEQ ID NO 212
<211> LENGTH: 119
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG 329

<400> SEQUENCE: 212

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Arg Asn Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Gly Gly Ile Ser Pro Phe Asp Tyr Trp Gly Gln Gly
            100                 105                 110

Thr Leu Val Thr Val Ser Ser
        115
```

<210> SEQ ID NO 213
<211> LENGTH: 5
<212> TYPE: PRT
<213> ORGANISM: Artificial Sequence
<220> FEATURE:
<223> OTHER INFORMATION: The Description of the artificial sequence:
      amino acid sequence of HCDR1 of MOG 329

<400> SEQUENCE: 213

```
Asn Tyr Ala Met Asn
1               5
```

<210> SEQ ID NO 214
<211> LENGTH: 17
<212> TYPE: PRT
<213> ORGANISM: Artificial Sequence
<220> FEATURE:
<223> OTHER INFORMATION: The Description of the artificial sequence:
      amino acid sequence of HCDR2 of MOG 329

<400> SEQUENCE: 214

```
Ala Ile Ser Gly Ser Gly Gly Ser Thr Tyr Tyr Ala Asp Ser Val Lys
1               5                   10                  15

Gly
```

```
<210> SEQ ID NO 215
<211> LENGTH: 10
<212> TYPE: PRT
<213> ORGANISM: Artificial Sequence
<220> FEATURE:
<223> OTHER INFORMATION: The Description of the artificial sequence:
      amino acid sequence of HCDR3 of MOG 329

<400> SEQUENCE: 215

Asp Tyr Gly Gly Ile Ser Pro Phe Asp Tyr
1               5                   10

<210> SEQ ID NO 216
<211> LENGTH: 321
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG 329

<400> SEQUENCE: 216
gacatccagt tgacccagtc tccatcctcc ctgtctgcat ctgtaggaga cagagtcacc      60
atcacttgcc gggcaagtca gggcattagc agtgctttag cctggtatca gcagaaacca     120
gggaaagctc ctaagctcct gatctatgat gcctccagtt tggaaagtgg ggtcccatca     180
aggttcagcg gcagtggatc tgggacagat ttcactctca ccatcagcag cctgcagcct     240
gaagattttg caacttatta ctgtcaacag tttaatagtt accctcacac ttttggccag     300
gggaccaaag tggatatcaa a                                                321

<210> SEQ ID NO 217
<211> LENGTH: 107
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG 329

<400> SEQUENCE: 217

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro His
                85                  90                  95

Thr Phe Gly Gln Gly Thr Lys Val Asp Ile Lys
            100                 105

<210> SEQ ID NO 218
<211> LENGTH: 11
<212> TYPE: PRT
<213> ORGANISM: Artificial Sequence
<220> FEATURE:
<223> OTHER INFORMATION: The Description of the artificial sequence:
      amino acid sequence of LCDR 1 of MOG 329

<400> SEQUENCE: 218
```

Arg Ala Ser Gln Gly Ile Ser Ser Ala Leu Ala
1               5                   10

<210> SEQ ID NO 219
<211> LENGTH: 7
<212> TYPE: PRT
<213> ORGANISM: Artificial Sequence
<220> FEATURE:
<223> OTHER INFORMATION: The Description of the artificial sequence:
      amino acid sequence of LCDR 2 of MOG 329

<400> SEQUENCE: 219

Asp Ala Ser Ser Leu Glu Ser
1               5

<210> SEQ ID NO 220
<211> LENGTH: 9
<212> TYPE: PRT
<213> ORGANISM: Artificial Sequence
<220> FEATURE:
<223> OTHER INFORMATION: The Description of the artificial sequence:
      amino acid sequence of LCDR 3 of MOG 329

<400> SEQUENCE: 220

Gln Gln Phe Asn Ser Tyr Pro His Thr
1               5

<210> SEQ ID NO 221
<211> LENGTH: 372
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG446

<400> SEQUENCE: 221
caggtgcagc tggtggagtc tgggggaggt gtggtacggc cggggggtc cctgagactc    60 tcctgtgcag cctctggatt cacctttgat gattatggca tgagctgggt ccgccaagct   120
ccagggaagg ggctggagtg ggtctctaat attaattgga atggtgatag cacaggttat   180
gtagactctg tgaagggccg attcaccatc tccagagaca cgccaagaa ctccctgtat    240 ctgcaaatga acagtctgag agccgaggac acggccttgt attactgtgc gagagcgagg   300
acctattact atgtttcggg gaggtactac tttgactact ggggccaggg aaccctggtc   360
actgtctcct ca                                                      372

<210> SEQ ID NO 222
<211> LENGTH: 124
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG446

<400> SEQUENCE: 222

Gln Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Asn Ile Asn Trp Asn Gly Asp Ser Thr Gly Tyr Val Asp Ser Val
    50                  55                  60

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Ala Arg Thr Tyr Tyr Tyr Val Ser Gly Arg Tyr Tyr Phe Asp
            100                 105                 110

Tyr Trp Gly Gln Gly Thr Leu Val Thr Val Ser Ser
        115                 120

<210> SEQ ID NO 223
<211> LENGTH: 5
<212> TYPE: PRT
<213> ORGANISM: Artificial Sequence
<220> FEATURE:
<223> OTHER INFORMATION: The Description of the artificial sequence:
      amino acid sequence of HCDR1 of MOG446

<400> SEQUENCE: 223

Asp Tyr Gly Met Ser
1               5

<210> SEQ ID NO 224
<211> LENGTH: 17
<212> TYPE: PRT
<213> ORGANISM: Artificial Sequence
<220> FEATURE:
<223> OTHER INFORMATION: The Description of the artificial sequence:
      amino acid sequence of HCDR2 of MOG446

<400> SEQUENCE: 224

Asn Ile Asn Trp Asn Gly Asp Ser Thr Gly Tyr Val Asp Ser Val Lys
1               5                   10                  15

Gly

<210> SEQ ID NO 225
<211> LENGTH: 15
<212> TYPE: PRT
<213> ORGANISM: Artificial Sequence
<220> FEATURE:
<223> OTHER INFORMATION: The Description of the artificial sequence:
      amino acid sequence of HCDR3 of MOG446

<400> SEQUENCE: 225

Ala Arg Thr Tyr Tyr Tyr Val Ser Gly Arg Tyr Tyr Phe Asp Tyr
1               5                   10                  15

<210> SEQ ID NO 226
<211> LENGTH: 321
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG446

<400> SEQUENCE: 226
gacatccaga tgacccagtc tccatcctcc ctgtctgcat ctgtaggaga cagagtcacc      60
atcacttgcc gggcaagtca gggcattagc agtgctttag cctggtatca gcagaaacca    120
gggaaagctc ctaagctcct gatctatgat gcctccagtt tggaaagtgg ggtcccatca    180
aggttcagcg gcagtggatc tgggacagat ttcactctca ccatcagcag cctgcagcct    240
gaagattttg caacttatta ctgtcaacag tttaatagtt acccgctcac tttcggcgga    300
gggaccaagg tggaaatcaa a                                              321
```

<210> SEQ ID NO 227
<211> LENGTH: 107
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG446

<400> SEQUENCE: 227

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 228
<211> LENGTH: 11
<212> TYPE: PRT
<213> ORGANISM: Artificial Sequence
<220> FEATURE:
<223> OTHER INFORMATION: The Description of the artificial sequence:
      amino acid sequence of LCDR1 of MOG446

<400> SEQUENCE: 228

Arg Ala Ser Gln Gly Ile Ser Ser Ala Leu Ala
1               5                   10

<210> SEQ ID NO 229
<211> LENGTH: 7
<212> TYPE: PRT
<213> ORGANISM: Artificial Sequence
<220> FEATURE:
<223> OTHER INFORMATION: The Description of the artificial sequence:
      amino acid sequence of LCDR2 of MOG446

<400> SEQUENCE: 229

Asp Ala Ser Ser Leu Glu Ser
1               5

<210> SEQ ID NO 230
<211> LENGTH: 9
<212> TYPE: PRT
<213> ORGANISM: Artificial Sequence
<220> FEATURE:
<223> OTHER INFORMATION: The Description of the artificial sequence:
      amino acid sequence of LCDR3 of MOG446

<400> SEQUENCE: 230

Gln Gln Phe Asn Ser Tyr Pro Leu Thr
1               5

<210> SEQ ID NO 231
<211> LENGTH: 366
<212> TYPE: DNA
<213> ORGANISM: Artificial Sequence
<220> FEATURE:
<223> OTHER INFORMATION: The Description of the artificial sequence:
base sequence encoding VH excluding signal sequence of MOG456

<400> SEQUENCE: 231

```
gaggtgcagc tggtggagtc tgggggaggc ctggtcaagc ctgggggtc  cctgagactc      60
tcctgtgcag cctctggatt caccttcagt agctatagca tgcactgggt ccgccaggct     120
ccagggaagg gctggagtg gtctcatcc attggtagta ggagtcgtta catatactac       180
gcagactcag tgaagggccg attcaccatc tccagagaca cgccaagaa ctcactgtat      240
ctgcaaatga acagcctgag agccgaggac acggctgtgt attactgtgc gaaagggtat    300
tacgatattt tgactggttc tctctttgac tactggggcc agggaaccct ggtcactgtc    360
tcctca                                                                366
```

<210> SEQ ID NO 232
<211> LENGTH: 122
<212> TYPE: PRT
<213> ORGANISM: Artificial Sequence
<220> FEATURE:
<223> OTHER INFORMATION: The Description of the artificial sequence:
amino acid sequence of VH excluding signal sequence of MOG 456

<400> SEQUENCE: 232

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met His Trp Val Arg Gln Ala Pro Gly Lys Gly Leu Glu Trp Val
        35                  40                  45

Ser Ser Ile Gly Ser Arg Ser Arg Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Tyr Tyr Asp Ile Leu Thr Gly Ser Leu Phe Asp Tyr Trp
            100                 105                 110

Gly Gln Gly Thr Leu Val Thr Val Ser Ser
        115                 120
```

<210> SEQ ID NO 233
<211> LENGTH: 5
<212> TYPE: PRT
<213> ORGANISM: Artificial Sequence
<220> FEATURE:
<223> OTHER INFORMATION: The Description of the artificial sequence:
amino acid sequence of HCDR1 of MOG456

<400> SEQUENCE: 233

```
Ser Tyr Ser Met His
1               5
```

<210> SEQ ID NO 234
<211> LENGTH: 17
<212> TYPE: PRT
<213> ORGANISM: Artificial Sequence
<220> FEATURE:
<223> OTHER INFORMATION: The Description of the artificial sequence:
amino acid sequence of HCDR2 of MOG456

<400> SEQUENCE: 234

```
Ser Ile Gly Ser Arg Ser Arg Tyr Ile Tyr Tyr Ala Asp Ser Val Lys
1               5                   10                  15

Gly

<210> SEQ ID NO 235
<211> LENGTH: 13
<212> TYPE: PRT
<213> ORGANISM: Artificial Sequence
<220> FEATURE:
<223> OTHER INFORMATION: The Description of the artificial sequence:
      amino acid sequence of HCDR3 of MOG 456

<400> SEQUENCE: 235

Gly Tyr Tyr Asp Ile Leu Thr Gly Ser Leu Phe Asp Tyr
1               5                   10

<210> SEQ ID NO 236
<211> LENGTH: 321
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG456

<400> SEQUENCE: 236
gacatcgtga tgacccagtc tccatcctca ctgtctgcat ctgtaggaga cagagtcacc      60
atcacttgtc gggcgagtca gggtattagc agtgctttag cctggtatca gcagaaacca     120
gggaaagctc ctaagctcct gatctatgat gcctccagtt tggaaagtgg ggtcccatca     180
aggttcagcg gcagtggatc tgggacagat ttcactctca ccatcagcag cctgcagcct     240
gaagattttg caacttatta ctgtcaacag tttaatagtt acccgtggac gttcggccaa     300
gggaccaagg tggagatcaa a                                               321

<210> SEQ ID NO 237
<211> LENGTH: 107
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG456

<400> SEQUENCE: 237

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Trp
                85                  90                  95

Thr Phe Gly Gln Gly Thr Lys Val Glu Ile Lys
            100                 105

<210> SEQ ID NO 238
<211> LENGTH: 11
<212> TYPE: PRT
```

<213> ORGANISM: Artificial Sequence
<220> FEATURE:
<223> OTHER INFORMATION: The Description of the artificial sequence: amino acid sequence of LCDR 1 of MOG 456

<400> SEQUENCE: 238

Arg Ala Ser Gln Gly Ile Ser Ser Ala Leu Ala
1               5                   10

<210> SEQ ID NO 239
<211> LENGTH: 7
<212> TYPE: PRT
<213> ORGANISM: Artificial Sequence
<220> FEATURE:
<223> OTHER INFORMATION: The Description of the artificial sequence: amino acid sequence of LCDR 2 of MOG 456

<400> SEQUENCE: 239

Asp Ala Ser Ser Leu Glu Ser
1               5

<210> SEQ ID NO 240
<211> LENGTH: 9
<212> TYPE: PRT
<213> ORGANISM: Artificial Sequence
<220> FEATURE:
<223> OTHER INFORMATION: The Description of the artificial sequence: amino acid sequence of LCDR 3 of MOG 456

<400> SEQUENCE: 240

Gln Gln Phe Asn Ser Tyr Pro Trp Thr
1               5

<210> SEQ ID NO 241
<211> LENGTH: 357
<212> TYPE: DNA
<213> ORGANISM: Artificial Sequence
<220> FEATURE:
<223> OTHER INFORMATION: The Description of the artificial sequence: base sequence encoding VH excluding signal sequence of MOG 473

<400> SEQUENCE: 241
caggtgcagc tggtggagtc tgggggaggc ctggtcaagc ctgggggtc cctgagactc      60 tcctgtgcag cctctggatt caccttcagt agctatagca tgcactgggt ccgccaggct     120
ccagggaagg ggctggagtg ggtttcggac attagtacta atagtagaac cagaaactat     180
gcagactctg tgaagggccg attcaccatc tccagagaca atgccaagaa ctcagtgtat     240
ctgcaaatgc acagcctgag ggacgaggac acggctgtgt actactgtgc gagagactac     300
ggtggtatct attactttga ctattggggc cagggaaccc tggtcactgt ctcctca        357

<210> SEQ ID NO 242
<211> LENGTH: 119
<212> TYPE: PRT
<213> ORGANISM: Artificial Sequence
<220> FEATURE:
<223> OTHER INFORMATION: The Description of the artificial sequence: amino acid sequence of VH excluding signal sequence of MOG 473

<400> SEQUENCE: 242

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met His Trp Val Arg Gln Ala Pro Gly Lys Gly Leu Glu Trp Val

```
                35                  40                  45
Ser Asp Ile Ser Thr Asn Ser Arg Thr Arg Asn Tyr Ala Asp Ser Val
         50                  55                  60
Lys Gly Arg Phe Thr Ile Ser Arg Asp Asn Ala Lys Asn Ser Val Tyr
 65                  70                  75                  80
Leu Gln Met His Ser Leu Arg Asp Glu Asp Thr Ala Val Tyr Tyr Cys
                 85                  90                  95
Ala Arg Asp Tyr Gly Gly Ile Tyr Tyr Phe Asp Tyr Trp Gly Gln Gly
            100                 105                 110
Thr Leu Val Thr Val Ser Ser
        115
```

<210> SEQ ID NO 243
<211> LENGTH: 5
<212> TYPE: PRT
<213> ORGANISM: Artificial Sequence
<220> FEATURE:
<223> OTHER INFORMATION: The Description of the artificial sequence:
      amino acid sequence of HCDR1 of MOG 473

<400> SEQUENCE: 243

```
Ser Tyr Ser Met His
1               5
```

<210> SEQ ID NO 244
<211> LENGTH: 17
<212> TYPE: PRT
<213> ORGANISM: Artificial Sequence
<220> FEATURE:
<223> OTHER INFORMATION: The Description of the artificial sequence:
      amino acid sequence of HCDR2 of MOG 473

<400> SEQUENCE: 244

```
Asp Ile Ser Thr Asn Ser Arg Thr Arg Asn Tyr Ala Asp Ser Val Lys
1               5                   10                  15

Gly
```

<210> SEQ ID NO 245
<211> LENGTH: 10
<212> TYPE: PRT
<213> ORGANISM: Artificial Sequence
<220> FEATURE:
<223> OTHER INFORMATION: The Description of the artificial sequence:
      amino acid sequence of HCDR3 of MOG 473

<400> SEQUENCE: 245

```
Asp Tyr Gly Gly Ile Tyr Tyr Phe Asp Tyr
1               5                   10
```

<210> SEQ ID NO 246
<211> LENGTH: 324
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG 473

<400> SEQUENCE: 246

```
gaaatagtga tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
```

```
gaagattttg cagtttatta ctgtcagcag cgtagcaact ggcctccgta cactttttggc      300 caggggacca agctggagat caaa                                              324
```

<210> SEQ ID NO 247
<211> LENGTH: 108
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG 473

<400> SEQUENCE: 247

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Tyr Thr Phe Gly Gln Gly Thr Lys Leu Glu Ile Lys
            100                 105

<210> SEQ ID NO 248
<211> LENGTH: 11
<212> TYPE: PRT
<213> ORGANISM: Artificial Sequence
<220> FEATURE:
<223> OTHER INFORMATION: The Description of the artificial sequence:
      amino acid sequence of LCDR1 of MOG 473

<400> SEQUENCE: 248

Arg Ala Ser Gln Ser Val Ser Ser Tyr Leu Ala
1               5                   10

<210> SEQ ID NO 249
<211> LENGTH: 7
<212> TYPE: PRT
<213> ORGANISM: Artificial Sequence
<220> FEATURE:
<223> OTHER INFORMATION: The Description of the artificial sequence:
      amino acid sequence of LCDR 2 of MOG 473

<400> SEQUENCE: 249

Asp Ala Ser Asn Arg Ala Thr
1               5

<210> SEQ ID NO 250
<211> LENGTH: 10
<212> TYPE: PRT
<213> ORGANISM: Artificial Sequence
<220> FEATURE:
<223> OTHER INFORMATION: The Description of the artificial sequence:
      amino acid sequence of LCDR 3 of MOG 473

<400> SEQUENCE: 250

Gln Gln Arg Ser Asn Trp Pro Pro Tyr Thr
1               5                   10

<210> SEQ ID NO 251
<211> LENGTH: 369
<212> TYPE: DNA
<213> ORGANISM: Artificial Sequence
<220> FEATURE:
<223> OTHER INFORMATION: The Description of the artificial sequence: base sequence encoding VH excluding signal sequence of MOG426

<400> SEQUENCE: 251

```
caggtccagc tggtacagtc tggagctgag gtgaagaagc ctggggcctc agtgaaggtc    60
tcctgcaagg cttctggtta cagctttaac agctatggta tcaactgggt gcgacaggcc   120
cctggacaag gcttgagtg gatgggatgg atcagcgctt acactggtaa aacaagttat   180
gcacagaagg tccagggcag agtcaccatg accacagaca gatccacgag cacagcctac   240
atggagctga ggagcctgag atctgacgac acggccatgt attactgtgc gagagagtac   300
gatattttga ctggttattc cgatgctttt gatacctggg gccaagggac aatggtcacc   360
gtctcttca                                                           369
```

<210> SEQ ID NO 252
<211> LENGTH: 123
<212> TYPE: PRT
<213> ORGANISM: Artificial Sequence
<220> FEATURE:
<223> OTHER INFORMATION: The Description of the artificial sequence: amino acid sequence of VH excluding signal sequence of MOG426

<400> SEQUENCE: 252

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Asn Ser Tyr
            20                  25                  30

Gly Ile Asn Trp Val Arg Gln Ala Pro Gly Gln Gly Leu Glu Trp Met
        35                  40                  45

Gly Trp Ile Ser Ala Tyr Thr Gly Lys Thr Ser Tyr Ala Gln Lys Val
    50                  55                  60

Gln Gly Arg Val Thr Met Thr Thr Asp Arg Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Glu Tyr Asp Ile Leu Thr Gly Tyr Ser Asp Ala Phe Asp Thr
            100                 105                 110

Trp Gly Gln Gly Thr Met Val Thr Val Ser Ser
        115                 120
```

<210> SEQ ID NO 253
<211> LENGTH: 321
<212> TYPE: DNA
<213> ORGANISM: Artificial Sequence
<220> FEATURE:
<223> OTHER INFORMATION: The Description of the artificial sequence: base sequence encoding VL excluding signal sequence of MOG426

<400> SEQUENCE: 253

```
gaaattgtgt tgacgcagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
```

```
gaagattttg cagtttatta ctgtcagcag cgtggcaact ggccgctcac tttcggcgga    300
gggaccaagc tggagatcaa a                                              321
```

<210> SEQ ID NO 254
<211> LENGTH: 107
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG426

<400> SEQUENCE: 254

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Gly Asn Trp Pro Leu
                85                  90                  95

Thr Phe Gly Gly Gly Thr Lys Leu Glu Ile Lys
            100                 105

<210> SEQ ID NO 255
<211> LENGTH: 369
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG428

<400> SEQUENCE: 255

```
gaggtccagc tggtacagtc tggagctgag gtgaagaagc ctggggcctc agtgaaggtc    60
tcctgcaagg cttctggtta cagctttaac agctatggta tcaactgggt gcgacaggcc    120
cctggacaag gcttgagtg  gatgggatgg atcagcgctt acactggtaa aacaagttat    180
gcacagaagg tccagggcag agtcaccatg accacagaca gatccacgag cacagcctac    240
atggagctga ggagcctgag atctgacgac acggccatgt attactgtgc gagagagtac    300
gatattttga ctggttattc cgatgctttt gatacctggg gccaagggac aatggtcacc    360
gtctcttca                                                            369
```

<210> SEQ ID NO 256
<211> LENGTH: 123
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG428

<400> SEQUENCE: 256

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Asn Ser Tyr
            20                  25                  30

Gly Ile Asn Trp Val Arg Gln Ala Pro Gly Gln Gly Leu Glu Trp Met

```
                35                  40                  45
Gly Trp Ile Ser Ala Tyr Thr Gly Lys Thr Ser Tyr Ala Gln Lys Val
 50                  55                  60

Gln Gly Arg Val Thr Met Thr Thr Asp Arg Ser Thr Ser Thr Ala Tyr
 65                  70                  75                  80

Met Glu Leu Arg Ser Leu Arg Ser Asp Asp Thr Ala Met Tyr Tyr Cys
                 85                  90                  95

Ala Arg Glu Tyr Asp Ile Leu Thr Gly Tyr Ser Asp Ala Phe Asp Thr
             100                 105                 110

Trp Gly Gln Gly Thr Met Val Thr Val Ser Ser
         115                 120
```

<210> SEQ ID NO 257
<211> LENGTH: 324
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG428

<400> SEQUENCE: 257
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcacctcg gacgttcggc   300
caagggacca gctggagat caaa                                           324

<210> SEQ ID NO 258
<211> LENGTH: 108
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG428

<400> SEQUENCE: 258

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Arg Thr Phe Gly Gln Gly Thr Lys Leu Glu Ile Lys
             100                 105
```

<210> SEQ ID NO 259
<211> LENGTH: 366
<212> TYPE: DNA
<213> ORGANISM: Artificial Sequence
<220> FEATURE:
<223> OTHER INFORMATION: The Description of the artificial sequence:

base sequence encoding VH excluding signal sequence of MOG 313

<400> SEQUENCE: 259

```
caggtgcagc tggtggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagtt attagtggta gtggtggtag cacatactac   180
gcagactccg tgaagggccg gttcaccatc tccagagaca attccaagaa cacgctgtat   240
ctgcaaatga acagcctgag agccgaggac acggccgtat attactgtgc gaaagcatat   300
tacgatattt tgactggttc cctctttgac tcctggggcc agggaaccct ggtcactgtc   360
tcctca                                                               366
```

<210> SEQ ID NO 260
<211> LENGTH: 122
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG 313

<400> SEQUENCE: 260

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Tyr Tyr Asp Ile Leu Thr Gly Ser Leu Phe Asp Ser Trp
            100                 105                 110

Gly Gln Gly Thr Leu Val Thr Val Ser Ser
        115                 120

<210> SEQ ID NO 261
<211> LENGTH: 321
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG 313

<400> SEQUENCE: 261

```
gacatcgtga tgacccagtc tccatcctcc ctgtctgcat ctgtaggaga cagagtcacc    60
atcacttgcc gggcaagtca gggcattagc agtgctttag cctggtatca gcagaaacca   120
gggaaagctc ctaagctcct gatctatgat gcctccagtt tggaaagtgg ggtcccatca   180
aggttcagcg gcagtggatc tgggacagat ttcactctca ccatcagcag cctgcagcct   240
gaagattttg caacttatta ctgtcaacag tttaatagtt accctctcac tttcggcgga   300
gggaccaagg tggaaatcaa a                                              321
```

<210> SEQ ID NO 262
<211> LENGTH: 107

```
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG

<400> SEQUENCE: 262

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 263
<211> LENGTH: 366
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG 314

<400> SEQUENCE: 263
caggtgcagc tggtggagtc tgggggaggc ttggtacagc ctgggggtc cctgagactc       60 tcctgtgcag cctctggatt cacctttagc agctatgcca tgagctgggt ccgccaggct      120
ccagggaagg ggctggagtg gtctcagct attagtggta gagtagtag cacatactac       180 gcagactccg tgaagggccg gttcaccatc tccagagaca attccaagaa cacgctgtat      240
ctgcaaatga acagcctgag agccgaggac acggccgtat attactgtgc gaaaggctat     300
tacgatattt tgactggttc cttctttgac tactggggcc agggaaccct ggtcaccgtc      360
tcctca                                                                 366

<210> SEQ ID NO 264
<211> LENGTH: 122
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG 314

<400> SEQUENCE: 264

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Arg Gly Ser Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Gly Tyr Tyr Asp Ile Leu Thr Gly Ser Phe Phe Asp Tyr Trp
            100                 105                 110

Gly Gln Gly Thr Leu Val Thr Val Ser Ser
        115                 120

<210> SEQ ID NO 265
<211> LENGTH: 321
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG 314

<400> SEQUENCE: 265
gacatccagt tgacccagtc tccatcctcc ctgtctgcat ctgtaggaga cagagtcacc      60
atcacttgcc gggcaagtca gggcattagc agtgctttag cctggtatca gcagaaacca    120
gggaaagctc ctaagctcct gatctatgat gcctccagtt tggaaagtgg ggtcccatca    180
aggttcagcg gcagtggatc tgggacagat ttcactctca ccatcagcag cctgcagcct    240
gaagattttg caacttatta ctgtcaacag tttaatagtt acccgtacac ttttggccag    300
gggaccaagc tggagatcaa a                                              321

<210> SEQ ID NO 266
<211> LENGTH: 107
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG 314

<400> SEQUENCE: 266

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys
            100                 105

<210> SEQ ID NO 267
<211> LENGTH: 366
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG 315

<400> SEQUENCE: 267
gaggtgcagc tggtggagtc tgggggaggc ttggtacagc ctggggggtc cctgagactc      60
tcctgtgcag cctctggatt cacctttagc acctatgcca tgagctgggt ccgccaggct    120
```

```
ccagggaagg ggctggagtg ggtctcagct attagtggta gtggtgttag cacatactac    180
gcagactccg tgaagggccg gttcaccctc tccagagaca attccaagaa cacgctgtat    240
ctgcaaatga acagcctgag agccgaggac acggccgtat attactgtgc gaaagcgtat    300
tacgatattt tgactggtaa tttccttgac tactggggcc agggaaccct ggtcactgtc    360
tcctca                                                                366
```

<210> SEQ ID NO 268
<211> LENGTH: 122
<212> TYPE: PRT
<213> ORGANISM: Artificial Sequence
<220> FEATURE:
<223> OTHER INFORMATION: The Description of the artificial sequence:
    amino acid sequence of VH excluding signal sequence of MOG 315

<400> SEQUENCE: 268

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Val Ser Thr Tyr Tyr Ala Asp Ser Val
    50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Tyr Tyr Asp Ile Leu Thr Gly Asn Phe Leu Asp Tyr Trp
            100                 105                 110

Gly Gln Gly Thr Leu Val Thr Val Ser Ser
        115                 120

<210> SEQ ID NO 269
<211> LENGTH: 321
<212> TYPE: DNA
<213> ORGANISM: Artificial Sequence
<220> FEATURE:
<223> OTHER INFORMATION: The Description of the artificial sequence:
    base sequence encoding VL excluding signal sequence of MOG 315

<400> SEQUENCE: 269

```
gccatccagt tgacccagtc tccatcctcc ctgtctgcat ctgtaggaga cagagtcacc     60
atcacttgcc gggcaagtca gggcattagc agtgctttag cctggtatca gcagaaacca    120
gggaaagctc ctaagctcct gatctatgat gcctccagtt tggaaagtgg ggtcccatca    180
aggttcagcg gcagtggatc tgggacagat ttcactctca ccatcagcag cctgcagcct    240
gaagattttg caacttatta ctgtcaacag tttaatagtt acccgctcac tttcggcgga    300
gggaccaagg tggaaatcaa a                                              321
```

<210> SEQ ID NO 270
<211> LENGTH: 107
<212> TYPE: PRT
<213> ORGANISM: Artificial Sequence
<220> FEATURE:
<223> OTHER INFORMATION: The Description of the artificial sequence:
    amino acid sequence of VL excluding signal sequence of MOG 315

<400> SEQUENCE: 270

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 271
<211> LENGTH: 366
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG331

<400> SEQUENCE: 271
gaggtgcagc tggtggagtc cggggggaggc ttggtatagc ctgggggggtc cctgagactc      60 tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg attcaccatc tccagagaca attccaagaa cacactgtat     240
ctgcaaatga acagcctgag agccgaggac acggccgtat attactgtgc gaaagcgtat     300
tacgatattt tgactggttc cttctttgac tactggggcc agggaaccct ggtcactgtc     360
tcctca                                                                366

<210> SEQ ID NO 272
<211> LENGTH: 122
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG331

<400> SEQUENCE: 272

Glu Val Gln Leu Val Glu Ser Gly Gly Gly Leu Val Tyr Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Tyr Tyr Asp Ile Leu Thr Gly Ser Phe Phe Asp Tyr Trp
            100                 105                 110

-continued

Gly Gln Gly Thr Leu Val Thr Val Ser Ser
        115                 120

<210> SEQ ID NO 273
<211> LENGTH: 321
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG331

<400> SEQUENCE: 273

```
gaaatagtga tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag actggagcct   240
gaagattttg cagtgtatta ctgtcagcag tatggtagct caccgctcac tttcggcgga   300
gggaccaagc tggagatcaa a                                             321
```

<210> SEQ ID NO 274
<211> LENGTH: 107
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG331

<400> SEQUENCE: 274

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Leu
                85                  90                  95

Thr Phe Gly Gly Gly Thr Lys Leu Glu Ile Lys
            100                 105

<210> SEQ ID NO 275
<211> LENGTH: 366
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG357

<400> SEQUENCE: 275

```
gaggtgcagc tggtggagac tgggggaggc ttggtacagc ctgggggtc cctgagactc     60 tcctgtgcag cctctggatt cacctttagc agctatgcca tgagctgggt ccgccaggct   120
ccagggaagg ggctggagtg gtctcagat attaatcata gtggtggtag cacatactac    180
gcagactccg tgaagggccg gttcaccatc tccagagaca attccaagca cacgctgtat   240
ctgcaaatga acagcctgag agccgaggac acggccgtat attactgtgc gaaagactat   300
```

```
tacgatattt tgactggttc cttctttgac tactggggcc agggaaccct ggtcactgtc    360
tcctca                                                               366
```

<210> SEQ ID NO 276
<211> LENGTH: 122
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG 357

<400> SEQUENCE: 276

```
Glu Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Asn His Ser Gly Gly Ser Thr Tyr Tyr Ala Asp Ser Val
    50                  55                  60

Lys Gly Arg Phe Thr Ile Ser Arg Asp Asn Ser Lys His Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Tyr Asp Ile Leu Thr Gly Ser Phe Phe Asp Tyr Trp
            100                 105                 110

Gly Gln Gly Thr Leu Val Thr Val Ser Ser
        115                 120
```

<210> SEQ ID NO 277
<211> LENGTH: 321
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG 357

<400> SEQUENCE: 277

```
gacatcgtga tgacccagtc tccatcctcc ctgtctgcat ctgtaggaga cagagtcacc    60
atcacttgcc gggcaagtca gggcattagc agtgctttag cctggtatca gcagaaacca   120
gggaaagctc ctaagctcct gatctatgat gcctccagtt tggaaagtgg ggtcccatca   180
aggttcagcg gcagtggatc tgggacagat ttcactctca ccatcagcag cctgcagcct   240
gaagattttg caacttatta ctgtcaacag tttaatagtt acccgtggac gttcggccaa   300
gggaccaagg tggagatcaa a                                             321
```

<210> SEQ ID NO 278
<211> LENGTH: 107
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG 357

<400> SEQUENCE: 278

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30
```

Leu Ala Trp Tyr Gln Gln Lys Pro Gly Lys Ala Pro Lys Leu Leu Ile
              35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Trp
              85                  90                  95

Thr Phe Gly Gln Gly Thr Lys Val Glu Ile Lys
             100                 105

<210> SEQ ID NO 279
<211> LENGTH: 366
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG 476

<400> SEQUENCE: 279
gaggtgcagc tggtggagtc tgggggaggc ttggtacagc ctggggggtc cctgagactc     60
tcctgtgcag cctctggatt cactttagc agctatgcca tgaactgggt ccgccaggct    120
ccagggaagg gctggagtg gtctcagct attagttata gtggtcgtag cacatactac    180
gcagactccg tgaagggccg attcaccatc tccagagaca attccaagaa cacgctgtat    240
ctgcaaatga acagcctgag agccgaggac acggccgtat attactgtgc aagggccctt    300
tacgatattt tgactggtgg cggatttgac tactggggcc agggaaccct ggtcaccgtc    360
tcttca                                                               366

<210> SEQ ID NO 280
<211> LENGTH: 122
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG 476

<400> SEQUENCE: 280

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
              20                  25                  30

Ala Met Asn Trp Val Arg Gln Ala Pro Gly Lys Gly Leu Glu Trp Val
          35                  40                  45

Ser Ala Ile Ser Tyr Ser Gly Arg Ser Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
              85                  90                  95

Ala Lys Gly Leu Tyr Asp Ile Leu Thr Gly Gly Phe Asp Tyr Trp
             100                 105                 110

Gly Gln Gly Thr Leu Val Thr Val Ser Ser
            115                 120

<210> SEQ ID NO 281
<211> LENGTH: 321
<212> TYPE: DNA

<213> ORGANISM: Artificial Sequence
<220> FEATURE:
<223> OTHER INFORMATION: The Description of the artificial sequence:
      base sequence encoding VL excluding signal sequence of MOG 476

<400> SEQUENCE: 281

```
gacatccaga tgacccagtc tccatcctcc ctgtctgcat ctgtaggaga cagagtcacc    60
atcacttgcc gggcaagtca gggcattagc agtgctttag cctggtatca gcagaaacca   120
gggaaagctc ctaagctcct gatctatgat gcctccagtt tggaaagtgg ggtcccatca   180
aggttcagcg gcagtggatc tgggacagat ttcactctca ccatcagcag cctgcagcct   240
gaagattttg caacttatta ctgtcaacag tttaatagtt acccgtccac ttttggccag   300
gggacacgac tggagattaa a                                              321
```

<210> SEQ ID NO 282
<211> LENGTH: 107
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG 476

<400> SEQUENCE: 282

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Ser Ser Ala
            20                  25                  30
Leu Ala Trp Tyr Gln Gln Lys Pro Gly Lys Ala Pro Lys Leu Leu Ile
        35                  40                  45
Tyr Asp Ala Ser Ser Leu Glu Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Phe Asn Ser Tyr Pro Ser
                85                  90                  95
Thr Phe Gly Gln Gly Thr Arg Leu Glu Ile Lys
            100                 105
```

<210> SEQ ID NO 283
<211> LENGTH: 381
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG 323

<400> SEQUENCE: 283

```
cggatcacct tgagggagtc tggtcctacg ctggtgaaac ccacacagac cctcacgctg    60
acctgcacct tctctgggtt ctcactcagc actagtggag tgggtgtggg ctggatccgt   120
cagcccccag gaaaggccct ggagtggctt gcactcattt ttgggatga tgatagtcac   180
tacagcccat ctctgaagag caggctcacc atcaccaagg acacctccaa aaaccaggtg   240
gtccttacaa tgaccaacat ggaccctgtg gacacagcca catattactg tgcacggtat   300
tactttggtt cggggagtta tttccctagc tactggtact cgatctctg ggccgtggc    360
accctggtca ccgtctcctc a                                              381
```

<210> SEQ ID NO 284
<211> LENGTH: 127

```
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG 323

<400> SEQUENCE: 284

Arg Ile Thr Leu Arg Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Phe Trp Asp Asp Ser His Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Tyr Tyr Phe Gly Ser Gly Ser Tyr Phe Pro Ser Tyr Trp
            100                 105                 110

Tyr Phe Asp Leu Trp Gly Arg Gly Thr Leu Val Thr Val Ser Ser
        115                 120                 125

<210> SEQ ID NO 285
<211> LENGTH: 321
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG 323

<400> SEQUENCE: 285
gaaatagtga tgacgcagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctcccac tttcggcgga     300
gggaccaagc tggagatcaa a                                                321

<210> SEQ ID NO 286
<211> LENGTH: 107
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG 323

<400> SEQUENCE: 286

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
```

```
                65                  70                  75                  80
Glu Asp Phe Ala Val Tyr Tyr Cys Gln Gln Arg Ser Asn Trp Pro Pro
                        85                  90                  95

Thr Phe Gly Gly Gly Thr Lys Leu Glu Ile Lys
            100                 105
```

<210> SEQ ID NO 287
<211> LENGTH: 381
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG 341

<400> SEQUENCE: 287

```
cggatcacct tgaaggagtc tggtcctacg ctggtgaaac ccacacagac cctcacgctg      60
acctgcacct tctctgggtt ctcactcagc actagtggag tgggtgtggg ctggatccgt     120
cagcccccag gaaaggccct ggagtggctt gcactcattt attgggatga tgataaacac     180
tacagcccat ctctgaagag caggctcacc atcaccaagg acacctccaa aaaccaggtg     240
gtccttacaa tgaccaacat ggaccctgtg gacacagcca catattactg tgcacggtat     300
tactttggtt cggggagtta ttcccctagc tactggtact tcgatctctg gggccgtggc     360
accctggtca ctgtctcctc a                                               381
```

<210> SEQ ID NO 288
<211> LENGTH: 127
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG 341

<400> SEQUENCE: 288

```
Arg Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asp Asp Asp Lys His Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Tyr Tyr Phe Gly Ser Gly Ser Tyr Ser Pro Ser Tyr Trp
            100                 105                 110

Tyr Phe Asp Leu Trp Gly Arg Gly Thr Leu Val Thr Val Ser Ser
        115                 120                 125
```

<210> SEQ ID NO 289
<211> LENGTH: 321
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG 341

<400> SEQUENCE: 289

```
gaaattgtgt tgacgcagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctccac  tttcggcgga     300 gggaccaagg tggagatcaa a                                               321
```

<210> SEQ ID NO 290
<211> LENGTH: 107
<212> TYPE: PRT
<213> ORGANISM: Artificial Sequence
<220> FEATURE:
<223> OTHER INFORMATION: The Description of the artificial sequence: amino acid sequence of VL excluding signal sequence of MOG 341

<400> SEQUENCE: 290

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Thr Phe Gly Gly Gly Thr Lys Val Glu Ile Lys
            100                 105
```

<210> SEQ ID NO 291
<211> LENGTH: 381
<212> TYPE: DNA
<213> ORGANISM: Artificial Sequence
<220> FEATURE:
<223> OTHER INFORMATION: The Description of the artificial sequence: base sequence encoding VH excluding signal sequence of MOG 354

<400> SEQUENCE: 291

```
cggatcacct tgagggagtc tggtcctacg ctggtgaaac ccacacagac cctcacgctg      60
acctgcacct cctctgggct ctcactcagc actagtggag tgggtgtggg ctggatccgt     120
cagcccccag gaaaggccct ggagtggctt gcactcattt tttgggatga tgatacacac     180
tacagcccat ctctgaagag caggctcacc atcaccaagg acacctccaa aaaccaggtg     240
gtccttacaa tgaccaacat ggaccctgtg gacacagcca catattactg tgcacggtat     300
tactttggtt cggggagtta tttccctagc tactggtact cgatctctg  gggccgtggc     360 accatggtca ccgtctcttc a                                               381
```

<210> SEQ ID NO 292
<211> LENGTH: 127
<212> TYPE: PRT
<213> ORGANISM: Artificial Sequence
<220> FEATURE:
<223> OTHER INFORMATION: The Description of the artificial sequence: amino acid sequence of VH excluding signal sequence of MOG 354

<400> SEQUENCE: 292

```
Arg Ile Thr Leu Arg Glu Ser Gly Pro Thr Leu Val Lys Pro Thr Gln
1               5                   10                  15

Thr Leu Thr Leu Thr Cys Thr Ser Ser Gly Leu Ser Leu Ser Thr Ser
                20                  25                  30

Gly Val Gly Val Gly Trp Ile Arg Gln Pro Pro Gly Lys Ala Leu Glu
            35                  40                  45

Trp Leu Ala Leu Ile Phe Trp Asp Asp Asp Thr His Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Tyr Tyr Phe Gly Ser Gly Ser Tyr Phe Pro Ser Tyr Trp
            100                 105                 110

Tyr Phe Asp Leu Trp Gly Arg Gly Thr Met Val Thr Val Ser Ser
            115                 120                 125
```

<210> SEQ ID NO 293
<211> LENGTH: 321
<212> TYPE: DNA
<213> ORGANISM: Artificial Sequence
<220> FEATURE:
<223> OTHER INFORMATION: The Description of the artificial sequence: base sequence encoding VL excluding signal sequence of MOG 354

<400> SEQUENCE: 293

```
gaaatagtga tgacgcagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggccgctcac tttcggcgga   300
gggaccaagg tggaaatcaa a                                             321
```

<210> SEQ ID NO 294
<211> LENGTH: 107
<212> TYPE: PRT
<213> ORGANISM: Artificial Sequence
<220> FEATURE:
<223> OTHER INFORMATION: The Description of the artificial sequence: amino acid sequence of VL excluding signal sequence of MOG 354

<400> SEQUENCE: 294

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105
```

<210> SEQ ID NO 295
<211> LENGTH: 381
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG 355

<400> SEQUENCE: 295

```
cggatcacct tgagggagtc tggtcctacg ctggtgaaac ccacacagac cctcacgctg      60
acctgcacct cctctgggct ctcactcagc actagtggag tgggtgtggg ctggatccgt     120
cagcccccag gaaaggccct ggagtggctt gcactcattt tttgggatga tgatacacac     180
tacagcccat ctctgaagag caggctcacc atcaccaagg acacctccaa aaaccaggtg     240
gtccttacaa tgaccaacat ggaccctgtg gacacagcca catattactg tgcacggtat     300
tactttggtt cggggagtta tttccctagc tactggtact cgatctctg gggccgtggc     360 accctggtca ctgtctcctc a                                                381
```

<210> SEQ ID NO 296
<211> LENGTH: 127
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG 355

<400> SEQUENCE: 296

```
Arg Ile Thr Leu Arg Glu Ser Gly Pro Thr Leu Val Lys Pro Thr Gln
1               5                   10                  15

Thr Leu Thr Leu Thr Cys Thr Ser Ser Gly Leu Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Phe Trp Asp Asp Asp Thr His Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Tyr Tyr Phe Gly Ser Gly Ser Tyr Phe Pro Ser Tyr Trp
            100                 105                 110

Tyr Phe Asp Leu Trp Gly Arg Gly Thr Leu Val Thr Val Ser Ser
        115                 120                 125
```

<210> SEQ ID NO 297
<211> LENGTH: 321
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG 355

<400> SEQUENCE: 297

```
gaaatagtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
```

```
gaagattttg cagtttatta ctgtcagcag cgtagcaact ggccgctcac tttcggcgga      300
gggaccaagc tggagatcaa a                                                321
```

<210> SEQ ID NO 298
<211> LENGTH: 107
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG 355

<400> SEQUENCE: 298

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Leu Glu Ile Lys
            100                 105
```

<210> SEQ ID NO 299
<211> LENGTH: 360
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG 308

<400> SEQUENCE: 299

```
gaggtgcagc tggtgcagtc cggggctgag gtgaggaagt ctgggtcctc ggtgaaggtc      60
tcctgcaagg cttctggagg caccttcagc agatatgcta tcagctgggt gcgacaggcc     120
cctggacaag gcttgagtg gatgggaggg atcatcccta tgtttagtac gacaaactac      180
gcacagaagt tccagggcag agtcacgatt accgcggacg aatccacgag cacagcctac     240
atggaactga gcagcctgag atctgaggac acggccgtgt attactgtgc gagagattgg     300
gcagtggctg gtatggggtt tgcctactgg ggccagggaa ccctggtcac cgtctcctca     360
```

<210> SEQ ID NO 300
<211> LENGTH: 120
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG 308

<400> SEQUENCE: 300

```
Glu Val Gln Leu Val Gln Ser Gly Ala Glu Val Arg Lys Ser Gly Ser
1               5                   10                  15

Ser Val Lys Val Ser Cys Lys Ala Ser Gly Gly Thr Phe Ser Arg Tyr
            20                  25                  30

Ala Ile Ser Trp Val Arg Gln Ala Pro Gly Gln Gly Leu Glu Trp Met
        35                  40                  45
```

Gly Gly Ile Ile Pro Met Phe Ser Thr Thr Asn Tyr Ala Gln Lys Phe
            50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Trp Ala Val Ala Gly Met Gly Phe Ala Tyr Trp Gly Gln
                100                 105                 110

Gly Thr Leu Val Thr Val Ser Ser
        115                 120

<210> SEQ ID NO 301
<211> LENGTH: 321
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG 308

<400> SEQUENCE: 301
gaaatagtga tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctccgac gttcggccaa     300
gggaccaaag tggatatcaa a                                               321

<210> SEQ ID NO 302
<211> LENGTH: 107
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG 308

<400> SEQUENCE: 302

Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Thr Phe Gly Gln Gly Thr Lys Val Asp Ile Lys
                100                 105

<210> SEQ ID NO 303
<211> LENGTH: 360
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG 316

<400> SEQUENCE: 303

```
gaagtgcagc tggtgcagtc cggggctgag gtgaagaagc ctgggtcctc ggtgaaggtc    60
tcctgcaagg cttctggagg caccttcagc agatatgcta tcagctgggt gcgacaggcc   120
cctggacaag gcttgagtg gatgggaggg atcatcccta tgtttaatac agcaaactac   180
gcacagaagt tccagggcag agtcacgatt accgcggacg aatccacgag cacagcctac   240
atggagctga gcagcctgag atctgaggac acggccgtgt attactgtgc gagagattgg   300
gcagtggctg gtatggggtt taactactgg ggccagggaa ccctggtcac cgtctcctca   360
```

<210> SEQ ID NO 304
<211> LENGTH: 120
<212> TYPE: PRT
<213> ORGANISM: Artificial Sequence
<220> FEATURE:
<223> OTHER INFORMATION: The Description of the artificial sequence: amino acid sequence of VH excluding signal sequence of MOG 316

<400> SEQUENCE: 304

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30

Ala Ile Ser Trp Val Arg Gln Ala Pro Gly Gln Gly Leu Glu Trp Met
        35                  40                  45

Gly Gly Ile Ile Pro Met Phe Asn Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Trp Ala Val Ala Gly Met Gly Phe Asn Tyr Trp Gly Gln
            100                 105                 110

Gly Thr Leu Val Thr Val Ser Ser
        115                 120
```

<210> SEQ ID NO 305
<211> LENGTH: 321
<212> TYPE: DNA
<213> ORGANISM: Artificial Sequence
<220> FEATURE:
<223> OTHER INFORMATION: The Description of the artificial sequence: base sequence encoding VL excluding signal sequence of MOG 316

<400> SEQUENCE: 305

```
gacatccaga tgacccagtc tccatcctcc ctgtctgcat ctgtaggaga cagagtcacc    60
atcacttgcc gggcaagtca gggcattaac agtgctttag cctggtatca gcagaaacca   120
gggaaagctc ctaagctcct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgccaacag tataatagtt acccgatcac cttcggccaa   300
gggacacgac tggagattaa a                                             321
```

<210> SEQ ID NO 306
<211> LENGTH: 107
<212> TYPE: PRT
<213> ORGANISM: Artificial Sequence
<220> FEATURE:

<223> OTHER INFORMATION: The Description of the artificial sequence:
      amino acid sequence of VL excluding signal sequence of MOG 316

<400> SEQUENCE: 306

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Ser Ala
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105

<210> SEQ ID NO 307
<211> LENGTH: 360
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG 319

<400> SEQUENCE: 307
caggtgcagc tggtgcaatc tggggctgag gtgaagaagc ctgggtcctc ggtgaaggtc      60
tcctgcaagg cttctggagg caccttcagc agatatgcta tcagctgggt gcgacaggcc     120
cctggacaag ggcttgagtg gatgggaggg atcatcccta tgtttagtac agcaaactac     180
gcacagaagt tccagggcag agtcacgatt accgcggacg aatccacgag cacagcctac     240
atggagctga gcagcctgag atctgacgac acggccgtgt attactgtgc gagagattgg     300
gcagtggctg gtatgggctt taactactgg ggccagggaa ccctggtcac tgtctcctca     360

<210> SEQ ID NO 308
<211> LENGTH: 120
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG 319

<400> SEQUENCE: 308

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30

Ala Ile Ser Trp Val Arg Gln Ala Pro Gly Gln Gly Leu Glu Trp Met
        35                  40                  45

Gly Gly Ile Ile Pro Met Phe Ser Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Asp Trp Ala Val Ala Gly Met Gly Phe Asn Tyr Trp Gly Gln

Gly Thr Leu Val Thr Val Ser Ser
        115                 120

<210> SEQ ID NO 309
<211> LENGTH: 324
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG 319

<400> SEQUENCE: 309
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccatt cactttcggc     300
cctgggacca aggtggaaat caaa                                            324

<210> SEQ ID NO 310
<211> LENGTH: 108
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG 319

<400> SEQUENCE: 310

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Glu Ile Lys
            100                 105

<210> SEQ ID NO 311
<211> LENGTH: 360
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG 320

<400> SEQUENCE: 311
caggtgcagc tggtgcagtc tggggctgag gtgaagaagc ctgggtcctc ggtgaaggtc      60
tcctgcaagg cttctggagg caccttcagc agatatgcta tcaactgggt gcgacaggcc     120
cctggacaag gcttgagtg gatgggaggg atcatcccta tgtttagtac agtaaattac     180
gcacagaagt tccagggcag agtcacgatt accgcggacg aatccacgag cacagcctac     240

```
atggagctga gcagcctgag atctgaggac acggccgtgt attactgtgc gagagattgg      300
gcagtggctg gtatggggtt tgactactgg ggccagggaa ccctggtcac cgtctcctca      360
```

<210> SEQ ID NO 312
<211> LENGTH: 120
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG 320

<400> SEQUENCE: 312

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30

Ala Ile Asn Trp Val Arg Gln Ala Pro Gly Gln Gly Leu Glu Trp Met
        35                  40                  45

Gly Gly Ile Ile Pro Met Phe Ser Thr Val Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Trp Ala Val Ala Gly Met Gly Phe Asp Tyr Trp Gly Gln
            100                 105                 110

Gly Thr Leu Val Thr Val Ser Ser
        115                 120

<210> SEQ ID NO 313
<211> LENGTH: 324
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG 320

<400> SEQUENCE: 313

```
gaaatagtgt tgacacagtc tccaggcacc ctgtctttgt ctccagggga aagagccacc      60
ctctcctgca gggccagtca gagtgttagc agcagctact tagcctggta ccagcagaaa      120
cctggccagg ctcccaggct cctcatctat ggtgcatcca gcagggccac tggcatccca      180
gacaggttca gtggcagtgg gtctgggaca gacttcactc tcaccatcag cagactggag      240
cctgaagatt ttgcagtgta ttactgtcag cagtatggta gctcaccatt cactttcggc      300
cctgggacca aagtggatat caaa                                             324
```

<210> SEQ ID NO 314
<211> LENGTH: 108
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG 320

<400> SEQUENCE: 314

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Phe Thr Phe Gly Pro Gly Thr Lys Val Asp Ile Lys
            100                 105

<210> SEQ ID NO 315
<211> LENGTH: 360
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG 338

<400> SEQUENCE: 315
caggtccagc tggtgcagtc tggggctgag gtgaagaagc ctgggtcctc ggtgaaggtc     60
tcctgcaagg cttctggagg caccttcagc agatatgcta tcagctgggt gcgacaggcc    120
cctggacaag gcttgagtg gatgggaggg atcatcccta tgtttaatac agcaaactac    180
gcacagaagt tccagggcag agtcacgatt accgcgacg aatccacgag cacagcctac    240
atggagctga gcagcctgag atctgaggac acggccgtgt attactgtgc gagagattgg    300
gcagtggctg gtatgggtt tgaccctgg ggccagggaa ccctggtcac tgtctcctca    360

<210> SEQ ID NO 316
<211> LENGTH: 120
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG 338

<400> SEQUENCE: 316

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Arg Tyr
             20                  25                  30

Ala Ile Ser Trp Val Arg Gln Ala Pro Gly Gln Gly Leu Glu Trp Met
            35                  40                  45

Gly Gly Ile Ile Pro Met Phe Asn Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Trp Ala Val Ala Gly Met Gly Phe Asp Pro Trp Gly Gln
            100                 105                 110

Gly Thr Leu Val Thr Val Ser Ser
        115                 120

<210> SEQ ID NO 317
<211> LENGTH: 321
<212> TYPE: DNA
<213> ORGANISM: Artificial Sequence
<220> FEATURE:

<223> OTHER INFORMATION: The Description of the artificial sequence:
     base sequence encoding VL excluding signal sequence of MOG 338

<400> SEQUENCE: 317

```
gaaattgtgt tgacgcagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtaacaact ggcctctcac tttcggcgga     300
gggaccaagc tggagatcaa a                                                321
```

<210> SEQ ID NO 318
<211> LENGTH: 107
<212> TYPE: PRT
<213> ORGANISM: Artificial Sequence
<220> FEATURE:
<223> OTHER INFORMATION: The Description of the artificial sequence:
     amino acid sequence of VL excluding signal sequence of MOG 338

<400> SEQUENCE: 318

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Asn Trp Pro Leu
                85                  90                  95

Thr Phe Gly Gly Gly Thr Lys Leu Glu Ile Lys
            100                 105

<210> SEQ ID NO 319
<211> LENGTH: 360
<212> TYPE: DNA
<213> ORGANISM: Artificial Sequence
<220> FEATURE:
<223> OTHER INFORMATION: The Description of the artificial sequence:
     base sequence encoding VH excluding signal sequence of MOG352

<400> SEQUENCE: 319

```
gaggtgcagc tggtgcagtc cggggctgag gtgaagaagc ctgggtcctc ggtgaaggtc      60
tcctgcaagg cttctggagg caccttcagc agatatgcta tcaactgggt gcgacaggcc    120
cctggacaag gcttgagtg gatgggaggg atcatcccta tgtttagtac agtaaactac    180
gcacagaagt tccagggcag agtcacgatt accgcggacg aatccacgag cacagcctac    240
atggagctga gcagcctgag atctgaggac acggccgtgt attactgtgc gagagattgg    300
gcagtggctg gtatggggtt tgactactgg ggccagggaa ccctggtcac tgtctcctca    360
```

<210> SEQ ID NO 320
<211> LENGTH: 120
<212> TYPE: PRT
<213> ORGANISM: Artificial Sequence
<220> FEATURE:
<223> OTHER INFORMATION: The Description of the artificial sequence:

amino acid sequence of VH excluding signal sequence of MOG352

<400> SEQUENCE: 320

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30

Ala Ile Asn Trp Val Arg Gln Ala Pro Gly Gln Gly Leu Glu Trp Met
        35                  40                  45

Gly Gly Ile Ile Pro Met Phe Ser Thr Val Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Trp Ala Val Ala Gly Met Gly Phe Asp Tyr Trp Gly Gln
            100                 105                 110

Gly Thr Leu Val Thr Val Ser Ser
        115                 120

<210> SEQ ID NO 321
<211> LENGTH: 321
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG352

<400> SEQUENCE: 321
gccatccaga tgacccagtc tccatcttcc gtgtctgcat ctgtaggaga cagagtcacc       60
atcacttgtc gggcgagtca gggtattagc agctggttag cctggtatca gcataaacca      120
gggaaagccc ctaagtccct gatctatgct gcatccagtt tgcaaagtgg ggtcccatca      180
aggttcagcg gcagtggatc tgggacagat ttcactctca ccatcagcag cctgcagcct      240
gaagattttg caacttatta ctgccaacag tataatagtt acccgctcac tttcggcgga      300
gggaccaaag tggatatcaa a                                                321

<210> SEQ ID NO 322
<211> LENGTH: 107
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG 352

<400> SEQUENCE: 322

Ala Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Asp Ile Lys
        100                 105

<210> SEQ ID NO 323
<211> LENGTH: 360
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG 359

<400> SEQUENCE: 323
gaggtccagc tggtgcagtc tggggctgag gtgaagaagc ctgggtcctc ggtgaaggtc    60
tcctgcaagg cttctggagg caccttcagc agatatgcta tcagctgggt gcgacaggcc   120
cctggacaag gcttgagtg gatgggaggg atcatccta tgtttaatac agcaaactac   180
gcacagaagt tccagggcag agtcacgatt accgcggacg aatccacgag cacagcctac   240
atggagctga gcagcctgag atctgaggac acggccgtgt attactgtgc gagagattgg   300
gcagtggctg gtatggggtt taactactgg ggccagggaa ccctggtcac tgtctcctca   360

<210> SEQ ID NO 324
<211> LENGTH: 120
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG 359

<400> SEQUENCE: 324

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30

Ala Ile Ser Trp Val Arg Gln Ala Pro Gly Gln Gly Leu Glu Trp Met
        35                  40                  45

Gly Gly Ile Ile Pro Met Phe Asn Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Trp Ala Val Ala Gly Met Gly Phe Asn Tyr Trp Gly Gln
            100                 105                 110

Gly Thr Leu Val Thr Val Ser Ser
        115                 120

<210> SEQ ID NO 325
<211> LENGTH: 324
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG 359

<400> SEQUENCE: 325
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180

```
gacaggttca gtggcagtgg gtctgggaca gacttcactc tcaccatcag cagactggag      240
cctgaagatt tgcagtgta ttactgtcag cagtatggta gctcaccgct cactttcggc      300
ggagggacca agctggagat caaa                                             324
```

<210> SEQ ID NO 326
<211> LENGTH: 108
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG 359

<400> SEQUENCE: 326

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Leu Glu Ile Lys
            100                 105
```

<210> SEQ ID NO 327
<211> LENGTH: 360
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG 478

<400> SEQUENCE: 327

```
gaggtccagc tggtacagtc tggggctgag gtgaagaagc ctgggtcctc ggtgaaggtc      60
tcctgcaagg cttctggagg caccttcagc agatatgcta tcagctgggt gcgacaggcc      120
cctggacaag gcttgagtg gatgggaggg atcatcccta tgtttgctac agcaaactac      180
gcacagaagt tccaggccag agtcacgatt accgcggacg aaaccacgag cacagcctac      240
atggagctga gcagcctgag atctgaggac acgggcgtgt attactgtgc gagagattgg      300
gcagtggctg ctatggggtt tgcccactgg ggccagggaa ccctggtcac tgtctcctca      360
```

<210> SEQ ID NO 328
<211> LENGTH: 120
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG 478

<400> SEQUENCE: 328

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30

Ala Ile Ser Trp Val Arg Gln Ala Pro Gly Gln Gly Leu Glu Trp Met
```

```
            35                  40                  45
Gly Gly Ile Ile Pro Met Phe Ala Thr Ala Asn Tyr Ala Gln Lys Phe
 50                  55                  60

Gln Ala Arg Val Thr Ile Thr Ala Asp Glu Thr Thr Ser Thr Ala Tyr
 65                  70                  75                  80

Met Glu Leu Ser Ser Leu Arg Ser Glu Asp Thr Gly Val Tyr Tyr Cys
                 85                  90                  95

Ala Arg Asp Trp Ala Val Ala Ala Met Gly Phe Ala His Trp Gly Gln
                100                 105                 110

Gly Thr Leu Val Thr Val Ser Ser
            115                 120

<210> SEQ ID NO 329
<211> LENGTH: 324
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG 478

<400> SEQUENCE: 329
gaaatagtga tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccgat caccttcggc     300
caagggacac gactggagat taaa                                            324

<210> SEQ ID NO 330
<211> LENGTH: 108
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG 478

<400> SEQUENCE: 330

Glu Ile Val Met Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Ile Thr Phe Gly Gln Gly Thr Arg Leu Glu Ile Lys
            100                 105

<210> SEQ ID NO 331
<211> LENGTH: 357
<212> TYPE: DNA
<213> ORGANISM: Artificial Sequence
<220> FEATURE:
<223> OTHER INFORMATION: The Description of the artificial sequence:
``` base sequence encoding VH excluding signal sequence of MOG 470

<400> SEQUENCE: 331
caggtgcagc tggtggagtc tgggggaggc ttggtacagc cggggggggtc cctgagactc     60 tcctgtgcag cctctggatt cacctttagc agctatgcca tgaactgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaagtga acagcctgag agccgaggac acggccgttt attactgtgc gagagactac    300
ggtggtatct ccccctttga ctactggggc cagggaaccc tggtcaccgt ctcctca       357

<210> SEQ ID NO 332
<211> LENGTH: 119
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG 470

<400> SEQUENCE: 332

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Val Asn Ser Leu Arg Ala Glu Asp Thr Ala Val Tyr Tyr Cys
                85                  90                  95

Ala Arg Asp Tyr Gly Gly Ile Ser Pro Phe Asp Tyr Trp Gly Gln Gly
            100                 105                 110

Thr Leu Val Thr Val Ser Ser
        115

<210> SEQ ID NO 333
<211> LENGTH: 321
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG 470

<400> SEQUENCE: 333
gaaatagtga tgacacagtc tccagccacc ctgtctttgt ctccagggga aagagccacc     60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag actggagcct    240
gaagattttg cagtgtatta ctgtcagcag tatggtagct caccgtacac ttttggccag    300
gggacacgac tggagattaa a                                              321

<210> SEQ ID NO 334
<211> LENGTH: 107
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG 470

<400> SEQUENCE: 334

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Tyr
                85                  90                  95

Thr Phe Gly Gln Gly Thr Arg Leu Glu Ile Lys
            100                 105

<210> SEQ ID NO 335
<211> LENGTH: 366
<212> TYPE: DNA
<213> ORGANISM: Artificial Sequence
<220> FEATURE:
<223> OTHER INFORMATION: The Description of the artificial sequence:
      base sequence encoding VH excluding signal sequence of MOG 418

<400> SEQUENCE: 335
caggtgtagc tggtgcagtc tgggggaggc tggtcaagc ctgggggtc cctgagactc      60
tcctgtgcag cctctggatt caccttcagt agctatagca tgcactgggt ccgccaggct    120
ccagggaagg gctggagtg gtctcatcc attagtcata gtagtagtta catatcctac     180
gcagactcag tgaagggccg attcaccatc tccagagaca cgccaagaa ttcactgtat    240
ctgcaaatga acagcctgag agccgaggac acggctgtgt attactgtgc gaaagggtat    300
tacgatattt tgactggttc tctctttgac tactggggcc agggaaccct ggtcaccgtc    360
tcctca                                                              366

<210> SEQ ID NO 336
<211> LENGTH: 122
<212> TYPE: PRT
<213> ORGANISM: Artificial Sequence
<220> FEATURE:
<223> OTHER INFORMATION: The Description of the artificial sequence:
      amino acid sequence of VH excluding signal sequence of MOG 418

<400> SEQUENCE: 336

Gln Val Tyr Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met His Trp Val Arg Gln Ala Pro Gly Lys Gly Leu Glu Trp Val
        35                  40                  45

Ser Ser Ile Ser His Ser Ser Ser Tyr Ile Ser Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys

```
                              85                  90                  95
Ala Lys Gly Tyr Tyr Asp Ile Leu Thr Gly Ser Leu Phe Asp Tyr Trp
                100                 105                 110

Gly Gln Gly Thr Leu Val Thr Val Ser Ser
            115                 120

<210> SEQ ID NO 337
<211> LENGTH: 321
<212> TYPE: DNA
<213> ORGANISM: Artificial Sequence
<220> FEATURE:
<223> OTHER INFORMATION: The Description of the artificial sequence:
      base sequence encoding VL excluding signal sequence of MOG 418

<400> SEQUENCE: 337
gaaattgtgt tgacgcagtc tccagccacc ctgtctttgt ctccagggga aagagccacc      60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag actggagcct    240
gaagattttg cagtgtatta ctgtcagcag tatggtagct caccattcac tttcggccct    300
gggaccaaag tggatatcaa a                                              321

<210> SEQ ID NO 338
<211> LENGTH: 107
<212> TYPE: PRT
<213> ORGANISM: Artificial Sequence
<220> FEATURE:
<223> OTHER INFORMATION: The Description of the artificial sequence:
      amino acid sequence of VL excluding signal sequence of MOG 418

<400> SEQUENCE: 338

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Phe
                85                  90                  95

Thr Phe Gly Pro Gly Thr Lys Val Asp Ile Lys
            100                 105
```